United States Patent
Tainsky et al.

(10) Patent No.: US 9,575,070 B2
(45) Date of Patent: Feb. 21, 2017

(54) NEOEPITOPE DETECTION OF DISEASE USING PROTEIN ARRAYS

(75) Inventors: Michael A. Tainsky, West Bloomfield, MI (US); Sorin Draghici, Troy, MI (US); Ho-Sheng Lin, Plymouth, MI (US)

(73) Assignee: Wayne State University, Detroit, MI (US)

( * ) Notice: Subject to any disclaimer, the term of this patent is extended or adjusted under 35 U.S.C. 154(b) by 783 days.

(21) Appl. No.: 11/903,312

(22) Filed: Sep. 21, 2007

(65) Prior Publication Data

US 2008/0267999 A1    Oct. 30, 2008

Related U.S. Application Data

(63) Continuation-in-part of application No. 11/060,867, filed on Feb. 17, 2005, now Pat. No. 7,964,536, which is a continuation-in-part of application No. 10/004,587, filed on Dec. 4, 2001, now Pat. No. 7,863,004.

(51) Int. Cl.
*G01N 33/68* (2006.01)
*C07K 14/00* (2006.01)

(52) U.S. Cl.
CPC .......... *G01N 33/68* (2013.01); *G01N 33/6893* (2013.01); *C07K 2319/00* (2013.01); *G01N 2800/32* (2013.01); *G01N 2800/36* (2013.01)

(58) Field of Classification Search
None
See application file for complete search history.

(56) References Cited

U.S. PATENT DOCUMENTS

| | | | |
|---|---|---|---|
| 3,654,090 A | | 4/1972 | Schuurs et al. |
| 3,817,837 A | | 6/1974 | Rubenstein et al. |
| 3,996,345 A | | 12/1976 | Ullman et al. |
| 4,020,151 A | | 4/1977 | Bolz et al. |
| 4,062,935 A | | 12/1977 | Masson et al. |
| 4,184,849 A | | 1/1980 | Cambiaso et al. |
| 4,275,149 A | | 6/1981 | Litman et al. |
| 4,318,980 A | | 3/1982 | Bogulaski et al. |
| 4,855,242 A | | 8/1989 | Soeldner et al. |
| 4,868,104 A | | 9/1989 | Kurn et al. |
| 4,946,778 A | | 8/1990 | Ladner et al. |
| 4,959,303 A | | 9/1990 | Milburn et al. |
| 5,185,243 A | | 2/1993 | Ullman et al. |
| 5,200,318 A | | 4/1993 | Rabin et al. |
| 5,766,905 A | * | 6/1998 | Studier et al. ............. 435/235.1 |
| 6,610,836 B1 | * | 8/2003 | Breton ................... C07K 14/26 435/320.1 |
| 7,781,565 B2 | * | 8/2010 | Pasqualini ............... C07K 7/06 424/192.1 |
| 2002/0081570 A1 | * | 6/2002 | Lilien et al. ..................... 435/5 |
| 2003/0105000 A1 | * | 6/2003 | Pero et al. ..................... 514/12 |
| 2003/0143667 A1 | * | 7/2003 | O'Brien et al. ............ 435/69.1 |
| 2003/0157597 A1 | * | 8/2003 | Raitano .................. C07K 16/30 435/69.1 |
| 2003/0236190 A1 | * | 12/2003 | Pillutla et al. .................. 514/12 |
| 2004/0170956 A1 | * | 9/2004 | Wellstein et al. .................. 435/5 |
| 2005/0095648 A1 | * | 5/2005 | Geysen et al. ................ 435/7.1 |
| 2006/0014138 A1 | * | 1/2006 | Chinnaiyan et al. ............ 435/5 |
| 2007/0197444 A1 | * | 8/2007 | Herman et al. ................. 514/13 |
| 2007/0202496 A1 | * | 8/2007 | Beretta ............................ 435/5 |
| 2008/0081768 A1 | * | 4/2008 | Watt ....................... C07K 1/047 506/9 |
| 2013/0122027 A1 | * | 5/2013 | Tainsky et al. ............ 424/184.1 |

OTHER PUBLICATIONS

Boon and Old (Curr. Opin. Immunol. 9:681 1997).*
Bei et al. (Int. J. Oncol. Dec. 2007 31:1301-1308).*
Boyd (The Basic Science of Oncology, 1992, McGraw-Hill, Inc., p. 379).*
Greenbaum et al. (Genome Biology, 2003, vol. 4, Issue 9, pp. 117.1-117.8).*
Brennan et al. (J. Autoimmunity, 1989, 2 (suppl.): 177-186).*
Hell et al. (Laboratory Investigation, 1995, 73: 492-496).*
Fu et al. (EMBO J., 1996, 15:43982-4401).*
Rudikoff et al, (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Holmes (Exp. Opin.Invest. Drugs, 2001, 10(3):511-519).*
Tanaka et al. (1985 Proc. Natl. Acad. Sci. USA 82:3400-3404.*
Brown et al. (The Laryngoscope, 2003, 113: 393-400).*
Tang et al. (GenBank AAL96264.2, multiple myeloma overexpression gene 2, Sep. 2, 2003).*
Fernandez et al. (Cancer Detection and Prevention, Jan. 2005, 29: 59-65).*

(Continued)

*Primary Examiner* — Peter J Reddig
(74) *Attorney, Agent, or Firm* — Kenneth Kohn

(57) ABSTRACT

A diagnostic device for and method of detecting the presence of head and neck squamous cell carcinoma (HNSCC) in a patient including a detector device for detecting a presence of at least one marker indicative of HNSCC, the detector device including a panel of markers for HNSCC. A diagnostic device for and method of staging HNSCC in a patient including a detector device for detecting a presence of at least one marker indicative of stages of HNSCC, the detector device including a panel of markers for HNSCC. Markers for head and neck squamous cell carcinoma selected from the markers listed in Table 5. Methods of personalized immunotherapy, making a personalized anticancer vaccine, and predicting a clinical outcome in a HNSCC patient. A method of making a panel of HNSCC markers.

9 Claims, 6 Drawing Sheets

(56) References Cited

OTHER PUBLICATIONS

Cesareni, G. (FEBS Jul. 1992, 307(1): 66-70).*

T7Select® 10-3 OrientExpress™ cDNA Cloning System Manual, Oligo(dT) (TB178-T7Select® System Manual downloaded May 17, 2016).*

* cited by examiner

Fig. 1

| Clones from patient | Source of sera | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 1 | 1 | | | | | | | | | | | |
| 2 | | 1 | | | | | | | | | | |
| 3 | | | 1 | | | | | | | | | |
| 4 | | | | 1 | | | | | | | | |
| 5 | | | | | 1 | | | | | | | |
| 6 | | | | | | 1 | | | | | | |
| 7 | | | | | | | 1 | | | | | |
| 8 | | | | | | | | 1 | | | | |
| 9 | | | | | | | | | 1 | | | |
| 10 | | | | | | | | | | 1 | | |
| 11 | | | | | | | | | | | ? | |
| 12 | | | | | | | | | | | | ? |

| Clones from patient | Source of sera | | | | | | | | | |
|---|---|---|---|---|---|---|---|---|---|---|
| | 1 | 2 | 3 | 4 | 5 | 6 | 7 | 8 | 9 | 10 |
| 2 | | 1 | | 1 | | | | 1 | | |
| 3 | | | 1 | | | 1 | | | | 1 |
| 5 | | | | | 1 | | | 1 | 1 | |
| 7 | | | | | | | 1 | | | 1 |
| 8 | | | | | | | | 1 | | |
| 9 | | | | | | | | | 1 | |
| 10 | | | | | | | | | | 1 |
| 1 | 1 | | | | | | | | | |
| 4 | | | | 1 | | | | | | |
| 6 | | | | | | 1 | | | | |

Fig. 2

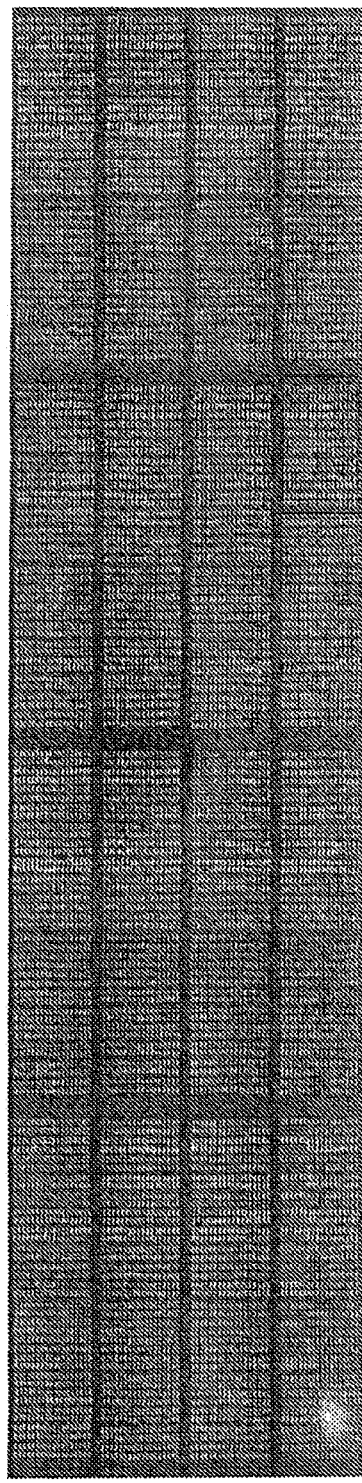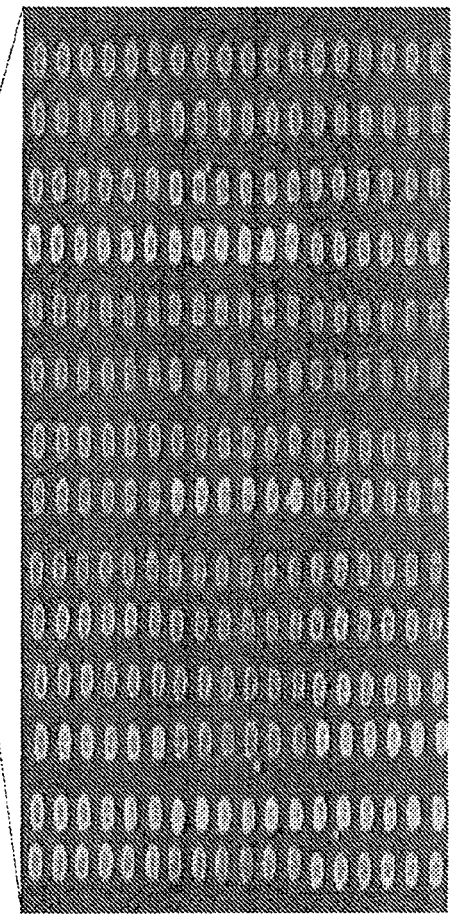
$$\text{Reactivity} = \frac{\text{Fluorescent intensity AlexaFluor647 (red)}}{\text{Fluorescent intensity AlexaFluor532 (green)}}$$
Fig. 4A
Fig. 4B

SEQUENCE LISTING

<160> NUMBER OF SEQ ID NOS: 1184

<210> SEQ ID NO 1
<211> LENGTH: 21
<212> TYPE: DNA
<213> ORGANISM: human

<400> SEQUENCE: 1
gttctatccg caacgttatg g                                              21

<210> SEQ ID NO 2
<211> LENGTH: 22
<212> TYPE: DNA
<213> ORGANISM: human

<400> SEQUENCE: 2
ggaggaaagt cgttttttgg gg                                             22

<210> SEQ ID NO 3
<211> LENGTH: 52
<212> TYPE: PRT
<213> ORGANISM: human

<400> SEQUENCE: 3

Ala Glu Met Phe Pro Glu Gly Ala Gly Pro Tyr Val Asp Leu Asp Glu
1               5                   10                  15

Ala Gly Gly Ser Thr Gly Leu Leu Met Asp Leu Ala Ala Asn Glu Lys
            20                  25                  30

Ala Val His Ala Asp Phe Phe Asn Asp Phe Glu Asp Leu Phe Asp Asp
        35                  40                  45

Asp Asp Ile Gln
    50

<210> SEQ ID NO 4
<211> LENGTH: 51
<212> TYPE: PRT
<213> ORGANISM: human

<400> SEQUENCE: 4

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 5
<211> LENGTH: 51
<212> TYPE: PRT
<213> ORGANISM: human

<400> SEQUENCE: 5

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

```
Asp Ile Gln
    50

<210> SEQ ID NO 6
<211> LENGTH: 51
<212> TYPE: PRT
<213> ORGANISM: human

<400> SEQUENCE: 6

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 7
<211> LENGTH: 30
<212> TYPE: PRT
<213> ORGANISM: human

<400> SEQUENCE: 7

Leu Val Ser Arg Pro Phe Gln His Gln Ala Ser Gly Trp Met Val Phe
1               5                   10                  15

Glu Asn Gly Ile Thr Met Leu Gln Asp Ser Ile Asn Trp Gly
            20                  25                  30

<210> SEQ ID NO 8
<211> LENGTH: 20
<212> TYPE: PRT
<213> ORGANISM: human

<400> SEQUENCE: 8

Ala Ser Gly Trp Met Val Phe Glu Asn Gly Ile Thr Met Leu Gln Asp
1               5                   10                  15

Ser Ile Asn Trp
            20

<210> SEQ ID NO 9
<211> LENGTH: 20
<212> TYPE: PRT
<213> ORGANISM: human

<400> SEQUENCE: 9

Ala Ser Gly Trp Met Val Phe Glu Asn Gly Ile Thr Met Leu Gln Asp
1               5                   10                  15

Ser Ile Asn Trp
            20

<210> SEQ ID NO 10
<211> LENGTH: 20
<212> TYPE: PRT
<213> ORGANISM: human

<400> SEQUENCE: 10

Ala Ser Gly Trp Met Val Phe Glu Asn Gly Ile Thr Met Leu Gln Asp
1               5                   10                  15

Ser Ile Asn Trp
            20
```

-continued

```
<210> SEQ ID NO 11
<211> LENGTH: 53
<212> TYPE: PRT
<213> ORGANISM: human

<400> SEQUENCE: 11

Pro Pro Trp Ser Pro Ile Val Glu Leu Leu Asp Ala Gln Val Ala Ala
1               5                   10                  15

Asp Pro Asp Lys Leu Val Glu Arg Phe Glu Leu Ala Val Asp Ala Leu
                20                  25                  30

Ser Pro Glu Val Tyr Thr Thr Tyr Phe Val Thr Lys Thr Leu Leu Leu
            35                  40                  45

Thr Ser Leu Phe Leu
    50

<210> SEQ ID NO 12
<211> LENGTH: 27
<212> TYPE: PRT
<213> ORGANISM: human

<400> SEQUENCE: 12

Leu Ala Val Asp Ala Leu Ser Pro Glu Val Tyr Thr Thr Tyr Phe Val
1               5                   10                  15

Thr Lys Thr Leu Leu Leu Thr Ser Leu Phe Leu
                20                  25

<210> SEQ ID NO 13
<211> LENGTH: 23
<212> TYPE: PRT
<213> ORGANISM: human

<400> SEQUENCE: 13

Asp Ala Leu Ser Pro Glu Tyr Thr Thr Tyr Phe Val Thr Lys Thr Leu
1               5                   10                  15

Leu Leu Thr Ser Leu Phe Leu
                20

<210> SEQ ID NO 14
<211> LENGTH: 27
<212> TYPE: PRT
<213> ORGANISM: human

<400> SEQUENCE: 14

Met Thr Tyr Asp Ala Leu Ser Pro Glu Leu Tyr Thr Thr Tyr Phe Val
1               5                   10                  15

Thr Lys Thr Leu Leu Leu Thr Ser Leu Phe Leu
                20                  25

<210> SEQ ID NO 15
<211> LENGTH: 52
<212> TYPE: PRT
<213> ORGANISM: human

<400> SEQUENCE: 15

Ala Glu Met Phe Pro Glu Gly Ala Gly Pro Tyr Val Asp Leu Asp Glu
1               5                   10                  15

Ala Gly Gly Ser Thr Gly Leu Leu Met Asp Leu Ala Ala Asn Glu Lys
                20                  25                  30

Ala Val His Ala Asp Phe Phe Asn Asp Phe Glu Asp Leu Phe Asp Asp
            35                  40                  45
```

```
Asp Asp Ile Gln
    50

<210> SEQ ID NO 16
<211> LENGTH: 51
<212> TYPE: PRT
<213> ORGANISM: human

<400> SEQUENCE: 16

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 17
<211> LENGTH: 51
<212> TYPE: PRT
<213> ORGANISM: human

<400> SEQUENCE: 17

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 18
<211> LENGTH: 51
<212> TYPE: PRT
<213> ORGANISM: human

<400> SEQUENCE: 18

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 19
<211> LENGTH: 30
<212> TYPE: PRT
<213> ORGANISM: human

<400> SEQUENCE: 19

Leu Val Ser Arg Pro Phe Gln His Gln Ala Ser Gly Trp Met Val Phe
1               5                   10                  15

Glu Asn Gly Ile Thr Met Leu Gln Asp Ser Ile Asn Trp Gly
            20                  25                  30

<210> SEQ ID NO 20
```

```
<211> LENGTH: 20
<212> TYPE: PRT
<213> ORGANISM: human

<400> SEQUENCE: 20

Ala Ser Gly Trp Met Val Phe Glu Asn Gly Ile Thr Met Leu Gln Asp
1               5                   10                  15

Ser Ile Asn Trp
            20

<210> SEQ ID NO 21
<211> LENGTH: 20
<212> TYPE: PRT
<213> ORGANISM: human

<400> SEQUENCE: 21

Ala Ser Gly Trp Met Val Phe Glu Asn Gly Ile Thr Met Leu Gln Asp
1               5                   10                  15

Ser Ile Asn Trp
            20

<210> SEQ ID NO 22
<211> LENGTH: 20
<212> TYPE: PRT
<213> ORGANISM: human

<400> SEQUENCE: 22

Ala Ser Gly Trp Met Val Phe Glu Asn Gly Ile Thr Met Leu Gln Asp
1               5                   10                  15

Ser Ile Asn Trp
            20

<210> SEQ ID NO 23
<211> LENGTH: 52
<212> TYPE: PRT
<213> ORGANISM: human

<400> SEQUENCE: 23

Gly Arg Lys Gly Leu Glu Phe Ala Arg Leu Val Lys Ser Tyr Glu Ala
1               5                   10                  15

Gln Asp Pro Glu Ile Ala Ser Leu Ser Gly Lys Leu Lys Ala Leu Phe
                20                  25                  30

Leu Pro Pro Met Thr Leu Pro Pro His Gly Pro Ala Ala Gly Gly Ser
            35                  40                  45

Val Ala Ala Ser
    50

<210> SEQ ID NO 24
<211> LENGTH: 48
<212> TYPE: PRT
<213> ORGANISM: human

<400> SEQUENCE: 24

Leu Glu Phe Ala Arg Leu Val Lys Ser Tyr Glu Ala Gln Asp Pro Glu
1               5                   10                  15

Ile Ala Ser Leu Ser Gly Lys Leu Lys Ala Leu Phe Leu Pro Pro Met
                20                  25                  30

Thr Leu Pro Pro His Gly Pro Ala Ala Gly Gly Ser Val Ala Ala Ser
            35                  40                  45

<210> SEQ ID NO 25
```

<211> LENGTH: 47
<212> TYPE: PRT
<213> ORGANISM: human

<400> SEQUENCE: 25

```
Leu Phe Ala Arg Leu Val Lys Ser Tyr Glu Ala Gln Asp Pro Glu Ile
1               5                   10                  15
Ala Ser Leu Ser Gly Lys Leu Lys Ala Leu Phe Leu Pro Pro Met Thr
            20                  25                  30
Leu Pro Pro His Gly Pro Ala Ala Gly Gly Ser Val Ala Ala Ser
        35                  40                  45
```

<210> SEQ ID NO 26
<211> LENGTH: 48
<212> TYPE: PRT
<213> ORGANISM: human

<400> SEQUENCE: 26

```
Leu Lys Phe Ala Arg Leu Val Lys Ser Tyr Glu Ala Gln Asp Pro Glu
1               5                   10                  15
Ile Ala Ser Leu Ser Gly Lys Leu Lys Ala Leu Phe Leu Pro Pro Met
            20                  25                  30
Thr Leu Pro Pro His Gly Pro Ala Ala Gly Gly Ser Val Ala Ala Ser
        35                  40                  45
```

<210> SEQ ID NO 27
<211> LENGTH: 28
<212> TYPE: PRT
<213> ORGANISM: human

<400> SEQUENCE: 27

```
Gly Trp Ser Ala Met Ala Gln Ser Trp Leu Thr Ala Thr Ser Thr Ser
1               5                   10                  15
Arg Val Gln Val Ile Leu Leu Pro Gln Pro Pro Glu
            20                  25
```

<210> SEQ ID NO 28
<211> LENGTH: 28
<212> TYPE: PRT
<213> ORGANISM: human

<400> SEQUENCE: 28

```
Gly Trp Ser Ala Met Ala Gln Ser Trp Leu Thr Ala Thr Ser Thr Ser
1               5                   10                  15
Arg Val Gln Val Ile Leu Leu Pro Gln Pro Pro Glu
            20                  25
```

<210> SEQ ID NO 29
<211> LENGTH: 25
<212> TYPE: PRT
<213> ORGANISM: human

<400> SEQUENCE: 29

```
Gly Trp Ser Ala Met Ala Gln Ser Trp Leu Thr Thr Ser Ser Val Gln
1               5                   10                  15
Val Ile Leu Leu Pro Gln Pro Pro Glu
            20                  25
```

<210> SEQ ID NO 30
<211> LENGTH: 28
<212> TYPE: PRT
<213> ORGANISM: human

```
<400> SEQUENCE: 30

Gly Trp Ser Ala Met Ala Gln Ser Trp Leu Thr Val Thr Ser Ala Ser
1               5                   10                  15

Gln Val Gln Val Ile Leu Leu Pro Gln Pro Pro Glu
            20                  25

<210> SEQ ID NO 31
<211> LENGTH: 52
<212> TYPE: PRT
<213> ORGANISM: human

<400> SEQUENCE: 31

Ala Glu Met Phe Pro Glu Gly Ala Gly Pro Tyr Val Asp Leu Asp Glu
1               5                   10                  15

Ala Gly Gly Ser Thr Gly Leu Leu Met Asp Leu Ala Ala Asn Glu Lys
            20                  25                  30

Ala Val His Ala Asp Phe Phe Asn Asp Phe Glu Asp Leu Phe Asp Asp
        35                  40                  45

Asp Asp Ile Gln
    50

<210> SEQ ID NO 32
<211> LENGTH: 51
<212> TYPE: PRT
<213> ORGANISM: human

<400> SEQUENCE: 32

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 33
<211> LENGTH: 51
<212> TYPE: PRT
<213> ORGANISM: human

<400> SEQUENCE: 33

Glu Met Phe Pro Glu Gly Ala Gly Pro Tyr Val Asp Leu Asp Glu Ala
1               5                   10                  15

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 34
<211> LENGTH: 51
<212> TYPE: PRT
<213> ORGANISM: human

<400> SEQUENCE: 34

Glu Met Phe Pro Glu Gly Ala Gly Pro Tyr Val Asp Leu Asp Glu Ala
1               5                   10                  15
```

Gly Gly Ser Thr Gly Leu Leu Met Asp Leu Ala Ala Asn Glu Lys Ala
            20                  25                  30

Val His Ala Asp Phe Phe Asn Asp Phe Glu Asp Leu Phe Asp Asp Asp
        35                  40                  45

Asp Ile Gln
    50

<210> SEQ ID NO 35
<211> LENGTH: 24
<212> TYPE: PRT
<213> ORGANISM: human

<400> SEQUENCE: 35

Lys Leu Leu His Gln Gly Ala Arg Arg Arg Gly Leu Arg Thr Pro
1               5                   10                  15

Ala Ser Val Pro Ile Ser Pro Ser
            20

<210> SEQ ID NO 36
<211> LENGTH: 22
<212> TYPE: PRT
<213> ORGANISM: human

<400> SEQUENCE: 36

Leu His Gln Gly Ala Arg Arg Arg Gly Leu Arg Thr Pro Ala Ser
1               5                   10                  15

Val Pro Ile Ser Pro Ser
            20

<210> SEQ ID NO 37
<211> LENGTH: 12
<212> TYPE: PRT
<213> ORGANISM: human

<400> SEQUENCE: 37

Leu Gln Gly Arg Arg Arg Leu Ser Val Pro Pro Ser
1               5                   10

<210> SEQ ID NO 38
<211> LENGTH: 19
<212> TYPE: PRT
<213> ORGANISM: human

<400> SEQUENCE: 38

Leu Gln Gln Gly Gly Arg Arg Gly Asp Leu Ser Ser Val Pro Thr
1               5                   10                  15

Ala Pro Ser

<210> SEQ ID NO 39
<211> LENGTH: 11
<212> TYPE: PRT
<213> ORGANISM: human

<400> SEQUENCE: 39

Ala Arg Arg Arg Arg Gly Leu Arg Thr Pro Ala
1               5                   10

<210> SEQ ID NO 40
<211> LENGTH: 9
<212> TYPE: PRT
<213> ORGANISM: human

```
<400> SEQUENCE: 40

Ala Arg Arg Arg Arg Leu Arg Thr Ala
1               5

<210> SEQ ID NO 41
<211> LENGTH: 10
<212> TYPE: PRT
<213> ORGANISM: human

<400> SEQUENCE: 41

Ala Arg Arg Arg Arg Leu Arg Thr Ala Ala
1               5                   10

<210> SEQ ID NO 42
<211> LENGTH: 15
<212> TYPE: PRT
<213> ORGANISM: human

<400> SEQUENCE: 42

Arg Arg Arg Arg Gly Leu Arg Thr Pro Ala Ser Val Pro Ile Ser
1               5                   10                  15

<210> SEQ ID NO 43
<211> LENGTH: 9
<212> TYPE: PRT
<213> ORGANISM: human

<400> SEQUENCE: 43

Arg Arg Arg Arg Ala Ser Pro Ile Ser
1               5

<210> SEQ ID NO 44
<211> LENGTH: 10
<212> TYPE: PRT
<213> ORGANISM: human

<400> SEQUENCE: 44

Arg Arg Arg Arg Ala Ser Ala Pro Ile Ser
1               5                   10

<210> SEQ ID NO 45
<211> LENGTH: 34
<212> TYPE: PRT
<213> ORGANISM: human

<400> SEQUENCE: 45

Val Ile Gln Glu Pro Gly Gly Arg Gly Asp Lys Leu Leu His Gln Gly
1               5                   10                  15

Ala Arg Arg Arg Arg Gly Leu Arg Thr Pro Ala Ser Val Pro Ile Ser
            20                  25                  30

Pro Ser

<210> SEQ ID NO 46
<211> LENGTH: 22
<212> TYPE: PRT
<213> ORGANISM: human
<220> FEATURE:
<221> NAME/KEY: misc_feature
<222> LOCATION: (9)..(9)
<223> OTHER INFORMATION: Xaa can be any naturally occurring amino acid

<400> SEQUENCE: 46

Leu His Gln Gly Ala Arg Arg Arg Xaa Gly Leu Arg Thr Pro Ala Ser
1               5                   10                  15
```

Val Pro Ile Ser Pro Ser
            20

<210> SEQ ID NO 47
<211> LENGTH: 12
<212> TYPE: PRT
<213> ORGANISM: human

<400> SEQUENCE: 47

Leu Gln Gly Arg Arg Leu Ser Val Pro Pro Ser
1               5                   10

<210> SEQ ID NO 48
<211> LENGTH: 19
<212> TYPE: PRT
<213> ORGANISM: human

<400> SEQUENCE: 48

Leu Gln Gln Gly Gly Arg Arg Gly Asp Leu Ser Ser Val Pro Thr
1               5                   10                  15

Ala Pro Ser

<210> SEQ ID NO 49
<211> LENGTH: 23
<212> TYPE: PRT
<213> ORGANISM: human

<400> SEQUENCE: 49

Gly Arg Val Ile Gln Glu Pro Gly Gly Arg Gly Asp Lys Leu Leu His
1               5                   10                  15

Gln Gly Ala Arg Arg Arg Arg
            20

<210> SEQ ID NO 50
<211> LENGTH: 15
<212> TYPE: PRT
<213> ORGANISM: human

<400> SEQUENCE: 50

Gly Arg Gln Pro Gly Gly Arg Gly Leu Leu Gly Arg Arg Arg
1               5                   10                  15

<210> SEQ ID NO 51
<211> LENGTH: 26
<212> TYPE: PRT
<213> ORGANISM: human

<400> SEQUENCE: 51

Gly Arg Gln Thr Pro Gly Gly Arg Gly Val Pro Leu Leu Asn Val Gly
1               5                   10                  15

Ser Arg Arg Ser Gln Pro Gly Gln Arg Arg
            20                  25

<210> SEQ ID NO 52
<211> LENGTH: 20
<212> TYPE: PRT
<213> ORGANISM: human

<400> SEQUENCE: 52

Gly Arg Gly Asp Lys Leu Leu His Gln Gly Ala Arg Arg Arg Arg Gly
1               5                   10                  15

Leu Arg Thr Pro

<210> SEQ ID NO 53
<211> LENGTH: 11
<212> TYPE: PRT
<213> ORGANISM: human

<400> SEQUENCE: 53

Gly Arg Gly Gly Ala Arg Arg Arg Arg Thr Pro
1               5                   10

<210> SEQ ID NO 54
<211> LENGTH: 14
<212> TYPE: PRT
<213> ORGANISM: human

<400> SEQUENCE: 54

Gly Arg Gly Gln Arg Gly Ala Arg Gln Arg Arg Arg Thr Pro
1               5                   10

<210> SEQ ID NO 55
<211> LENGTH: 5
<212> TYPE: PRT
<213> ORGANISM: human

<400> SEQUENCE: 55

Asn Ser Ser Val Asp
1               5

<210> SEQ ID NO 56
<211> LENGTH: 5
<212> TYPE: PRT
<213> ORGANISM: human

<400> SEQUENCE: 56

Asn Ser Ser Val Asp
1               5

<210> SEQ ID NO 57
<211> LENGTH: 5
<212> TYPE: PRT
<213> ORGANISM: human

<400> SEQUENCE: 57

Asn Ser Ser Val Asp
1               5

<210> SEQ ID NO 58
<211> LENGTH: 5
<212> TYPE: PRT
<213> ORGANISM: human

<400> SEQUENCE: 58

Asn Ser Ser Val Asp
1               5

<210> SEQ ID NO 59
<211> LENGTH: 20
<212> TYPE: PRT
<213> ORGANISM: human

<400> SEQUENCE: 59

Gly Ser Gly Lys Ile Lys Lys Ser Val Leu Trp Asp Arg Lys Val Gly
1               5                   10                  15

Ile Arg Lys Asn
            20

<210> SEQ ID NO 60
<211> LENGTH: 13
<212> TYPE: PRT
<213> ORGANISM: human

<400> SEQUENCE: 60

Ser Gly Lys Ile Lys Lys Ser Val Leu Trp Asp Arg Lys
1               5                   10

<210> SEQ ID NO 61
<211> LENGTH: 9
<212> TYPE: PRT
<213> ORGANISM: human

<400> SEQUENCE: 61

Ser Gly Ile Lys Lys Val Leu Asp Lys
1               5

<210> SEQ ID NO 62
<211> LENGTH: 13
<212> TYPE: PRT
<213> ORGANISM: human

<400> SEQUENCE: 62

Ser Gly Pro Ile Lys Lys Pro Val Leu Arg Asp Met Lys
1               5                   10

<210> SEQ ID NO 63
<211> LENGTH: 6
<212> TYPE: PRT
<213> ORGANISM: human

<400> SEQUENCE: 63

Ser Val Leu Trp Asp Arg
1               5

<210> SEQ ID NO 64
<211> LENGTH: 6
<212> TYPE: PRT
<213> ORGANISM: human

<400> SEQUENCE: 64

Ser Val Leu Trp Asp Arg
1               5

<210> SEQ ID NO 65
<211> LENGTH: 6
<212> TYPE: PRT
<213> ORGANISM: human

<400> SEQUENCE: 65

Ser Val Leu Trp Asp Arg
1               5

<210> SEQ ID NO 66
<211> LENGTH: 6
<212> TYPE: PRT
<213> ORGANISM: human

<400> SEQUENCE: 66

Lys Lys Ser Val Leu Trp
1               5

```
<210> SEQ ID NO 67
<211> LENGTH: 6
<212> TYPE: PRT
<213> ORGANISM: human

<400> SEQUENCE: 67

Lys Lys Ser Val Leu Trp
1               5

<210> SEQ ID NO 68
<211> LENGTH: 6
<212> TYPE: PRT
<213> ORGANISM: human

<400> SEQUENCE: 68

Lys Lys Ser Val Leu Trp
1               5

<210> SEQ ID NO 69
<211> LENGTH: 56
<212> TYPE: PRT
<213> ORGANISM: human
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid

<400> SEQUENCE: 69

Gly Ser Arg Lys Ile Xaa Trp Thr Ala Leu Trp Glu Thr Lys Val Gly
1               5                   10                  15

Leu Cys Leu Lys Leu Lys Met Asp Glu Pro Cys Leu Ser His Ala Cys
                20                  25                  30

Tyr Pro Asn Thr Leu Gly Gly Gln Gly Gly Arg Ile Thr Arg Xaa Arg
            35                  40                  45

Leu Arg Pro Ser Trp Pro Thr Gln
    50                  55

<210> SEQ ID NO 70
<211> LENGTH: 17
<212> TYPE: PRT
<213> ORGANISM: human

<400> SEQUENCE: 70

His Ala Cys Tyr Pro Asn Thr Leu Gly Gly Gln Gly Gly Arg Ile Thr
1               5                   10                  15

Arg

<210> SEQ ID NO 71
<211> LENGTH: 15
<212> TYPE: PRT
<213> ORGANISM: human

<400> SEQUENCE: 71

His Ala Cys Pro Thr Leu Gly Gly Gln Gly Gly Arg Ile Thr Arg
1               5                   10                  15

<210> SEQ ID NO 72
<211> LENGTH: 17
<212> TYPE: PRT
```

<213> ORGANISM: human

<400> SEQUENCE: 72

His Ala Cys Asn Pro Ser Thr Leu Gly Gly Gln Gly Gly Arg Ile Thr
1               5                   10                  15

Arg

<210> SEQ ID NO 73
<211> LENGTH: 17
<212> TYPE: PRT
<213> ORGANISM: human

<400> SEQUENCE: 73

His Ala Cys Tyr Pro Asn Thr Leu Gly Gly Gln Gly Gly Arg Ile Thr
1               5                   10                  15

Arg

<210> SEQ ID NO 74
<211> LENGTH: 14
<212> TYPE: PRT
<213> ORGANISM: human

<400> SEQUENCE: 74

His Ala Cys Pro Thr Leu Gly Gly Gly Gly Arg Ile Thr Arg
1               5                   10

<210> SEQ ID NO 75
<211> LENGTH: 17
<212> TYPE: PRT
<213> ORGANISM: human

<400> SEQUENCE: 75

His Ala Cys Asn Pro Ser Thr Leu Gly Gly Arg Gly Gly Arg Ile Thr
1               5                   10                  15

Arg

<210> SEQ ID NO 76
<211> LENGTH: 16
<212> TYPE: PRT
<213> ORGANISM: human

<400> SEQUENCE: 76

His Ala Cys Tyr Pro Asn Thr Leu Gly Gly Gln Gly Gly Arg Ile Thr
1               5                   10                  15

<210> SEQ ID NO 77
<211> LENGTH: 13
<212> TYPE: PRT
<213> ORGANISM: human

<400> SEQUENCE: 77

His Cys Pro Thr Leu Gly Gly Gln Gly Gly Arg Ile Thr
1               5                   10

<210> SEQ ID NO 78
<211> LENGTH: 13
<212> TYPE: PRT
<213> ORGANISM: human

<400> SEQUENCE: 78

His Cys Pro Thr Leu Gly Gly Gln Gly Gly Arg Ile Thr
1               5                   10

<210> SEQ ID NO 79
<211> LENGTH: 15
<212> TYPE: PRT
<213> ORGANISM: human

<400> SEQUENCE: 79

Leu Ala Gln Leu Gln His Gly Lys Asn Leu Gln Pro Tyr Arg Asp
1               5                   10                  15

<210> SEQ ID NO 80
<211> LENGTH: 12
<212> TYPE: PRT
<213> ORGANISM: human

<400> SEQUENCE: 80

Leu Gln His Gly Lys Asn Leu Gln Pro Tyr Arg Asp
1               5                   10

<210> SEQ ID NO 81
<211> LENGTH: 8
<212> TYPE: PRT
<213> ORGANISM: human

<400> SEQUENCE: 81

Leu Gln His Gly Pro Tyr Arg Asp
1               5

<210> SEQ ID NO 82
<211> LENGTH: 9
<212> TYPE: PRT
<213> ORGANISM: human

<400> SEQUENCE: 82

Leu Gln His Gly Ser Pro Tyr Arg Asp
1               5

<210> SEQ ID NO 83
<211> LENGTH: 8
<212> TYPE: PRT
<213> ORGANISM: human

<400> SEQUENCE: 83

Lys Asn Leu Gln Pro Tyr Arg Asp
1               5

<210> SEQ ID NO 84
<211> LENGTH: 6
<212> TYPE: PRT
<213> ORGANISM: human

<400> SEQUENCE: 84

Lys Asn Leu Pro Tyr Arg
1               5

<210> SEQ ID NO 85
<211> LENGTH: 8
<212> TYPE: PRT
<213> ORGANISM: human

<400> SEQUENCE: 85

Lys Asn Leu Leu Pro Tyr Arg Asn
1               5

<210> SEQ ID NO 86

```
<211> LENGTH: 13
<212> TYPE: PRT
<213> ORGANISM: human

<400> SEQUENCE: 86

Leu Ala Gln Leu Gln His Gly Lys Asn Leu Gln Pro Tyr
1               5                   10

<210> SEQ ID NO 87
<211> LENGTH: 9
<212> TYPE: PRT
<213> ORGANISM: human

<400> SEQUENCE: 87

Leu Gln Leu His Gly Lys Leu Pro Tyr
1               5

<210> SEQ ID NO 88
<211> LENGTH: 14
<212> TYPE: PRT
<213> ORGANISM: human

<400> SEQUENCE: 88

Leu Ser Gln Leu Thr His Gly Ile Lys Glu Leu Gly Pro Tyr
1               5                   10

<210> SEQ ID NO 89
<211> LENGTH: 13
<212> TYPE: PRT
<213> ORGANISM: human

<400> SEQUENCE: 89

Leu Ala Gln Leu Gln His Gly Lys Asn Leu Gln Pro Tyr
1               5                   10

<210> SEQ ID NO 90
<211> LENGTH: 9
<212> TYPE: PRT
<213> ORGANISM: human

<400> SEQUENCE: 90

Leu Gln Leu His Gly Lys Leu Pro Tyr
1               5

<210> SEQ ID NO 91
<211> LENGTH: 14
<212> TYPE: PRT
<213> ORGANISM: human

<400> SEQUENCE: 91

Leu Ser Gln Leu Thr His Gly Ile Lys Glu Leu Gly Pro Tyr
1               5                   10

<210> SEQ ID NO 92
<211> LENGTH: 15
<212> TYPE: PRT
<213> ORGANISM: human

<400> SEQUENCE: 92

Leu Ala Gln Leu Gln His Gly Lys Asn Leu Gln Pro Tyr Arg Asp
1               5                   10                  15

<210> SEQ ID NO 93
<211> LENGTH: 10
<212> TYPE: PRT
```

<213> ORGANISM: human

<400> SEQUENCE: 93

Leu Gln Leu His Gly Leu Pro Tyr Arg Asp
1               5                   10

<210> SEQ ID NO 94
<211> LENGTH: 19
<212> TYPE: PRT
<213> ORGANISM: human

<400> SEQUENCE: 94

Leu Ser Gln Leu Thr His Gly Ile Thr Glu Leu Gly Pro Tyr Thr Leu
1               5                   10                  15

Asp Arg Asp

<210> SEQ ID NO 95
<211> LENGTH: 13
<212> TYPE: PRT
<213> ORGANISM: human

<400> SEQUENCE: 95

Leu Ala Gln Leu Gln His Gly Lys Asn Leu Gln Pro Tyr
1               5                   10

<210> SEQ ID NO 96
<211> LENGTH: 8
<212> TYPE: PRT
<213> ORGANISM: human

<400> SEQUENCE: 96

Leu Gln Leu His Gly Leu Pro Tyr
1               5

<210> SEQ ID NO 97
<211> LENGTH: 14
<212> TYPE: PRT
<213> ORGANISM: human

<400> SEQUENCE: 97

Leu Ser Gln Leu Thr His Gly Ile Thr Glu Leu Gly Pro Tyr
1               5                   10

<210> SEQ ID NO 98
<211> LENGTH: 4
<212> TYPE: PRT
<213> ORGANISM: human

<400> SEQUENCE: 98

Asn Ser Ser Leu
1

<210> SEQ ID NO 99
<211> LENGTH: 4
<212> TYPE: PRT
<213> ORGANISM: human

<400> SEQUENCE: 99

Asn Ser Ser Leu
1

<210> SEQ ID NO 100
<211> LENGTH: 4
<212> TYPE: PRT

<213> ORGANISM: human

<400> SEQUENCE: 100

Asn Ser Ser Leu
1

<210> SEQ ID NO 101
<211> LENGTH: 4
<212> TYPE: PRT
<213> ORGANISM: human

<400> SEQUENCE: 101

Asn Ser Ser Leu
1

<210> SEQ ID NO 102
<211> LENGTH: 19
<212> TYPE: PRT
<213> ORGANISM: human

<400> SEQUENCE: 102

Val Asp Ser Arg Thr Arg Ser Met Thr Tyr Ser Lys Ser Ser Thr Ala
1               5                   10                  15

Thr Pro Arg

<210> SEQ ID NO 103
<211> LENGTH: 18
<212> TYPE: PRT
<213> ORGANISM: human

<400> SEQUENCE: 103

Val Asp Ser Arg Thr Arg Ser Met Thr Tyr Ser Lys Ser Ser Thr Ala
1               5                   10                  15

Thr Pro

<210> SEQ ID NO 104
<211> LENGTH: 14
<212> TYPE: PRT
<213> ORGANISM: human

<400> SEQUENCE: 104

Val Asp Ser Arg Thr Arg Ser Thr Lys Ser Thr Ala Thr Pro
1               5                   10

<210> SEQ ID NO 105
<211> LENGTH: 27
<212> TYPE: PRT
<213> ORGANISM: human

<400> SEQUENCE: 105

Val Asp Ser Arg Thr Tyr Leu Leu Asp Phe Arg Ser Ile Asp Asp Glu
1               5                   10                  15

Ile Thr Glu Ala Lys Ser Gly Thr Ala Thr Pro
            20                  25

<210> SEQ ID NO 106
<211> LENGTH: 11
<212> TYPE: PRT
<213> ORGANISM: human

<400> SEQUENCE: 106

Ser Arg Thr Arg Ser Met Thr Tyr Ser Lys Ser
1               5                   10

<210> SEQ ID NO 107
<211> LENGTH: 8
<212> TYPE: PRT
<213> ORGANISM: human

<400> SEQUENCE: 107

Ser Arg Arg Ser Thr Tyr Ser Ser
1               5

<210> SEQ ID NO 108
<211> LENGTH: 11
<212> TYPE: PRT
<213> ORGANISM: human

<400> SEQUENCE: 108

Ser Arg Ser Arg Ser Arg Thr Tyr Ser Arg Ser
1               5                   10

<210> SEQ ID NO 109
<211> LENGTH: 12
<212> TYPE: PRT
<213> ORGANISM: human

<400> SEQUENCE: 109

Arg Thr Arg Ser Met Thr Tyr Ser Lys Ser Ser Thr
1               5                   10

<210> SEQ ID NO 110
<211> LENGTH: 9
<212> TYPE: PRT
<213> ORGANISM: human

<400> SEQUENCE: 110

Arg Thr Arg Ser Tyr Ser Ser Ser Thr
1               5

<210> SEQ ID NO 111
<211> LENGTH: 18
<212> TYPE: PRT
<213> ORGANISM: human

<400> SEQUENCE: 111

Arg Thr Arg Ser Val Ser Tyr Ser His Ser Arg Ser Arg Ser Arg Ser
1               5                   10                  15

Ser Thr

<210> SEQ ID NO 112
<211> LENGTH: 64
<212> TYPE: PRT
<213> ORGANISM: human

<400> SEQUENCE: 112

Leu Pro Arg Val Gln Ala Gln Gly Gly Arg Val Pro Glu Thr Glu
1               5                   10                  15

Gly Ala Gly Gly Gly Arg Gly Arg Gln Gly Arg Ala Gly Ala Pro Ala
                20                  25                  30

Gly Arg Gly Thr Ala Ala Ala Gln Gly Gly Ala Glu Leu Gly Ala Glu
            35                  40                  45

Ala Gly Gly Asp Ala Gln Glu Gly Ser Leu Arg Pro His Ser Ser Asn
        50                  55                  60

```
<210> SEQ ID NO 113
<211> LENGTH: 37
<212> TYPE: PRT
<213> ORGANISM: human

<400> SEQUENCE: 113

Gly Gly Arg Val Pro Glu Glu Thr Glu Ala Gly Gly Arg Gly
1               5                   10                  15

Arg Gln Gly Arg Ala Gly Ala Pro Ala Gly Arg Gly Thr Ala Ala Ala
            20                  25                  30

Gln Gly Gly Ala Glu
        35

<210> SEQ ID NO 114
<211> LENGTH: 19
<212> TYPE: PRT
<213> ORGANISM: human

<400> SEQUENCE: 114

Gly Gly Arg Gly Gly Gly Arg Gly Arg Gly Arg Ala Gly Gly Arg Gly
1               5                   10                  15

Gly Gly Ala

<210> SEQ ID NO 115
<211> LENGTH: 23
<212> TYPE: PRT
<213> ORGANISM: human

<400> SEQUENCE: 115

Gly Gly Arg Gly Gly Gly Arg Gly Arg Gly Arg Ala Gly Ser Gln Gly
1               5                   10                  15

Gly Arg Gly Gly Gly Ala Gln
            20

<210> SEQ ID NO 116
<211> LENGTH: 23
<212> TYPE: PRT
<213> ORGANISM: human

<400> SEQUENCE: 116

Gly Gly Gly Arg Gly Arg Gln Gly Arg Ala Gly Ala Pro Ala Gly Arg
1               5                   10                  15

Gly Thr Ala Ala Ala Gln Gly
            20

<210> SEQ ID NO 117
<211> LENGTH: 17
<212> TYPE: PRT
<213> ORGANISM: human

<400> SEQUENCE: 117

Gly Gly Gly Arg Gly Arg Gly Arg Ala Gly Ala Ala Gly Gly Ala Ala
1               5                   10                  15

Gly

<210> SEQ ID NO 118
<211> LENGTH: 23
<212> TYPE: PRT
<213> ORGANISM: human

<400> SEQUENCE: 118

Gly Gly Gly Arg Gly Arg Gly Arg Ala Arg Gly Ala Ala Ala Gly Ser
```

```
                1               5                   10                  15
Gly Val Pro Ala Ala Pro Gly
                20

<210> SEQ ID NO 119
<211> LENGTH: 43
<212> TYPE: PRT
<213> ORGANISM: human

<400> SEQUENCE: 119

Ala Gln Gly Gly Arg Val Pro Glu Glu Thr Glu Ala Gly Gly Gly
1               5                   10                  15

Arg Gly Arg Gln Gly Arg Ala Gly Ala Pro Ala Gly Arg Gly Thr Ala
                20                  25                  30

Ala Ala Gln Gly Gly Ala Glu Leu Gly Ala Glu
        35                  40

<210> SEQ ID NO 120
<211> LENGTH: 24
<212> TYPE: PRT
<213> ORGANISM: human

<400> SEQUENCE: 120

Ala Gly Gly Arg Val Pro Gly Ala Gly Gly Arg Arg Ala Ala Thr
1               5                   10                  15

Ala Gly Ala Glu Leu Gly Ala Glu
                20

<210> SEQ ID NO 121
<211> LENGTH: 56
<212> TYPE: PRT
<213> ORGANISM: human

<400> SEQUENCE: 121

Ala Asn Gly Gly Arg Val Pro Gly Asn Gly Ala Gly Leu Gly Pro Gly
1               5                   10                  15

Arg Leu Glu Arg Glu Ala Ala Ala Ala Ala Thr Thr Pro Ala Pro
                20                  25                  30

Thr Ala Gly Ala Leu Tyr Ser Gly Ser Glu Gly Asp Ser Glu Ser Gly
        35                  40                  45

Glu Glu Glu Glu Leu Gly Ala Glu
    50                  55

<210> SEQ ID NO 122
<211> LENGTH: 14
<212> TYPE: PRT
<213> ORGANISM: human

<400> SEQUENCE: 122

Gln Thr Thr Pro Gly Asp Cys Pro Asp Thr Ala Thr Leu Pro
1               5                   10

<210> SEQ ID NO 123
<211> LENGTH: 7
<212> TYPE: PRT
<213> ORGANISM: human

<400> SEQUENCE: 123

Thr Pro Gly Asp Cys Pro Asp
1               5
```

```
<210> SEQ ID NO 124
<211> LENGTH: 6
<212> TYPE: PRT
<213> ORGANISM: human

<400> SEQUENCE: 124

Thr Pro Gly Asp Cys Pro
1               5

<210> SEQ ID NO 125
<211> LENGTH: 7
<212> TYPE: PRT
<213> ORGANISM: human

<400> SEQUENCE: 125

Thr Pro Gly Asp Cys Pro Asn
1               5

<210> SEQ ID NO 126
<211> LENGTH: 6
<212> TYPE: PRT
<213> ORGANISM: human

<400> SEQUENCE: 126

Thr Pro Gly Asp Cys Pro
1               5

<210> SEQ ID NO 127
<211> LENGTH: 6
<212> TYPE: PRT
<213> ORGANISM: human

<400> SEQUENCE: 127

Thr Pro Gly Asp Cys Pro
1               5

<210> SEQ ID NO 128
<211> LENGTH: 6
<212> TYPE: PRT
<213> ORGANISM: human

<400> SEQUENCE: 128

Thr Pro Gly Asp Cys Pro
1               5

<210> SEQ ID NO 129
<211> LENGTH: 13
<212> TYPE: PRT
<213> ORGANISM: human

<400> SEQUENCE: 129

Thr Thr Pro Gly Asp Cys Pro Asp Thr Ala Thr Leu Pro
1               5                   10

<210> SEQ ID NO 130
<211> LENGTH: 11
<212> TYPE: PRT
<213> ORGANISM: human

<400> SEQUENCE: 130

Thr Thr Pro Gly Cys Pro Thr Ala Thr Leu Pro
1               5                   10

<210> SEQ ID NO 131
<211> LENGTH: 16
```

```
<212> TYPE: PRT
<213> ORGANISM: human

<400> SEQUENCE: 131

Thr Thr Pro Gly Cys Asn Pro Gln Leu Thr Tyr Thr Ala Thr Leu Pro
1               5                   10                  15

<210> SEQ ID NO 132
<211> LENGTH: 4
<212> TYPE: PRT
<213> ORGANISM: human

<400> SEQUENCE: 132

Asn Ser Ser Val
1

<210> SEQ ID NO 133
<211> LENGTH: 4
<212> TYPE: PRT
<213> ORGANISM: human

<400> SEQUENCE: 133

Asn Ser Ser Val
1

<210> SEQ ID NO 134
<211> LENGTH: 4
<212> TYPE: PRT
<213> ORGANISM: human

<400> SEQUENCE: 134

Asn Ser Ser Val
1

<210> SEQ ID NO 135
<211> LENGTH: 4
<212> TYPE: PRT
<213> ORGANISM: human

<400> SEQUENCE: 135

Asn Ser Ser Val
1

<210> SEQ ID NO 136
<211> LENGTH: 35
<212> TYPE: PRT
<213> ORGANISM: human

<400> SEQUENCE: 136

Glu Arg Gly Lys Lys Arg Lys Ile Arg Glu Met Leu Gln Asp Met Val
1               5                   10                  15

Pro Val Val Val Glu Glu Glu Thr Leu Arg Thr Asn Val Leu Ser Ile
            20                  25                  30

Gly Asn Lys
        35

<210> SEQ ID NO 137
<211> LENGTH: 15
<212> TYPE: PRT
<213> ORGANISM: human

<400> SEQUENCE: 137

Lys Ile Arg Glu Met Leu Gln Asp Met Val Pro Val Val Val Glu
1               5                   10                  15
```

<210> SEQ ID NO 138
<211> LENGTH: 10
<212> TYPE: PRT
<213> ORGANISM: human

<400> SEQUENCE: 138

Lys Ile Met Gln Asp Met Val Pro Val Val
1               5                   10

<210> SEQ ID NO 139
<211> LENGTH: 18
<212> TYPE: PRT
<213> ORGANISM: human

<400> SEQUENCE: 139

Lys Ile Gln Val Met Glu Gln His Phe Gln Asp Met Val Pro Val Ile
1               5                   10                  15

Val Asp

<210> SEQ ID NO 140
<211> LENGTH: 24
<212> TYPE: PRT
<213> ORGANISM: human

<400> SEQUENCE: 140

Arg Lys Ile Arg Glu Met Leu Gln Asp Met Val Pro Val Val Val Glu
1               5                   10                  15

Glu Glu Thr Leu Arg Thr Asn Val
            20

<210> SEQ ID NO 141
<211> LENGTH: 12
<212> TYPE: PRT
<213> ORGANISM: human

<400> SEQUENCE: 141

Arg Ile Arg Glu Leu Gln Asp Thr Leu Arg Thr Val
1               5                   10

<210> SEQ ID NO 142
<211> LENGTH: 16
<212> TYPE: PRT
<213> ORGANISM: human

<400> SEQUENCE: 142

Arg Arg Ile Arg Glu Leu Leu Gln Asp Thr Leu Thr Arg Thr Gly Val
1               5                   10                  15

<210> SEQ ID NO 143
<211> LENGTH: 22
<212> TYPE: PRT
<213> ORGANISM: human

<400> SEQUENCE: 143

Lys Arg Lys Ile Arg Glu Met Leu Gln Asp Met Val Pro Val Val Val
1               5                   10                  15

Glu Glu Glu Thr Leu Arg
            20

<210> SEQ ID NO 144
<211> LENGTH: 12
<212> TYPE: PRT

```
<213> ORGANISM: human

<400> SEQUENCE: 144

Lys Arg Arg Glu Met Gln Met Glu Glu Thr Leu Arg
1               5                   10

<210> SEQ ID NO 145
<211> LENGTH: 22
<212> TYPE: PRT
<213> ORGANISM: human

<400> SEQUENCE: 145

Lys Arg Arg Glu Arg Glu Met Gln Gln Glu Met Met Leu Arg Asp Glu
1               5                   10                  15

Glu Thr Met Glu Leu Arg
            20

<210> SEQ ID NO 146
<211> LENGTH: 14
<212> TYPE: PRT
<213> ORGANISM: human

<400> SEQUENCE: 146

Arg Lys Gly Lys Lys Ser Lys Arg Arg Lys Trp Leu Asn Ser
1               5                   10

<210> SEQ ID NO 147
<211> LENGTH: 13
<212> TYPE: PRT
<213> ORGANISM: human

<400> SEQUENCE: 147

Arg Lys Gly Lys Lys Ser Lys Arg Arg Lys Trp Leu Asn
1               5                   10

<210> SEQ ID NO 148
<211> LENGTH: 10
<212> TYPE: PRT
<213> ORGANISM: human

<400> SEQUENCE: 148

Arg Lys Lys Ser Lys Arg Arg Lys Trp Leu
1               5                   10

<210> SEQ ID NO 149
<211> LENGTH: 20
<212> TYPE: PRT
<213> ORGANISM: human

<400> SEQUENCE: 149

Arg Lys Ser Lys Arg His Ser Ser Lys Arg Lys Ser Met Ser
1               5                   10                  15

Ser Trp Leu Asp
            20

<210> SEQ ID NO 150
<211> LENGTH: 6
<212> TYPE: PRT
<213> ORGANISM: human

<400> SEQUENCE: 150

Arg Arg Lys Trp Leu Asn
1               5
```

<210> SEQ ID NO 151
<211> LENGTH: 6
<212> TYPE: PRT
<213> ORGANISM: human

<400> SEQUENCE: 151

Arg Arg Lys Trp Leu Asn
1               5

<210> SEQ ID NO 152
<211> LENGTH: 6
<212> TYPE: PRT
<213> ORGANISM: human

<400> SEQUENCE: 152

Arg Arg Lys Trp Leu Asn
1               5

<210> SEQ ID NO 153
<211> LENGTH: 10
<212> TYPE: PRT
<213> ORGANISM: human

<400> SEQUENCE: 153

Arg Lys Gly Lys Lys Ser Lys Arg Arg Lys
1               5                   10

<210> SEQ ID NO 154
<211> LENGTH: 7
<212> TYPE: PRT
<213> ORGANISM: human

<400> SEQUENCE: 154

Arg Lys Gly Lys Lys Arg Lys
1               5

<210> SEQ ID NO 155
<211> LENGTH: 10
<212> TYPE: PRT
<213> ORGANISM: human

<400> SEQUENCE: 155

Arg Lys Gly Lys Lys Ala Arg Arg Lys Lys
1               5                   10

<210> SEQ ID NO 156
<211> LENGTH: 4
<212> TYPE: PRT
<213> ORGANISM: human

<400> SEQUENCE: 156

Thr Lys Ala Lys
1

<210> SEQ ID NO 157
<211> LENGTH: 4
<212> TYPE: PRT
<213> ORGANISM: human

<400> SEQUENCE: 157

Thr Lys Ala Lys
1

<210> SEQ ID NO 158

```
<211> LENGTH: 4
<212> TYPE: PRT
<213> ORGANISM: human

<400> SEQUENCE: 158

Thr Lys Ala Lys
1

<210> SEQ ID NO 159
<211> LENGTH: 4
<212> TYPE: PRT
<213> ORGANISM: human

<400> SEQUENCE: 159

Thr Lys Ala Lys
1

<210> SEQ ID NO 160
<211> LENGTH: 4
<212> TYPE: PRT
<213> ORGANISM: human

<400> SEQUENCE: 160

Pro Asn Ser Gly
1

<210> SEQ ID NO 161
<211> LENGTH: 4
<212> TYPE: PRT
<213> ORGANISM: human

<400> SEQUENCE: 161

Pro Asn Ser Gly
1

<210> SEQ ID NO 162
<211> LENGTH: 4
<212> TYPE: PRT
<213> ORGANISM: human

<400> SEQUENCE: 162

Pro Asn Ser Gly
1

<210> SEQ ID NO 163
<211> LENGTH: 4
<212> TYPE: PRT
<213> ORGANISM: human

<400> SEQUENCE: 163

Pro Asn Ser Gly
1

<210> SEQ ID NO 164
<211> LENGTH: 4
<212> TYPE: PRT
<213> ORGANISM: human

<400> SEQUENCE: 164

Asn Ser Ser Ala
1

<210> SEQ ID NO 165
<211> LENGTH: 4
<212> TYPE: PRT
```

```
<213> ORGANISM: human

<400> SEQUENCE: 165

Asn Ser Ser Ala
1

<210> SEQ ID NO 166
<211> LENGTH: 4
<212> TYPE: PRT
<213> ORGANISM: human

<400> SEQUENCE: 166

Asn Ser Ser Ala
1

<210> SEQ ID NO 167
<211> LENGTH: 4
<212> TYPE: PRT
<213> ORGANISM: human

<400> SEQUENCE: 167

Asn Ser Ser Ala
1

<210> SEQ ID NO 168
<211> LENGTH: 9
<212> TYPE: PRT
<213> ORGANISM: human

<400> SEQUENCE: 168

Arg Arg Leu Lys Lys Phe Cys Ile Thr
1               5

<210> SEQ ID NO 169
<211> LENGTH: 8
<212> TYPE: PRT
<213> ORGANISM: human

<400> SEQUENCE: 169

Arg Arg Leu Lys Lys Phe Cys Ile
1               5

<210> SEQ ID NO 170
<211> LENGTH: 8
<212> TYPE: PRT
<213> ORGANISM: human

<400> SEQUENCE: 170

Arg Arg Leu Lys Lys Phe Cys Ile
1               5

<210> SEQ ID NO 171
<211> LENGTH: 11
<212> TYPE: PRT
<213> ORGANISM: human

<400> SEQUENCE: 171

Arg Arg Leu Lys Lys Arg Gly Ile Phe Cys Ile
1               5                   10

<210> SEQ ID NO 172
<211> LENGTH: 6
<212> TYPE: PRT
<213> ORGANISM: human
```

```
<400> SEQUENCE: 172

Leu Lys Lys Phe Cys Ile
1               5

<210> SEQ ID NO 173
<211> LENGTH: 6
<212> TYPE: PRT
<213> ORGANISM: human

<400> SEQUENCE: 173

Leu Lys Lys Phe Cys Ile
1               5

<210> SEQ ID NO 174
<211> LENGTH: 6
<212> TYPE: PRT
<213> ORGANISM: human

<400> SEQUENCE: 174

Leu Lys Lys Phe Cys Ile
1               5

<210> SEQ ID NO 175
<211> LENGTH: 6
<212> TYPE: PRT
<213> ORGANISM: human

<400> SEQUENCE: 175

Arg Arg Leu Lys Lys Phe
1               5

<210> SEQ ID NO 176
<211> LENGTH: 6
<212> TYPE: PRT
<213> ORGANISM: human

<400> SEQUENCE: 176

Arg Arg Leu Lys Lys Phe
1               5

<210> SEQ ID NO 177
<211> LENGTH: 6
<212> TYPE: PRT
<213> ORGANISM: human

<400> SEQUENCE: 177

Arg Arg Leu Lys Lys Phe
1               5

<210> SEQ ID NO 178
<211> LENGTH: 26
<212> TYPE: PRT
<213> ORGANISM: human

<400> SEQUENCE: 178

Ile Phe Ala Gly Gly Gly Gly Pro Ala Gly Pro Gly Arg Ala Gly Thr
1               5                   10                  15

Gly Gly Gly Arg Val Ala Ser Ala Thr Arg
            20                  25

<210> SEQ ID NO 179
<211> LENGTH: 22
<212> TYPE: PRT
<213> ORGANISM: human
```

<400> SEQUENCE: 179

Phe Ala Gly Gly Gly Pro Ala Gly Pro Gly Arg Ala Gly Thr Gly
1               5                   10                  15

Gly Gly Arg Val Ala Ser
            20

<210> SEQ ID NO 180
<211> LENGTH: 18
<212> TYPE: PRT
<213> ORGANISM: human

<400> SEQUENCE: 180

Phe Gly Gly Gly Pro Ala Pro Gly Arg Ala Gly Thr Gly Gly Val
1               5                   10                  15

Ala Ser

<210> SEQ ID NO 181
<211> LENGTH: 32
<212> TYPE: PRT
<213> ORGANISM: human

<400> SEQUENCE: 181

Phe His Gly Gly Gln Pro Thr Gly Ala Pro Leu Asp Cys Ala Ala
1               5                   10                  15

Pro Gly Ala His Tyr Arg Ala Gly Thr Gly Gly Pro Val Ala Ser
            20                  25                  30

<210> SEQ ID NO 182
<211> LENGTH: 20
<212> TYPE: PRT
<213> ORGANISM: human

<400> SEQUENCE: 182

Gly Gly Gly Gly Pro Ala Gly Pro Gly Arg Ala Gly Thr Gly Gly
1               5                   10                  15

Arg Val Ala Ser
            20

<210> SEQ ID NO 183
<211> LENGTH: 15
<212> TYPE: PRT
<213> ORGANISM: human

<400> SEQUENCE: 183

Gly Gly Gly Gly Pro Gly Pro Gly Gly Thr Gly Gly Ala Ser
1               5                   10                  15

<210> SEQ ID NO 184
<211> LENGTH: 21
<212> TYPE: PRT
<213> ORGANISM: human

<400> SEQUENCE: 184

Gly Gly Gly Gly Pro Gly Gly Ser Ala Ser Gly Pro Gly Gly Thr Gly
1               5                   10                  15

Gly Gly Lys Ala Ser
            20

<210> SEQ ID NO 185
<211> LENGTH: 15
<212> TYPE: PRT

<213> ORGANISM: human

<400> SEQUENCE: 185

Ala Gly Gly Gly Gly Pro Ala Gly Pro Gly Arg Ala Gly Thr Gly
1               5                   10                  15

<210> SEQ ID NO 186
<211> LENGTH: 11
<212> TYPE: PRT
<213> ORGANISM: human

<400> SEQUENCE: 186

Ala Gly Gly Gly Gly Pro Gly Pro Gly Gly Gly
1               5                   10

<210> SEQ ID NO 187
<211> LENGTH: 13
<212> TYPE: PRT
<213> ORGANISM: human

<400> SEQUENCE: 187

Ala Gly Gly Gly Gly Pro Gly Gly Pro Gly Gly Ser Gly
1               5                   10

<210> SEQ ID NO 188
<211> LENGTH: 17
<212> TYPE: PRT
<213> ORGANISM: human

<400> SEQUENCE: 188

Val Lys Ile Met Thr Leu Lys Ser Arg Gln Arg Ser Tyr Lys Asn Pro
1               5                   10                  15

Gly

<210> SEQ ID NO 189
<211> LENGTH: 8
<212> TYPE: PRT
<213> ORGANISM: human

<400> SEQUENCE: 189

Thr Leu Lys Ser Arg Gln Arg Ser
1               5

<210> SEQ ID NO 190
<211> LENGTH: 7
<212> TYPE: PRT
<213> ORGANISM: human

<400> SEQUENCE: 190

Thr Leu Lys Arg Gln Arg Ser
1               5

<210> SEQ ID NO 191
<211> LENGTH: 8
<212> TYPE: PRT
<213> ORGANISM: human

<400> SEQUENCE: 191

Thr Leu Lys Glu Arg Gln Arg Ser
1               5

<210> SEQ ID NO 192
<211> LENGTH: 15
<212> TYPE: PRT

```
<213> ORGANISM: human

<400> SEQUENCE: 192

Val Lys Ile Met Thr Leu Lys Ser Arg Gln Arg Ser Tyr Lys Asn
1               5                   10                  15

<210> SEQ ID NO 193
<211> LENGTH: 9
<212> TYPE: PRT
<213> ORGANISM: human

<400> SEQUENCE: 193

Val Lys Thr Leu Lys Arg Ser Lys Asn
1               5

<210> SEQ ID NO 194
<211> LENGTH: 14
<212> TYPE: PRT
<213> ORGANISM: human

<400> SEQUENCE: 194

Val Lys Leu Leu Thr Leu Lys Pro Arg Glu Thr Ser Lys Asn
1               5                   10

<210> SEQ ID NO 195
<211> LENGTH: 9
<212> TYPE: PRT
<213> ORGANISM: human

<400> SEQUENCE: 195

Leu Lys Ser Arg Gln Arg Ser Tyr Lys
1               5

<210> SEQ ID NO 196
<211> LENGTH: 7
<212> TYPE: PRT
<213> ORGANISM: human

<400> SEQUENCE: 196

Leu Ser Arg Gln Arg Tyr Lys
1               5

<210> SEQ ID NO 197
<211> LENGTH: 9
<212> TYPE: PRT
<213> ORGANISM: human

<400> SEQUENCE: 197

Leu Gln Ser Arg Gln Arg Asp Tyr Lys
1               5

<210> SEQ ID NO 198
<211> LENGTH: 14
<212> TYPE: PRT
<213> ORGANISM: human

<400> SEQUENCE: 198

Arg Pro Ala Arg Ser Arg Arg Met Met Ala Trp Gly Lys Ala
1               5                   10

<210> SEQ ID NO 199
<211> LENGTH: 8
<212> TYPE: PRT
<213> ORGANISM: human
```

<400> SEQUENCE: 199

Arg Pro Ala Arg Ser Arg Arg Met
1               5

<210> SEQ ID NO 200
<211> LENGTH: 7
<212> TYPE: PRT
<213> ORGANISM: human

<400> SEQUENCE: 200

Arg Pro Arg Ser Arg Arg Met
1               5

<210> SEQ ID NO 201
<211> LENGTH: 8
<212> TYPE: PRT
<213> ORGANISM: human

<400> SEQUENCE: 201

Arg Pro Glu Arg Ser Arg Arg Met
1               5

<210> SEQ ID NO 202
<211> LENGTH: 7
<212> TYPE: PRT
<213> ORGANISM: human

<400> SEQUENCE: 202

Arg Arg Met Met Ala Trp Gly
1               5

<210> SEQ ID NO 203
<211> LENGTH: 6
<212> TYPE: PRT
<213> ORGANISM: human

<400> SEQUENCE: 203

Arg Arg Met Ala Trp Gly
1               5

<210> SEQ ID NO 204
<211> LENGTH: 7
<212> TYPE: PRT
<213> ORGANISM: human

<400> SEQUENCE: 204

Arg Arg Thr Met Ala Trp Gly
1               5

<210> SEQ ID NO 205
<211> LENGTH: 10
<212> TYPE: PRT
<213> ORGANISM: human

<400> SEQUENCE: 205

Pro Ala Arg Ser Arg Arg Met Met Ala Trp
1               5                   10

<210> SEQ ID NO 206
<211> LENGTH: 8
<212> TYPE: PRT
<213> ORGANISM: human

<400> SEQUENCE: 206

```
Pro Ala Arg Arg Met Met Ala Trp
1               5
```

<210> SEQ ID NO 207
<211> LENGTH: 12
<212> TYPE: PRT
<213> ORGANISM: human

<400> SEQUENCE: 207

```
Pro Ala Gln Pro Arg His Arg Met Met Ser Ala Trp
1               5                   10
```

<210> SEQ ID NO 208
<211> LENGTH: 36
<212> TYPE: PRT
<213> ORGANISM: human

<400> SEQUENCE: 208

```
Asp Trp Arg Val Pro Arg Pro Ala Pro His His Arg Leu Gly Ala Arg
1               5                   10                  15

Arg Leu Pro Asn Leu His Ala Ala Pro Gly Arg Ala Ala Pro Arg Ala
                20                  25                  30

Ala Ser Gly Leu
        35
```

<210> SEQ ID NO 209
<211> LENGTH: 17
<212> TYPE: PRT
<213> ORGANISM: human

<400> SEQUENCE: 209

```
Pro Arg Pro Ala Pro His His Arg Leu Gly Ala Arg Arg Leu Pro Asn
1               5                   10                  15

Leu
```

<210> SEQ ID NO 210
<211> LENGTH: 11
<212> TYPE: PRT
<213> ORGANISM: human

<400> SEQUENCE: 210

```
Pro Arg Pro Ala Pro Ala Arg Arg Leu Pro Leu
1               5                   10
```

<210> SEQ ID NO 211
<211> LENGTH: 12
<212> TYPE: PRT
<213> ORGANISM: human

<400> SEQUENCE: 211

```
Pro Arg Pro Ala Pro Ala Arg Arg Leu Pro Gly Leu
1               5                   10
```

<210> SEQ ID NO 212
<211> LENGTH: 35
<212> TYPE: PRT
<213> ORGANISM: human

<400> SEQUENCE: 212

```
Trp Arg Val Pro Arg Pro Ala Pro His His Arg Leu Gly Ala Arg Arg
1               5                   10                  15

Leu Pro Asn Leu His Ala Ala Pro Gly Arg Ala Ala Pro Arg Ala Ala
                20                  25                  30
```

Ser Gly Leu
        35

<210> SEQ ID NO 213
<211> LENGTH: 18
<212> TYPE: PRT
<213> ORGANISM: human

<400> SEQUENCE: 213

Trp Pro Arg Pro Arg Leu Pro Leu Ala Pro Gly Arg Ala Ala Arg Ala
1               5                   10                  15

Ser Leu

<210> SEQ ID NO 214
<211> LENGTH: 29
<212> TYPE: PRT
<213> ORGANISM: human

<400> SEQUENCE: 214

Trp Pro Arg Pro Arg Ala Leu Pro Leu Arg Gly Ala Val Gly Ser Cys
1               5                   10                  15

Pro Pro Gly Arg Ala Ala Arg Gly Ala Ser Asp Leu
            20                  25

<210> SEQ ID NO 215
<211> LENGTH: 31
<212> TYPE: PRT
<213> ORGANISM: human

<400> SEQUENCE: 215

Trp Arg Val Pro Arg Pro Ala Pro His His Arg Leu Gly Ala Arg Arg
1               5                   10                  15

Leu Pro Asn Leu His Ala Ala Pro Gly Arg Ala Ala Pro Arg Ala
            20                  25                  30

<210> SEQ ID NO 216
<211> LENGTH: 19
<212> TYPE: PRT
<213> ORGANISM: human

<400> SEQUENCE: 216

Trp Arg Val Arg Pro His Leu Pro Leu Ala Ala Pro Gly Arg Ala Ala
1               5                   10                  15

Pro Arg Ala

<210> SEQ ID NO 217
<211> LENGTH: 34
<212> TYPE: PRT
<213> ORGANISM: human

<400> SEQUENCE: 217

Trp Arg Val Arg Pro Asp Asp Val His Leu Pro Pro Leu Pro Ala Ala
1               5                   10                  15

Pro Gly Pro Arg Arg Arg Arg Pro Arg Thr Pro Pro Ala Ala Pro
            20                  25                  30

Arg Ala

<210> SEQ ID NO 218
<211> LENGTH: 6
<212> TYPE: PRT
<213> ORGANISM: human

<400> SEQUENCE: 218

Asn Ser Ser Cys Ser Glu
1               5

<210> SEQ ID NO 219
<211> LENGTH: 6
<212> TYPE: PRT
<213> ORGANISM: human

<400> SEQUENCE: 219

Asn Ser Ser Cys Ser Glu
1               5

<210> SEQ ID NO 220
<211> LENGTH: 5
<212> TYPE: PRT
<213> ORGANISM: human

<400> SEQUENCE: 220

Ser Ser Cys Ser Glu
1               5

<210> SEQ ID NO 221
<211> LENGTH: 6
<212> TYPE: PRT
<213> ORGANISM: human

<400> SEQUENCE: 221

Asp Ser Ser Cys Ser Glu
1               5

<210> SEQ ID NO 222
<211> LENGTH: 6
<212> TYPE: PRT
<213> ORGANISM: human

<400> SEQUENCE: 222

Asn Ser Ser Cys Ser Glu
1               5

<210> SEQ ID NO 223
<211> LENGTH: 5
<212> TYPE: PRT
<213> ORGANISM: human

<400> SEQUENCE: 223

Asn Ser Cys Ser Glu
1               5

<210> SEQ ID NO 224
<211> LENGTH: 6
<212> TYPE: PRT
<213> ORGANISM: human

<400> SEQUENCE: 224

Asn Ser Thr Cys Ser Glu
1               5

<210> SEQ ID NO 225
<211> LENGTH: 6
<212> TYPE: PRT
<213> ORGANISM: human

<400> SEQUENCE: 225

```
Asn Ser Ser Cys Ser Glu
1               5

<210> SEQ ID NO 226
<211> LENGTH: 5
<212> TYPE: PRT
<213> ORGANISM: human

<400> SEQUENCE: 226

Asn Ser Cys Ser Glu
1               5

<210> SEQ ID NO 227
<211> LENGTH: 6
<212> TYPE: PRT
<213> ORGANISM: human

<400> SEQUENCE: 227

Asn Asn Ser Cys Ser Glu
1               5

<210> SEQ ID NO 228
<211> LENGTH: 27
<212> TYPE: PRT
<213> ORGANISM: human

<400> SEQUENCE: 228

Arg Gly Asp Lys Leu Leu His Gln Gly Ala Arg Arg Arg Gly Leu
1               5                   10                  15

Arg Thr Pro Ala Ser Val Pro Ile Ser Pro Ser
            20                  25

<210> SEQ ID NO 229
<211> LENGTH: 22
<212> TYPE: PRT
<213> ORGANISM: human

<400> SEQUENCE: 229

Leu His Gln Gly Ala Arg Arg Arg Gly Leu Arg Thr Pro Ala Ser
1               5                   10                  15

Val Pro Ile Ser Pro Ser
            20

<210> SEQ ID NO 230
<211> LENGTH: 12
<212> TYPE: PRT
<213> ORGANISM: human

<400> SEQUENCE: 230

Leu Gln Gly Arg Arg Arg Leu Ser Val Pro Pro Ser
1               5                   10

<210> SEQ ID NO 231
<211> LENGTH: 19
<212> TYPE: PRT
<213> ORGANISM: human

<400> SEQUENCE: 231

Leu Gln Gln Gly Gly Arg Arg Arg Gly Asp Leu Ser Ser Val Pro Thr
1               5                   10                  15

Ala Pro Ser
```

```
<210> SEQ ID NO 232
<211> LENGTH: 13
<212> TYPE: PRT
<213> ORGANISM: human

<400> SEQUENCE: 232

Arg Arg Arg Arg Gly Leu Arg Thr Pro Ala Ser Val Pro
1               5                   10

<210> SEQ ID NO 233
<211> LENGTH: 11
<212> TYPE: PRT
<213> ORGANISM: human

<400> SEQUENCE: 233

Arg Arg Arg Arg Leu Arg Thr Pro Ala Val Pro
1               5                   10

<210> SEQ ID NO 234
<211> LENGTH: 18
<212> TYPE: PRT
<213> ORGANISM: human

<400> SEQUENCE: 234

Arg Arg Arg Arg Pro Leu Leu Arg Leu Pro Arg Arg Thr Pro Ala Lys
1               5                   10                  15

Val Pro

<210> SEQ ID NO 235
<211> LENGTH: 35
<212> TYPE: PRT
<213> ORGANISM: human
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 235

Arg Cys Ser Ser Xaa Asn Arg Xaa Gly Arg Glu Gly Cys Pro Arg Ser
1               5                   10                  15

Cys Gly Leu Arg Asn Glu Ser Gln Leu His Val Ala Arg Cys Trp Gly
            20                  25                  30

Leu Pro Gly
        35

<210> SEQ ID NO 236
<211> LENGTH: 15
<212> TYPE: PRT
<213> ORGANISM: human

<400> SEQUENCE: 236

Gln Gly Arg Glu Gly Cys Pro Arg Ser Cys Gly Leu Arg Asn Glu
1               5                   10                  15

<210> SEQ ID NO 237
<211> LENGTH: 11
<212> TYPE: PRT
<213> ORGANISM: human

<400> SEQUENCE: 237

Gln Gly Arg Glu Gly Cys Pro Cys Gly Leu Arg
```

```
1               5                   10
```

<210> SEQ ID NO 238
<211> LENGTH: 14
<212> TYPE: PRT
<213> ORGANISM: human

<400> SEQUENCE: 238

```
Gln Gly Ala Arg Glu Gly Cys Pro Cys Gly Leu Arg His Gln
1               5                   10
```

<210> SEQ ID NO 239
<211> LENGTH: 21
<212> TYPE: PRT
<213> ORGANISM: human

<400> SEQUENCE: 239

```
Arg Gln Gly Arg Glu Gly Cys Pro Arg Ser Cys Gly Leu Arg Asn Glu
1               5                   10                  15

Ser Gln Leu His Val
            20
```

<210> SEQ ID NO 240
<211> LENGTH: 14
<212> TYPE: PRT
<213> ORGANISM: human

<400> SEQUENCE: 240

```
Arg Gly Arg Glu Gly Cys Pro Arg Cys Arg Ser Leu His Val
1               5                   10
```

<210> SEQ ID NO 241
<211> LENGTH: 18
<212> TYPE: PRT
<213> ORGANISM: human

<400> SEQUENCE: 241

```
Arg Pro Gly Leu Arg Glu Gly Cys Pro Arg Cys Arg Gln Ser Val Leu
1               5                   10                  15

His Val
```

<210> SEQ ID NO 242
<211> LENGTH: 11
<212> TYPE: PRT
<213> ORGANISM: human

<400> SEQUENCE: 242

```
Arg Gln Gly Arg Glu Gly Cys Pro Arg Ser Cys
1               5                   10
```

<210> SEQ ID NO 243
<211> LENGTH: 9
<212> TYPE: PRT
<213> ORGANISM: human

<400> SEQUENCE: 243

```
Arg Gln Gly Arg Glu Gly Cys Arg Cys
1               5
```

<210> SEQ ID NO 244
<211> LENGTH: 12
<212> TYPE: PRT
<213> ORGANISM: human

```
<400> SEQUENCE: 244

Arg Gln Gly Arg Glu Gly Ala Cys His Arg Ala Cys
1               5                   10

<210> SEQ ID NO 245
<211> LENGTH: 24
<212> TYPE: PRT
<213> ORGANISM: human

<400> SEQUENCE: 245

Glu Arg Pro Ser Lys Arg Tyr Leu His Gln Ala Ala Gly Gly Gly Glu
1               5                   10                  15

Arg Lys Glu Arg Gln Leu Cys Ser
            20

<210> SEQ ID NO 246
<211> LENGTH: 15
<212> TYPE: PRT
<213> ORGANISM: human

<400> SEQUENCE: 246

Tyr Leu His Gln Ala Ala Gly Gly Gly Glu Arg Lys Glu Arg Gln
1               5                   10                  15

<210> SEQ ID NO 247
<211> LENGTH: 12
<212> TYPE: PRT
<213> ORGANISM: human

<400> SEQUENCE: 247

Tyr Leu Gln Ala Gly Gly Gly Arg Lys Glu Arg Gln
1               5                   10

<210> SEQ ID NO 248
<211> LENGTH: 22
<212> TYPE: PRT
<213> ORGANISM: human

<400> SEQUENCE: 248

Tyr Leu Gln Ala Glu Gly Gly Gly Asp Arg Gln Leu Gly Asp Arg Glu
1               5                   10                  15

Lys Glu Leu Ile Arg Gln
            20

<210> SEQ ID NO 249
<211> LENGTH: 15
<212> TYPE: PRT
<213> ORGANISM: human

<400> SEQUENCE: 249

Tyr Leu His Gln Ala Ala Gly Gly Gly Glu Arg Lys Glu Arg Gln
1               5                   10                  15

<210> SEQ ID NO 250
<211> LENGTH: 12
<212> TYPE: PRT
<213> ORGANISM: human

<400> SEQUENCE: 250

Tyr Leu Gln Ala Gly Gly Gly Arg Lys Glu Arg Gln
1               5                   10

<210> SEQ ID NO 251
```

```
<211> LENGTH: 22
<212> TYPE: PRT
<213> ORGANISM: human

<400> SEQUENCE: 251

Tyr Leu Gln Ala Glu Gly Gly Asp Arg Gln Leu Gly Asp Arg Glu
1               5                   10                  15

Lys Glu Leu Ile Arg Gln
            20

<210> SEQ ID NO 252
<211> LENGTH: 16
<212> TYPE: PRT
<213> ORGANISM: human

<400> SEQUENCE: 252

Leu His Gln Ala Ala Gly Gly Gly Glu Arg Lys Glu Arg Gln Leu Cys
1               5                   10                  15

<210> SEQ ID NO 253
<211> LENGTH: 8
<212> TYPE: PRT
<213> ORGANISM: human

<400> SEQUENCE: 253

Leu His Glu Arg Lys Gln Leu Cys
1               5

<210> SEQ ID NO 254
<211> LENGTH: 11
<212> TYPE: PRT
<213> ORGANISM: human

<400> SEQUENCE: 254

Leu His His Glu Arg Lys Ala Lys Gln Leu Cys
1               5                   10

<210> SEQ ID NO 255
<211> LENGTH: 6
<212> TYPE: PRT
<213> ORGANISM: human

<400> SEQUENCE: 255

Ser Ser Gln Gly His Phe
1               5

<210> SEQ ID NO 256
<211> LENGTH: 6
<212> TYPE: PRT
<213> ORGANISM: human

<400> SEQUENCE: 256

Ser Ser Gln Gly His Phe
1               5

<210> SEQ ID NO 257
<211> LENGTH: 6
<212> TYPE: PRT
<213> ORGANISM: human

<400> SEQUENCE: 257

Ser Ser Gln Gly His Phe
1               5
```

```
<210> SEQ ID NO 258
<211> LENGTH: 6
<212> TYPE: PRT
<213> ORGANISM: human

<400> SEQUENCE: 258

Ser Ser Gln Gly His Phe
1               5

<210> SEQ ID NO 259
<211> LENGTH: 5
<212> TYPE: PRT
<213> ORGANISM: human

<400> SEQUENCE: 259

Ser Gln Gly His Phe
1               5

<210> SEQ ID NO 260
<211> LENGTH: 5
<212> TYPE: PRT
<213> ORGANISM: human

<400> SEQUENCE: 260

Ser Gln Gly His Phe
1               5

<210> SEQ ID NO 261
<211> LENGTH: 5
<212> TYPE: PRT
<213> ORGANISM: human

<400> SEQUENCE: 261

Ser Gln Gly His Phe
1               5

<210> SEQ ID NO 262
<211> LENGTH: 5
<212> TYPE: PRT
<213> ORGANISM: human

<400> SEQUENCE: 262

Ser Ser Gln Gly His
1               5

<210> SEQ ID NO 263
<211> LENGTH: 5
<212> TYPE: PRT
<213> ORGANISM: human

<400> SEQUENCE: 263

Ser Ser Gln Gly His
1               5

<210> SEQ ID NO 264
<211> LENGTH: 5
<212> TYPE: PRT
<213> ORGANISM: human

<400> SEQUENCE: 264

Ser Ser Gln Gly His
1               5

<210> SEQ ID NO 265
<211> LENGTH: 20
```

<212> TYPE: PRT
<213> ORGANISM: human

<400> SEQUENCE: 265

Gly Ser Gly Lys Ile Lys Lys Ser Val Leu Trp Asp Arg Lys Val Gly
1               5                   10                  15

Ile Arg Lys Asn
            20

<210> SEQ ID NO 266
<211> LENGTH: 11
<212> TYPE: PRT
<213> ORGANISM: human

<400> SEQUENCE: 266

Lys Ser Val Leu Trp Asp Arg Lys Val Glu Ile
1               5                   10

<210> SEQ ID NO 267
<211> LENGTH: 8
<212> TYPE: PRT
<213> ORGANISM: human

<400> SEQUENCE: 267

Lys Ser Trp Arg Lys Val Glu Ile
1               5

<210> SEQ ID NO 268
<211> LENGTH: 12
<212> TYPE: PRT
<213> ORGANISM: human

<400> SEQUENCE: 268

Lys Ser Ile Arg Met Trp Glu Arg Lys Val Glu Ile
1               5                   10

<210> SEQ ID NO 269
<211> LENGTH: 15
<212> TYPE: PRT
<213> ORGANISM: human

<400> SEQUENCE: 269

Ser Gly Lys Ile Lys Lys Ser Val Leu Trp Asp Arg Lys Val Glu
1               5                   10                  15

<210> SEQ ID NO 270
<211> LENGTH: 10
<212> TYPE: PRT
<213> ORGANISM: human

<400> SEQUENCE: 270

Ser Gly Ile Lys Lys Val Leu Asp Lys Glu
1               5                   10

<210> SEQ ID NO 271
<211> LENGTH: 15
<212> TYPE: PRT
<213> ORGANISM: human

<400> SEQUENCE: 271

Ser Gly Pro Ile Lys Lys Pro Val Leu Arg Asp Met Lys Glu Glu
1               5                   10                  15

<210> SEQ ID NO 272

<211> LENGTH: 8
<212> TYPE: PRT
<213> ORGANISM: human

<400> SEQUENCE: 272

Leu Trp Asp Arg Lys Val Gly Ile
1               5

<210> SEQ ID NO 273
<211> LENGTH: 7
<212> TYPE: PRT
<213> ORGANISM: human

<400> SEQUENCE: 273

Leu Asp Arg Lys Val Gly Ile
1               5

<210> SEQ ID NO 274
<211> LENGTH: 8
<212> TYPE: PRT
<213> ORGANISM: human

<400> SEQUENCE: 274

Leu Ser Asp Arg Lys Val Gly Ile
1               5

<210> SEQ ID NO 275
<211> LENGTH: 15
<212> TYPE: PRT
<213> ORGANISM: human

<400> SEQUENCE: 275

Ala Arg Arg Trp Ser Arg Ser Thr Leu Cys Arg Ser Ile Cys Leu
1               5                   10                  15

<210> SEQ ID NO 276
<211> LENGTH: 8
<212> TYPE: PRT
<213> ORGANISM: human

<400> SEQUENCE: 276

Arg Arg Trp Ser Arg Ser Thr Leu
1               5

<210> SEQ ID NO 277
<211> LENGTH: 7
<212> TYPE: PRT
<213> ORGANISM: human

<400> SEQUENCE: 277

Arg Arg Trp Ser Ser Thr Leu
1               5

<210> SEQ ID NO 278
<211> LENGTH: 8
<212> TYPE: PRT
<213> ORGANISM: human

<400> SEQUENCE: 278

Arg Arg Trp Ser Pro Ser Thr Leu
1               5

<210> SEQ ID NO 279
<211> LENGTH: 10
<212> TYPE: PRT

<213> ORGANISM: human

<400> SEQUENCE: 279

Ser Arg Ser Thr Leu Cys Arg Ser Ile Cys
1               5                   10

<210> SEQ ID NO 280
<211> LENGTH: 8
<212> TYPE: PRT
<213> ORGANISM: human

<400> SEQUENCE: 280

Ser Arg Ser Leu Cys Ser Ile Cys
1               5

<210> SEQ ID NO 281
<211> LENGTH: 9
<212> TYPE: PRT
<213> ORGANISM: human

<400> SEQUENCE: 281

Ser Arg Ser Arg Leu Cys Ser Ile Cys
1               5

<210> SEQ ID NO 282
<211> LENGTH: 10
<212> TYPE: PRT
<213> ORGANISM: human

<400> SEQUENCE: 282

Leu Ile Gln His Gln His Leu Gly Gln Ile
1               5                   10

<210> SEQ ID NO 283
<211> LENGTH: 7
<212> TYPE: PRT
<213> ORGANISM: human

<400> SEQUENCE: 283

Leu Ile Gln His Gln His Leu
1               5

<210> SEQ ID NO 284
<211> LENGTH: 7
<212> TYPE: PRT
<213> ORGANISM: human

<400> SEQUENCE: 284

Leu Ile Gln His Gln Asn Leu
1               5

<210> SEQ ID NO 285
<211> LENGTH: 7
<212> TYPE: PRT
<213> ORGANISM: human

<400> SEQUENCE: 285

Leu Ile Gln His Gln Asn Leu
1               5

<210> SEQ ID NO 286
<211> LENGTH: 7
<212> TYPE: PRT
<213> ORGANISM: human

<400> SEQUENCE: 286

Leu Ile Gln His Gln His Leu
1               5

<210> SEQ ID NO 287
<211> LENGTH: 7
<212> TYPE: PRT
<213> ORGANISM: human

<400> SEQUENCE: 287

Leu Ile Gln His Gln His Leu
1               5

<210> SEQ ID NO 288
<211> LENGTH: 8
<212> TYPE: PRT
<213> ORGANISM: human

<400> SEQUENCE: 288

Leu Ile Gln Gln His Gln His Leu
1               5

<210> SEQ ID NO 289
<211> LENGTH: 9
<212> TYPE: PRT
<213> ORGANISM: human

<400> SEQUENCE: 289

Leu Ile Gln His Gln His Leu Gly Gln
1               5

<210> SEQ ID NO 290
<211> LENGTH: 7
<212> TYPE: PRT
<213> ORGANISM: human

<400> SEQUENCE: 290

Leu Ile Gln His Leu Gly Gln
1               5

<210> SEQ ID NO 291
<211> LENGTH: 9
<212> TYPE: PRT
<213> ORGANISM: human

<400> SEQUENCE: 291

Leu Ile Gln Tyr Val His Leu Gly Gln
1               5

<210> SEQ ID NO 292
<211> LENGTH: 23
<212> TYPE: PRT
<213> ORGANISM: human

<400> SEQUENCE: 292

Arg Pro His Cys Glu Leu Trp Gly Met Leu Ala Pro Thr Asp Cys Cys
1               5                   10                  15

His Leu His Arg Ser Ser Phe
            20

<210> SEQ ID NO 293
<211> LENGTH: 6
<212> TYPE: PRT
<213> ORGANISM: human

-continued

<400> SEQUENCE: 293

Pro Thr Asp Cys Cys His
1               5

<210> SEQ ID NO 294
<211> LENGTH: 6
<212> TYPE: PRT
<213> ORGANISM: human

<400> SEQUENCE: 294

Pro Thr Asp Cys Cys His
1               5

<210> SEQ ID NO 295
<211> LENGTH: 6
<212> TYPE: PRT
<213> ORGANISM: human

<400> SEQUENCE: 295

Pro Thr Asp Cys Cys His
1               5

<210> SEQ ID NO 296
<211> LENGTH: 6
<212> TYPE: PRT
<213> ORGANISM: human

<400> SEQUENCE: 296

His Leu His Arg Ser Ser
1               5

<210> SEQ ID NO 297
<211> LENGTH: 5
<212> TYPE: PRT
<213> ORGANISM: human

<400> SEQUENCE: 297

His His Arg Ser Ser
1               5

<210> SEQ ID NO 298
<211> LENGTH: 6
<212> TYPE: PRT
<213> ORGANISM: human

<400> SEQUENCE: 298

His Arg His Arg Ser Ser
1               5

<210> SEQ ID NO 299
<211> LENGTH: 12
<212> TYPE: PRT
<213> ORGANISM: human

<400> SEQUENCE: 299

Leu Ala Pro Thr Asp Cys Cys His Leu His Arg Ser
1               5                   10

<210> SEQ ID NO 300
<211> LENGTH: 8
<212> TYPE: PRT
<213> ORGANISM: human

<400> SEQUENCE: 300

```
Leu Pro Thr Asp His Leu Arg Ser
1               5

<210> SEQ ID NO 301
<211> LENGTH: 12
<212> TYPE: PRT
<213> ORGANISM: human

<400> SEQUENCE: 301

Leu Pro Pro Thr Asp Tyr Ala His Leu Gln Arg Ser
1               5                   10

<210> SEQ ID NO 302
<211> LENGTH: 7
<212> TYPE: PRT
<213> ORGANISM: human

<400> SEQUENCE: 302

Leu Trp Gly Met Leu Ala Pro
1               5

<210> SEQ ID NO 303
<211> LENGTH: 6
<212> TYPE: PRT
<213> ORGANISM: human

<400> SEQUENCE: 303

Leu Trp Gly Leu Ala Pro
1               5

<210> SEQ ID NO 304
<211> LENGTH: 7
<212> TYPE: PRT
<213> ORGANISM: human

<400> SEQUENCE: 304

Leu Trp Gly Leu Leu Ala Pro
1               5

<210> SEQ ID NO 305
<211> LENGTH: 30
<212> TYPE: PRT
<213> ORGANISM: human

<400> SEQUENCE: 305

Pro His Asn Thr Phe Ser Ala Tyr Pro Glu Cys Pro Asp Val Thr Arg
1               5                   10                  15

Thr Thr Pro Met His Thr Pro His Glu Thr Ser Tyr His Leu
            20                  25                  30

<210> SEQ ID NO 306
<211> LENGTH: 19
<212> TYPE: PRT
<213> ORGANISM: human

<400> SEQUENCE: 306

His Asn Thr Phe Ser Ala Tyr Pro Glu Cys Pro Asp Val Thr Arg Thr
1               5                   10                  15

Thr Pro Met

<210> SEQ ID NO 307
<211> LENGTH: 12
<212> TYPE: PRT
```

```
<213> ORGANISM: human

<400> SEQUENCE: 307

His Thr Ser Ala Tyr Pro Glu Pro Val Thr Thr Met
1               5                   10

<210> SEQ ID NO 308
<211> LENGTH: 23
<212> TYPE: PRT
<213> ORGANISM: human

<400> SEQUENCE: 308

His Ser Thr Val Ser Ala Tyr Pro Glu Pro Ser Lys Val Thr Ser Pro
1               5                   10                  15

Asn Val Thr Thr Ser Thr Met
            20

<210> SEQ ID NO 309
<211> LENGTH: 16
<212> TYPE: PRT
<213> ORGANISM: human

<400> SEQUENCE: 309

Asp Val Thr Arg Thr Thr Pro Met His Thr Pro His Glu Thr Ser Tyr
1               5                   10                  15

<210> SEQ ID NO 310
<211> LENGTH: 10
<212> TYPE: PRT
<213> ORGANISM: human

<400> SEQUENCE: 310

Asp Val Thr Thr Pro Pro Glu Thr Ser Tyr
1               5                   10

<210> SEQ ID NO 311
<211> LENGTH: 15
<212> TYPE: PRT
<213> ORGANISM: human

<400> SEQUENCE: 311

Asp Val Thr Trp Thr Ser Pro Pro Ser Val Ala Glu Thr Ser Tyr
1               5                   10                  15

<210> SEQ ID NO 312
<211> LENGTH: 16
<212> TYPE: PRT
<213> ORGANISM: human

<400> SEQUENCE: 312

Ala Tyr Pro Glu Cys Pro Asp Val Thr Arg Thr Thr Pro Met His Thr
1               5                   10                  15

<210> SEQ ID NO 313
<211> LENGTH: 9
<212> TYPE: PRT
<213> ORGANISM: human

<400> SEQUENCE: 313

Ala Tyr Glu Pro Val Thr Pro Met Thr
1               5

<210> SEQ ID NO 314
<211> LENGTH: 14
```

```
<212> TYPE: PRT
<213> ORGANISM: human

<400> SEQUENCE: 314

Ala Tyr Ser Glu Pro Pro Lys Val Thr Ser Pro Met Val Thr
1               5                   10

<210> SEQ ID NO 315
<211> LENGTH: 16
<212> TYPE: PRT
<213> ORGANISM: human

<400> SEQUENCE: 315

Asp Val Thr Arg Thr Thr Pro Met His Thr Pro His Glu Thr Ser Tyr
1               5                   10                  15

<210> SEQ ID NO 316
<211> LENGTH: 11
<212> TYPE: PRT
<213> ORGANISM: human

<400> SEQUENCE: 316

Asp Val Thr Arg Thr Met His Thr Pro Thr Tyr
1               5                   10

<210> SEQ ID NO 317
<211> LENGTH: 14
<212> TYPE: PRT
<213> ORGANISM: human

<400> SEQUENCE: 317

Asp Val Thr Arg Thr Met His Phe Gly Thr Pro Thr Ala Tyr
1               5                   10

<210> SEQ ID NO 318
<211> LENGTH: 29
<212> TYPE: PRT
<213> ORGANISM: human

<400> SEQUENCE: 318

Pro Asn Ser Ser Pro His Asn Thr Phe Ser Ala Tyr Pro Glu Cys Pro
1               5                   10                  15

Asp Val Thr Arg Thr Thr Pro Met His Thr Pro His Glu
            20                  25

<210> SEQ ID NO 319
<211> LENGTH: 16
<212> TYPE: PRT
<213> ORGANISM: human

<400> SEQUENCE: 319

Pro Ser Ser Pro Asn Phe Ser Asp Val Arg Thr Pro Thr Pro His Glu
1               5                   10                  15

<210> SEQ ID NO 320
<211> LENGTH: 32
<212> TYPE: PRT
<213> ORGANISM: human

<400> SEQUENCE: 320

Pro Asp Ser Ser Pro Asn Ala Phe Ser Thr Ser Gly Asp Val Val Ser
1               5                   10                  15

Arg Asn Gln Ser Phe Leu Arg Thr Pro Ile Gln Arg Thr Pro His Glu
            20                  25                  30
```

<210> SEQ ID NO 321
<211> LENGTH: 14
<212> TYPE: PRT
<213> ORGANISM: human

<400> SEQUENCE: 321

Ser Ala Tyr Pro Glu Cys Pro Asp Val Thr Arg Thr Thr Pro
1               5                   10

<210> SEQ ID NO 322
<211> LENGTH: 10
<212> TYPE: PRT
<213> ORGANISM: human

<400> SEQUENCE: 322

Ser Ala Tyr Cys Pro Asp Thr Thr Thr Pro
1               5                   10

<210> SEQ ID NO 323
<211> LENGTH: 15
<212> TYPE: PRT
<213> ORGANISM: human

<400> SEQUENCE: 323

Ser Ala Tyr Ala Val Cys Pro Asp Ile Thr Ala Thr Val Thr Pro
1               5                   10                  15

<210> SEQ ID NO 324
<211> LENGTH: 14
<212> TYPE: PRT
<213> ORGANISM: human

<400> SEQUENCE: 324

Glu Cys Pro Asp Val Thr Arg Thr Thr Pro Met His Thr Pro
1               5                   10

<210> SEQ ID NO 325
<211> LENGTH: 9
<212> TYPE: PRT
<213> ORGANISM: human

<400> SEQUENCE: 325

Glu Cys Pro Val Arg Thr Pro Thr Pro
1               5

<210> SEQ ID NO 326
<211> LENGTH: 20
<212> TYPE: PRT
<213> ORGANISM: human

<400> SEQUENCE: 326

Glu Cys Pro Val Arg Arg Asn Gly Gln Gly Asp Ala Pro Pro Thr Pro
1               5                   10                  15

Leu Pro Thr Pro
            20

<210> SEQ ID NO 327
<211> LENGTH: 36
<212> TYPE: PRT
<213> ORGANISM: human

<400> SEQUENCE: 327

Gly Arg Val Ile Gln Glu Pro Gly Gly Arg Gly Asp Lys Leu Leu His

```
            1               5                  10                  15
Gln Gly Ala Arg Arg Arg Arg Gly Leu Arg Thr Pro Ala Ser Val Pro
            20                  25                  30

Ile Ser Pro Ser
        35
```

<210> SEQ ID NO 328
<211> LENGTH: 22
<212> TYPE: PRT
<213> ORGANISM: human

<400> SEQUENCE: 328

```
Leu His Gln Gly Ala Arg Arg Arg Arg Gly Leu Arg Thr Pro Ala Ser
1               5                  10                  15

Val Pro Ile Ser Pro Ser
            20
```

<210> SEQ ID NO 329
<211> LENGTH: 12
<212> TYPE: PRT
<213> ORGANISM: human

<400> SEQUENCE: 329

```
Leu Gln Gly Arg Arg Arg Leu Ser Val Pro Pro Ser
1               5                  10
```

<210> SEQ ID NO 330
<211> LENGTH: 19
<212> TYPE: PRT
<213> ORGANISM: human

<400> SEQUENCE: 330

```
Leu Gln Gln Gly Gly Arg Arg Arg Gly Asp Leu Ser Ser Val Pro Thr
1               5                  10                  15

Ala Pro Ser
```

<210> SEQ ID NO 331
<211> LENGTH: 22
<212> TYPE: PRT
<213> ORGANISM: human

<400> SEQUENCE: 331

```
Leu His Gln Gly Ala Arg Arg Arg Arg Gly Leu Arg Thr Pro Ala Ser
1               5                  10                  15

Val Pro Ile Ser Pro Ser
            20
```

<210> SEQ ID NO 332
<211> LENGTH: 12
<212> TYPE: PRT
<213> ORGANISM: human

<400> SEQUENCE: 332

```
Leu Gln Gly Arg Arg Arg Leu Ser Val Pro Pro Ser
1               5                  10
```

<210> SEQ ID NO 333
<211> LENGTH: 19
<212> TYPE: PRT
<213> ORGANISM: human

<400> SEQUENCE: 333

```
Leu Gln Gln Gly Gly Arg Arg Arg Gly Asp Leu Ser Ser Val Pro Thr
1               5                   10                  15

Ala Pro Ser

<210> SEQ ID NO 334
<211> LENGTH: 23
<212> TYPE: PRT
<213> ORGANISM: human

<400> SEQUENCE: 334

Gly Arg Val Ile Gln Glu Pro Gly Arg Gly Asp Lys Leu Leu His
1               5                   10                  15

Gln Gly Ala Arg Arg Arg Arg
                20

<210> SEQ ID NO 335
<211> LENGTH: 13
<212> TYPE: PRT
<213> ORGANISM: human

<400> SEQUENCE: 335

Gly Arg Gln Pro Gly Gly Arg Gly Leu Leu Gly Arg Arg
1               5                   10

<210> SEQ ID NO 336
<211> LENGTH: 26
<212> TYPE: PRT
<213> ORGANISM: human

<400> SEQUENCE: 336

Gly Arg Gln Thr Pro Gly Gly Arg Gly Val Pro Leu Leu Asn Val Gly
1               5                   10                  15

Ser Arg Arg Ser Gln Pro Gly Gln Arg Arg
                20                  25

<210> SEQ ID NO 337
<211> LENGTH: 20
<212> TYPE: PRT
<213> ORGANISM: human

<400> SEQUENCE: 337

Gly Ser Gly Lys Ile Lys Lys Ser Val Leu Trp Asp Arg Lys Val Gly
1               5                   10                  15

Ile Arg Lys Asn
                20

<210> SEQ ID NO 338
<211> LENGTH: 13
<212> TYPE: PRT
<213> ORGANISM: human

<400> SEQUENCE: 338

Ser Gly Lys Ile Lys Lys Ser Val Leu Trp Asp Arg Lys
1               5                   10

<210> SEQ ID NO 339
<211> LENGTH: 9
<212> TYPE: PRT
<213> ORGANISM: human

<400> SEQUENCE: 339

Ser Gly Ile Lys Lys Val Leu Asp Lys
1               5
```

<210> SEQ ID NO 340
<211> LENGTH: 13
<212> TYPE: PRT
<213> ORGANISM: human

<400> SEQUENCE: 340

Ser Gly Pro Ile Lys Lys Pro Val Leu Arg Asp Met Lys
1               5                   10

<210> SEQ ID NO 341
<211> LENGTH: 6
<212> TYPE: PRT
<213> ORGANISM: human

<400> SEQUENCE: 341

Ser Val Leu Trp Asp Arg
1               5

<210> SEQ ID NO 342
<211> LENGTH: 6
<212> TYPE: PRT
<213> ORGANISM: human

<400> SEQUENCE: 342

Ser Val Leu Trp Asp Arg
1               5

<210> SEQ ID NO 343
<211> LENGTH: 6
<212> TYPE: PRT
<213> ORGANISM: human

<400> SEQUENCE: 343

Ser Val Leu Trp Asp Arg
1               5

<210> SEQ ID NO 344
<211> LENGTH: 6
<212> TYPE: PRT
<213> ORGANISM: human

<400> SEQUENCE: 344

Lys Lys Ser Val Leu Trp
1               5

<210> SEQ ID NO 345
<211> LENGTH: 6
<212> TYPE: PRT
<213> ORGANISM: human

<400> SEQUENCE: 345

Lys Lys Ser Val Leu Trp
1               5

<210> SEQ ID NO 346
<211> LENGTH: 6
<212> TYPE: PRT
<213> ORGANISM: human

<400> SEQUENCE: 346

Lys Lys Ser Val Leu Trp
1               5

```
<210> SEQ ID NO 347
<211> LENGTH: 4
<212> TYPE: PRT
<213> ORGANISM: human

<400> SEQUENCE: 347

Thr Gln Leu Val
1

<210> SEQ ID NO 348
<211> LENGTH: 4
<212> TYPE: PRT
<213> ORGANISM: human

<400> SEQUENCE: 348

Thr Gln Leu Val
1

<210> SEQ ID NO 349
<211> LENGTH: 4
<212> TYPE: PRT
<213> ORGANISM: human

<400> SEQUENCE: 349

Thr Gln Leu Val
1

<210> SEQ ID NO 350
<211> LENGTH: 4
<212> TYPE: PRT
<213> ORGANISM: human

<400> SEQUENCE: 350

Thr Gln Leu Val
1

<210> SEQ ID NO 351
<211> LENGTH: 16
<212> TYPE: PRT
<213> ORGANISM: human

<400> SEQUENCE: 351

Gly Val Ser Val Asn Glu Ala Ser Tyr Asp Gly Lys Tyr Ser Ser Tyr
1               5                   10                  15

<210> SEQ ID NO 352
<211> LENGTH: 14
<212> TYPE: PRT
<213> ORGANISM: human

<400> SEQUENCE: 352

Trp Val Asn Glu Ala Ser Tyr Asp Gly Lys Tyr Ser Ser Tyr
1               5                   10

<210> SEQ ID NO 353
<211> LENGTH: 9
<212> TYPE: PRT
<213> ORGANISM: human

<400> SEQUENCE: 353

Trp Val Ser Tyr Asp Gly Lys Tyr Tyr
1               5

<210> SEQ ID NO 354
<211> LENGTH: 14
```

<212> TYPE: PRT
<213> ORGANISM: human

<400> SEQUENCE: 354

Trp Val Ala Val Ile Ser Tyr Asp Gly Lys Tyr Glu Asn Tyr
1               5                   10

<210> SEQ ID NO 355
<211> LENGTH: 11
<212> TYPE: PRT
<213> ORGANISM: human

<400> SEQUENCE: 355

Trp Val Asn Glu Ala Ser Tyr Asp Gly Lys Tyr
1               5                   10

<210> SEQ ID NO 356
<211> LENGTH: 8
<212> TYPE: PRT
<213> ORGANISM: human

<400> SEQUENCE: 356

Trp Val Ser Tyr Asp Gly Lys Tyr
1               5

<210> SEQ ID NO 357
<211> LENGTH: 11
<212> TYPE: PRT
<213> ORGANISM: human

<400> SEQUENCE: 357

Trp Val Ala Val Ile Ser Tyr Asp Gly Lys Tyr
1               5                   10

<210> SEQ ID NO 358
<211> LENGTH: 8
<212> TYPE: PRT
<213> ORGANISM: human

<400> SEQUENCE: 358

Val Ser Val Asn Glu Ala Ser Tyr
1               5

<210> SEQ ID NO 359
<211> LENGTH: 7
<212> TYPE: PRT
<213> ORGANISM: human

<400> SEQUENCE: 359

Val Ser Val Asn Glu Ala Tyr
1               5

<210> SEQ ID NO 360
<211> LENGTH: 8
<212> TYPE: PRT
<213> ORGANISM: human

<400> SEQUENCE: 360

Val Ser Val Asn Glu Ala Pro Tyr
1               5

<210> SEQ ID NO 361
<211> LENGTH: 25
<212> TYPE: PRT
<213> ORGANISM: human

<400> SEQUENCE: 361

Gly Ala Ala Gln Pro Arg Asn Ala Glu Arg Arg Arg Val Arg Gly
1               5                   10                  15

Pro Val Arg Ala Ala Glu Met Leu Arg
            20                  25

<210> SEQ ID NO 362
<211> LENGTH: 12
<212> TYPE: PRT
<213> ORGANISM: human

<400> SEQUENCE: 362

Gln Pro Arg Asn Ala Glu Arg Arg Arg Val Arg
1               5                   10

<210> SEQ ID NO 363
<211> LENGTH: 10
<212> TYPE: PRT
<213> ORGANISM: human

<400> SEQUENCE: 363

Gln Pro Arg Ala Glu Arg Arg Val Arg
1               5                   10

<210> SEQ ID NO 364
<211> LENGTH: 13
<212> TYPE: PRT
<213> ORGANISM: human

<400> SEQUENCE: 364

Gln Pro Val Arg Glu Ala Glu Arg Arg His Arg Val Arg
1               5                   10

<210> SEQ ID NO 365
<211> LENGTH: 17
<212> TYPE: PRT
<213> ORGANISM: human

<400> SEQUENCE: 365

Ala Glu Arg Arg Arg Arg Val Arg Gly Pro Val Arg Ala Ala Glu Met
1               5                   10                  15

Leu

<210> SEQ ID NO 366
<211> LENGTH: 11
<212> TYPE: PRT
<213> ORGANISM: human

<400> SEQUENCE: 366

Ala Glu Arg Arg Arg Arg Gly Arg Ala Met Leu
1               5                   10

<210> SEQ ID NO 367
<211> LENGTH: 18
<212> TYPE: PRT
<213> ORGANISM: human

<400> SEQUENCE: 367

Ala Glu Arg Arg Ser Arg Ser Arg Gly Ala Ile Arg Asn Ala Cys Gln
1               5                   10                  15

Met Leu

<210> SEQ ID NO 368
<211> LENGTH: 17
<212> TYPE: PRT
<213> ORGANISM: human

<400> SEQUENCE: 368

Pro Arg Asn Ala Glu Arg Arg Arg Val Arg Gly Pro Val Arg Ala
1               5                   10                  15
Ala

<210> SEQ ID NO 369
<211> LENGTH: 12
<212> TYPE: PRT
<213> ORGANISM: human

<400> SEQUENCE: 369

Pro Arg Ala Arg Arg Arg Arg Gly Arg Ala Ala
1               5                   10

<210> SEQ ID NO 370
<211> LENGTH: 15
<212> TYPE: PRT
<213> ORGANISM: human

<400> SEQUENCE: 370

Pro Arg Ala Ala Ala Arg Arg Arg Arg Gly Ala Arg Ala Ala
1               5                   10                  15

<210> SEQ ID NO 371
<211> LENGTH: 5
<212> TYPE: PRT
<213> ORGANISM: human

<400> SEQUENCE: 371

Asn Ser Ser His His
1               5

<210> SEQ ID NO 372
<211> LENGTH: 5
<212> TYPE: PRT
<213> ORGANISM: human

<400> SEQUENCE: 372

Asn Ser Ser His His
1               5

<210> SEQ ID NO 373
<211> LENGTH: 5
<212> TYPE: PRT
<213> ORGANISM: human

<400> SEQUENCE: 373

Asn Ser Ser His His
1               5

<210> SEQ ID NO 374
<211> LENGTH: 5
<212> TYPE: PRT
<213> ORGANISM: human

<400> SEQUENCE: 374

Asn Ser Ser His His
1               5

<210> SEQ ID NO 375
<211> LENGTH: 28
<212> TYPE: PRT
<213> ORGANISM: human

<400> SEQUENCE: 375

Leu Gly Thr Ser Thr Ala Gln Gln His Gly Gly Trp Cys Pro Glu Ala
1               5                   10                  15

Ser Lys Asp Gly Pro His Pro Ser Thr Phe Pro Gln
            20                  25

<210> SEQ ID NO 376
<211> LENGTH: 21
<212> TYPE: PRT
<213> ORGANISM: human

<400> SEQUENCE: 376

Gln His Gly Gly Trp Cys Pro Glu Ala Ser Lys Asp Gly Pro His Pro
1               5                   10                  15

Ser Thr Phe Pro Gln
            20

<210> SEQ ID NO 377
<211> LENGTH: 15
<212> TYPE: PRT
<213> ORGANISM: human

<400> SEQUENCE: 377

Gln His Gly Gly Cys Pro Lys Gly Pro His Pro Ser Thr Pro Gln
1               5                   10                  15

<210> SEQ ID NO 378
<211> LENGTH: 22
<212> TYPE: PRT
<213> ORGANISM: human

<400> SEQUENCE: 378

Gln His Gly Gly Cys Pro Ala Lys Ala Leu Pro Gly Pro His Pro Gly
1               5                   10                  15

Val Val Ser Thr Pro Gln
            20

<210> SEQ ID NO 379
<211> LENGTH: 7
<212> TYPE: PRT
<213> ORGANISM: human

<400> SEQUENCE: 379

Gly Trp Cys Pro Glu Ala Ser
1               5

<210> SEQ ID NO 380
<211> LENGTH: 7
<212> TYPE: PRT
<213> ORGANISM: human

<400> SEQUENCE: 380

Gly Trp Cys Pro Glu Ala Ser
1               5

<210> SEQ ID NO 381
<211> LENGTH: 7
<212> TYPE: PRT

```
<213> ORGANISM: human

<400> SEQUENCE: 381

Gly Trp Cys Pro Glu Ala Ser
1               5

<210> SEQ ID NO 382
<211> LENGTH: 9
<212> TYPE: PRT
<213> ORGANISM: human

<400> SEQUENCE: 382

Gln His Gly Gly Trp Cys Pro Glu Ala
1               5

<210> SEQ ID NO 383
<211> LENGTH: 8
<212> TYPE: PRT
<213> ORGANISM: human

<400> SEQUENCE: 383

Gln His Gly Trp Cys Pro Glu Ala
1               5

<210> SEQ ID NO 384
<211> LENGTH: 10
<212> TYPE: PRT
<213> ORGANISM: human

<400> SEQUENCE: 384

Gln His Gly Pro Trp Cys Pro Pro Glu Ala
1               5                   10

<210> SEQ ID NO 385
<211> LENGTH: 4
<212> TYPE: PRT
<213> ORGANISM: human

<400> SEQUENCE: 385

Asp Cys Ser Cys
1

<210> SEQ ID NO 386
<211> LENGTH: 4
<212> TYPE: PRT
<213> ORGANISM: human

<400> SEQUENCE: 386

Asp Cys Ser Cys
1

<210> SEQ ID NO 387
<211> LENGTH: 4
<212> TYPE: PRT
<213> ORGANISM: human

<400> SEQUENCE: 387

Asp Cys Ser Cys
1

<210> SEQ ID NO 388
<211> LENGTH: 4
<212> TYPE: PRT
<213> ORGANISM: human
```

```
<400> SEQUENCE: 388

Asp Cys Ser Cys
1

<210> SEQ ID NO 389
<211> LENGTH: 17
<212> TYPE: PRT
<213> ORGANISM: human

<400> SEQUENCE: 389

Asn Arg Ser Arg Trp Ile Cys Gly Pro Leu Gly Leu Ile Lys Ala Leu
1               5                   10                  15

Val

<210> SEQ ID NO 390
<211> LENGTH: 13
<212> TYPE: PRT
<213> ORGANISM: human

<400> SEQUENCE: 390

Trp Ile Cys Gly Pro Leu Gly Leu Ile Lys Ala Leu Val
1               5                   10

<210> SEQ ID NO 391
<211> LENGTH: 8
<212> TYPE: PRT
<213> ORGANISM: human

<400> SEQUENCE: 391

Trp Cys Pro Leu Gly Ala Leu Val
1               5

<210> SEQ ID NO 392
<211> LENGTH: 10
<212> TYPE: PRT
<213> ORGANISM: human

<400> SEQUENCE: 392

Trp Leu Cys Ser Pro Leu Gly Ala Leu Val
1               5                   10

<210> SEQ ID NO 393
<211> LENGTH: 9
<212> TYPE: PRT
<213> ORGANISM: human

<400> SEQUENCE: 393

Gly Pro Leu Gly Leu Ile Lys Ala Leu
1               5

<210> SEQ ID NO 394
<211> LENGTH: 7
<212> TYPE: PRT
<213> ORGANISM: human

<400> SEQUENCE: 394

Gly Pro Leu Gly Leu Ile Leu
1               5

<210> SEQ ID NO 395
<211> LENGTH: 9
<212> TYPE: PRT
<213> ORGANISM: human
```

<400> SEQUENCE: 395

Gly Pro Leu Gly Leu Ile Arg Asn Leu
1               5

<210> SEQ ID NO 396
<211> LENGTH: 5
<212> TYPE: PRT
<213> ORGANISM: human

<400> SEQUENCE: 396

Trp Ile Cys Gly Pro
1               5

<210> SEQ ID NO 397
<211> LENGTH: 5
<212> TYPE: PRT
<213> ORGANISM: human

<400> SEQUENCE: 397

Trp Ile Cys Gly Pro
1               5

<210> SEQ ID NO 398
<211> LENGTH: 5
<212> TYPE: PRT
<213> ORGANISM: human

<400> SEQUENCE: 398

Trp Ile Cys Gly Pro
1               5

<210> SEQ ID NO 399
<211> LENGTH: 14
<212> TYPE: PRT
<213> ORGANISM: human

<400> SEQUENCE: 399

Arg Lys Gly Lys Lys Ser Lys Arg Arg Lys Trp Leu Asn Ser
1               5                   10

<210> SEQ ID NO 400
<211> LENGTH: 13
<212> TYPE: PRT
<213> ORGANISM: human

<400> SEQUENCE: 400

Arg Lys Gly Lys Lys Ser Lys Arg Arg Lys Trp Leu Asn
1               5                   10

<210> SEQ ID NO 401
<211> LENGTH: 10
<212> TYPE: PRT
<213> ORGANISM: human

<400> SEQUENCE: 401

Arg Lys Lys Ser Lys Arg Arg Lys Trp Leu
1               5                   10

<210> SEQ ID NO 402
<211> LENGTH: 20
<212> TYPE: PRT
<213> ORGANISM: human

<400> SEQUENCE: 402

-continued

Arg Lys Ser Lys Arg His Ser Ser Lys Arg Arg Lys Ser Met Ser
1               5                   10                  15

Ser Trp Leu Asp
            20

<210> SEQ ID NO 403
<211> LENGTH: 9
<212> TYPE: PRT
<213> ORGANISM: human

<400> SEQUENCE: 403

Lys Lys Ser Lys Arg Arg Lys Trp Leu
1               5

<210> SEQ ID NO 404
<211> LENGTH: 7
<212> TYPE: PRT
<213> ORGANISM: human

<400> SEQUENCE: 404

Lys Lys Lys Arg Lys Trp Leu
1               5

<210> SEQ ID NO 405
<211> LENGTH: 9
<212> TYPE: PRT
<213> ORGANISM: human

<400> SEQUENCE: 405

Lys Lys Lys Lys Lys Arg Lys Trp Leu
1               5

<210> SEQ ID NO 406
<211> LENGTH: 7
<212> TYPE: PRT
<213> ORGANISM: human

<400> SEQUENCE: 406

Lys Lys Ser Lys Arg Arg Lys
1               5

<210> SEQ ID NO 407
<211> LENGTH: 7
<212> TYPE: PRT
<213> ORGANISM: human

<400> SEQUENCE: 407

Lys Lys Ser Lys Arg Arg Lys
1               5

<210> SEQ ID NO 408
<211> LENGTH: 7
<212> TYPE: PRT
<213> ORGANISM: human

<400> SEQUENCE: 408

Lys Lys Ser Lys Arg Arg Lys
1               5

<210> SEQ ID NO 409
<211> LENGTH: 6
<212> TYPE: PRT
<213> ORGANISM: human

<400> SEQUENCE: 409

```
Arg Arg Lys Trp Leu Asn
1               5

<210> SEQ ID NO 410
<211> LENGTH: 6
<212> TYPE: PRT
<213> ORGANISM: human

<400> SEQUENCE: 410

Arg Arg Lys Trp Leu Asn
1               5

<210> SEQ ID NO 411
<211> LENGTH: 6
<212> TYPE: PRT
<213> ORGANISM: human

<400> SEQUENCE: 411

Arg Arg Lys Trp Leu Asn
1               5

<210> SEQ ID NO 412
<211> LENGTH: 11
<212> TYPE: PRT
<213> ORGANISM: human

<400> SEQUENCE: 412

Arg Lys Gly Lys Lys Ser Lys Arg Arg Lys Trp
1               5                   10

<210> SEQ ID NO 413
<211> LENGTH: 8
<212> TYPE: PRT
<213> ORGANISM: human

<400> SEQUENCE: 413

Arg Lys Lys Lys Arg Arg Lys Trp
1               5

<210> SEQ ID NO 414
<211> LENGTH: 10
<212> TYPE: PRT
<213> ORGANISM: human

<400> SEQUENCE: 414

Arg Lys Lys Lys Glu Asn Arg Arg Lys Trp
1               5                   10

<210> SEQ ID NO 415
<211> LENGTH: 6
<212> TYPE: PRT
<213> ORGANISM: human

<400> SEQUENCE: 415

Gly Asp Pro Asn Ser Ser
1               5

<210> SEQ ID NO 416
<211> LENGTH: 5
<212> TYPE: PRT
<213> ORGANISM: human

<400> SEQUENCE: 416

Gly Asp Pro Asn Ser
```

```
1               5
```

<210> SEQ ID NO 417
<211> LENGTH: 5
<212> TYPE: PRT
<213> ORGANISM: human

<400> SEQUENCE: 417

```
Gly Asp Pro Asn Ser
1               5
```

<210> SEQ ID NO 418
<211> LENGTH: 5
<212> TYPE: PRT
<213> ORGANISM: human

<400> SEQUENCE: 418

```
Gly Asp Pro Asn Ser
1               5
```

<210> SEQ ID NO 419
<211> LENGTH: 5
<212> TYPE: PRT
<213> ORGANISM: human

<400> SEQUENCE: 419

```
Asp Pro Asn Ser Ser
1               5
```

<210> SEQ ID NO 420
<211> LENGTH: 5
<212> TYPE: PRT
<213> ORGANISM: human

<400> SEQUENCE: 420

```
Asp Pro Asn Ser Ser
1               5
```

<210> SEQ ID NO 421
<211> LENGTH: 5
<212> TYPE: PRT
<213> ORGANISM: human

<400> SEQUENCE: 421

```
Asp Pro Asn Ser Ser
1               5
```

<210> SEQ ID NO 422
<211> LENGTH: 36
<212> TYPE: PRT
<213> ORGANISM: human

<400> SEQUENCE: 422

```
Gly Arg Val Ile Gln Glu Pro Gly Gly Arg Gly Asp Lys Leu Leu His
1               5                   10                  15

Gln Gly Ala Arg Arg Arg Arg Gly Leu Arg Thr Pro Ala Ser Val Pro
            20                  25                  30

Ile Ser Pro Ser
        35
```

<210> SEQ ID NO 423
<211> LENGTH: 22
<212> TYPE: PRT
<213> ORGANISM: human

```
<400> SEQUENCE: 423

Leu His Gln Gly Ala Arg Arg Arg Gly Leu Arg Thr Pro Ala Ser
1               5                   10                  15

Val Pro Ile Ser Pro Ser
            20

<210> SEQ ID NO 424
<211> LENGTH: 12
<212> TYPE: PRT
<213> ORGANISM: human

<400> SEQUENCE: 424

Leu Gln Gly Arg Arg Arg Leu Ser Val Pro Pro Ser
1               5                   10

<210> SEQ ID NO 425
<211> LENGTH: 19
<212> TYPE: PRT
<213> ORGANISM: human

<400> SEQUENCE: 425

Leu Gln Gln Gly Gly Arg Arg Arg Gly Asp Leu Ser Ser Val Pro Thr
1               5                   10                  15

Ala Pro Ser

<210> SEQ ID NO 426
<211> LENGTH: 22
<212> TYPE: PRT
<213> ORGANISM: human

<400> SEQUENCE: 426

Leu His Gln Gly Ala Arg Arg Arg Gly Leu Arg Thr Pro Ala Ser
1               5                   10                  15

Val Pro Ile Ser Pro Ser
            20

<210> SEQ ID NO 427
<211> LENGTH: 12
<212> TYPE: PRT
<213> ORGANISM: human

<400> SEQUENCE: 427

Leu Gln Gly Arg Arg Arg Leu Ser Val Pro Pro Ser
1               5                   10

<210> SEQ ID NO 428
<211> LENGTH: 19
<212> TYPE: PRT
<213> ORGANISM: human

<400> SEQUENCE: 428

Leu Gln Gln Gly Gly Arg Arg Arg Gly Asp Leu Ser Ser Val Pro Thr
1               5                   10                  15

Ala Pro Ser

<210> SEQ ID NO 429
<211> LENGTH: 23
<212> TYPE: PRT
<213> ORGANISM: human

<400> SEQUENCE: 429
```

```
Gly Arg Val Ile Gln Glu Pro Gly Gly Arg Gly Asp Lys Leu Leu His
1               5                   10                  15

Gln Gly Ala Arg Arg Arg
            20

<210> SEQ ID NO 430
<211> LENGTH: 15
<212> TYPE: PRT
<213> ORGANISM: human

<400> SEQUENCE: 430

Gly Arg Gln Pro Gly Gly Arg Gly Leu Leu Gly Arg Arg Arg Arg
1               5                   10                  15

<210> SEQ ID NO 431
<211> LENGTH: 26
<212> TYPE: PRT
<213> ORGANISM: human

<400> SEQUENCE: 431

Gly Arg Gln Thr Pro Gly Gly Arg Gly Val Pro Leu Leu Asn Val Gly
1               5                   10                  15

Ser Arg Arg Ser Gln Pro Gly Gln Arg Arg
            20                  25

<210> SEQ ID NO 432
<211> LENGTH: 11
<212> TYPE: PRT
<213> ORGANISM: human

<400> SEQUENCE: 432

Val Gly Asn Gly Glu Gly Arg Leu Glu Val Leu
1               5                   10

<210> SEQ ID NO 433
<211> LENGTH: 7
<212> TYPE: PRT
<213> ORGANISM: human

<400> SEQUENCE: 433

Glu Gly Arg Leu Glu Val Leu
1               5

<210> SEQ ID NO 434
<211> LENGTH: 7
<212> TYPE: PRT
<213> ORGANISM: human

<400> SEQUENCE: 434

Glu Gly Arg Leu Glu Val Leu
1               5

<210> SEQ ID NO 435
<211> LENGTH: 7
<212> TYPE: PRT
<213> ORGANISM: human

<400> SEQUENCE: 435

Glu Gly Arg Leu Glu Val Leu
1               5

<210> SEQ ID NO 436
<211> LENGTH: 7
<212> TYPE: PRT
```

```
<213> ORGANISM: human

<400> SEQUENCE: 436

Gly Glu Gly Arg Leu Glu Val
1               5

<210> SEQ ID NO 437
<211> LENGTH: 7
<212> TYPE: PRT
<213> ORGANISM: human

<400> SEQUENCE: 437

Gly Glu Gly Arg Leu Glu Val
1               5

<210> SEQ ID NO 438
<211> LENGTH: 7
<212> TYPE: PRT
<213> ORGANISM: human

<400> SEQUENCE: 438

Gly Glu Gly Arg Leu Glu Val
1               5

<210> SEQ ID NO 439
<211> LENGTH: 8
<212> TYPE: PRT
<213> ORGANISM: human

<400> SEQUENCE: 439

Gly Glu Gly Arg Leu Glu Val Leu
1               5

<210> SEQ ID NO 440
<211> LENGTH: 6
<212> TYPE: PRT
<213> ORGANISM: human

<400> SEQUENCE: 440

Gly Gly Arg Leu Glu Leu
1               5

<210> SEQ ID NO 441
<211> LENGTH: 8
<212> TYPE: PRT
<213> ORGANISM: human

<400> SEQUENCE: 441

Gly Gln Gly Arg Leu Glu Ile Leu
1               5

<210> SEQ ID NO 442
<211> LENGTH: 14
<212> TYPE: PRT
<213> ORGANISM: human

<400> SEQUENCE: 442

Gly Ser Arg Val Arg Met Ser Gly Lys Lys Lys Glu Arg Lys
1               5                   10

<210> SEQ ID NO 443
<211> LENGTH: 10
<212> TYPE: PRT
<213> ORGANISM: human
```

<400> SEQUENCE: 443

Val Arg Met Ser Gly Lys Lys Lys Glu Arg
1               5                   10

<210> SEQ ID NO 444
<211> LENGTH: 8
<212> TYPE: PRT
<213> ORGANISM: human

<400> SEQUENCE: 444

Val Arg Met Lys Lys Lys Glu Arg
1               5

<210> SEQ ID NO 445
<211> LENGTH: 10
<212> TYPE: PRT
<213> ORGANISM: human

<400> SEQUENCE: 445

Val Arg Met Glu Glu Lys Lys Lys Glu Arg
1               5                   10

<210> SEQ ID NO 446
<211> LENGTH: 8
<212> TYPE: PRT
<213> ORGANISM: human

<400> SEQUENCE: 446

Met Ser Gly Lys Lys Lys Glu Arg
1               5

<210> SEQ ID NO 447
<211> LENGTH: 7
<212> TYPE: PRT
<213> ORGANISM: human

<400> SEQUENCE: 447

Ser Gly Lys Lys Lys Glu Arg
1               5

<210> SEQ ID NO 448
<211> LENGTH: 8
<212> TYPE: PRT
<213> ORGANISM: human

<400> SEQUENCE: 448

Leu Ser Gly Lys Lys Lys Glu Arg
1               5

<210> SEQ ID NO 449
<211> LENGTH: 10
<212> TYPE: PRT
<213> ORGANISM: human

<400> SEQUENCE: 449

Val Arg Met Ser Gly Lys Lys Lys Glu Arg
1               5                   10

<210> SEQ ID NO 450
<211> LENGTH: 7
<212> TYPE: PRT
<213> ORGANISM: human

<400> SEQUENCE: 450

Val Arg Ser Lys Lys Lys Arg
1               5

<210> SEQ ID NO 451
<211> LENGTH: 10
<212> TYPE: PRT
<213> ORGANISM: human

<400> SEQUENCE: 451

Val Arg Leu Ser Glu Lys Lys Lys Asp Arg
1               5                   10

<210> SEQ ID NO 452
<211> LENGTH: 5
<212> TYPE: PRT
<213> ORGANISM: human

<400> SEQUENCE: 452

Asn Ser Ser Val Ser
1               5

<210> SEQ ID NO 453
<211> LENGTH: 5
<212> TYPE: PRT
<213> ORGANISM: human

<400> SEQUENCE: 453

Asn Ser Ser Val Ser
1               5

<210> SEQ ID NO 454
<211> LENGTH: 5
<212> TYPE: PRT
<213> ORGANISM: human

<400> SEQUENCE: 454

Asn Ser Ser Val Ser
1               5

<210> SEQ ID NO 455
<211> LENGTH: 5
<212> TYPE: PRT
<213> ORGANISM: human

<400> SEQUENCE: 455

Asn Ser Ser Val Ser
1               5

<210> SEQ ID NO 456
<211> LENGTH: 4
<212> TYPE: PRT
<213> ORGANISM: human

<400> SEQUENCE: 456

Ser Ile Cys Ala
1

<210> SEQ ID NO 457
<211> LENGTH: 4
<212> TYPE: PRT
<213> ORGANISM: human

<400> SEQUENCE: 457

Ser Ile Cys Ala
1

<210> SEQ ID NO 458
<211> LENGTH: 4
<212> TYPE: PRT
<213> ORGANISM: human

<400> SEQUENCE: 458

Ser Ile Cys Ala
1

<210> SEQ ID NO 459
<211> LENGTH: 4
<212> TYPE: PRT
<213> ORGANISM: human

<400> SEQUENCE: 459

Ser Ile Cys Ala
1

<210> SEQ ID NO 460
<211> LENGTH: 11
<212> TYPE: PRT
<213> ORGANISM: human

<400> SEQUENCE: 460

Gln Leu Arg Ile Ser Thr Thr Arg Ser Trp Thr
1               5                   10

<210> SEQ ID NO 461
<211> LENGTH: 10
<212> TYPE: PRT
<213> ORGANISM: human

<400> SEQUENCE: 461

Gln Leu Arg Ile Ser Thr Thr Arg Ser Trp
1               5                   10

<210> SEQ ID NO 462
<211> LENGTH: 7
<212> TYPE: PRT
<213> ORGANISM: human

<400> SEQUENCE: 462

Gln Leu Arg Ser Thr Arg Trp
1               5

<210> SEQ ID NO 463
<211> LENGTH: 10
<212> TYPE: PRT
<213> ORGANISM: human

<400> SEQUENCE: 463

Gln Leu Arg Asp Ser Thr Ala Arg Ala Trp
1               5                   10

<210> SEQ ID NO 464
<211> LENGTH: 6
<212> TYPE: PRT
<213> ORGANISM: human

<400> SEQUENCE: 464

Ser Thr Thr Arg Ser Trp
1               5

```
<210> SEQ ID NO 465
<211> LENGTH: 6
<212> TYPE: PRT
<213> ORGANISM: human

<400> SEQUENCE: 465

Ser Thr Thr Arg Ser Trp
1               5

<210> SEQ ID NO 466
<211> LENGTH: 6
<212> TYPE: PRT
<213> ORGANISM: human

<400> SEQUENCE: 466

Ser Thr Thr Arg Ser Trp
1               5

<210> SEQ ID NO 467
<211> LENGTH: 8
<212> TYPE: PRT
<213> ORGANISM: human

<400> SEQUENCE: 467

Arg Ile Ser Thr Thr Arg Ser Trp
1               5

<210> SEQ ID NO 468
<211> LENGTH: 6
<212> TYPE: PRT
<213> ORGANISM: human

<400> SEQUENCE: 468

Arg Ile Ser Thr Ser Trp
1               5

<210> SEQ ID NO 469
<211> LENGTH: 8
<212> TYPE: PRT
<213> ORGANISM: human

<400> SEQUENCE: 469

Arg Ile Ser Ser Thr Ser Ser Trp
1               5

<210> SEQ ID NO 470
<211> LENGTH: 7
<212> TYPE: PRT
<213> ORGANISM: human

<400> SEQUENCE: 470

Arg Ile Ser Thr Thr Arg Ser
1               5

<210> SEQ ID NO 471
<211> LENGTH: 6
<212> TYPE: PRT
<213> ORGANISM: human

<400> SEQUENCE: 471

Arg Ile Ser Thr Arg Ser
1               5

<210> SEQ ID NO 472
<211> LENGTH: 9
```

<212> TYPE: PRT
<213> ORGANISM: human

<400> SEQUENCE: 472

Arg Ile Ser Thr Ser Pro Ile Arg Ser
1               5

<210> SEQ ID NO 473
<211> LENGTH: 36
<212> TYPE: PRT
<213> ORGANISM: human

<400> SEQUENCE: 473

Gly Arg Val Ile Gln Glu Pro Gly Gly Arg Gly Asp Lys Leu Leu His
1               5                   10                  15

Gln Gly Ala Arg Arg Arg Gly Leu Arg Thr Pro Ala Ser Val Pro
            20                  25                  30

Ile Ser Pro Ser
        35

<210> SEQ ID NO 474
<211> LENGTH: 22
<212> TYPE: PRT
<213> ORGANISM: human

<400> SEQUENCE: 474

Leu His Gln Gly Ala Arg Arg Arg Gly Leu Arg Thr Pro Ala Ser
1               5                   10                  15

Val Pro Ile Ser Pro Ser
            20

<210> SEQ ID NO 475
<211> LENGTH: 12
<212> TYPE: PRT
<213> ORGANISM: human

<400> SEQUENCE: 475

Leu Gln Gly Arg Arg Arg Leu Ser Val Pro Pro Ser
1               5                   10

<210> SEQ ID NO 476
<211> LENGTH: 19
<212> TYPE: PRT
<213> ORGANISM: human

<400> SEQUENCE: 476

Leu Gln Gln Gly Gly Arg Arg Gly Asp Leu Ser Ser Val Pro Thr
1               5                   10                  15

Ala Pro Ser

<210> SEQ ID NO 477
<211> LENGTH: 22
<212> TYPE: PRT
<213> ORGANISM: human

<400> SEQUENCE: 477

Leu His Gln Gly Ala Arg Arg Arg Gly Leu Arg Thr Pro Ala Ser
1               5                   10                  15

Val Pro Ile Ser Pro Ser
            20

<210> SEQ ID NO 478

```
<211> LENGTH: 12
<212> TYPE: PRT
<213> ORGANISM: human

<400> SEQUENCE: 478

Leu Gln Gly Arg Arg Leu Ser Val Pro Pro Ser
1               5                   10

<210> SEQ ID NO 479
<211> LENGTH: 19
<212> TYPE: PRT
<213> ORGANISM: human

<400> SEQUENCE: 479

Leu Gln Gln Gly Gly Arg Arg Gly Asp Leu Ser Ser Val Pro Thr
1               5                   10                  15

Ala Pro Ser

<210> SEQ ID NO 480
<211> LENGTH: 23
<212> TYPE: PRT
<213> ORGANISM: human

<400> SEQUENCE: 480

Gly Arg Val Ile Gln Glu Pro Gly Gly Arg Gly Asp Lys Leu Leu His
1               5                   10                  15

Gln Gly Ala Arg Arg Arg Arg
                20

<210> SEQ ID NO 481
<211> LENGTH: 15
<212> TYPE: PRT
<213> ORGANISM: human

<400> SEQUENCE: 481

Gly Arg Gln Pro Gly Gly Arg Gly Leu Leu Gly Arg Arg Arg Arg
1               5                   10                  15

<210> SEQ ID NO 482
<211> LENGTH: 26
<212> TYPE: PRT
<213> ORGANISM: human

<400> SEQUENCE: 482

Gly Arg Gln Thr Pro Gly Gly Arg Gly Val Pro Leu Leu Asn Val Gly
1               5                   10                  15

Ser Arg Arg Ser Gln Pro Gly Gln Arg Arg
                20                  25

<210> SEQ ID NO 483
<211> LENGTH: 5
<212> TYPE: PRT
<213> ORGANISM: human

<400> SEQUENCE: 483

Asp Met Ser Tyr Lys
1               5

<210> SEQ ID NO 484
<211> LENGTH: 5
<212> TYPE: PRT
<213> ORGANISM: human

<400> SEQUENCE: 484
```

Asp Met Ser Tyr Lys
1               5

<210> SEQ ID NO 485
<211> LENGTH: 4
<212> TYPE: PRT
<213> ORGANISM: human

<400> SEQUENCE: 485

Met Ser Tyr Lys
1

<210> SEQ ID NO 486
<211> LENGTH: 5
<212> TYPE: PRT
<213> ORGANISM: human

<400> SEQUENCE: 486

Glu Met Ser Tyr Lys
1               5

<210> SEQ ID NO 487
<211> LENGTH: 4
<212> TYPE: PRT
<213> ORGANISM: human

<400> SEQUENCE: 487

Asp Met Ser Tyr
1

<210> SEQ ID NO 488
<211> LENGTH: 4
<212> TYPE: PRT
<213> ORGANISM: human

<400> SEQUENCE: 488

Asp Met Ser Tyr
1

<210> SEQ ID NO 489
<211> LENGTH: 4
<212> TYPE: PRT
<213> ORGANISM: human

<400> SEQUENCE: 489

Asp Met Ser Tyr
1

<210> SEQ ID NO 490
<211> LENGTH: 27
<212> TYPE: PRT
<213> ORGANISM: human

<400> SEQUENCE: 490

Arg Gly Asp Lys Leu Leu His Gln Gly Ala Arg Arg Arg Gly Leu
1               5                   10                  15

Arg Thr Pro Ala Ser Val Pro Ile Ser Pro Ser
            20                  25

<210> SEQ ID NO 491
<211> LENGTH: 22
<212> TYPE: PRT
<213> ORGANISM: human

```
<400> SEQUENCE: 491

Leu His Gln Gly Ala Arg Arg Arg Gly Leu Arg Thr Pro Ala Ser
1               5                   10                  15

Val Pro Ile Ser Pro Ser
            20

<210> SEQ ID NO 492
<211> LENGTH: 12
<212> TYPE: PRT
<213> ORGANISM: human

<400> SEQUENCE: 492

Leu Gln Gly Arg Arg Arg Leu Ser Val Pro Pro Ser
1               5                   10

<210> SEQ ID NO 493
<211> LENGTH: 19
<212> TYPE: PRT
<213> ORGANISM: human

<400> SEQUENCE: 493

Leu Gln Gln Gly Gly Arg Arg Arg Gly Asp Leu Ser Ser Val Pro Thr
1               5                   10                  15

Ala Pro Ser

<210> SEQ ID NO 494
<211> LENGTH: 13
<212> TYPE: PRT
<213> ORGANISM: human

<400> SEQUENCE: 494

Arg Arg Arg Arg Gly Leu Arg Thr Pro Ala Ser Val Pro
1               5                   10

<210> SEQ ID NO 495
<211> LENGTH: 11
<212> TYPE: PRT
<213> ORGANISM: human

<400> SEQUENCE: 495

Arg Arg Arg Arg Leu Arg Thr Pro Ala Val Pro
1               5                   10

<210> SEQ ID NO 496
<211> LENGTH: 18
<212> TYPE: PRT
<213> ORGANISM: human

<400> SEQUENCE: 496

Arg Arg Arg Arg Pro Leu Leu Arg Leu Pro Arg Arg Thr Pro Ala Lys
1               5                   10                  15

Val Pro

<210> SEQ ID NO 497
<211> LENGTH: 14
<212> TYPE: PRT
<213> ORGANISM: human

<400> SEQUENCE: 497

Arg Pro Ala Arg Ser Arg Arg Met Met Ala Trp Gly Lys Ala
1               5                   10
```

```
<210> SEQ ID NO 498
<211> LENGTH: 8
<212> TYPE: PRT
<213> ORGANISM: human

<400> SEQUENCE: 498

Arg Pro Ala Arg Ser Arg Arg Met
1               5

<210> SEQ ID NO 499
<211> LENGTH: 7
<212> TYPE: PRT
<213> ORGANISM: human

<400> SEQUENCE: 499

Arg Pro Arg Ser Arg Arg Met
1               5

<210> SEQ ID NO 500
<211> LENGTH: 8
<212> TYPE: PRT
<213> ORGANISM: human

<400> SEQUENCE: 500

Arg Pro Glu Arg Ser Arg Arg Met
1               5

<210> SEQ ID NO 501
<211> LENGTH: 7
<212> TYPE: PRT
<213> ORGANISM: human

<400> SEQUENCE: 501

Arg Arg Met Met Ala Trp Gly
1               5

<210> SEQ ID NO 502
<211> LENGTH: 6
<212> TYPE: PRT
<213> ORGANISM: human

<400> SEQUENCE: 502

Arg Arg Met Ala Trp Gly
1               5

<210> SEQ ID NO 503
<211> LENGTH: 7
<212> TYPE: PRT
<213> ORGANISM: human

<400> SEQUENCE: 503

Arg Arg Thr Met Ala Trp Gly
1               5

<210> SEQ ID NO 504
<211> LENGTH: 10
<212> TYPE: PRT
<213> ORGANISM: human

<400> SEQUENCE: 504

Arg Pro Ala Arg Ser Arg Arg Met Met Ala
1               5                   10

<210> SEQ ID NO 505
<211> LENGTH: 8
```

```
<212> TYPE: PRT
<213> ORGANISM: human

<400> SEQUENCE: 505

Arg Ala Arg Arg Arg Met Met Ala
1               5

<210> SEQ ID NO 506
<211> LENGTH: 14
<212> TYPE: PRT
<213> ORGANISM: human

<400> SEQUENCE: 506

Arg Lys Ala Arg Asn Arg Arg Gln Glu Trp Asn Met Met Ala
1               5                   10

<210> SEQ ID NO 507
<211> LENGTH: 29
<212> TYPE: PRT
<213> ORGANISM: human

<400> SEQUENCE: 507

Ala Glu Thr Val Gly Pro Gly Arg Glu Glu Gly Cys Trp Gln Arg Gly
1               5                   10                  15

Arg Pro Asn Glu Glu Thr Thr Cys Pro Ser Ser Arg Ser
            20                  25

<210> SEQ ID NO 508
<211> LENGTH: 13
<212> TYPE: PRT
<213> ORGANISM: human

<400> SEQUENCE: 508

Gly Pro Gly Arg Glu Glu Gly Cys Trp Gln Arg Gly Arg
1               5                   10

<210> SEQ ID NO 509
<211> LENGTH: 11
<212> TYPE: PRT
<213> ORGANISM: human

<400> SEQUENCE: 509

Gly Pro Gly Arg Gly Cys Trp Gln Arg Gly Arg
1               5                   10

<210> SEQ ID NO 510
<211> LENGTH: 14
<212> TYPE: PRT
<213> ORGANISM: human

<400> SEQUENCE: 510

Gly Pro Gly Arg Gly Cys Gly Trp Val Gln Arg Gly Arg
1               5                   10

<210> SEQ ID NO 511
<211> LENGTH: 7
<212> TYPE: PRT
<213> ORGANISM: human

<400> SEQUENCE: 511

Glu Gly Cys Trp Gln Arg Gly
1               5

<210> SEQ ID NO 512
```

```
<211> LENGTH: 6
<212> TYPE: PRT
<213> ORGANISM: human

<400> SEQUENCE: 512

Glu Gly Cys Trp Arg Gly
1               5

<210> SEQ ID NO 513
<211> LENGTH: 7
<212> TYPE: PRT
<213> ORGANISM: human

<400> SEQUENCE: 513

Glu Gly Cys Trp Glu Arg Gly
1               5

<210> SEQ ID NO 514
<211> LENGTH: 7
<212> TYPE: PRT
<213> ORGANISM: human

<400> SEQUENCE: 514

Val Gly Pro Gly Arg Glu Glu
1               5

<210> SEQ ID NO 515
<211> LENGTH: 7
<212> TYPE: PRT
<213> ORGANISM: human

<400> SEQUENCE: 515

Val Gly Pro Gly Arg Glu Glu
1               5

<210> SEQ ID NO 516
<211> LENGTH: 7
<212> TYPE: PRT
<213> ORGANISM: human
<220> FEATURE:
<221> NAME/KEY: misc_feature
<222> LOCATION: (86)..(86)
<223> OTHER INFORMATION: Xaa can be any naturally occurring amino acid

<400> SEQUENCE: 516

Val Gly Pro Gly Arg Glu Glu
1               5

<210> SEQ ID NO 517
<211> LENGTH: 94
<212> TYPE: PRT
<213> ORGANISM: human
<220> FEATURE:
<221> NAME/KEY: misc_feature
<222> LOCATION: (86)..(86)
<223> OTHER INFORMATION: Xaa can be any naturally occurring amino acid

<400> SEQUENCE: 517

Pro Ile Asp Gly Leu Ala Thr Ser Ala Ile Met Ala Cys Glu Val Thr
1               5                   10                  15

Thr Leu Thr His Lys Pro Trp Asn Asn Ser Val Lys Ala Gly Thr Leu
            20                  25                  30

Ile Thr Lys Ser Phe Leu Ser Ser Ala Gln Ser Thr Lys Ile Phe Cys
        35                  40                  45

Cys Leu Trp Asp Leu Val Cys Lys Gln Leu Lys Gly Asp Ala Ala Gln
```

```
            50                  55                  60
Gly Leu Ala Val Asp Gly Asn Val Lys Glu Gln Ser Ile His Lys Leu
 65                  70                  75                  80

His Asn Thr Ala Arg Xaa Ser Leu Arg Pro His Ser Ser Asn
                 85                  90
```

<210> SEQ ID NO 518
<211> LENGTH: 35
<212> TYPE: PRT
<213> ORGANISM: human

<400> SEQUENCE: 518

```
Ala Gln Ser Thr Lys Ile Phe Cys Cys Leu Trp Asp Leu Val Cys Lys
 1               5                   10                  15

Gln Leu Lys Gly Asp Ala Ala Gln Gly Leu Ala Val Asp Gly Asn Val
                20                  25                  30

Lys Glu Gln
         35
```

<210> SEQ ID NO 519
<211> LENGTH: 23
<212> TYPE: PRT
<213> ORGANISM: human

<400> SEQUENCE: 519

```
Ala Gln Ser Lys Ile Phe Cys Cys Leu Trp Val Lys Gln Leu Asp Ala
 1               5                   10                  15

Ala Gln Gly Leu Gly Val Glu
                20
```

<210> SEQ ID NO 520
<211> LENGTH: 34
<212> TYPE: PRT
<213> ORGANISM: human

<400> SEQUENCE: 520

```
Ala Gln Ser Met Lys Ile Phe Cys Cys Leu Trp Asn Phe Val Tyr Lys
 1               5                   10                  15

Gln Leu Glu Asp Ala Ala Gln Gly Leu Thr Met Gly Gly Asp Val Glu
                20                  25                  30

Glu His
```

<210> SEQ ID NO 521
<211> LENGTH: 31
<212> TYPE: PRT
<213> ORGANISM: human

<400> SEQUENCE: 521

```
Lys Ile Phe Cys Cys Leu Trp Asp Leu Val Cys Lys Gln Leu Lys Gly
 1               5                   10                  15

Asp Ala Ala Gln Gly Leu Ala Val Asp Gly Asn Val Lys Glu Gln
                20                  25                  30
```

<210> SEQ ID NO 522
<211> LENGTH: 20
<212> TYPE: PRT
<213> ORGANISM: human

<400> SEQUENCE: 522

```
Lys Ile Phe Cys Cys Leu Trp Val Lys Gln Leu Asp Ala Ala Gln Gly
 1               5                   10                  15
```

Leu Gly Val Glu
            20

<210> SEQ ID NO 523
<211> LENGTH: 30
<212> TYPE: PRT
<213> ORGANISM: human

<400> SEQUENCE: 523

Lys Ile Phe Cys Cys Leu Trp Asn Phe Val Tyr Lys Gln Leu Glu Asp
1               5                   10                  15

Ala Ala Gln Gly Leu Thr Met Gly Gly Asp Val Glu Glu His
            20                  25                  30

<210> SEQ ID NO 524
<211> LENGTH: 12
<212> TYPE: PRT
<213> ORGANISM: human

<400> SEQUENCE: 524

Cys Leu Trp Asp Leu Val Cys Lys Gln Leu Lys Gly
1               5                   10

<210> SEQ ID NO 525
<211> LENGTH: 10
<212> TYPE: PRT
<213> ORGANISM: human

<400> SEQUENCE: 525

Cys Leu Trp Asp Leu Val Cys Gln Lys Gly
1               5                   10

<210> SEQ ID NO 526
<211> LENGTH: 14
<212> TYPE: PRT
<213> ORGANISM: human

<400> SEQUENCE: 526

Cys Leu Ser Leu Gln Trp Asp Leu Val Cys Glu Gln Lys Gly
1               5                   10

<210> SEQ ID NO 527
<211> LENGTH: 36
<212> TYPE: PRT
<213> ORGANISM: human

<400> SEQUENCE: 527

Gly Arg Val Ile Gln Glu Pro Gly Gly Arg Gly Asp Lys Leu Leu His
1               5                   10                  15

Gln Gly Ala Arg Arg Arg Arg Gly Leu Arg Thr Pro Ala Ser Val Pro
            20                  25                  30

Ile Ser Pro Ser
            35

<210> SEQ ID NO 528
<211> LENGTH: 22
<212> TYPE: PRT
<213> ORGANISM: human

<400> SEQUENCE: 528

Leu His Gln Gly Ala Arg Arg Arg Arg Gly Leu Arg Thr Pro Ala Ser
1               5                   10                  15

Val Pro Ile Ser Pro Ser
            20

<210> SEQ ID NO 529
<211> LENGTH: 12
<212> TYPE: PRT
<213> ORGANISM: human

<400> SEQUENCE: 529

Leu Gln Gly Arg Arg Leu Ser Val Pro Pro Ser
1               5                   10

<210> SEQ ID NO 530
<211> LENGTH: 19
<212> TYPE: PRT
<213> ORGANISM: human

<400> SEQUENCE: 530

Leu Gln Gln Gly Gly Arg Arg Gly Asp Leu Ser Ser Val Pro Thr
1               5                   10                  15

Ala Pro Ser

<210> SEQ ID NO 531
<211> LENGTH: 22
<212> TYPE: PRT
<213> ORGANISM: human

<400> SEQUENCE: 531

Leu His Gln Gly Ala Arg Arg Arg Gly Leu Arg Thr Pro Ala Ser
1               5                   10                  15

Val Pro Ile Ser Pro Ser
            20

<210> SEQ ID NO 532
<211> LENGTH: 12
<212> TYPE: PRT
<213> ORGANISM: human

<400> SEQUENCE: 532

Leu Gln Gly Arg Arg Arg Leu Ser Val Pro Pro Ser
1               5                   10

<210> SEQ ID NO 533
<211> LENGTH: 19
<212> TYPE: PRT
<213> ORGANISM: human

<400> SEQUENCE: 533

Leu Gln Gln Gly Gly Arg Arg Arg Gly Asp Leu Ser Ser Val Pro Thr
1               5                   10                  15

Ala Pro Ser

<210> SEQ ID NO 534
<211> LENGTH: 23
<212> TYPE: PRT
<213> ORGANISM: human

<400> SEQUENCE: 534

Gly Arg Val Ile Gln Glu Pro Gly Gly Arg Gly Asp Lys Leu Leu His
1               5                   10                  15

Gln Gly Ala Arg Arg Arg
            20

<210> SEQ ID NO 535
<211> LENGTH: 15
<212> TYPE: PRT
<213> ORGANISM: human

<400> SEQUENCE: 535

Gly Arg Gln Pro Gly Gly Arg Gly Leu Leu Gly Arg Arg Arg Arg
1               5                   10                  15

<210> SEQ ID NO 536
<211> LENGTH: 26
<212> TYPE: PRT
<213> ORGANISM: human

<400> SEQUENCE: 536

Gly Arg Gln Thr Pro Gly Gly Arg Gly Val Pro Leu Leu Asn Val Gly
1               5                   10                  15

Ser Arg Arg Ser Gln Pro Gly Gln Arg Arg
            20                  25

<210> SEQ ID NO 537
<211> LENGTH: 36
<212> TYPE: PRT
<213> ORGANISM: human

<400> SEQUENCE: 537

Gly Arg Val Ile Gln Glu Pro Gly Gly Gly Asp Lys Leu Leu His
1               5                   10                  15

Gln Gly Ala Arg Arg Arg Arg Gly Leu Arg Thr Pro Ala Ser Val Pro
            20                  25                  30

Ile Ser Pro Ser
        35

<210> SEQ ID NO 538
<211> LENGTH: 22
<212> TYPE: PRT
<213> ORGANISM: human

<400> SEQUENCE: 538

Leu His Gln Gly Ala Arg Arg Arg Arg Gly Leu Arg Thr Pro Ala Ser
1               5                   10                  15

Val Pro Ile Ser Pro Ser
            20

<210> SEQ ID NO 539
<211> LENGTH: 12
<212> TYPE: PRT
<213> ORGANISM: human

<400> SEQUENCE: 539

Leu Gln Gly Arg Arg Arg Leu Ser Val Pro Pro Ser
1               5                   10

<210> SEQ ID NO 540
<211> LENGTH: 19
<212> TYPE: PRT
<213> ORGANISM: human

<400> SEQUENCE: 540

Leu Gln Gln Gly Gly Arg Arg Arg Gly Asp Leu Ser Ser Val Pro Thr
1               5                   10                  15

Ala Pro Ser

<210> SEQ ID NO 541
<211> LENGTH: 22
<212> TYPE: PRT
<213> ORGANISM: human

<400> SEQUENCE: 541

Leu His Gln Gly Ala Arg Arg Arg Gly Leu Arg Thr Pro Ala Ser
1               5                   10                  15

Val Pro Ile Ser Pro Ser
            20

<210> SEQ ID NO 542
<211> LENGTH: 12
<212> TYPE: PRT
<213> ORGANISM: human

<400> SEQUENCE: 542

Leu Gln Gly Arg Arg Arg Leu Ser Val Pro Pro Ser
1               5                   10

<210> SEQ ID NO 543
<211> LENGTH: 19
<212> TYPE: PRT
<213> ORGANISM: human

<400> SEQUENCE: 543

Leu Gln Gln Gly Gly Arg Arg Gly Asp Leu Ser Ser Val Pro Thr
1               5                   10                  15

Ala Pro Ser

<210> SEQ ID NO 544
<211> LENGTH: 23
<212> TYPE: PRT
<213> ORGANISM: human

<400> SEQUENCE: 544

Gly Arg Val Ile Gln Glu Pro Gly Gly Arg Gly Asp Lys Leu Leu His
1               5                   10                  15

Gln Gly Ala Arg Arg Arg Arg
            20

<210> SEQ ID NO 545
<211> LENGTH: 15
<212> TYPE: PRT
<213> ORGANISM: human

<400> SEQUENCE: 545

Gly Arg Gln Pro Gly Gly Arg Gly Leu Leu Gly Arg Arg Arg Arg
1               5                   10                  15

<210> SEQ ID NO 546
<211> LENGTH: 26
<212> TYPE: PRT
<213> ORGANISM: human

<400> SEQUENCE: 546

Gly Arg Gln Thr Pro Gly Gly Arg Gly Val Pro Leu Leu Asn Val Gly
1               5                   10                  15

Ser Arg Arg Ser Gln Pro Gly Gln Arg Arg
            20                  25

```
<210> SEQ ID NO 547
<211> LENGTH: 6
<212> TYPE: PRT
<213> ORGANISM: human

<400> SEQUENCE: 547

Ser Ser Gln Gly His Phe
1               5

<210> SEQ ID NO 548
<211> LENGTH: 6
<212> TYPE: PRT
<213> ORGANISM: human

<400> SEQUENCE: 548

Ser Ser Gln Gly His Phe
1               5

<210> SEQ ID NO 549
<211> LENGTH: 6
<212> TYPE: PRT
<213> ORGANISM: human

<400> SEQUENCE: 549

Ser Ser Gln Gly His Phe
1               5

<210> SEQ ID NO 550
<211> LENGTH: 6
<212> TYPE: PRT
<213> ORGANISM: human

<400> SEQUENCE: 550

Ser Ser Gln Gly His Phe
1               5

<210> SEQ ID NO 551
<211> LENGTH: 5
<212> TYPE: PRT
<213> ORGANISM: human

<400> SEQUENCE: 551

Ser Ser Gln Gly His
1               5

<210> SEQ ID NO 552
<211> LENGTH: 5
<212> TYPE: PRT
<213> ORGANISM: human

<400> SEQUENCE: 552

Ser Ser Gln Gly His
1               5

<210> SEQ ID NO 553
<211> LENGTH: 5
<212> TYPE: PRT
<213> ORGANISM: human

<400> SEQUENCE: 553

Ser Ser Gln Gly His
1               5

<210> SEQ ID NO 554
<211> LENGTH: 64
```

```
<212> TYPE: PRT
<213> ORGANISM: human

<400> SEQUENCE: 554

Leu Pro Arg Val Gln Ala Gln Gly Gly Arg Val Pro Glu Glu Thr Glu
1               5                   10                  15

Gly Ala Gly Gly Arg Gly Arg Gln Gly Arg Ala Gly Ala Pro Ala
            20                  25                  30

Gly Arg Gly Thr Ala Ala Ala Gln Gly Gly Ala Glu Leu Gly Ala Glu
        35                  40                  45

Ala Gly Gly Asp Ala Gln Glu Gly Ser Leu Arg Pro His Ser Ser Asn
    50                  55                  60

<210> SEQ ID NO 555
<211> LENGTH: 37
<212> TYPE: PRT
<213> ORGANISM: human

<400> SEQUENCE: 555

Gly Gly Arg Val Pro Glu Glu Thr Glu Gly Ala Gly Gly Arg Gly
1               5                   10                  15

Arg Gln Gly Arg Ala Gly Ala Pro Ala Gly Arg Gly Thr Ala Ala Ala
            20                  25                  30

Gln Gly Gly Ala Glu
        35

<210> SEQ ID NO 556
<211> LENGTH: 19
<212> TYPE: PRT
<213> ORGANISM: human

<400> SEQUENCE: 556

Gly Gly Arg Gly Gly Arg Gly Arg Gly Arg Ala Gly Gly Arg Gly
1               5                   10                  15

Gly Gly Ala

<210> SEQ ID NO 557
<211> LENGTH: 23
<212> TYPE: PRT
<213> ORGANISM: human

<400> SEQUENCE: 557

Gly Gly Arg Gly Gly Arg Gly Arg Gly Arg Ala Gly Ser Gln Gly
1               5                   10                  15

Gly Arg Gly Gly Gly Ala Gln
            20

<210> SEQ ID NO 558
<211> LENGTH: 16
<212> TYPE: PRT
<213> ORGANISM: human

<400> SEQUENCE: 558

Gly Gly Gly Arg Gly Arg Gln Gly Arg Ala Gly Ala Pro Ala Gly Arg
1               5                   10                  15

<210> SEQ ID NO 559
<211> LENGTH: 10
<212> TYPE: PRT
<213> ORGANISM: human

<400> SEQUENCE: 559
```

Gly Gly Arg Gly Arg Gly Arg Ala Gly Arg
1               5                   10

<210> SEQ ID NO 560
<211> LENGTH: 12
<212> TYPE: PRT
<213> ORGANISM: human

<400> SEQUENCE: 560

Gly Gly Ala Arg Gly Arg Gly Arg Gly Ala Gly Arg
1               5                   10

<210> SEQ ID NO 561
<211> LENGTH: 23
<212> TYPE: PRT
<213> ORGANISM: human

<400> SEQUENCE: 561

Gly Gly Gly Arg Gly Arg Gln Gly Arg Ala Gly Ala Pro Ala Gly Arg
1               5                   10                  15

Gly Thr Ala Ala Ala Gln Gly
            20

<210> SEQ ID NO 562
<211> LENGTH: 17
<212> TYPE: PRT
<213> ORGANISM: human

<400> SEQUENCE: 562

Gly Gly Gly Arg Gly Arg Gly Arg Ala Gly Ala Ala Gly Gly Ala Ala
1               5                   10                  15

Gly

<210> SEQ ID NO 563
<211> LENGTH: 23
<212> TYPE: PRT
<213> ORGANISM: human

<400> SEQUENCE: 563

Gly Gly Gly Arg Gly Arg Gly Arg Ala Arg Gly Ala Ala Ala Gly Ser
1               5                   10                  15

Gly Val Pro Ala Ala Pro Gly
            20

<210> SEQ ID NO 564
<211> LENGTH: 15
<212> TYPE: PRT
<213> ORGANISM: human

<400> SEQUENCE: 564

Pro Ser Ser Ala Arg Pro Ala Cys Val Cys Pro Ser Ser Ser Asp
1               5                   10                  15

<210> SEQ ID NO 565
<211> LENGTH: 11
<212> TYPE: PRT
<213> ORGANISM: human

<400> SEQUENCE: 565

Pro Ser Arg Pro Cys Val Cys Pro Ser Ser Asp
1               5                   10

```
<210> SEQ ID NO 566
<211> LENGTH: 11
<212> TYPE: PRT
<213> ORGANISM: human

<400> SEQUENCE: 566

Pro Ser Arg Pro Cys Val Cys Pro Ser Ser Asp
1               5                   10

<210> SEQ ID NO 567
<211> LENGTH: 15
<212> TYPE: PRT
<213> ORGANISM: human

<400> SEQUENCE: 567

Pro Ser Arg Pro Ser Cys Val Cys Pro Gly Ser Ala Arg Ser Asp
1               5                   10                  15

<210> SEQ ID NO 568
<211> LENGTH: 19
<212> TYPE: PRT
<213> ORGANISM: human

<400> SEQUENCE: 568

Pro Pro Ser Ser Ala Arg Pro Ala Cys Val Cys Pro Ser Ser Asp
1               5                   10                  15

Pro Pro Phe

<210> SEQ ID NO 569
<211> LENGTH: 10
<212> TYPE: PRT
<213> ORGANISM: human

<400> SEQUENCE: 569

Pro Pro Ser Ser Ala Arg Pro Ala Pro Pro
1               5                   10

<210> SEQ ID NO 570
<211> LENGTH: 11
<212> TYPE: PRT
<213> ORGANISM: human

<400> SEQUENCE: 570

Pro Pro Ser Ser Ala Arg Pro Ala Pro Pro Tyr
1               5                   10

<210> SEQ ID NO 571
<211> LENGTH: 21
<212> TYPE: PRT
<213> ORGANISM: human

<400> SEQUENCE: 571

Val Val Ser Pro Pro Ser Ser Ala Arg Pro Ala Cys Val Cys Pro Ser
1               5                   10                  15

Ser Ser Asp Pro Pro
            20

<210> SEQ ID NO 572
<211> LENGTH: 12
<212> TYPE: PRT
<213> ORGANISM: human

<400> SEQUENCE: 572

Val Val Pro Pro Ala Arg Pro Cys Pro Ser Pro Pro
```

```
1               5                   10

<210> SEQ ID NO 573
<211> LENGTH: 15
<212> TYPE: PRT
<213> ORGANISM: human

<400> SEQUENCE: 573

Val Val Pro Pro Pro Ala Arg Pro Cys Pro Thr Ser Gly Pro Pro
1               5                   10                  15

<210> SEQ ID NO 574
<211> LENGTH: 5
<212> TYPE: PRT
<213> ORGANISM: human

<400> SEQUENCE: 574

Asn Ser Ser Lys Glu
1               5

<210> SEQ ID NO 575
<211> LENGTH: 5
<212> TYPE: PRT
<213> ORGANISM: human

<400> SEQUENCE: 575

Asn Ser Ser Lys Glu
1               5

<210> SEQ ID NO 576
<211> LENGTH: 5
<212> TYPE: PRT
<213> ORGANISM: human

<400> SEQUENCE: 576

Asn Ser Ser Lys Glu
1               5

<210> SEQ ID NO 577
<211> LENGTH: 4
<212> TYPE: PRT
<213> ORGANISM: human
<220> FEATURE:
<221> NAME/KEY: misc_feature
<222> LOCATION: (19)..(19)
<223> OTHER INFORMATION: Xaa can be any naturally occurring amino acid

<400> SEQUENCE: 577

Asn Ser Lys Glu
1

<210> SEQ ID NO 578
<211> LENGTH: 79
<212> TYPE: PRT
<213> ORGANISM: human
<220> FEATURE:
<221> NAME/KEY: misc_feature
<222> LOCATION: (19)..(19)
<223> OTHER INFORMATION: Xaa can be any naturally occurring amino acid

<400> SEQUENCE: 578

Ala Met Arg Ala Ser Arg Arg Phe Ser Ser Asn Ala Arg Ala Pro
1               5                   10                  15

Gly Gly Xaa His Arg Pro Ala Gly Gly Gly Ala Gly Gly Ala Gly
                20                  25                  30
```

```
Gln His Gly Ala Asp Gln Arg Pro Ala Glu Gly Gln Pro Ala Asp
         35                  40                  45

Arg Pro Asp Gln His Arg Pro Glu Pro Gly Ala Gln Pro Arg Pro Glu
 50                  55                  60

Glu Arg Glu Cys Ser Ala Ala Gly Thr Pro Glu Gln Gly Ala
 65                  70                  75
```

<210> SEQ ID NO 579
<211> LENGTH: 22
<212> TYPE: PRT
<213> ORGANISM: human

<400> SEQUENCE: 579

```
Arg Pro Ala Glu Glu Gly Gln Pro Ala Asp Arg Pro Asp Gln His Arg
 1               5                  10                  15

Pro Glu Pro Gly Ala Gln
             20
```

<210> SEQ ID NO 580
<211> LENGTH: 20
<212> TYPE: PRT
<213> ORGANISM: human

<400> SEQUENCE: 580

```
Arg Pro Glu Glu Gly Pro Ala Pro His Arg Pro Glu Pro Gly Gln Pro
 1               5                  10                  15

Glu Glu Arg Glu
         20
```

<210> SEQ ID NO 581
<211> LENGTH: 41
<212> TYPE: PRT
<213> ORGANISM: human

<400> SEQUENCE: 581

```
Arg Pro Glu Gly Glu Glu Gly Pro Ala Glu Pro Glu Glu His Ser
 1               5                  10                  15

Val Arg Ile Cys Met Ser Pro Gly Pro Glu Pro Gly Gln Ile Leu
             20                  25                  30

Ser Val Lys Met Pro Glu Glu Arg Glu
         35                  40
```

<210> SEQ ID NO 582
<211> LENGTH: 23
<212> TYPE: PRT
<213> ORGANISM: human

<400> SEQUENCE: 582

```
Glu Glu Gly Gln Pro Ala Asp Arg Pro Asp Gln His Arg Pro Glu Pro
 1               5                  10                  15

Gly Ala Gln Pro Arg Pro Glu
             20
```

<210> SEQ ID NO 583
<211> LENGTH: 17
<212> TYPE: PRT
<213> ORGANISM: human

<400> SEQUENCE: 583

```
Glu Glu Gly Ala Pro Asp Gln His Arg Pro Glu Pro Gly Pro Arg Pro
 1               5                  10                  15
```

Glu

<210> SEQ ID NO 584
<211> LENGTH: 46
<212> TYPE: PRT
<213> ORGANISM: human

<400> SEQUENCE: 584

Glu Glu Gly Ser Ala Ala Pro Asp Gln His Thr His Pro Lys Glu Ala
1               5                   10                  15

Ala Thr Asp Pro Pro Ala Pro Arg Thr Pro Glu Pro Pro Gly Ser
            20                  25                  30

Pro Pro Ser Ser Pro Pro Pro Ala Ser Leu Gly Arg Pro Glu
        35                  40                  45

<210> SEQ ID NO 585
<211> LENGTH: 36
<212> TYPE: PRT
<213> ORGANISM: human

<400> SEQUENCE: 585

Gly Gln Pro Ala Asp Arg Pro Asp Gln His Arg Pro Glu Pro Gly Ala
1               5                   10                  15

Gln Pro Arg Pro Glu Glu Arg Glu Cys Ser Ala Ala Ala Gly Thr Pro
            20                  25                  30

Glu Gln Gly Ala
        35

<210> SEQ ID NO 586
<211> LENGTH: 21
<212> TYPE: PRT
<213> ORGANISM: human

<400> SEQUENCE: 586

Gly Gln Pro Ala Pro Asp Arg Pro Pro Gly Ala Arg Glu Glu Ala Gly
1               5                   10                  15

Thr Pro Glu Gly Ala
            20

<210> SEQ ID NO 587
<211> LENGTH: 32
<212> TYPE: PRT
<213> ORGANISM: human

<400> SEQUENCE: 587

Gly Gln Pro Ala Glu Pro Asp Ala Pro Arg Ser Ser Pro Gly Pro Gly
1               5                   10                  15

Ala Arg Glu Glu Gly Ala Gly Gly Ala Ala Thr Pro Glu Asp Gly Ala
            20                  25                  30

<210> SEQ ID NO 588
<211> LENGTH: 49
<212> TYPE: PRT
<213> ORGANISM: human

<400> SEQUENCE: 588

Gly Gly Gly Ala Gly Gly Ala Gly Gln His Gly Ala Asp Gln Arg
1               5                   10                  15

Pro Ala Glu Glu Gly Gln Pro Ala Asp Arg Pro Asp Gln His Arg Pro
            20                  25                  30

Glu Pro Gly Ala Gln Pro Arg Pro Glu Glu Arg Glu Cys Ser Ala Ala

-continued

```
                35                  40                  45
Ala

<210> SEQ ID NO 589
<211> LENGTH: 26
<212> TYPE: PRT
<213> ORGANISM: human

<400> SEQUENCE: 589

Gly Gly Gly Ala Gly Gly Ala Gly His Ala Arg Glu Glu Gly Pro Pro
1               5                   10                  15

Gly Pro Arg Glu Glu Arg Glu Cys Ala Ala
            20                  25

<210> SEQ ID NO 590
<211> LENGTH: 46
<212> TYPE: PRT
<213> ORGANISM: human

<400> SEQUENCE: 590

Gly Gly Gly Ala Gly Gly Ala Gly Leu His Phe Ala Gly His Arg Arg
1               5                   10                  15

Arg Glu Glu Gly Pro Ala Pro Thr Gly Ser Arg Pro Arg Gly Ala Ala
            20                  25                  30

Asp Gln Glu Leu Glu Leu Leu Arg Glu Cys Leu Gly Ala Ala
        35                  40                  45

<210> SEQ ID NO 591
<211> LENGTH: 6
<212> TYPE: PRT
<213> ORGANISM: human

<400> SEQUENCE: 591

Asp Gln Arg Pro Ala Glu
1               5

<210> SEQ ID NO 592
<211> LENGTH: 5
<212> TYPE: PRT
<213> ORGANISM: human

<400> SEQUENCE: 592

Asp Arg Pro Ala Glu
1               5

<210> SEQ ID NO 593
<211> LENGTH: 6
<212> TYPE: PRT
<213> ORGANISM: human
<220> FEATURE:
<221> NAME/KEY: misc_feature
<222> LOCATION: (7)..(7)
<223> OTHER INFORMATION: Xaa can be any naturally occurring amino acid

<400> SEQUENCE: 593

Asp Glu Arg Pro Ala Glu
1               5

<210> SEQ ID NO 594
<211> LENGTH: 16
<212> TYPE: PRT
<213> ORGANISM: human
<220> FEATURE:
<221> NAME/KEY: misc_feature
```

<222> LOCATION: (7)..(7)
<223> OTHER INFORMATION: Xaa can be any naturally occurring amino acid

<400> SEQUENCE: 594

Ala Arg Ala Pro Gly Gly Xaa His Arg Pro Ala Gly Gly Gly Ala Gly
1               5                   10                  15

<210> SEQ ID NO 595
<211> LENGTH: 10
<212> TYPE: PRT
<213> ORGANISM: human

<400> SEQUENCE: 595

Ala Arg Gly Gly Pro Gly Gly Gly Ala Gly
1               5                   10

<210> SEQ ID NO 596
<211> LENGTH: 12
<212> TYPE: PRT
<213> ORGANISM: human

<400> SEQUENCE: 596

Ala Arg Asp Gly Gly Pro Glu Gly Gly Gly Ala Gly
1               5                   10

<210> SEQ ID NO 597
<211> LENGTH: 9
<212> TYPE: PRT
<213> ORGANISM: human

<400> SEQUENCE: 597

Gly Gly Gly Ala Gly Gly Gly Ala Gly
1               5

<210> SEQ ID NO 598
<211> LENGTH: 7
<212> TYPE: PRT
<213> ORGANISM: human

<400> SEQUENCE: 598

Gly Gly Gly Gly Gly Ala Gly
1               5

<210> SEQ ID NO 599
<211> LENGTH: 9
<212> TYPE: PRT
<213> ORGANISM: human
<220> FEATURE:
<221> NAME/KEY: misc_feature
<222> LOCATION: (26)..(26)
<223> OTHER INFORMATION: Xaa can be any naturally occurring amino acid

<400> SEQUENCE: 599

Gly Gly Pro Glu Gly Gly Gly Ala Gly
1               5

<210> SEQ ID NO 600
<211> LENGTH: 29
<212> TYPE: PRT
<213> ORGANISM: human
<220> FEATURE:
<221> NAME/KEY: misc_feature
<222> LOCATION: (26)..(26)
<223> OTHER INFORMATION: Xaa can be any naturally occurring amino acid

<400> SEQUENCE: 600

```
Trp Asp Cys Ala Thr Ala Cys Gln Pro Gly Ser Gln Arg Asp Ser Val
1               5                   10                  15

Ser Lys Lys Lys Lys Lys Gly Gly Xaa Gly Lys Asn
            20                  25
```

<210> SEQ ID NO 601
<211> LENGTH: 16
<212> TYPE: PRT
<213> ORGANISM: human

<400> SEQUENCE: 601

```
Gln Pro Gly Ser Gln Arg Asp Ser Val Ser Lys Lys Lys Lys Lys Lys
1               5                   10                  15
```

<210> SEQ ID NO 602
<211> LENGTH: 14
<212> TYPE: PRT
<213> ORGANISM: human

<400> SEQUENCE: 602

```
Pro Gly Ser Arg Asp Ser Val Ser Lys Lys Lys Lys Lys Lys
1               5                   10
```

<210> SEQ ID NO 603
<211> LENGTH: 25
<212> TYPE: PRT
<213> ORGANISM: human

<400> SEQUENCE: 603

```
Glu Pro Gly Ser Cys His Ser Thr Pro Ala Trp Ala Thr Glu Arg Asp
1               5                   10                  15

Ser Val Ser Lys Lys Lys Lys Lys Lys
            20                  25
```

<210> SEQ ID NO 604
<211> LENGTH: 11
<212> TYPE: PRT
<213> ORGANISM: human

<400> SEQUENCE: 604

```
Arg Asp Ser Val Ser Lys Lys Lys Lys Lys Lys
1               5                   10
```

<210> SEQ ID NO 605
<211> LENGTH: 6
<212> TYPE: PRT
<213> ORGANISM: human

<400> SEQUENCE: 605

```
Arg Val Ser Lys Lys Lys
1               5
```

<210> SEQ ID NO 606
<211> LENGTH: 11
<212> TYPE: PRT
<213> ORGANISM: human

<400> SEQUENCE: 606

```
Arg Asn Pro Val Ser Thr Lys Ser Thr Lys Lys
1               5                   10
```

<210> SEQ ID NO 607
<211> LENGTH: 25
<212> TYPE: PRT

<213> ORGANISM: human

<400> SEQUENCE: 607

Trp Asp Cys Ala Thr Ala Cys Gln Pro Gly Ser Gln Arg Asp Ser Val
1               5                   10                  15

Ser Lys Lys Lys Lys Lys Arg Gly
            20                  25

<210> SEQ ID NO 608
<211> LENGTH: 16
<212> TYPE: PRT
<213> ORGANISM: human

<400> SEQUENCE: 608

Gln Pro Gly Ser Gln Arg Asp Ser Val Ser Lys Lys Lys Lys Lys Lys
1               5                   10                  15

<210> SEQ ID NO 609
<211> LENGTH: 14
<212> TYPE: PRT
<213> ORGANISM: human

<400> SEQUENCE: 609

Pro Gly Ser Arg Asp Ser Val Ser Lys Lys Lys Lys Lys Lys
1               5                   10

<210> SEQ ID NO 610
<211> LENGTH: 25
<212> TYPE: PRT
<213> ORGANISM: human

<400> SEQUENCE: 610

Glu Pro Gly Ser Cys His Ser Thr Pro Ala Trp Ala Thr Glu Arg Asp
1               5                   10                  15

Ser Val Ser Lys Lys Lys Lys Lys
            20                  25

<210> SEQ ID NO 611
<211> LENGTH: 11
<212> TYPE: PRT
<213> ORGANISM: human

<400> SEQUENCE: 611

Arg Asp Ser Val Ser Lys Lys Lys Lys Lys
1               5                   10

<210> SEQ ID NO 612
<211> LENGTH: 6
<212> TYPE: PRT
<213> ORGANISM: human

<400> SEQUENCE: 612

Arg Val Ser Lys Lys Lys
1               5

<210> SEQ ID NO 613
<211> LENGTH: 11
<212> TYPE: PRT
<213> ORGANISM: human

<400> SEQUENCE: 613

Arg Asn Pro Val Ser Thr Lys Ser Thr Lys Lys
1               5                   10

<210> SEQ ID NO 614
<211> LENGTH: 25
<212> TYPE: PRT
<213> ORGANISM: human

<400> SEQUENCE: 614

Trp Asp Cys Ala Thr Ala Cys Gln Pro Gly Ser Gln Arg Asp Ser Val
1               5                   10                  15

Ser Lys Lys Lys Lys Lys Arg Gly
            20                  25

<210> SEQ ID NO 615
<211> LENGTH: 16
<212> TYPE: PRT
<213> ORGANISM: human

<400> SEQUENCE: 615

Gln Pro Gly Ser Gln Arg Asp Ser Val Ser Lys Lys Lys Lys Lys Lys
1               5                   10                  15

<210> SEQ ID NO 616
<211> LENGTH: 14
<212> TYPE: PRT
<213> ORGANISM: human

<400> SEQUENCE: 616

Pro Gly Ser Arg Asp Ser Val Ser Lys Lys Lys Lys Lys Lys
1               5                   10

<210> SEQ ID NO 617
<211> LENGTH: 25
<212> TYPE: PRT
<213> ORGANISM: human

<400> SEQUENCE: 617

Glu Pro Gly Ser Cys His Ser Thr Pro Ala Trp Ala Thr Glu Arg Asp
1               5                   10                  15

Ser Val Ser Lys Lys Lys Lys Lys Lys
            20                  25

<210> SEQ ID NO 618
<211> LENGTH: 11
<212> TYPE: PRT
<213> ORGANISM: human

<400> SEQUENCE: 618

Arg Asp Ser Val Ser Lys Lys Lys Lys Lys Lys
1               5                   10

<210> SEQ ID NO 619
<211> LENGTH: 6
<212> TYPE: PRT
<213> ORGANISM: human

<400> SEQUENCE: 619

Arg Val Ser Lys Lys Lys
1               5

<210> SEQ ID NO 620
<211> LENGTH: 11
<212> TYPE: PRT
<213> ORGANISM: human

<400> SEQUENCE: 620

Arg Asn Pro Val Ser Thr Lys Ser Thr Lys Lys
1               5                   10

<210> SEQ ID NO 621
<211> LENGTH: 5
<212> TYPE: PRT
<213> ORGANISM: human

<400> SEQUENCE: 621

Asn Ser Ser Gly Val
1               5

<210> SEQ ID NO 622
<211> LENGTH: 5
<212> TYPE: PRT
<213> ORGANISM: human

<400> SEQUENCE: 622

Asn Ser Ser Gly Val
1               5

<210> SEQ ID NO 623
<211> LENGTH: 5
<212> TYPE: PRT
<213> ORGANISM: human

<400> SEQUENCE: 623

Asn Ser Ser Gly Val
1               5

<210> SEQ ID NO 624
<211> LENGTH: 5
<212> TYPE: PRT
<213> ORGANISM: human

<400> SEQUENCE: 624

Asn Ser Ser Gly Val
1               5

<210> SEQ ID NO 625
<211> LENGTH: 33
<212> TYPE: PRT
<213> ORGANISM: human

<400> SEQUENCE: 625

Gly Arg Gly Gly Gly Gly Gly Arg Gly Gly Gly Gly Arg Ile Arg Arg
1               5                   10                  15

Arg Lys Pro Gln Glu Pro Glu Lys Gln Arg Ala Glu Val Gln Ile Gln
                20                  25                  30

Gly

<210> SEQ ID NO 626
<211> LENGTH: 17
<212> TYPE: PRT
<213> ORGANISM: human

<400> SEQUENCE: 626

Gly Arg Gly Gly Gly Gly Gly Arg Gly Gly Gly Gly Ile Gly Gly
1               5                   10                  15

Arg

<210> SEQ ID NO 627

```
<211> LENGTH: 16
<212> TYPE: PRT
<213> ORGANISM: human

<400> SEQUENCE: 627

Gly Arg Gly Gly Gly Gly Arg Gly Gly Gly Gly Gly Gly Gly Gly Arg
1               5                   10                  15

<210> SEQ ID NO 628
<211> LENGTH: 19
<212> TYPE: PRT
<213> ORGANISM: human

<400> SEQUENCE: 628

Gly Arg Gly Gly Arg Gly Gly Arg Gly Gly Gly Gly Phe Arg
1               5                   10                  15

Gly Gly Arg

<210> SEQ ID NO 629
<211> LENGTH: 16
<212> TYPE: PRT
<213> ORGANISM: human

<400> SEQUENCE: 629

Gly Arg Gly Gly Gly Gly Gly Arg Gly Gly Gly Gly Ile Arg Arg
1               5                   10                  15

<210> SEQ ID NO 630
<211> LENGTH: 13
<212> TYPE: PRT
<213> ORGANISM: human

<400> SEQUENCE: 630

Gly Arg Gly Gly Gly Gly Arg Gly Gly Gly Gly Arg Arg
1               5                   10

<210> SEQ ID NO 631
<211> LENGTH: 19
<212> TYPE: PRT
<213> ORGANISM: human

<400> SEQUENCE: 631

Gly Arg Gly Gly Gly Ala Trp Gly Pro Gly Arg Gly Gly Ala Gly Gly
1               5                   10                  15

Leu Arg Arg

<210> SEQ ID NO 632
<211> LENGTH: 11
<212> TYPE: PRT
<213> ORGANISM: human

<400> SEQUENCE: 632

Ala Asp His Lys Val Arg Ser Leu Arg Pro Ala
1               5                   10

<210> SEQ ID NO 633
<211> LENGTH: 7
<212> TYPE: PRT
<213> ORGANISM: human

<400> SEQUENCE: 633

Val Arg Ser Leu Arg Pro Ala
1               5
```

<210> SEQ ID NO 634
<211> LENGTH: 7
<212> TYPE: PRT
<213> ORGANISM: human

<400> SEQUENCE: 634

Val Arg Ser Leu Arg Pro Ala
1               5

<210> SEQ ID NO 635
<211> LENGTH: 7
<212> TYPE: PRT
<213> ORGANISM: human

<400> SEQUENCE: 635

Val Arg Ser Leu Arg Pro Ala
1               5

<210> SEQ ID NO 636
<211> LENGTH: 15
<212> TYPE: PRT
<213> ORGANISM: human

<400> SEQUENCE: 636

Pro Asn Ser Ser Ala Asp His Lys Val Arg Ser Leu Arg Pro Ala
1               5                   10                  15

<210> SEQ ID NO 637
<211> LENGTH: 9
<212> TYPE: PRT
<213> ORGANISM: human

<400> SEQUENCE: 637

Pro Asn Ser Ala Asp Val Arg Arg Ala
1               5

<210> SEQ ID NO 638
<211> LENGTH: 13
<212> TYPE: PRT
<213> ORGANISM: human

<400> SEQUENCE: 638

Pro Asn Asn Ser Ala Asp Pro Arg Val Arg Arg Ala Ala
1               5                   10

<210> SEQ ID NO 639
<211> LENGTH: 9
<212> TYPE: PRT
<213> ORGANISM: human

<400> SEQUENCE: 639

Asp His Lys Val Arg Ser Leu Arg Pro
1               5

<210> SEQ ID NO 640
<211> LENGTH: 7
<212> TYPE: PRT
<213> ORGANISM: human

<400> SEQUENCE: 640

Asp His Lys Ser Leu Arg Pro
1               5

<210> SEQ ID NO 641

```
<211> LENGTH: 11
<212> TYPE: PRT
<213> ORGANISM: human

<400> SEQUENCE: 641

Asp His Lys Ile Ala Lys Gln Ser Leu Arg Pro
1               5                   10

<210> SEQ ID NO 642
<211> LENGTH: 5
<212> TYPE: PRT
<213> ORGANISM: human

<400> SEQUENCE: 642

Asn Ser Ser Leu Phe
1               5

<210> SEQ ID NO 643
<211> LENGTH: 5
<212> TYPE: PRT
<213> ORGANISM: human

<400> SEQUENCE: 643

Asn Ser Ser Leu Phe
1               5

<210> SEQ ID NO 644
<211> LENGTH: 5
<212> TYPE: PRT
<213> ORGANISM: human

<400> SEQUENCE: 644

Asn Ser Ser Leu Phe
1               5

<210> SEQ ID NO 645
<211> LENGTH: 5
<212> TYPE: PRT
<213> ORGANISM: human

<400> SEQUENCE: 645

Asn Ser Ser Leu Phe
1               5

<210> SEQ ID NO 646
<211> LENGTH: 9
<212> TYPE: PRT
<213> ORGANISM: human

<400> SEQUENCE: 646

Pro Arg Gln Ser Phe Thr Leu Val Ala
1               5

<210> SEQ ID NO 647
<211> LENGTH: 7
<212> TYPE: PRT
<213> ORGANISM: human

<400> SEQUENCE: 647

Arg Gln Ser Phe Thr Leu Val
1               5

<210> SEQ ID NO 648
<211> LENGTH: 7
<212> TYPE: PRT
```

```
<213> ORGANISM: human

<400> SEQUENCE: 648

Arg Gln Ser Phe Thr Leu Val
1               5

<210> SEQ ID NO 649
<211> LENGTH: 7
<212> TYPE: PRT
<213> ORGANISM: human

<400> SEQUENCE: 649

Arg Gln Ser Phe Thr Leu Val
1               5

<210> SEQ ID NO 650
<211> LENGTH: 9
<212> TYPE: PRT
<213> ORGANISM: human

<400> SEQUENCE: 650

Pro Arg Gln Ser Phe Thr Leu Val Ala
1               5

<210> SEQ ID NO 651
<211> LENGTH: 7
<212> TYPE: PRT
<213> ORGANISM: human

<400> SEQUENCE: 651

Pro Gln Ser Phe Thr Val Ala
1               5

<210> SEQ ID NO 652
<211> LENGTH: 9
<212> TYPE: PRT
<213> ORGANISM: human

<400> SEQUENCE: 652

Pro Lys Gln Ser Phe Thr Met Val Ala
1               5

<210> SEQ ID NO 653
<211> LENGTH: 7
<212> TYPE: PRT
<213> ORGANISM: human

<400> SEQUENCE: 653

Arg Val Gly Arg Lys Val Gln
1               5

<210> SEQ ID NO 654
<211> LENGTH: 8
<212> TYPE: PRT
<213> ORGANISM: human

<400> SEQUENCE: 654

Ser Arg Val Gly Arg Lys Val Gln
1               5

<210> SEQ ID NO 655
<211> LENGTH: 7
<212> TYPE: PRT
<213> ORGANISM: human
```

<400> SEQUENCE: 655

Ser Arg Val Arg Lys Val Gln
1               5

<210> SEQ ID NO 656
<211> LENGTH: 8
<212> TYPE: PRT
<213> ORGANISM: human

<400> SEQUENCE: 656

Ser Arg Val Pro Arg Lys Val Gln
1               5

<210> SEQ ID NO 657
<211> LENGTH: 6
<212> TYPE: PRT
<213> ORGANISM: human

<400> SEQUENCE: 657

Val Gly Arg Lys Val Gln
1               5

<210> SEQ ID NO 658
<211> LENGTH: 6
<212> TYPE: PRT
<213> ORGANISM: human

<400> SEQUENCE: 658

Val Gly Arg Lys Val Gln
1               5

<210> SEQ ID NO 659
<211> LENGTH: 6
<212> TYPE: PRT
<213> ORGANISM: human

<400> SEQUENCE: 659

Val Gly Arg Lys Val Gln
1               5

<210> SEQ ID NO 660
<211> LENGTH: 5
<212> TYPE: PRT
<213> ORGANISM: human

<400> SEQUENCE: 660

Gly Arg Lys Val Gln
1               5

<210> SEQ ID NO 661
<211> LENGTH: 5
<212> TYPE: PRT
<213> ORGANISM: human

<400> SEQUENCE: 661

Gly Arg Lys Val Gln
1               5

<210> SEQ ID NO 662
<211> LENGTH: 5
<212> TYPE: PRT
<213> ORGANISM: human

<400> SEQUENCE: 662

-continued

```
Gly Arg Lys Val Gln
1               5

<210> SEQ ID NO 663
<211> LENGTH: 36
<212> TYPE: PRT
<213> ORGANISM: human

<400> SEQUENCE: 663

Leu Gln Pro Gly Arg Gln Ser Glu Thr Pro Ser Gln Lys Lys Lys
1               5                   10                  15

Lys Asn Leu Gly Gly Met Gly Thr Gly Ala His Pro Phe Asp Pro Ser
            20                  25                  30

Thr Leu Gly Ser
        35

<210> SEQ ID NO 664
<211> LENGTH: 17
<212> TYPE: PRT
<213> ORGANISM: human

<400> SEQUENCE: 664

Leu Gln Pro Gly Arg Gln Ser Glu Thr Pro Ser Gln Lys Lys Lys Lys
1               5                   10                  15

Lys

<210> SEQ ID NO 665
<211> LENGTH: 17
<212> TYPE: PRT
<213> ORGANISM: human

<400> SEQUENCE: 665

Leu Gln Pro Gly Arg Gln Ser Glu Thr Pro Ser Gln Lys Lys Lys Lys
1               5                   10                  15

Lys

<210> SEQ ID NO 666
<211> LENGTH: 17
<212> TYPE: PRT
<213> ORGANISM: human

<400> SEQUENCE: 666

Leu Gln Pro Gly Arg Gln Ser Glu Thr Pro Ser Gln Lys Lys Lys Lys
1               5                   10                  15

Lys

<210> SEQ ID NO 667
<211> LENGTH: 17
<212> TYPE: PRT
<213> ORGANISM: human

<400> SEQUENCE: 667

Leu Gln Pro Gly Arg Gln Ser Glu Thr Pro Ser Gln Lys Lys Lys Lys
1               5                   10                  15

Lys

<210> SEQ ID NO 668
<211> LENGTH: 15
<212> TYPE: PRT
<213> ORGANISM: human

<400> SEQUENCE: 668
```

```
Leu Gln Pro Gly Gln Ser Glu Thr Pro Ser Gln Lys Lys Lys
1               5                   10                  15

<210> SEQ ID NO 669
<211> LENGTH: 17
<212> TYPE: PRT
<213> ORGANISM: human

<400> SEQUENCE: 669

Leu Gln Pro Gly Leu Gln Ser Glu Thr Pro Ser Gln Lys Lys Thr Lys
1               5                   10                  15

Lys

<210> SEQ ID NO 670
<211> LENGTH: 24
<212> TYPE: PRT
<213> ORGANISM: human

<400> SEQUENCE: 670

His Arg Gly Ser Pro Ser Asn Val Gly Ala Phe Arg Ile Gly Arg Glu
1               5                   10                  15

Ser Val Lys Glu Ser Leu Phe Tyr
            20

<210> SEQ ID NO 671
<211> LENGTH: 13
<212> TYPE: PRT
<213> ORGANISM: human

<400> SEQUENCE: 671

Phe Arg Ile Gly Arg Glu Ser Val Lys Glu Ser Leu Phe
1               5                   10

<210> SEQ ID NO 672
<211> LENGTH: 8
<212> TYPE: PRT
<213> ORGANISM: human

<400> SEQUENCE: 672

Phe Ile Arg Val Lys Ser Leu Phe
1               5

<210> SEQ ID NO 673
<211> LENGTH: 13
<212> TYPE: PRT
<213> ORGANISM: human

<400> SEQUENCE: 673

Phe Thr Ile Ser Arg Asp Asn Val Lys Asn Ser Leu Phe
1               5                   10

<210> SEQ ID NO 674
<211> LENGTH: 14
<212> TYPE: PRT
<213> ORGANISM: human

<400> SEQUENCE: 674

Gly Ala Phe Arg Ile Gly Arg Glu Ser Val Lys Glu Ser Leu
1               5                   10

<210> SEQ ID NO 675
<211> LENGTH: 11
<212> TYPE: PRT
```

```
<213> ORGANISM: human

<400> SEQUENCE: 675

Gly Phe Arg Gly Arg Glu Val Lys Glu Ser Leu
1               5                   10

<210> SEQ ID NO 676
<211> LENGTH: 21
<212> TYPE: PRT
<213> ORGANISM: human

<400> SEQUENCE: 676

Gly Glu Phe Arg Val Gly Arg Leu Lys His Glu Arg Val Lys Val Pro
1               5                   10                  15

Arg Gly Glu Ser Leu
            20

<210> SEQ ID NO 677
<211> LENGTH: 4
<212> TYPE: PRT
<213> ORGANISM: human

<400> SEQUENCE: 677

Arg Gly Ser Pro
1

<210> SEQ ID NO 678
<211> LENGTH: 4
<212> TYPE: PRT
<213> ORGANISM: human

<400> SEQUENCE: 678

Arg Gly Ser Pro
1

<210> SEQ ID NO 679
<211> LENGTH: 4
<212> TYPE: PRT
<213> ORGANISM: human

<400> SEQUENCE: 679

Arg Gly Ser Pro
1

<210> SEQ ID NO 680
<211> LENGTH: 14
<212> TYPE: PRT
<213> ORGANISM: human

<400> SEQUENCE: 680

Gly Ala Phe Arg Ile Gly Arg Glu Ser Val Lys Glu Ser Leu
1               5                   10

<210> SEQ ID NO 681
<211> LENGTH: 11
<212> TYPE: PRT
<213> ORGANISM: human

<400> SEQUENCE: 681

Gly Phe Arg Gly Arg Glu Val Lys Glu Ser Leu
1               5                   10

<210> SEQ ID NO 682
<211> LENGTH: 21
```

<212> TYPE: PRT
<213> ORGANISM: human

<400> SEQUENCE: 682

Gly Glu Phe Arg Val Gly Arg Leu Lys His Glu Arg Val Lys Val Pro
1               5                   10                  15

Arg Gly Glu Ser Leu
            20

<210> SEQ ID NO 683
<211> LENGTH: 6
<212> TYPE: PRT
<213> ORGANISM: human

<400> SEQUENCE: 683

Asn Ser Ser Val Gly Cys
1               5

<210> SEQ ID NO 684
<211> LENGTH: 5
<212> TYPE: PRT
<213> ORGANISM: human

<400> SEQUENCE: 684

Asn Ser Ser Val Gly
1               5

<210> SEQ ID NO 685
<211> LENGTH: 5
<212> TYPE: PRT
<213> ORGANISM: human

<400> SEQUENCE: 685

Asn Ser Ser Val Gly
1               5

<210> SEQ ID NO 686
<211> LENGTH: 5
<212> TYPE: PRT
<213> ORGANISM: human
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (41)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature

```
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid

<400> SEQUENCE: 686

Asn Ser Ser Val Gly
1               5

<210> SEQ ID NO 687
<211> LENGTH: 56
<212> TYPE: PRT
<213> ORGANISM: human
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(39)
<223> OTHER INFORMATION: Xaa can be any naturally occurring amino acid
<220> FEATURE:
<221> NAME/KEY: misc_feature
<222> LOCATION: (41)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid

<400> SEQUENCE: 687

Trp Asp Cys Ala Thr Ala Cys Gln Pro Gly Ser Gln Arg Asp Ser Val
1               5                   10                  15

Ser Lys Lys Lys Lys Lys Lys Gly Gly Xaa Glu Lys Xaa Xaa Gly Xaa
            20                  25                  30

Gly Xaa Phe Phe Xaa Xaa Xaa Lys Xaa Xaa Xaa Xaa Phe Xaa Arg Xaa
```

```
                35                  40                  45

Phe Xaa Pro Xaa Phe Xaa Xaa Lys
    50                  55

<210> SEQ ID NO 688
<211> LENGTH: 16
<212> TYPE: PRT
<213> ORGANISM: human

<400> SEQUENCE: 688

Gln Pro Gly Ser Gln Arg Asp Ser Val Ser Lys Lys Lys Lys Lys Lys
1               5                   10                  15

<210> SEQ ID NO 689
<211> LENGTH: 14
<212> TYPE: PRT
<213> ORGANISM: human

<400> SEQUENCE: 689

Pro Gly Ser Arg Asp Ser Val Ser Lys Lys Lys Lys Lys Lys
1               5                   10

<210> SEQ ID NO 690
<211> LENGTH: 25
<212> TYPE: PRT
<213> ORGANISM: human

<400> SEQUENCE: 690

Glu Pro Gly Ser Cys His Ser Thr Pro Ala Trp Ala Thr Glu Arg Asp
1               5                   10                  15

Ser Val Ser Lys Lys Lys Lys Lys
            20                  25

<210> SEQ ID NO 691
<211> LENGTH: 10
<212> TYPE: PRT
<213> ORGANISM: human

<400> SEQUENCE: 691

Asp Ser Val Ser Lys Lys Lys Lys Lys Lys
1               5                   10

<210> SEQ ID NO 692
<211> LENGTH: 8
<212> TYPE: PRT
<213> ORGANISM: human

<400> SEQUENCE: 692

Val Ser Lys Lys Lys Lys Lys Lys
1               5

<210> SEQ ID NO 693
<211> LENGTH: 10
<212> TYPE: PRT
<213> ORGANISM: human

<400> SEQUENCE: 693

Glu Thr Val Ser Lys Lys Lys Lys Lys Lys
1               5                   10

<210> SEQ ID NO 694
<211> LENGTH: 5
<212> TYPE: PRT
<213> ORGANISM: human
```

<400> SEQUENCE: 694

Ala Arg Gln Val Phe
1               5

<210> SEQ ID NO 695
<211> LENGTH: 5
<212> TYPE: PRT
<213> ORGANISM: human

<400> SEQUENCE: 695

Ala Arg Gln Val Phe
1               5

<210> SEQ ID NO 696
<211> LENGTH: 5
<212> TYPE: PRT
<213> ORGANISM: human

<400> SEQUENCE: 696

Ala Arg Gln Val Phe
1               5

<210> SEQ ID NO 697
<211> LENGTH: 5
<212> TYPE: PRT
<213> ORGANISM: human

<400> SEQUENCE: 697

Ala Arg Gln Val Phe
1               5

<210> SEQ ID NO 698
<211> LENGTH: 25
<212> TYPE: PRT
<213> ORGANISM: human

<400> SEQUENCE: 698

Trp Asp Cys Ala Thr Ala Cys Gln Pro Gly Ser Gln Arg Asp Ser Val
1               5                   10                  15

Ser Lys Lys Lys Lys Lys Lys Arg Gly
            20                  25

<210> SEQ ID NO 699
<211> LENGTH: 16
<212> TYPE: PRT
<213> ORGANISM: human

<400> SEQUENCE: 699

Gln Pro Gly Ser Gln Arg Asp Ser Val Ser Lys Lys Lys Lys Lys Lys
1               5                   10                  15

<210> SEQ ID NO 700
<211> LENGTH: 14
<212> TYPE: PRT
<213> ORGANISM: human

<400> SEQUENCE: 700

Pro Gly Ser Arg Asp Ser Val Ser Lys Lys Lys Lys Lys Lys
1               5                   10

<210> SEQ ID NO 701
<211> LENGTH: 25
<212> TYPE: PRT

```
<213> ORGANISM: human

<400> SEQUENCE: 701

Glu Pro Gly Ser Cys His Ser Thr Pro Ala Trp Ala Thr Glu Arg Asp
1               5                   10                  15
Ser Val Ser Lys Lys Lys Lys Lys
            20                  25

<210> SEQ ID NO 702
<211> LENGTH: 11
<212> TYPE: PRT
<213> ORGANISM: human

<400> SEQUENCE: 702

Arg Asp Ser Val Ser Lys Lys Lys Lys Lys
1               5                   10

<210> SEQ ID NO 703
<211> LENGTH: 6
<212> TYPE: PRT
<213> ORGANISM: human

<400> SEQUENCE: 703

Arg Val Ser Lys Lys Lys
1               5

<210> SEQ ID NO 704
<211> LENGTH: 11
<212> TYPE: PRT
<213> ORGANISM: human

<400> SEQUENCE: 704

Arg Asn Pro Val Ser Thr Lys Ser Thr Lys Lys
1               5                   10

<210> SEQ ID NO 705
<211> LENGTH: 25
<212> TYPE: PRT
<213> ORGANISM: human

<400> SEQUENCE: 705

Trp Asp Cys Ala Thr Ala Cys Gln Pro Gly Ser Gln Arg Asp Ser Val
1               5                   10                  15
Ser Lys Lys Lys Lys Lys Lys Arg Gly
            20                  25

<210> SEQ ID NO 706
<211> LENGTH: 16
<212> TYPE: PRT
<213> ORGANISM: human

<400> SEQUENCE: 706

Gln Pro Gly Ser Gln Arg Asp Ser Val Ser Lys Lys Lys Lys Lys Lys
1               5                   10                  15

<210> SEQ ID NO 707
<211> LENGTH: 14
<212> TYPE: PRT
<213> ORGANISM: human

<400> SEQUENCE: 707

Pro Gly Ser Arg Asp Ser Val Ser Lys Lys Lys Lys Lys Lys
1               5                   10
```

<210> SEQ ID NO 708
<211> LENGTH: 25
<212> TYPE: PRT
<213> ORGANISM: human

<400> SEQUENCE: 708

Glu Pro Gly Ser Cys His Ser Thr Pro Ala Trp Ala Thr Glu Arg Asp
1               5                   10                  15

Ser Val Ser Lys Lys Lys Lys Lys
            20                  25

<210> SEQ ID NO 709
<211> LENGTH: 11
<212> TYPE: PRT
<213> ORGANISM: human

<400> SEQUENCE: 709

Arg Asp Ser Val Ser Lys Lys Lys Lys Lys
1               5                   10

<210> SEQ ID NO 710
<211> LENGTH: 6
<212> TYPE: PRT
<213> ORGANISM: human

<400> SEQUENCE: 710

Arg Val Ser Lys Lys Lys
1               5

<210> SEQ ID NO 711
<211> LENGTH: 11
<212> TYPE: PRT
<213> ORGANISM: human

<400> SEQUENCE: 711

Arg Asn Pro Val Ser Thr Lys Ser Thr Lys Lys
1               5                   10

<210> SEQ ID NO 712
<211> LENGTH: 25
<212> TYPE: PRT
<213> ORGANISM: human

<400> SEQUENCE: 712

Trp Asp Cys Ala Thr Ala Cys Gln Pro Gly Ser Gln Arg Asp Ser Val
1               5                   10                  15

Ser Lys Lys Lys Lys Lys Arg Gly
            20                  25

<210> SEQ ID NO 713
<211> LENGTH: 16
<212> TYPE: PRT
<213> ORGANISM: human

<400> SEQUENCE: 713

Gln Pro Gly Ser Gln Arg Asp Ser Val Ser Lys Lys Lys Lys Lys
1               5                   10                  15

<210> SEQ ID NO 714
<211> LENGTH: 14
<212> TYPE: PRT
<213> ORGANISM: human

<400> SEQUENCE: 714

```
Pro Gly Ser Arg Asp Ser Val Ser Lys Lys Lys Lys Lys
1               5                   10
```

<210> SEQ ID NO 715
<211> LENGTH: 25
<212> TYPE: PRT
<213> ORGANISM: human

<400> SEQUENCE: 715

```
Glu Pro Gly Ser Cys His Ser Thr Pro Ala Trp Ala Thr Glu Arg Asp
1               5                   10                  15

Ser Val Ser Lys Lys Lys Lys Lys Lys
            20                  25
```

<210> SEQ ID NO 716
<211> LENGTH: 11
<212> TYPE: PRT
<213> ORGANISM: human

<400> SEQUENCE: 716

```
Arg Asp Ser Val Ser Lys Lys Lys Lys Lys Lys
1               5                   10
```

<210> SEQ ID NO 717
<211> LENGTH: 6
<212> TYPE: PRT
<213> ORGANISM: human

<400> SEQUENCE: 717

```
Arg Val Ser Lys Lys Lys
1               5
```

<210> SEQ ID NO 718
<211> LENGTH: 11
<212> TYPE: PRT
<213> ORGANISM: human

<400> SEQUENCE: 718

```
Arg Asn Pro Val Ser Thr Lys Ser Thr Lys Lys
1               5                   10
```

<210> SEQ ID NO 719
<211> LENGTH: 30
<212> TYPE: PRT
<213> ORGANISM: human

<400> SEQUENCE: 719

```
Tyr Lys Gln Arg Arg Val Lys Arg Glu His Pro Asn Arg Lys Gln
1               5                   10                  15

Leu Lys Asp Ile Leu Leu Ala Ser His Gly Gly Pro Ser Pro
            20                  25                  30
```

<210> SEQ ID NO 720
<211> LENGTH: 21
<212> TYPE: PRT
<213> ORGANISM: human

<400> SEQUENCE: 720

```
Gln Arg Arg Arg Val Lys Arg Glu His Pro Asn Arg Lys Gln Leu Lys
1               5                   10                  15

Asp Ile Leu Leu Ala
            20
```

<210> SEQ ID NO 721
<211> LENGTH: 13
<212> TYPE: PRT
<213> ORGANISM: human

<400> SEQUENCE: 721

Arg Arg Arg Val Arg Glu Asn Arg Lys Leu Asp Leu Ala
1               5                   10

<210> SEQ ID NO 722
<211> LENGTH: 30
<212> TYPE: PRT
<213> ORGANISM: human

<400> SEQUENCE: 722

Glu Arg Arg Arg Val Arg Arg Glu Arg Asn Lys Leu Ala Ala Ala Lys
1               5                   10                  15

Cys Arg Asn Arg Arg Lys Glu Leu Thr Asp Phe Leu Gln Ala
            20                  25                  30

<210> SEQ ID NO 723
<211> LENGTH: 15
<212> TYPE: PRT
<213> ORGANISM: human

<400> SEQUENCE: 723

Lys Gln Arg Arg Val Lys Arg Glu His Pro Asn Arg Lys Gln
1               5                   10                  15

<210> SEQ ID NO 724
<211> LENGTH: 10
<212> TYPE: PRT
<213> ORGANISM: human

<400> SEQUENCE: 724

Lys Arg Arg Lys Arg Glu Pro Asn Arg Gln
1               5                   10

<210> SEQ ID NO 725
<211> LENGTH: 19
<212> TYPE: PRT
<213> ORGANISM: human

<400> SEQUENCE: 725

Lys Glu Lys Arg Arg Gln Lys Arg Glu Lys His Lys Leu Asn Pro Asn
1               5                   10                  15

Arg Asn Gln

<210> SEQ ID NO 726
<211> LENGTH: 14
<212> TYPE: PRT
<213> ORGANISM: human

<400> SEQUENCE: 726

Leu Lys Asp Ile Leu Leu Ala Ser His Gly Gly Pro Ser Pro
1               5                   10

<210> SEQ ID NO 727
<211> LENGTH: 9
<212> TYPE: PRT
<213> ORGANISM: human

<400> SEQUENCE: 727

-continued

Leu Lys Asp Ile Leu Ala Pro Ser Pro
1               5

<210> SEQ ID NO 728
<211> LENGTH: 12
<212> TYPE: PRT
<213> ORGANISM: human
<220> FEATURE:
<221> NAME/KEY: misc_feature
<222> LOCATION: (26)..(26)
<223> OTHER INFORMATION: Xaa can be any naturally occurring amino acid

<400> SEQUENCE: 728

Leu Lys Asp Ile Met Leu Ala Asn Gln Pro Ser Pro
1               5                   10

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

-continued

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743
<211> LENGTH: 37
<212> TYPE: PRT
<213> ORGANISM: human

<400> SEQUENCE: 743

Glu Met Lys Arg His Ile Ser Thr Leu Arg Trp Lys Thr Cys Leu Asn
1               5                   10                  15

Ala Asn Met Lys Glu Leu Leu Glu Ile Lys Val Thr Gly Lys Ile Arg
            20                  25                  30

Tyr Asn Gln Gly Leu
        35

<210> SEQ ID NO 744
<211> LENGTH: 21
<212> TYPE: PRT
<213> ORGANISM: human

<400> SEQUENCE: 744

Ile Ser Thr Leu Arg Trp Lys Thr Cys Leu Asn Ala Asn Met Lys Glu
1               5                   10                  15

Leu Leu Glu Ile Lys
            20

<210> SEQ ID NO 745
<211> LENGTH: 14
<212> TYPE: PRT
<213> ORGANISM: human

<400> SEQUENCE: 745

Ile Thr Leu Lys Thr Cys Leu Asn Ala Lys Glu Leu Ile Lys
1               5                   10

```
<210> SEQ ID NO 746
<211> LENGTH: 24
<212> TYPE: PRT
<213> ORGANISM: human

<400> SEQUENCE: 746

Ile Ala Thr Leu Lys Asn Gly Val Gln Thr Cys Leu Asn Pro Asp Ser
1               5                   10                  15

Ala Asp Val Lys Glu Leu Ile Lys
                20

<210> SEQ ID NO 747
<211> LENGTH: 13
<212> TYPE: PRT
<213> ORGANISM: human

<400> SEQUENCE: 747

Met Lys Glu Leu Leu Glu Ile Lys Val Thr Gly Lys Ile
1               5                   10

<210> SEQ ID NO 748
<211> LENGTH: 9
<212> TYPE: PRT
<213> ORGANISM: human

<400> SEQUENCE: 748

Met Glu Leu Glu Lys Val Thr Gly Lys
1               5

<210> SEQ ID NO 749
<211> LENGTH: 12
<212> TYPE: PRT
<213> ORGANISM: human

<400> SEQUENCE: 749

Met Glu Glu Leu Val Glu Lys Val Thr Gly Lys Val
1               5                   10

<210> SEQ ID NO 750
<211> LENGTH: 6
<212> TYPE: PRT
<213> ORGANISM: human

<400> SEQUENCE: 750

Thr Leu Arg Trp Lys Thr
1               5

<210> SEQ ID NO 751
<211> LENGTH: 6
<212> TYPE: PRT
<213> ORGANISM: human

<400> SEQUENCE: 751

Thr Leu Arg Trp Lys Thr
1               5

<210> SEQ ID NO 752
<211> LENGTH: 6
<212> TYPE: PRT
<213> ORGANISM: human

<400> SEQUENCE: 752

Thr Leu Arg Trp Lys Thr
1               5
```

<210> SEQ ID NO 753
<211> LENGTH: 11
<212> TYPE: PRT
<213> ORGANISM: human

<400> SEQUENCE: 753

Cys Ile Asn Met Asp Ser Pro Pro Lys Gln Cys
1               5                   10

<210> SEQ ID NO 754
<211> LENGTH: 7
<212> TYPE: PRT
<213> ORGANISM: human

<400> SEQUENCE: 754

Ile Asn Met Asp Ser Pro Pro
1               5

<210> SEQ ID NO 755
<211> LENGTH: 6
<212> TYPE: PRT
<213> ORGANISM: human

<400> SEQUENCE: 755

Asn Met Asp Ser Pro Pro
1               5

<210> SEQ ID NO 756
<211> LENGTH: 7
<212> TYPE: PRT
<213> ORGANISM: human

<400> SEQUENCE: 756

Val Asn Met Asp Ser Pro Pro
1               5

<210> SEQ ID NO 757
<211> LENGTH: 7
<212> TYPE: PRT
<213> ORGANISM: human

<400> SEQUENCE: 757

Met Asp Ser Pro Pro Lys Gln
1               5

<210> SEQ ID NO 758
<211> LENGTH: 7
<212> TYPE: PRT
<213> ORGANISM: human

<400> SEQUENCE: 758

Met Asp Ser Pro Pro Lys Gln
1               5

<210> SEQ ID NO 759
<211> LENGTH: 9
<212> TYPE: PRT
<213> ORGANISM: human

<400> SEQUENCE: 759

Met Asp Ser Pro Pro His Gln Lys Gln
1               5

```
<210> SEQ ID NO 760
<211> LENGTH: 10
<212> TYPE: PRT
<213> ORGANISM: human

<400> SEQUENCE: 760

Cys Ile Asn Met Asp Ser Pro Pro Lys Gln
1               5                   10

<210> SEQ ID NO 761
<211> LENGTH: 8
<212> TYPE: PRT
<213> ORGANISM: human

<400> SEQUENCE: 761

Cys Ile Asn Asp Ser Pro Lys Gln
1               5

<210> SEQ ID NO 762
<211> LENGTH: 12
<212> TYPE: PRT
<213> ORGANISM: human

<400> SEQUENCE: 762

Cys Ile Asn Ala Ala Pro Asp Ser Pro Ser Lys Gln
1               5                   10

<210> SEQ ID NO 763
<211> LENGTH: 7
<212> TYPE: PRT
<213> ORGANISM: human

<400> SEQUENCE: 763

Gly Ala Gly Trp Glu Trp Val
1               5

<210> SEQ ID NO 764
<211> LENGTH: 5
<212> TYPE: PRT
<213> ORGANISM: human

<400> SEQUENCE: 764

Gly Trp Glu Trp Val
1               5

<210> SEQ ID NO 765
<211> LENGTH: 5
<212> TYPE: PRT
<213> ORGANISM: human

<400> SEQUENCE: 765

Gly Trp Glu Trp Val
1               5

<210> SEQ ID NO 766
<211> LENGTH: 5
<212> TYPE: PRT
<213> ORGANISM: human

<400> SEQUENCE: 766

Gly Trp Glu Trp Val
1               5

<210> SEQ ID NO 767
<211> LENGTH: 5
```

```
<212> TYPE: PRT
<213> ORGANISM: human

<400> SEQUENCE: 767

Ala Gly Trp Glu Trp
1               5

<210> SEQ ID NO 768
<211> LENGTH: 5
<212> TYPE: PRT
<213> ORGANISM: human

<400> SEQUENCE: 768

Ala Gly Trp Glu Trp
1               5

<210> SEQ ID NO 769
<211> LENGTH: 5
<212> TYPE: PRT
<213> ORGANISM: human

<400> SEQUENCE: 769

Ala Gly Trp Glu Trp
1               5

<210> SEQ ID NO 770
<211> LENGTH: 57
<212> TYPE: PRT
<213> ORGANISM: human

<400> SEQUENCE: 770

Pro Leu Cys Leu Ala Ser Leu Leu Ser Phe Ile Val Cys Leu Phe His
1               5                   10                  15

Phe Arg Tyr Leu Pro Thr Ile Leu Leu Pro Pro Ile Leu Lys His Lys
            20                  25                  30

Cys Asn Asp Arg Met His Leu Thr Cys Phe Gly Ser Ala Lys Ala Leu
        35                  40                  45

Met Tyr Ser Leu Ser Asn Asn Arg Cys
    50                  55

<210> SEQ ID NO 771
<211> LENGTH: 9
<212> TYPE: PRT
<213> ORGANISM: human

<400> SEQUENCE: 771

Val Cys Leu Phe His Phe Arg Tyr Leu
1               5

<210> SEQ ID NO 772
<211> LENGTH: 8
<212> TYPE: PRT
<213> ORGANISM: human

<400> SEQUENCE: 772

Val Cys Leu Phe His Phe Arg Tyr
1               5

<210> SEQ ID NO 773
<211> LENGTH: 9
<212> TYPE: PRT
<213> ORGANISM: human

<400> SEQUENCE: 773
```

Val Cys Leu Phe His Phe Arg Tyr Met
1               5

<210> SEQ ID NO 774
<211> LENGTH: 23
<212> TYPE: PRT
<213> ORGANISM: human

<400> SEQUENCE: 774

Ser Pro Leu Cys Leu Ala Ser Leu Leu Ser Phe Ile Val Cys Leu Phe
1               5                   10                  15

His Phe Arg Tyr Leu Pro Thr
            20

<210> SEQ ID NO 775
<211> LENGTH: 14
<212> TYPE: PRT
<213> ORGANISM: human

<400> SEQUENCE: 775

Ser Cys Ala Ser Leu Ser Phe Val Cys Phe Arg Leu Pro Thr
1               5                   10

<210> SEQ ID NO 776
<211> LENGTH: 44
<212> TYPE: PRT
<213> ORGANISM: human

<400> SEQUENCE: 776

Ser Arg Met Cys Met Ala Ile Ser Ile Cys Gln Met Leu Ser Met Leu
1               5                   10                  15

Ser Phe Val Val Cys Ala Phe Arg Tyr Arg His Met Phe Lys Arg Gly
            20                  25                  30

Trp Pro Met Gly Thr Cys Cys Leu Phe Leu Pro Thr
            35                  40

<210> SEQ ID NO 777
<211> LENGTH: 5
<212> TYPE: PRT
<213> ORGANISM: human

<400> SEQUENCE: 777

Asn Ser Phe His Asn
1               5

<210> SEQ ID NO 778
<211> LENGTH: 5
<212> TYPE: PRT
<213> ORGANISM: human

<400> SEQUENCE: 778

Asn Ser Phe His Asn
1               5

<210> SEQ ID NO 779
<211> LENGTH: 5
<212> TYPE: PRT
<213> ORGANISM: human

<400> SEQUENCE: 779

Asn Ser Phe His Asn
1               5

```
<210> SEQ ID NO 780
<211> LENGTH: 5
<212> TYPE: PRT
<213> ORGANISM: human

<400> SEQUENCE: 780

Asn Ser Phe His Asn
1               5

<210> SEQ ID NO 781
<211> LENGTH: 12
<212> TYPE: PRT
<213> ORGANISM: human

<400> SEQUENCE: 781

Gly Ile Thr Gly Ser Arg Pro Ala Trp Pro Thr Trp
1               5                   10

<210> SEQ ID NO 782
<211> LENGTH: 7
<212> TYPE: PRT
<213> ORGANISM: human

<400> SEQUENCE: 782

Arg Pro Ala Trp Pro Thr Trp
1               5

<210> SEQ ID NO 783
<211> LENGTH: 7
<212> TYPE: PRT
<213> ORGANISM: human

<400> SEQUENCE: 783

Arg Pro Ala Trp Pro Thr Trp
1               5

<210> SEQ ID NO 784
<211> LENGTH: 7
<212> TYPE: PRT
<213> ORGANISM: human

<400> SEQUENCE: 784

Arg Pro Ala Trp Pro Thr Trp
1               5

<210> SEQ ID NO 785
<211> LENGTH: 23
<212> TYPE: PRT
<213> ORGANISM: human

<400> SEQUENCE: 785

Val Arg Leu Val Arg Thr Glu Glu Arg Leu Glu Leu Arg Thr Arg Ser
1               5                   10                  15

Trp Asn Trp Gly Leu Val Gln
            20

<210> SEQ ID NO 786
<211> LENGTH: 7
<212> TYPE: PRT
<213> ORGANISM: human

<400> SEQUENCE: 786

Arg Ser Trp Asn Trp Gly Leu
1               5
```

-continued

<210> SEQ ID NO 787
<211> LENGTH: 7
<212> TYPE: PRT
<213> ORGANISM: human

<400> SEQUENCE: 787

Arg Ser Trp Asn Trp Gly Leu
1               5

<210> SEQ ID NO 788
<211> LENGTH: 7
<212> TYPE: PRT
<213> ORGANISM: human

<400> SEQUENCE: 788

Arg Ser Trp Asn Trp Gly Leu
1               5

<210> SEQ ID NO 789
<211> LENGTH: 18
<212> TYPE: PRT
<213> ORGANISM: human

<400> SEQUENCE: 789

Val Arg Leu Val Arg Thr Glu Glu Arg Leu Glu Leu Arg Thr Arg Ser
1               5                   10                  15

Trp Asn

<210> SEQ ID NO 790
<211> LENGTH: 10
<212> TYPE: PRT
<213> ORGANISM: human

<400> SEQUENCE: 790

Val Arg Leu Val Arg Thr Glu Leu Thr Trp
1               5                   10

<210> SEQ ID NO 791
<211> LENGTH: 15
<212> TYPE: PRT
<213> ORGANISM: human

<400> SEQUENCE: 791

Val Arg Leu Val Arg Thr Met Glu Leu Leu Thr Gln Asn Trp Asp
1               5                   10                  15

<210> SEQ ID NO 792
<211> LENGTH: 15
<212> TYPE: PRT
<213> ORGANISM: human

<400> SEQUENCE: 792

Leu Val Arg Thr Glu Glu Arg Leu Glu Leu Arg Thr Arg Ser Trp
1               5                   10                  15

<210> SEQ ID NO 793
<211> LENGTH: 10
<212> TYPE: PRT
<213> ORGANISM: human

<400> SEQUENCE: 793

Leu Val Arg Glu Glu Arg Arg Thr Ser Trp
1               5                   10

<210> SEQ ID NO 794
<211> LENGTH: 15
<212> TYPE: PRT
<213> ORGANISM: human

<400> SEQUENCE: 794

Leu Val Gln Gly Ala Arg Ser Glu Glu Arg Arg Thr Lys Ser Trp
1               5                   10                  15

<210> SEQ ID NO 795
<211> LENGTH: 6
<212> TYPE: PRT
<213> ORGANISM: human

<400> SEQUENCE: 795

Val Phe Asn Cys Trp Phe
1               5

<210> SEQ ID NO 796
<211> LENGTH: 6
<212> TYPE: PRT
<213> ORGANISM: human

<400> SEQUENCE: 796

Val Phe Asn Cys Trp Phe
1               5

<210> SEQ ID NO 797
<211> LENGTH: 5
<212> TYPE: PRT
<213> ORGANISM: human

<400> SEQUENCE: 797

Val Phe Cys Trp Phe
1               5

<210> SEQ ID NO 798
<211> LENGTH: 6
<212> TYPE: PRT
<213> ORGANISM: human

<400> SEQUENCE: 798

Val Phe Asp Cys Trp Phe
1               5

<210> SEQ ID NO 799
<211> LENGTH: 5
<212> TYPE: PRT
<213> ORGANISM: human

<400> SEQUENCE: 799

Val Phe Asn Cys Trp
1               5

<210> SEQ ID NO 800
<211> LENGTH: 4
<212> TYPE: PRT
<213> ORGANISM: human

<400> SEQUENCE: 800

Val Phe Cys Trp
1

```
<210> SEQ ID NO 801
<211> LENGTH: 5
<212> TYPE: PRT
<213> ORGANISM: human
<220> FEATURE:
<221> NAME/KEY: misc_feature
<222> LOCATION: (14)..(14)
<223> OTHER INFORMATION: Xaa can be any naturally occurring amino acid

<400> SEQUENCE: 801

Val Phe Asp Cys Trp
1               5

<210> SEQ ID NO 802
<211> LENGTH: 16
<212> TYPE: PRT
<213> ORGANISM: human
<220> FEATURE:
<221> NAME/KEY: misc_feature
<222> LOCATION: (14)..(14)
<223> OTHER INFORMATION: Xaa can be any naturally occurring amino acid

<400> SEQUENCE: 802

His Leu Lys Lys Lys Lys Lys Lys Lys Arg Gly Thr Gly Xaa Leu Arg
1               5                   10                  15

<210> SEQ ID NO 803
<211> LENGTH: 9
<212> TYPE: PRT
<213> ORGANISM: human

<400> SEQUENCE: 803

His Leu Lys Lys Lys Lys Lys Lys Lys
1               5

<210> SEQ ID NO 804
<211> LENGTH: 9
<212> TYPE: PRT
<213> ORGANISM: human

<400> SEQUENCE: 804

His Leu Lys Lys Lys Lys Lys Lys Lys
1               5

<210> SEQ ID NO 805
<211> LENGTH: 9
<212> TYPE: PRT
<213> ORGANISM: human

<400> SEQUENCE: 805

His Leu Lys Lys Lys Lys Lys Lys Lys
1               5

<210> SEQ ID NO 806
<211> LENGTH: 9
<212> TYPE: PRT
<213> ORGANISM: human

<400> SEQUENCE: 806

Lys Lys Lys Lys Lys Lys Lys Arg Gly
1               5

<210> SEQ ID NO 807
<211> LENGTH: 9
<212> TYPE: PRT
<213> ORGANISM: human
```

```
<400> SEQUENCE: 807

Lys Lys Lys Lys Lys Lys Arg Gly
1               5

<210> SEQ ID NO 808
<211> LENGTH: 9
<212> TYPE: PRT
<213> ORGANISM: human

<400> SEQUENCE: 808

Lys Lys Lys Lys Lys Lys Lys Arg Gly
1               5

<210> SEQ ID NO 809
<211> LENGTH: 10
<212> TYPE: PRT
<213> ORGANISM: human

<400> SEQUENCE: 809

Leu Lys Lys Lys Lys Lys Lys Lys Arg Gly
1               5                   10

<210> SEQ ID NO 810
<211> LENGTH: 9
<212> TYPE: PRT
<213> ORGANISM: human

<400> SEQUENCE: 810

Leu Lys Lys Lys Lys Lys Lys Lys Gly
1               5

<210> SEQ ID NO 811
<211> LENGTH: 10
<212> TYPE: PRT
<213> ORGANISM: human

<400> SEQUENCE: 811

Leu Lys Lys Lys Lys Lys Lys Lys Lys Gly
1               5                   10

<210> SEQ ID NO 812
<211> LENGTH: 11
<212> TYPE: PRT
<213> ORGANISM: human

<400> SEQUENCE: 812

Thr Asn Ser Ile Phe Gly Ser Leu Glu Ser Tyr
1               5                   10

<210> SEQ ID NO 813
<211> LENGTH: 10
<212> TYPE: PRT
<213> ORGANISM: human

<400> SEQUENCE: 813

Thr Asn Ser Ile Phe Gly Ser Leu Glu Ser
1               5                   10

<210> SEQ ID NO 814
<211> LENGTH: 8
<212> TYPE: PRT
<213> ORGANISM: human

<400> SEQUENCE: 814
```

```
Thr Asn Ser Phe Gly Leu Glu Ser
1               5

<210> SEQ ID NO 815
<211> LENGTH: 10
<212> TYPE: PRT
<213> ORGANISM: human

<400> SEQUENCE: 815

Thr Asn Ser Val Phe Gly Gly Leu Glu Ser
1               5                   10

<210> SEQ ID NO 816
<211> LENGTH: 10
<212> TYPE: PRT
<213> ORGANISM: human

<400> SEQUENCE: 816

Asn Ser Ile Phe Gly Ser Leu Glu Ser Tyr
1               5                   10

<210> SEQ ID NO 817
<211> LENGTH: 7
<212> TYPE: PRT
<213> ORGANISM: human

<400> SEQUENCE: 817

Asn Ile Phe Leu Glu Ser Tyr
1               5

<210> SEQ ID NO 818
<211> LENGTH: 10
<212> TYPE: PRT
<213> ORGANISM: human

<400> SEQUENCE: 818

Asn Asp Ile Phe Ala Asp Leu Glu Ser Tyr
1               5                   10

<210> SEQ ID NO 819
<211> LENGTH: 7
<212> TYPE: PRT
<213> ORGANISM: human

<400> SEQUENCE: 819

Ile Phe Gly Ser Leu Glu Ser
1               5

<210> SEQ ID NO 820
<211> LENGTH: 6
<212> TYPE: PRT
<213> ORGANISM: human

<400> SEQUENCE: 820

Phe Gly Ser Leu Glu Ser
1               5

<210> SEQ ID NO 821
<211> LENGTH: 7
<212> TYPE: PRT
<213> ORGANISM: human

<400> SEQUENCE: 821

Val Phe Gly Ser Leu Glu Ser
1               5
```

<210> SEQ ID NO 822
<211> LENGTH: 18
<212> TYPE: PRT
<213> ORGANISM: human

<400> SEQUENCE: 822

Pro Val Leu Ser Ser His Lys Asn Glu Ala Arg Asp Lys Gly Lys Cys
1               5                   10                  15

His Pro

<210> SEQ ID NO 823
<211> LENGTH: 12
<212> TYPE: PRT
<213> ORGANISM: human

<400> SEQUENCE: 823

Lys Asn Glu Ala Arg Asp Lys Gly Lys Cys His Pro
1               5                   10

<210> SEQ ID NO 824
<211> LENGTH: 8
<212> TYPE: PRT
<213> ORGANISM: human

<400> SEQUENCE: 824

Lys Glu Ala Lys Gly Lys Cys Pro
1               5

<210> SEQ ID NO 825
<211> LENGTH: 17
<212> TYPE: PRT
<213> ORGANISM: human

<400> SEQUENCE: 825

Lys Lys Glu Ala Lys Glu Lys Gly Thr Trp Val Gln Leu Lys Cys Gln
1               5                   10                  15

Pro

<210> SEQ ID NO 826
<211> LENGTH: 9
<212> TYPE: PRT
<213> ORGANISM: human

<400> SEQUENCE: 826

Ser His Lys Asn Glu Ala Arg Asp Lys
1               5

<210> SEQ ID NO 827
<211> LENGTH: 7
<212> TYPE: PRT
<213> ORGANISM: human

<400> SEQUENCE: 827

Ser His Lys Glu Ala Arg Lys
1               5

<210> SEQ ID NO 828
<211> LENGTH: 9
<212> TYPE: PRT
<213> ORGANISM: human

<400> SEQUENCE: 828

Ser His Lys Trp Glu Ala Arg Glu Lys
1               5

<210> SEQ ID NO 829
<211> LENGTH: 6
<212> TYPE: PRT
<213> ORGANISM: human

<400> SEQUENCE: 829

Asn Glu Ala Arg Asp Lys
1               5

<210> SEQ ID NO 830
<211> LENGTH: 6
<212> TYPE: PRT
<213> ORGANISM: human

<400> SEQUENCE: 830

Asn Glu Ala Arg Asp Lys
1               5

<210> SEQ ID NO 831
<211> LENGTH: 6
<212> TYPE: PRT
<213> ORGANISM: human

<400> SEQUENCE: 831

Asn Glu Ala Arg Asp Lys
1               5

<210> SEQ ID NO 832
<211> LENGTH: 17
<212> TYPE: PRT
<213> ORGANISM: human

<400> SEQUENCE: 832

Pro Ala Gly Ile Ser Arg Glu Leu Val Asp Lys Leu Ala Ala Ala Leu
1               5                   10                  15

Glu

<210> SEQ ID NO 833
<211> LENGTH: 9
<212> TYPE: PRT
<213> ORGANISM: human

<400> SEQUENCE: 833

Val Asp Lys Leu Ala Ala Ala Leu Glu
1               5

<210> SEQ ID NO 834
<211> LENGTH: 9
<212> TYPE: PRT
<213> ORGANISM: human

<400> SEQUENCE: 834

Val Asp Lys Leu Ala Ala Ala Leu Glu
1               5

<210> SEQ ID NO 835
<211> LENGTH: 9
<212> TYPE: PRT
<213> ORGANISM: human

<400> SEQUENCE: 835

Val Asp Lys Leu Ala Ala Ala Leu Glu
1               5

<210> SEQ ID NO 836
<211> LENGTH: 9
<212> TYPE: PRT
<213> ORGANISM: human

<400> SEQUENCE: 836

Ala Gly Ile Ser Arg Glu Leu Val Asp
1               5

<210> SEQ ID NO 837
<211> LENGTH: 7
<212> TYPE: PRT
<213> ORGANISM: human

<400> SEQUENCE: 837

Ala Gly Ile Ser Glu Leu Asp
1               5

<210> SEQ ID NO 838
<211> LENGTH: 9
<212> TYPE: PRT
<213> ORGANISM: human

<400> SEQUENCE: 838

Ala Gly Ile Ser Lys Glu Leu Ile Asp
1               5

<210> SEQ ID NO 839
<211> LENGTH: 8
<212> TYPE: PRT
<213> ORGANISM: human

<400> SEQUENCE: 839

Ser Arg Glu Leu Val Asp Lys Leu
1               5

<210> SEQ ID NO 840
<211> LENGTH: 6
<212> TYPE: PRT
<213> ORGANISM: human

<400> SEQUENCE: 840

Ser Arg Leu Val Lys Leu
1               5

<210> SEQ ID NO 841
<211> LENGTH: 8
<212> TYPE: PRT
<213> ORGANISM: human

<400> SEQUENCE: 841

Ser Arg Asp Leu Val Asn Lys Leu
1               5

<210> SEQ ID NO 842
<211> LENGTH: 23
<212> TYPE: PRT
<213> ORGANISM: human

<400> SEQUENCE: 842

His Thr Gln Gly Cys Leu Pro Met Ala Cys Ala Ala Ser Asp Ser Pro
1               5                   10                  15

Ala Cys Val Val Cys Ser His
            20

<210> SEQ ID NO 843
<211> LENGTH: 10
<212> TYPE: PRT
<213> ORGANISM: human

<400> SEQUENCE: 843

Asp Ser Pro Ala Cys Val Val Cys Ser His
1               5                   10

<210> SEQ ID NO 844
<211> LENGTH: 9
<212> TYPE: PRT
<213> ORGANISM: human

<400> SEQUENCE: 844

Asp Ser Pro Cys Val Val Cys Ser His
1               5

<210> SEQ ID NO 845
<211> LENGTH: 10
<212> TYPE: PRT
<213> ORGANISM: human

<400> SEQUENCE: 845

Asp Ser Pro Met Cys Val Val Cys Ser His
1               5                   10

<210> SEQ ID NO 846
<211> LENGTH: 19
<212> TYPE: PRT
<213> ORGANISM: human

<400> SEQUENCE: 846

His Thr Gln Gly Cys Leu Pro Met Ala Cys Ala Ala Ser Asp Ser Pro
1               5                   10                  15

Ala Cys Val

<210> SEQ ID NO 847
<211> LENGTH: 11
<212> TYPE: PRT
<213> ORGANISM: human

<400> SEQUENCE: 847

His Gly Cys Pro Met Ala Cys Ser Pro Cys Val
1               5                   10

<210> SEQ ID NO 848
<211> LENGTH: 16
<212> TYPE: PRT
<213> ORGANISM: human

<400> SEQUENCE: 848

His Ser Ser Gly Cys Pro Met Ala Cys Pro Gly Ser Pro Cys Cys Val
1               5                   10                  15

<210> SEQ ID NO 849
<211> LENGTH: 10
<212> TYPE: PRT
<213> ORGANISM: human

<400> SEQUENCE: 849

Leu Pro Met Ala Cys Ala Ala Ser Asp Ser
1               5                   10

<210> SEQ ID NO 850
<211> LENGTH: 8
<212> TYPE: PRT
<213> ORGANISM: human

<400> SEQUENCE: 850

Leu Pro Met Ala Cys Ala Ser Ser
1               5

<210> SEQ ID NO 851
<211> LENGTH: 11
<212> TYPE: PRT
<213> ORGANISM: human

<400> SEQUENCE: 851

Leu Pro Met Ala Cys Pro Ala Leu Ser Glu Ser
1               5                   10

<210> SEQ ID NO 852
<211> LENGTH: 9
<212> TYPE: PRT
<213> ORGANISM: human

<400> SEQUENCE: 852

Val Gln Lys Ser Gly Trp Gly Leu Ala
1               5

<210> SEQ ID NO 853
<211> LENGTH: 8
<212> TYPE: PRT
<213> ORGANISM: human

<400> SEQUENCE: 853

Val Gln Lys Ser Gly Trp Gly Leu
1               5

<210> SEQ ID NO 854
<211> LENGTH: 6
<212> TYPE: PRT
<213> ORGANISM: human

<400> SEQUENCE: 854

Val Lys Ser Gly Trp Leu
1               5

<210> SEQ ID NO 855
<211> LENGTH: 8
<212> TYPE: PRT
<213> ORGANISM: human

<400> SEQUENCE: 855

Val Asp Lys Ser Gly Trp Ser Leu
1               5

<210> SEQ ID NO 856
<211> LENGTH: 6
<212> TYPE: PRT
<213> ORGANISM: human

<400> SEQUENCE: 856

Val Gln Lys Ser Gly Trp

```
1               5

<210> SEQ ID NO 857
<211> LENGTH: 5
<212> TYPE: PRT
<213> ORGANISM: human

<400> SEQUENCE: 857

Gln Lys Ser Gly Trp
1               5

<210> SEQ ID NO 858
<211> LENGTH: 6
<212> TYPE: PRT
<213> ORGANISM: human

<400> SEQUENCE: 858

Ile Gln Lys Ser Gly Trp
1               5

<210> SEQ ID NO 859
<211> LENGTH: 8
<212> TYPE: PRT
<213> ORGANISM: human

<400> SEQUENCE: 859

Lys Lys Lys Lys Lys Gly Val Gly
1               5

<210> SEQ ID NO 860
<211> LENGTH: 7
<212> TYPE: PRT
<213> ORGANISM: human

<400> SEQUENCE: 860

Lys Lys Lys Lys Lys Gly Val
1               5

<210> SEQ ID NO 861
<211> LENGTH: 7
<212> TYPE: PRT
<213> ORGANISM: human

<400> SEQUENCE: 861

Lys Lys Lys Lys Lys Gly Val
1               5

<210> SEQ ID NO 862
<211> LENGTH: 7
<212> TYPE: PRT
<213> ORGANISM: human

<400> SEQUENCE: 862

Lys Lys Lys Lys Lys Gly Val
1               5

<210> SEQ ID NO 863
<211> LENGTH: 8
<212> TYPE: PRT
<213> ORGANISM: human

<400> SEQUENCE: 863

Lys Lys Lys Lys Lys Gly Val Gly
1               5
```

```
<210> SEQ ID NO 864
<211> LENGTH: 7
<212> TYPE: PRT
<213> ORGANISM: human

<400> SEQUENCE: 864

Lys Lys Lys Lys Lys Gly Gly
1               5

<210> SEQ ID NO 865
<211> LENGTH: 8
<212> TYPE: PRT
<213> ORGANISM: human

<400> SEQUENCE: 865

Lys Lys Lys Lys Lys Gly Gly Gly
1               5

<210> SEQ ID NO 866
<211> LENGTH: 6
<212> TYPE: PRT
<213> ORGANISM: human

<400> SEQUENCE: 866

Lys Lys Lys Lys Lys Gly
1               5

<210> SEQ ID NO 867
<211> LENGTH: 6
<212> TYPE: PRT
<213> ORGANISM: human

<400> SEQUENCE: 867

Lys Lys Lys Lys Lys Gly
1               5

<210> SEQ ID NO 868
<211> LENGTH: 6
<212> TYPE: PRT
<213> ORGANISM: human

<400> SEQUENCE: 868

Lys Lys Lys Lys Lys Gly
1               5

<210> SEQ ID NO 869
<211> LENGTH: 20
<212> TYPE: PRT
<213> ORGANISM: human

<400> SEQUENCE: 869

Leu Met Leu Pro Gly Leu Ser Leu Pro Gly Thr Leu Gly Val Arg Gly
1               5                   10                  15

Ser Leu Ser Lys
            20

<210> SEQ ID NO 870
<211> LENGTH: 19
<212> TYPE: PRT
<213> ORGANISM: human

<400> SEQUENCE: 870

Leu Met Leu Pro Gly Leu Ser Leu Pro Gly Thr Leu Gly Val Arg Gly
1               5                   10                  15
```

-continued

Ser Leu Ser

<210> SEQ ID NO 871
<211> LENGTH: 16
<212> TYPE: PRT
<213> ORGANISM: human

<400> SEQUENCE: 871

Leu Met Leu Pro Gly Leu Ser Leu Pro Thr Leu Gly Arg Ser Leu Ser
1               5                   10                  15

<210> SEQ ID NO 872
<211> LENGTH: 38
<212> TYPE: PRT
<213> ORGANISM: human

<400> SEQUENCE: 872

Leu Met Leu Trp Val Pro Gly Ser Ser Gly Asp Val Val Met Thr Gln
1               5                   10                  15

Ser Pro Leu Ser Leu Pro Val Thr Leu Gly Gln Pro Ala Ser Ile Ser
            20                  25                  30

Cys Arg Ser Ser Leu Ser
        35

<210> SEQ ID NO 873
<211> LENGTH: 9
<212> TYPE: PRT
<213> ORGANISM: human

<400> SEQUENCE: 873

Pro Gly Leu Ser Leu Pro Gly Thr Leu
1               5

<210> SEQ ID NO 874
<211> LENGTH: 8
<212> TYPE: PRT
<213> ORGANISM: human

<400> SEQUENCE: 874

Pro Gly Leu Ser Leu Pro Thr Leu
1               5

<210> SEQ ID NO 875
<211> LENGTH: 9
<212> TYPE: PRT
<213> ORGANISM: human

<400> SEQUENCE: 875

Pro Gly Leu Ser Leu Pro Ala Thr Leu
1               5

<210> SEQ ID NO 876
<211> LENGTH: 12
<212> TYPE: PRT
<213> ORGANISM: human

<400> SEQUENCE: 876

Leu Met Leu Pro Gly Leu Ser Leu Pro Gly Thr Leu
1               5                   10

<210> SEQ ID NO 877
<211> LENGTH: 9
<212> TYPE: PRT

<213> ORGANISM: human

<400> SEQUENCE: 877

Leu Leu Gly Leu Leu Pro Gly Thr Leu
1               5

<210> SEQ ID NO 878
<211> LENGTH: 12
<212> TYPE: PRT
<213> ORGANISM: human

<400> SEQUENCE: 878

Leu Leu Leu Ala Gly Leu Leu Leu Pro Gly Thr Leu
1               5                   10

<210> SEQ ID NO 879
<211> LENGTH: 9
<212> TYPE: PRT
<213> ORGANISM: human

<400> SEQUENCE: 879

Leu Pro Gly Leu Ser Leu Pro Gly Thr
1               5

<210> SEQ ID NO 880
<211> LENGTH: 8
<212> TYPE: PRT
<213> ORGANISM: human

<400> SEQUENCE: 880

Leu Pro Gly Leu Leu Pro Gly Thr
1               5

<210> SEQ ID NO 881
<211> LENGTH: 9
<212> TYPE: PRT
<213> ORGANISM: human

<400> SEQUENCE: 881

Leu Pro Gly Leu Asp Leu Pro Gly Thr
1               5

<210> SEQ ID NO 882
<211> LENGTH: 7
<212> TYPE: PRT
<213> ORGANISM: human

<400> SEQUENCE: 882

Gln Ile Met Arg Ser Gly Val
1               5

<210> SEQ ID NO 883
<211> LENGTH: 7
<212> TYPE: PRT
<213> ORGANISM: human

<400> SEQUENCE: 883

Gln Ile Met Arg Ser Gly Val
1               5

<210> SEQ ID NO 884
<211> LENGTH: 7
<212> TYPE: PRT
<213> ORGANISM: human

```
<400> SEQUENCE: 884

Gln Ile Met Arg Ser Gly Val
1               5

<210> SEQ ID NO 885
<211> LENGTH: 7
<212> TYPE: PRT
<213> ORGANISM: human

<400> SEQUENCE: 885

Gln Ile Met Arg Ser Gly Val
1               5

<210> SEQ ID NO 886
<211> LENGTH: 7
<212> TYPE: PRT
<213> ORGANISM: human

<400> SEQUENCE: 886

Gln Ile Met Arg Ser Gly Val
1               5

<210> SEQ ID NO 887
<211> LENGTH: 7
<212> TYPE: PRT
<213> ORGANISM: human

<400> SEQUENCE: 887

Gln Ile Met Arg Ser Gly Val
1               5

<210> SEQ ID NO 888
<211> LENGTH: 8
<212> TYPE: PRT
<213> ORGANISM: human

<400> SEQUENCE: 888

Gln Ile Met Leu Arg Ser Gly Val
1               5

<210> SEQ ID NO 889
<211> LENGTH: 6
<212> TYPE: PRT
<213> ORGANISM: human

<400> SEQUENCE: 889

Gln Ile Met Arg Ser Gly
1               5

<210> SEQ ID NO 890
<211> LENGTH: 5
<212> TYPE: PRT
<213> ORGANISM: human

<400> SEQUENCE: 890

Gln Ile Met Arg Gly
1               5

<210> SEQ ID NO 891
<211> LENGTH: 6
<212> TYPE: PRT
<213> ORGANISM: human

<400> SEQUENCE: 891
```

```
Gln Ile Met Arg Thr Gly
1               5

<210> SEQ ID NO 892
<211> LENGTH: 4
<212> TYPE: PRT
<213> ORGANISM: human

<400> SEQUENCE: 892

Ser Arg Tyr Trp
1

<210> SEQ ID NO 893
<211> LENGTH: 4
<212> TYPE: PRT
<213> ORGANISM: human

<400> SEQUENCE: 893

Ser Arg Tyr Trp
1

<210> SEQ ID NO 894
<211> LENGTH: 4
<212> TYPE: PRT
<213> ORGANISM: human

<400> SEQUENCE: 894

Ser Arg Tyr Trp
1

<210> SEQ ID NO 895
<211> LENGTH: 4
<212> TYPE: PRT
<213> ORGANISM: human
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 895

Ser Arg Tyr Trp
1

<210> SEQ ID NO 896
<211> LENGTH: 18
<212> TYPE: PRT
<213> ORGANISM: human
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 896

Thr Asn Gly Ser Lys Lys Glu Lys Lys Leu Xaa Phe Leu Xaa Xaa Xaa
1               5                   10                  15

Xaa Lys

<210> SEQ ID NO 897
<211> LENGTH: 10
```

```
<212> TYPE: PRT
<213> ORGANISM: human

<400> SEQUENCE: 897

Thr Asn Gly Ser Lys Lys Glu Lys Lys Leu
1               5                   10

<210> SEQ ID NO 898
<211> LENGTH: 8
<212> TYPE: PRT
<213> ORGANISM: human

<400> SEQUENCE: 898

Thr Gly Ser Lys Lys Lys Lys Leu
1               5

<210> SEQ ID NO 899
<211> LENGTH: 10
<212> TYPE: PRT
<213> ORGANISM: human

<400> SEQUENCE: 899

Thr Arg Gly Ser Lys Lys Lys Lys Lys Leu
1               5                   10

<210> SEQ ID NO 900
<211> LENGTH: 6
<212> TYPE: PRT
<213> ORGANISM: human

<400> SEQUENCE: 900

Lys Lys Glu Lys Lys Leu
1               5

<210> SEQ ID NO 901
<211> LENGTH: 6
<212> TYPE: PRT
<213> ORGANISM: human

<400> SEQUENCE: 901

Lys Lys Glu Lys Lys Leu
1               5

<210> SEQ ID NO 902
<211> LENGTH: 6
<212> TYPE: PRT
<213> ORGANISM: human

<400> SEQUENCE: 902

Lys Lys Glu Lys Lys Leu
1               5

<210> SEQ ID NO 903
<211> LENGTH: 9
<212> TYPE: PRT
<213> ORGANISM: human

<400> SEQUENCE: 903

Thr Asn Gly Ser Lys Lys Glu Lys Lys
1               5

<210> SEQ ID NO 904
<211> LENGTH: 9
<212> TYPE: PRT
<213> ORGANISM: human
```

<400> SEQUENCE: 904

Thr Asn Gly Ser Lys Lys Glu Lys Lys
1               5

<210> SEQ ID NO 905
<211> LENGTH: 20
<212> TYPE: PRT
<213> ORGANISM: human

<400> SEQUENCE: 905

Thr Asn Gly Gln Pro Asp Gln Gln Ala Ala Pro Lys Ala Pro Ser Lys
1               5                   10                  15

Lys Glu Lys Lys
        20

<210> SEQ ID NO 906
<211> LENGTH: 6
<212> TYPE: PRT
<213> ORGANISM: human

<400> SEQUENCE: 906

Ser Lys Lys Glu Lys Lys
1               5

<210> SEQ ID NO 907
<211> LENGTH: 6
<212> TYPE: PRT
<213> ORGANISM: human

<400> SEQUENCE: 907

Ser Lys Lys Glu Lys Lys
1               5

<210> SEQ ID NO 908
<211> LENGTH: 6
<212> TYPE: PRT
<213> ORGANISM: human

<400> SEQUENCE: 908

Ser Lys Lys Glu Lys Lys
1               5

<210> SEQ ID NO 909
<211> LENGTH: 22
<212> TYPE: PRT
<213> ORGANISM: human

<400> SEQUENCE: 909

Gly Glu Thr Pro Glu Leu Ile Thr Thr Asn Thr Ser Gln Leu Asn Phe
1               5                   10                  15

Arg Lys Gln Ile Val Pro
        20

<210> SEQ ID NO 910
<211> LENGTH: 7
<212> TYPE: PRT
<213> ORGANISM: human

<400> SEQUENCE: 910

Ile Thr Thr Asn Thr Ser Gln
1               5

<210> SEQ ID NO 911
<211> LENGTH: 7
<212> TYPE: PRT
<213> ORGANISM: human

<400> SEQUENCE: 911

Ile Thr Thr Asn Thr Ser Gln
1               5

<210> SEQ ID NO 912
<211> LENGTH: 7
<212> TYPE: PRT
<213> ORGANISM: human

<400> SEQUENCE: 912

Ile Thr Thr Asn Thr Ser Gln
1               5

<210> SEQ ID NO 913
<211> LENGTH: 18
<212> TYPE: PRT
<213> ORGANISM: human

<400> SEQUENCE: 913

Gly Glu Thr Pro Glu Leu Ile Thr Thr Asn Thr Ser Gln Leu Asn Phe
1               5                   10                  15

Arg Lys

<210> SEQ ID NO 914
<211> LENGTH: 10
<212> TYPE: PRT
<213> ORGANISM: human

<400> SEQUENCE: 914

Gly Thr Pro Thr Ser Leu Asn Phe Arg Lys
1               5                   10

<210> SEQ ID NO 915
<211> LENGTH: 14
<212> TYPE: PRT
<213> ORGANISM: human

<400> SEQUENCE: 915

Gly Gln Thr Pro Ala Thr Ser Glu Leu Asn Phe Leu Arg Lys
1               5                   10

<210> SEQ ID NO 916
<211> LENGTH: 8
<212> TYPE: PRT
<213> ORGANISM: human

<400> SEQUENCE: 916

Glu Leu Ile Thr Thr Asn Thr Ser
1               5

<210> SEQ ID NO 917
<211> LENGTH: 7
<212> TYPE: PRT
<213> ORGANISM: human

<400> SEQUENCE: 917

Glu Leu Ile Thr Thr Asn Ser
1               5

```
<210> SEQ ID NO 918
<211> LENGTH: 8
<212> TYPE: PRT
<213> ORGANISM: human
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 918

Glu Leu Ile Thr Thr Asn Asn Ser
1               5

<210> SEQ ID NO 919
<211> LENGTH: 19
<212> TYPE: PRT
<213> ORGANISM: human
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 919

Pro Arg Met Arg Trp Gly Xaa Xaa Xaa Val Ala Xaa Trp Pro Val Pro
1               5                   10                  15
Ser His Trp

<210> SEQ ID NO 920
<211> LENGTH: 7
<212> TYPE: PRT
<213> ORGANISM: human

<400> SEQUENCE: 920

Arg Ser Trp Asn Trp Gly Leu
1               5

<210> SEQ ID NO 921
<211> LENGTH: 7
<212> TYPE: PRT
<213> ORGANISM: human

<400> SEQUENCE: 921

Arg Ser Trp Asn Trp Gly Leu
1               5

<210> SEQ ID NO 922
<211> LENGTH: 7
<212> TYPE: PRT
<213> ORGANISM: human

<400> SEQUENCE: 922

Arg Ser Trp Asn Trp Gly Leu
1               5

<210> SEQ ID NO 923
<211> LENGTH: 18
<212> TYPE: PRT
<213> ORGANISM: human

<400> SEQUENCE: 923
```

Val Arg Leu Val Arg Thr Glu Glu Arg Leu Glu Leu Arg Thr Arg Ser
1               5                   10                  15

Trp Asn

<210> SEQ ID NO 924
<211> LENGTH: 10
<212> TYPE: PRT
<213> ORGANISM: human

<400> SEQUENCE: 924

Val Arg Leu Val Arg Thr Glu Leu Thr Trp
1               5                   10

<210> SEQ ID NO 925
<211> LENGTH: 15
<212> TYPE: PRT
<213> ORGANISM: human

<400> SEQUENCE: 925

Val Arg Leu Val Arg Thr Met Glu Leu Leu Thr Gln Asn Trp Asp
1               5                   10                  15

<210> SEQ ID NO 926
<211> LENGTH: 15
<212> TYPE: PRT
<213> ORGANISM: human

<400> SEQUENCE: 926

Leu Val Arg Thr Glu Glu Arg Leu Glu Leu Thr Arg Ser Trp
1               5                   10                  15

<210> SEQ ID NO 927
<211> LENGTH: 10
<212> TYPE: PRT
<213> ORGANISM: human

<400> SEQUENCE: 927

Leu Val Arg Glu Glu Arg Arg Thr Ser Trp
1               5                   10

<210> SEQ ID NO 928
<211> LENGTH: 15
<212> TYPE: PRT
<213> ORGANISM: human

<400> SEQUENCE: 928

Leu Val Gln Gly Ala Arg Ser Glu Glu Arg Arg Thr Lys Ser Trp
1               5                   10                  15

<210> SEQ ID NO 929
<211> LENGTH: 12
<212> TYPE: PRT
<213> ORGANISM: human

<400> SEQUENCE: 929

Arg Leu Glu Leu Arg Thr Arg Ser Trp Asn Trp Gly
1               5                   10

<210> SEQ ID NO 930
<211> LENGTH: 9
<212> TYPE: PRT
<213> ORGANISM: human

<400> SEQUENCE: 930

Arg Leu Glu Arg Thr Arg Asn Trp Gly
1               5

<210> SEQ ID NO 931
<211> LENGTH: 10
<212> TYPE: PRT
<213> ORGANISM: human

<400> SEQUENCE: 931

Arg Leu Glu Thr Arg Thr Arg Asn Trp Gly
1               5                   10

<210> SEQ ID NO 932
<211> LENGTH: 7
<212> TYPE: PRT
<213> ORGANISM: human

<400> SEQUENCE: 932

Glu Glu Arg Leu Glu Leu Arg
1               5

<210> SEQ ID NO 933
<211> LENGTH: 7
<212> TYPE: PRT
<213> ORGANISM: human

<400> SEQUENCE: 933

Glu Glu Arg Leu Glu Leu Arg
1               5

<210> SEQ ID NO 934
<211> LENGTH: 7
<212> TYPE: PRT
<213> ORGANISM: human

<400> SEQUENCE: 934

Glu Glu Arg Leu Glu Leu Arg
1               5

<210> SEQ ID NO 935
<211> LENGTH: 11
<212> TYPE: PRT
<213> ORGANISM: human

<400> SEQUENCE: 935

Glu Glu Arg Leu Glu Leu Arg Thr Arg Ser Trp
1               5                   10

<210> SEQ ID NO 936
<211> LENGTH: 8
<212> TYPE: PRT
<213> ORGANISM: human

<400> SEQUENCE: 936

Glu Glu Arg Leu Glu Arg Ser Trp
1               5

<210> SEQ ID NO 937
<211> LENGTH: 8
<212> TYPE: PRT
<213> ORGANISM: human
<220> FEATURE:
<221> NAME/KEY: misc_feature
<222> LOCATION: (35)..(35)
<223> OTHER INFORMATION: Xaa can be any naturally occurring amino acid

```
<400> SEQUENCE: 937

Glu Glu Arg Leu Glu Arg Ser Trp
1               5

<210> SEQ ID NO 938
<211> LENGTH: 40
<212> TYPE: PRT
<213> ORGANISM: human
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 938

Arg Glu Met Arg Leu Lys Asn Thr Lys Leu Gln Ser Asp Lys Arg Asn
1               5                   10                  15

Asn Phe Gly Pro Gly Ala Val Val His Thr Cys Asn Pro Ser Thr Ser
            20                  25                  30

Gly Gly Xaa Val Gly Arg Ile Thr
        35                  40

<210> SEQ ID NO 939
<211> LENGTH: 22
<212> TYPE: PRT
<213> ORGANISM: human
<220> FEATURE:
<221> NAME/KEY: misc_feature
<222> LOCATION: (17)..(17)
<223> OTHER INFORMATION: Xaa can be any naturally occurring amino acid

<400> SEQUENCE: 939

Gly Pro Gly Ala Val Val His Thr Cys Asn Pro Ser Thr Ser Gly Gly
1               5                   10                  15

Xaa Val Gly Arg Ile Thr
            20

<210> SEQ ID NO 940
<211> LENGTH: 17
<212> TYPE: PRT
<213> ORGANISM: human

<400> SEQUENCE: 940

Gly Pro Gly Ala Val His Cys Asn Pro Ser Thr Gly Gly Gly Arg Ile
1               5                   10                  15

Thr

<210> SEQ ID NO 941
<211> LENGTH: 22
<212> TYPE: PRT
<213> ORGANISM: human
<220> FEATURE:
<221> NAME/KEY: misc_feature
<222> LOCATION: (16)..(16)
<223> OTHER INFORMATION: Xaa can be any naturally occurring amino acid

<400> SEQUENCE: 941

Gly Pro Gly Ala Val Ala His Ala Cys Asn Pro Ser Thr Leu Gly Gly
1               5                   10                  15

Arg Gly Gly Arg Ile Thr
            20
```

```
<210> SEQ ID NO 942
<211> LENGTH: 21
<212> TYPE: PRT
<213> ORGANISM: human
<220> FEATURE:
<221> NAME/KEY: misc_feature
<222> LOCATION: (16)..(16)
<223> OTHER INFORMATION: Xaa can be any naturally occurring amino acid

<400> SEQUENCE: 942

Pro Gly Ala Val Val His Thr Cys Asn Pro Ser Thr Ser Gly Gly Xaa
1               5                   10                  15

Val Gly Arg Ile Thr
            20

<210> SEQ ID NO 943
<211> LENGTH: 16
<212> TYPE: PRT
<213> ORGANISM: human

<400> SEQUENCE: 943

Pro Gly Val Val His Cys Asn Pro Ser Thr Gly Gly Gly Arg Ile Thr
1               5                   10                  15

<210> SEQ ID NO 944
<211> LENGTH: 21
<212> TYPE: PRT
<213> ORGANISM: human
<220> FEATURE:
<221> NAME/KEY: misc_feature
<222> LOCATION: (21)..(21)
<223> OTHER INFORMATION: Xaa can be any naturally occurring amino acid

<400> SEQUENCE: 944

Pro Gly Thr Val Val His Ala Cys Asn Pro Ser Thr Leu Gly Gly Gln
1               5                   10                  15

Gly Gly Arg Ile Thr
            20

<210> SEQ ID NO 945
<211> LENGTH: 26
<212> TYPE: PRT
<213> ORGANISM: human
<220> FEATURE:
<221> NAME/KEY: misc_feature
<222> LOCATION: (21)..(21)
<223> OTHER INFORMATION: Xaa can be any naturally occurring amino acid

<400> SEQUENCE: 945

Arg Asn Asn Phe Gly Pro Gly Ala Val Val His Thr Cys Asn Pro Ser
1               5                   10                  15

Thr Ser Gly Gly Xaa Val Gly Arg Ile Thr
            20                  25

<210> SEQ ID NO 946
<211> LENGTH: 19
<212> TYPE: PRT
<213> ORGANISM: human

<400> SEQUENCE: 946

Arg Asn Gly Pro Gly Ala Val His Cys Asn Pro Ser Thr Gly Gly Gly
1               5                   10                  15

Arg Ile Thr
```

<210> SEQ ID NO 947
<211> LENGTH: 25
<212> TYPE: PRT
<213> ORGANISM: human

<400> SEQUENCE: 947

Arg Asn Gly Trp Pro Gly Ala Val Ala His Ala Cys Asn Pro Ser Thr
1               5                   10                  15

Leu Gly Gly Gln Gly Gly Arg Ile Thr
            20                  25

<210> SEQ ID NO 948
<211> LENGTH: 12
<212> TYPE: PRT
<213> ORGANISM: human

<400> SEQUENCE: 948

Gly Ile Thr Gly Ser Arg Pro Ala Trp Pro Thr Trp
1               5                   10

<210> SEQ ID NO 949
<211> LENGTH: 8
<212> TYPE: PRT
<213> ORGANISM: human

<400> SEQUENCE: 949

Ser Arg Pro Ala Trp Pro Thr Trp
1               5

<210> SEQ ID NO 950
<211> LENGTH: 8
<212> TYPE: PRT
<213> ORGANISM: human

<400> SEQUENCE: 950

Ser Arg Pro Ala Trp Pro Thr Trp
1               5

<210> SEQ ID NO 951
<211> LENGTH: 8
<212> TYPE: PRT
<213> ORGANISM: human

<400> SEQUENCE: 951

Ser Arg Pro Ala Trp Pro Thr Trp
1               5

<210> SEQ ID NO 952
<211> LENGTH: 7
<212> TYPE: PRT
<213> ORGANISM: human

<400> SEQUENCE: 952

Arg Pro Ala Trp Pro Thr Trp
1               5

<210> SEQ ID NO 953
<211> LENGTH: 7
<212> TYPE: PRT
<213> ORGANISM: human

<400> SEQUENCE: 953

Arg Pro Ala Trp Pro Thr Trp
1               5

```
<210> SEQ ID NO 954
<211> LENGTH: 7
<212> TYPE: PRT
<213> ORGANISM: human

<400> SEQUENCE: 954

Arg Pro Ala Trp Pro Thr Trp
1               5

<210> SEQ ID NO 955
<211> LENGTH: 8
<212> TYPE: PRT
<213> ORGANISM: human

<400> SEQUENCE: 955

Ser Arg Pro Ala Trp Pro Thr Trp
1               5

<210> SEQ ID NO 956
<211> LENGTH: 7
<212> TYPE: PRT
<213> ORGANISM: human

<400> SEQUENCE: 956

Ser Arg Pro Ala Trp Thr Trp
1               5

<210> SEQ ID NO 957
<211> LENGTH: 8
<212> TYPE: PRT
<213> ORGANISM: human

<400> SEQUENCE: 957

Ser Arg Pro Ala Trp Ala Thr Trp
1               5

<210> SEQ ID NO 958
<211> LENGTH: 4
<212> TYPE: PRT
<213> ORGANISM: human

<400> SEQUENCE: 958

Asn Ser Ser Ala
1

<210> SEQ ID NO 959
<211> LENGTH: 4
<212> TYPE: PRT
<213> ORGANISM: human

<400> SEQUENCE: 959

Asn Ser Ser Ala
1

<210> SEQ ID NO 960
<211> LENGTH: 4
<212> TYPE: PRT
<213> ORGANISM: human

<400> SEQUENCE: 960

Asn Ser Ser Ala
1
```

```
<210> SEQ ID NO 961
<211> LENGTH: 4
<212> TYPE: PRT
<213> ORGANISM: human

<400> SEQUENCE: 961

Asn Ser Ser Ala
1

<210> SEQ ID NO 962
<211> LENGTH: 5
<212> TYPE: PRT
<213> ORGANISM: human

<400> SEQUENCE: 962

Asn Ser Asn Ile Tyr
1               5

<210> SEQ ID NO 963
<211> LENGTH: 5
<212> TYPE: PRT
<213> ORGANISM: human

<400> SEQUENCE: 963

Asn Ser Asn Ile Tyr
1               5

<210> SEQ ID NO 964
<211> LENGTH: 5
<212> TYPE: PRT
<213> ORGANISM: human

<400> SEQUENCE: 964

Asn Ser Asn Ile Tyr
1               5

<210> SEQ ID NO 965
<211> LENGTH: 5
<212> TYPE: PRT
<213> ORGANISM: human

<400> SEQUENCE: 965

Asn Ser Asn Ile Tyr
1               5

<210> SEQ ID NO 966
<211> LENGTH: 12
<212> TYPE: PRT
<213> ORGANISM: human

<400> SEQUENCE: 966

Leu Thr Leu Arg Thr Lys Thr Thr Thr Val Thr Val
1               5                   10

<210> SEQ ID NO 967
<211> LENGTH: 7
<212> TYPE: PRT
<213> ORGANISM: human

<400> SEQUENCE: 967

Thr Leu Arg Thr Lys Thr Thr
1               5

<210> SEQ ID NO 968
<211> LENGTH: 7
```

```
<212> TYPE: PRT
<213> ORGANISM: human

<400> SEQUENCE: 968

Thr Leu Arg Thr Lys Thr Thr
1               5

<210> SEQ ID NO 969
<211> LENGTH: 7
<212> TYPE: PRT
<213> ORGANISM: human

<400> SEQUENCE: 969

Thr Leu Arg Thr Lys Thr Thr
1               5

<210> SEQ ID NO 970
<211> LENGTH: 8
<212> TYPE: PRT
<213> ORGANISM: human

<400> SEQUENCE: 970

Thr Leu Arg Thr Lys Thr Thr Thr
1               5

<210> SEQ ID NO 971
<211> LENGTH: 8
<212> TYPE: PRT
<213> ORGANISM: human

<400> SEQUENCE: 971

Thr Leu Arg Thr Lys Thr Thr Thr
1               5

<210> SEQ ID NO 972
<211> LENGTH: 9
<212> TYPE: PRT
<213> ORGANISM: human

<400> SEQUENCE: 972

Thr Leu Arg Thr Ser Lys Thr Thr Thr
1               5

<210> SEQ ID NO 973
<211> LENGTH: 9
<212> TYPE: PRT
<213> ORGANISM: human

<400> SEQUENCE: 973

Arg Thr Lys Thr Thr Thr Val Thr Val
1               5

<210> SEQ ID NO 974
<211> LENGTH: 7
<212> TYPE: PRT
<213> ORGANISM: human

<400> SEQUENCE: 974

Arg Thr Thr Thr Thr Thr Val
1               5

<210> SEQ ID NO 975
<211> LENGTH: 9
<212> TYPE: PRT
<213> ORGANISM: human
```

```
<400> SEQUENCE: 975

Arg Thr Thr Thr Thr Thr Leu Thr Val
1               5

<210> SEQ ID NO 976
<211> LENGTH: 12
<212> TYPE: PRT
<213> ORGANISM: human

<400> SEQUENCE: 976

Thr Arg Gly Thr Lys Arg Ser Trp Tyr His Ser Phe
1               5                   10

<210> SEQ ID NO 977
<211> LENGTH: 11
<212> TYPE: PRT
<213> ORGANISM: human

<400> SEQUENCE: 977

Thr Arg Gly Thr Lys Arg Ser Trp Tyr His Ser
1               5                   10

<210> SEQ ID NO 978
<211> LENGTH: 8
<212> TYPE: PRT
<213> ORGANISM: human

<400> SEQUENCE: 978

Thr Arg Lys Arg Trp Tyr His Ser
1               5

<210> SEQ ID NO 979
<211> LENGTH: 10
<212> TYPE: PRT
<213> ORGANISM: human

<400> SEQUENCE: 979

Thr Arg Thr Ser Lys Arg Trp Tyr His Ser
1               5                   10

<210> SEQ ID NO 980
<211> LENGTH: 8
<212> TYPE: PRT
<213> ORGANISM: human

<400> SEQUENCE: 980

Gly Thr Lys Arg Ser Trp Tyr His
1               5

<210> SEQ ID NO 981
<211> LENGTH: 7
<212> TYPE: PRT
<213> ORGANISM: human

<400> SEQUENCE: 981

Gly Thr Arg Ser Trp Tyr His
1               5

<210> SEQ ID NO 982
<211> LENGTH: 8
<212> TYPE: PRT
<213> ORGANISM: human

<400> SEQUENCE: 982
```

Gly Thr Val Arg Ser Trp Tyr His
1               5

<210> SEQ ID NO 983
<211> LENGTH: 8
<212> TYPE: PRT
<213> ORGANISM: human

<400> SEQUENCE: 983

Arg Gly Thr Lys Arg Ser Trp Tyr
1               5

<210> SEQ ID NO 984
<211> LENGTH: 6
<212> TYPE: PRT
<213> ORGANISM: human

<400> SEQUENCE: 984

Arg Gly Lys Ser Trp Tyr
1               5

<210> SEQ ID NO 985
<211> LENGTH: 8
<212> TYPE: PRT
<213> ORGANISM: human

<400> SEQUENCE: 985

Arg Gly Lys Lys Trp Ser Trp Tyr
1               5

<210> SEQ ID NO 986
<211> LENGTH: 20
<212> TYPE: PRT
<213> ORGANISM: human

<400> SEQUENCE: 986

Phe Phe Val Phe Tyr Leu Gln Ser Arg Ile Met Thr Asp Thr Lys Ile
1               5                   10                  15

Ser Pro Leu His
            20

<210> SEQ ID NO 987
<211> LENGTH: 18
<212> TYPE: PRT
<213> ORGANISM: human

<400> SEQUENCE: 987

Val Phe Tyr Leu Gln Ser Arg Ile Met Thr Asp Thr Lys Ile Ser Pro
1               5                   10                  15

Leu His

<210> SEQ ID NO 988
<211> LENGTH: 11
<212> TYPE: PRT
<213> ORGANISM: human

<400> SEQUENCE: 988

Val Tyr Ser Arg Ile Met Lys Ile Ser Pro Leu
1               5                   10

<210> SEQ ID NO 989
<211> LENGTH: 25
<212> TYPE: PRT

<213> ORGANISM: human

<400> SEQUENCE: 989

Val Tyr Tyr Thr Val Pro Leu Val Arg His Met Glu Ser Arg Ile Met
1               5                   10                  15

Ile Pro Leu Lys Ile Ser Pro Leu Gln
            20                  25

<210> SEQ ID NO 990
<211> LENGTH: 11
<212> TYPE: PRT
<213> ORGANISM: human

<400> SEQUENCE: 990

Arg Ile Met Thr Asp Thr Lys Ile Ser Pro Leu
1               5                   10

<210> SEQ ID NO 991
<211> LENGTH: 9
<212> TYPE: PRT
<213> ORGANISM: human

<400> SEQUENCE: 991

Arg Ile Met Thr Asp Thr Ile Ser Pro
1               5

<210> SEQ ID NO 992
<211> LENGTH: 12
<212> TYPE: PRT
<213> ORGANISM: human

<400> SEQUENCE: 992

Arg Ile Asn Met Thr Asp Thr Gly Ile Ser Pro Met
1               5                   10

<210> SEQ ID NO 993
<211> LENGTH: 9
<212> TYPE: PRT
<213> ORGANISM: human

<400> SEQUENCE: 993

Ile Met Thr Asp Thr Lys Ile Ser Pro
1               5

<210> SEQ ID NO 994
<211> LENGTH: 8
<212> TYPE: PRT
<213> ORGANISM: human

<400> SEQUENCE: 994

Ile Met Thr Asp Thr Lys Ile Pro
1               5

<210> SEQ ID NO 995
<211> LENGTH: 10
<212> TYPE: PRT
<213> ORGANISM: human
<220> FEATURE:
<221> NAME/KEY: misc_feature
<222> LOCATION: (13)..(13)
<223> OTHER INFORMATION: Xaa can be any naturally occurring amino acid

<400> SEQUENCE: 995

Ile Met Thr Asp Thr Glu Lys Ile His Pro
1               5                   10

<210> SEQ ID NO 996
<211> LENGTH: 16
<212> TYPE: PRT
<213> ORGANISM: human
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 996

Pro Cys Glu Met Glu Leu Glu Ser Pro His Pro Ala Xaa Cys His Leu
1               5                   10                  15

<210> SEQ ID NO 997
<211> LENGTH: 13
<212> TYPE: PRT
<213> ORGANISM: human
<220> FEATURE:
<221> NAME/KEY: misc_feature
<222> LOCATION: (10)..(10)
<223> OTHER INFORMATION: Xaa can be any naturally occurring amino acid

<400> SEQUENCE: 997

Met Glu Leu Glu Ser Pro His Pro Ala Xaa Cys His Leu
1               5                   10

<210> SEQ ID NO 998
<211> LENGTH: 11
<212> TYPE: PRT
<213> ORGANISM: human

<400> SEQUENCE: 998

Met Glu Leu Glu Ser Pro His Pro Cys His Leu
1               5                   10

<210> SEQ ID NO 999
<211> LENGTH: 15
<212> TYPE: PRT
<213> ORGANISM: human

<400> SEQUENCE: 999

Met Glu Leu Glu Ser Met Pro His Ser Val Pro Ser Cys His Leu
1               5                   10                  15

<210> SEQ ID NO 1000
<211> LENGTH: 10
<212> TYPE: PRT
<213> ORGANISM: human

<400> SEQUENCE: 1000

Glu Met Glu Gly Pro Ser Pro His Pro Ala
1               5                   10

<210> SEQ ID NO 1001
<211> LENGTH: 8
<212> TYPE: PRT
<213> ORGANISM: human

<400> SEQUENCE: 1001

Glu Met Glu Gly Pro Pro Pro Ala
1               5

<210> SEQ ID NO 1002
<211> LENGTH: 11
<212> TYPE: PRT
<213> ORGANISM: human
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1002

Glu Met Glu Gly Pro Asn Val Pro Asn Pro Ala
1               5                   10

<210> SEQ ID NO 1003
<211> LENGTH: 9
<212> TYPE: PRT
<213> ORGANISM: human
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1003

Ser Pro His Pro Ala Xaa Cys His Leu
1               5

<210> SEQ ID NO 1004
<211> LENGTH: 6
<212> TYPE: PRT
<213> ORGANISM: human

<400> SEQUENCE: 1004

Ser Pro His Pro Cys His
1               5

<210> SEQ ID NO 1005
<211> LENGTH: 9
<212> TYPE: PRT
<213> ORGANISM: human

<400> SEQUENCE: 1005

Ser Pro His Pro Ser Leu Cys His Met
1               5

<210> SEQ ID NO 1006
<211> LENGTH: 9
<212> TYPE: PRT
<213> ORGANISM: human

<400> SEQUENCE: 1006

Gly Cys Glu Met Glu Gly Gln Ser Pro
1               5

<210> SEQ ID NO 1007
<211> LENGTH: 9
<212> TYPE: PRT
<213> ORGANISM: human

<400> SEQUENCE: 1007

Gly Cys Glu Met Glu Gly Gln Ser Pro
1               5

<210> SEQ ID NO 1008
<211> LENGTH: 13
<212> TYPE: PRT
<213> ORGANISM: human

<400> SEQUENCE: 1008

Gly Cys Leu Ile Tyr Glu Met Ile Glu Gly Gln Ser Pro
1               5                   10

<210> SEQ ID NO 1009
<211> LENGTH: 7
<212> TYPE: PRT
<213> ORGANISM: human

<400> SEQUENCE: 1009

Met Glu Leu Glu Ser Pro His
1               5

<210> SEQ ID NO 1010
<211> LENGTH: 6
<212> TYPE: PRT
<213> ORGANISM: human

<400> SEQUENCE: 1010

Met Glu Glu Ser Pro His
1               5

<210> SEQ ID NO 1011
<211> LENGTH: 7
<212> TYPE: PRT
<213> ORGANISM: human

<400> SEQUENCE: 1011

Met Glu Ile Glu Ser Pro His
1               5

<210> SEQ ID NO 1012
<211> LENGTH: 4
<212> TYPE: PRT
<213> ORGANISM: human

<400> SEQUENCE: 1012

Asn Ser Ser Ala
1

<210> SEQ ID NO 1013
<211> LENGTH: 4
<212> TYPE: PRT
<213> ORGANISM: human

<400> SEQUENCE: 1013

Asn Ser Ser Ala
1

<210> SEQ ID NO 1014
<211> LENGTH: 4
<212> TYPE: PRT
<213> ORGANISM: human

<400> SEQUENCE: 1014

Asn Ser Ser Ala
1

<210> SEQ ID NO 1015
<211> LENGTH: 4
<212> TYPE: PRT
<213> ORGANISM: human

<400> SEQUENCE: 1015

Asn Ser Ser Ala
1

<210> SEQ ID NO 1016
<211> LENGTH: 11
<212> TYPE: PRT
<213> ORGANISM: human

<400> SEQUENCE: 1016

Gly Trp Gln Glu Arg Arg Asn Lys Leu Thr Lys
1               5                   10

<210> SEQ ID NO 1017
<211> LENGTH: 7
<212> TYPE: PRT
<213> ORGANISM: human

<400> SEQUENCE: 1017

Gln Glu Arg Arg Asn Lys Leu
1               5

<210> SEQ ID NO 1018
<211> LENGTH: 6
<212> TYPE: PRT
<213> ORGANISM: human

<400> SEQUENCE: 1018

Glu Arg Arg Asn Lys Leu
1               5

<210> SEQ ID NO 1019
<211> LENGTH: 7
<212> TYPE: PRT
<213> ORGANISM: human

<400> SEQUENCE: 1019

Glu Glu Arg Arg Asn Lys Leu
1               5

<210> SEQ ID NO 1020
<211> LENGTH: 9
<212> TYPE: PRT
<213> ORGANISM: human

<400> SEQUENCE: 1020

Gly Trp Gln Glu Arg Arg Asn Lys Leu
1               5

<210> SEQ ID NO 1021
<211> LENGTH: 6
<212> TYPE: PRT
<213> ORGANISM: human

<400> SEQUENCE: 1021

Gly Trp Glu Arg Arg Leu
1               5

<210> SEQ ID NO 1022
<211> LENGTH: 9
<212> TYPE: PRT
<213> ORGANISM: human

<400> SEQUENCE: 1022

Gly Trp Glu Glu Arg Arg Asp Ile Leu

```
<210> SEQ ID NO 1023
<211> LENGTH: 6
<212> TYPE: PRT
<213> ORGANISM: human

<400> SEQUENCE: 1023

Glu Arg Arg Asn Lys Leu
1               5

<210> SEQ ID NO 1024
<211> LENGTH: 6
<212> TYPE: PRT
<213> ORGANISM: human

<400> SEQUENCE: 1024

Glu Arg Arg Asn Lys Leu
1               5

<210> SEQ ID NO 1025
<211> LENGTH: 6
<212> TYPE: PRT
<213> ORGANISM: human

<400> SEQUENCE: 1025

Glu Arg Arg Asn Lys Leu
1               5

<210> SEQ ID NO 1026
<211> LENGTH: 9
<212> TYPE: PRT
<213> ORGANISM: human

<400> SEQUENCE: 1026

Trp Gln Glu Arg Arg Asn Lys Leu Thr
1               5

<210> SEQ ID NO 1027
<211> LENGTH: 7
<212> TYPE: PRT
<213> ORGANISM: human

<400> SEQUENCE: 1027

Trp Glu Arg Arg Asn Leu Thr
1               5

<210> SEQ ID NO 1028
<211> LENGTH: 11
<212> TYPE: PRT
<213> ORGANISM: human

<400> SEQUENCE: 1028

Trp Arg Glu Arg Arg Asn Ala Ile Arg Leu Thr
1               5                   10

<210> SEQ ID NO 1029
<211> LENGTH: 23
<212> TYPE: PRT
<213> ORGANISM: human

<400> SEQUENCE: 1029

Val Glu Gly Lys Val Ala Arg Cys Gln Ser Lys Ser Pro Gly Phe Glu
1               5                   10                  15
```

```
Asp Gly Leu Phe Gly Lys Phe
            20
```

<210> SEQ ID NO 1030
<211> LENGTH: 10
<212> TYPE: PRT
<213> ORGANISM: human

<400> SEQUENCE: 1030

```
Cys Gln Ser Lys Ser Pro Gly Phe Glu Asp
1               5                   10
```

<210> SEQ ID NO 1031
<211> LENGTH: 7
<212> TYPE: PRT
<213> ORGANISM: human

<400> SEQUENCE: 1031

```
Cys Gln Ser Lys Ser Pro Gly
1               5
```

<210> SEQ ID NO 1032
<211> LENGTH: 10
<212> TYPE: PRT
<213> ORGANISM: human

<400> SEQUENCE: 1032

```
Cys Gln Ser Lys Ser Pro Gly Leu Asp Asn
1               5                   10
```

<210> SEQ ID NO 1033
<211> LENGTH: 16
<212> TYPE: PRT
<213> ORGANISM: human

<400> SEQUENCE: 1033

```
Lys Val Ala Arg Cys Gln Ser Lys Ser Pro Gly Phe Glu Asp Gly Leu
1               5                   10                  15
```

<210> SEQ ID NO 1034
<211> LENGTH: 9
<212> TYPE: PRT
<213> ORGANISM: human

<400> SEQUENCE: 1034

```
Lys Val Arg Cys Gly Phe Glu Asp Leu
1               5
```

<210> SEQ ID NO 1035
<211> LENGTH: 11
<212> TYPE: PRT
<213> ORGANISM: human

<400> SEQUENCE: 1035

```
Lys Val Gly Arg Cys Gly Phe Glu Asp Asn Leu
1               5                   10
```

<210> SEQ ID NO 1036
<211> LENGTH: 9
<212> TYPE: PRT
<213> ORGANISM: human

<400> SEQUENCE: 1036

```
Val Ala Arg Cys Gln Ser Lys Ser Pro
1               5
```

<210> SEQ ID NO 1037
<211> LENGTH: 7
<212> TYPE: PRT
<213> ORGANISM: human

<400> SEQUENCE: 1037

Val Ala Arg Cys Gln Lys Pro
1               5

<210> SEQ ID NO 1038
<211> LENGTH: 9
<212> TYPE: PRT
<213> ORGANISM: human

<400> SEQUENCE: 1038

Val Ala Arg Cys Gln Cys Lys Gly Pro
1               5

<210> SEQ ID NO 1039
<211> LENGTH: 8
<212> TYPE: PRT
<213> ORGANISM: human

<400> SEQUENCE: 1039

Leu Thr Ser Lys Thr Gln Arg Lys
1               5

<210> SEQ ID NO 1040
<211> LENGTH: 8
<212> TYPE: PRT
<213> ORGANISM: human

<400> SEQUENCE: 1040

Leu Thr Ser Lys Thr Gln Arg Lys
1               5

<210> SEQ ID NO 1041
<211> LENGTH: 8
<212> TYPE: PRT
<213> ORGANISM: human

<400> SEQUENCE: 1041

Leu Thr Ser Lys Thr Gln Arg Lys
1               5

<210> SEQ ID NO 1042
<211> LENGTH: 9
<212> TYPE: PRT
<213> ORGANISM: human

<400> SEQUENCE: 1042

Leu Thr Leu Ser Lys Thr Gln Arg Lys
1               5

<210> SEQ ID NO 1043
<211> LENGTH: 8
<212> TYPE: PRT
<213> ORGANISM: human

<400> SEQUENCE: 1043

Leu Thr Ser Lys Thr Gln Arg Lys
1               5

```
<210> SEQ ID NO 1044
<211> LENGTH: 8
<212> TYPE: PRT
<213> ORGANISM: human

<400> SEQUENCE: 1044

Leu Thr Ser Lys Thr Gln Arg Lys
1               5

<210> SEQ ID NO 1045
<211> LENGTH: 9
<212> TYPE: PRT
<213> ORGANISM: human

<400> SEQUENCE: 1045

Leu Thr Leu Ser Lys Thr Gln Arg Lys
1               5

<210> SEQ ID NO 1046
<211> LENGTH: 8
<212> TYPE: PRT
<213> ORGANISM: human

<400> SEQUENCE: 1046

Leu Thr Ser Lys Thr Gln Arg Lys
1               5

<210> SEQ ID NO 1047
<211> LENGTH: 8
<212> TYPE: PRT
<213> ORGANISM: human

<400> SEQUENCE: 1047

Leu Thr Ser Lys Thr Gln Arg Lys
1               5

<210> SEQ ID NO 1048
<211> LENGTH: 9
<212> TYPE: PRT
<213> ORGANISM: human

<400> SEQUENCE: 1048

Leu Thr Leu Ser Lys Thr Gln Arg Lys
1               5

<210> SEQ ID NO 1049
<211> LENGTH: 6
<212> TYPE: PRT
<213> ORGANISM: human

<400> SEQUENCE: 1049

Thr Ser Lys Thr Gln Arg
1               5

<210> SEQ ID NO 1050
<211> LENGTH: 6
<212> TYPE: PRT
<213> ORGANISM: human

<400> SEQUENCE: 1050

Thr Ser Lys Thr Gln Arg
1               5

<210> SEQ ID NO 1051
<211> LENGTH: 6
```

```
<212> TYPE: PRT
<213> ORGANISM: human

<400> SEQUENCE: 1051

Thr Ser Lys Thr Gln Arg
1               5

<210> SEQ ID NO 1052
<211> LENGTH: 6
<212> TYPE: PRT
<213> ORGANISM: human

<400> SEQUENCE: 1052

Thr Ser Lys Thr Gln Arg
1               5

<210> SEQ ID NO 1053
<211> LENGTH: 6
<212> TYPE: PRT
<213> ORGANISM: human

<400> SEQUENCE: 1053

Thr Ser Lys Thr Gln Arg
1               5

<210> SEQ ID NO 1054
<211> LENGTH: 6
<212> TYPE: PRT
<213> ORGANISM: human

<400> SEQUENCE: 1054

Thr Ser Lys Thr Gln Arg
1               5

<210> SEQ ID NO 1055
<211> LENGTH: 7
<212> TYPE: PRT
<213> ORGANISM: human

<400> SEQUENCE: 1055

Thr Ser Lys Thr Gln Arg Lys
1               5

<210> SEQ ID NO 1056
<211> LENGTH: 6
<212> TYPE: PRT
<213> ORGANISM: human

<400> SEQUENCE: 1056

Thr Ser Lys Thr Arg Lys
1               5

<210> SEQ ID NO 1057
<211> LENGTH: 7
<212> TYPE: PRT
<213> ORGANISM: human

<400> SEQUENCE: 1057

Thr Ser Lys Thr Lys Arg Lys
1               5

<210> SEQ ID NO 1058
<211> LENGTH: 5
<212> TYPE: PRT
<213> ORGANISM: human
```

<400> SEQUENCE: 1058

Lys Thr Gln Arg Lys
1               5

<210> SEQ ID NO 1059
<211> LENGTH: 5
<212> TYPE: PRT
<213> ORGANISM: human

<400> SEQUENCE: 1059

Lys Thr Gln Arg Lys
1               5

<210> SEQ ID NO 1060
<211> LENGTH: 5
<212> TYPE: PRT
<213> ORGANISM: human

<400> SEQUENCE: 1060

Lys Thr Gln Arg Lys
1               5

<210> SEQ ID NO 1061
<211> LENGTH: 6
<212> TYPE: PRT
<213> ORGANISM: human

<400> SEQUENCE: 1061

Gly Asp Pro Asn Ser Ser
1               5

<210> SEQ ID NO 1062
<211> LENGTH: 5
<212> TYPE: PRT
<213> ORGANISM: human

<400> SEQUENCE: 1062

Gly Asp Pro Asn Ser
1               5

<210> SEQ ID NO 1063
<211> LENGTH: 5
<212> TYPE: PRT
<213> ORGANISM: human

<400> SEQUENCE: 1063

Gly Asp Pro Asn Ser
1               5

<210> SEQ ID NO 1064
<211> LENGTH: 5
<212> TYPE: PRT
<213> ORGANISM: human

<400> SEQUENCE: 1064

Gly Asp Pro Asn Ser
1               5

<210> SEQ ID NO 1065
<211> LENGTH: 5
<212> TYPE: PRT
<213> ORGANISM: human

<400> SEQUENCE: 1065

```
Asp Pro Asn Ser Ser
1               5

<210> SEQ ID NO 1066
<211> LENGTH: 5
<212> TYPE: PRT
<213> ORGANISM: human

<400> SEQUENCE: 1066

Asp Pro Asn Ser Ser
1               5

<210> SEQ ID NO 1067
<211> LENGTH: 5
<212> TYPE: PRT
<213> ORGANISM: human

<400> SEQUENCE: 1067

Asp Pro Asn Ser Ser
1               5

<210> SEQ ID NO 1068
<211> LENGTH: 7
<212> TYPE: PRT
<213> ORGANISM: human

<400> SEQUENCE: 1068

Gly Asp Pro Asn Ser Val Tyr
1               5

<210> SEQ ID NO 1069
<211> LENGTH: 7
<212> TYPE: PRT
<213> ORGANISM: human

<400> SEQUENCE: 1069

Gly Asp Pro Asn Ser Val Tyr
1               5

<210> SEQ ID NO 1070
<211> LENGTH: 6
<212> TYPE: PRT
<213> ORGANISM: human

<400> SEQUENCE: 1070

Gly Pro Asn Ser Val Tyr
1               5

<210> SEQ ID NO 1071
<211> LENGTH: 7
<212> TYPE: PRT
<213> ORGANISM: human

<400> SEQUENCE: 1071

Gly Gly Pro Asn Ser Val Tyr
1               5

<210> SEQ ID NO 1072
<211> LENGTH: 26
<212> TYPE: PRT
<213> ORGANISM: human

<400> SEQUENCE: 1072

Tyr Val Tyr Arg Leu Pro Ile Arg Ser Leu Thr Gly Gly Ala Gly Gly
```

-continued

```
                1               5                  10                 15
Gly Gly Arg Gln Glu Ala Trp Met Gly Thr
        20                  25

<210> SEQ ID NO 1073
<211> LENGTH: 14
<212> TYPE: PRT
<213> ORGANISM: human

<400> SEQUENCE: 1073

Leu Thr Gly Gly Ala Gly Gly Gly Arg Gln Glu Ala Trp
1               5                   10

<210> SEQ ID NO 1074
<211> LENGTH: 11
<212> TYPE: PRT
<213> ORGANISM: human

<400> SEQUENCE: 1074

Leu Gly Gly Ala Gly Gly Gly Gly Arg Glu Trp
1               5                   10

<210> SEQ ID NO 1075
<211> LENGTH: 15
<212> TYPE: PRT
<213> ORGANISM: human

<400> SEQUENCE: 1075

Leu Ala Gly Gly Ala Gly Gly Gly Ala Gly Arg Lys Glu Asp Trp
1               5                   10                  15

<210> SEQ ID NO 1076
<211> LENGTH: 4
<212> TYPE: PRT
<213> ORGANISM: human

<400> SEQUENCE: 1076

Val Trp Ala Ala
1

<210> SEQ ID NO 1077
<211> LENGTH: 4
<212> TYPE: PRT
<213> ORGANISM: human

<400> SEQUENCE: 1077

Val Trp Ala Ala
1

<210> SEQ ID NO 1078
<211> LENGTH: 4
<212> TYPE: PRT
<213> ORGANISM: human

<400> SEQUENCE: 1078

Val Trp Ala Ala
1

<210> SEQ ID NO 1079
<211> LENGTH: 4
<212> TYPE: PRT
<213> ORGANISM: human

<400> SEQUENCE: 1079
```

Val Trp Ala Ala
1

<210> SEQ ID NO 1080
<211> LENGTH: 10
<212> TYPE: PRT
<213> ORGANISM: human

<400> SEQUENCE: 1080

Cys Thr Asn Gly Ile Leu Leu Lys Lys Ile
1               5                   10

<210> SEQ ID NO 1081
<211> LENGTH: 8
<212> TYPE: PRT
<213> ORGANISM: human

<400> SEQUENCE: 1081

Asn Gly Ile Leu Leu Lys Lys Ile
1               5

<210> SEQ ID NO 1082
<211> LENGTH: 7
<212> TYPE: PRT
<213> ORGANISM: human

<400> SEQUENCE: 1082

Asn Ile Leu Leu Lys Lys Ile
1               5

<210> SEQ ID NO 1083
<211> LENGTH: 8
<212> TYPE: PRT
<213> ORGANISM: human

<400> SEQUENCE: 1083

Asn Ser Ile Leu Leu Lys Lys Ile
1               5

<210> SEQ ID NO 1084
<211> LENGTH: 7
<212> TYPE: PRT
<213> ORGANISM: human

<400> SEQUENCE: 1084

Cys Thr Asn Gly Ile Leu Leu
1               5

<210> SEQ ID NO 1085
<211> LENGTH: 6
<212> TYPE: PRT
<213> ORGANISM: human

<400> SEQUENCE: 1085

Cys Thr Asn Gly Leu Leu
1               5

<210> SEQ ID NO 1086
<211> LENGTH: 7
<212> TYPE: PRT
<213> ORGANISM: human

<400> SEQUENCE: 1086

Cys Thr Asn Gly Val Leu Leu
1               5

<210> SEQ ID NO 1087
<211> LENGTH: 8
<212> TYPE: PRT
<213> ORGANISM: human

<400> SEQUENCE: 1087

Asn Gly Ile Leu Leu Lys Lys Ile
1               5

<210> SEQ ID NO 1088
<211> LENGTH: 6
<212> TYPE: PRT
<213> ORGANISM: human

<400> SEQUENCE: 1088

Asn Gly Ile Leu Lys Ile
1               5

<210> SEQ ID NO 1089
<211> LENGTH: 8
<212> TYPE: PRT
<213> ORGANISM: human

<400> SEQUENCE: 1089

Asn Gly Ile Met Leu Arg Lys Ile
1               5

<210> SEQ ID NO 1090
<211> LENGTH: 9
<212> TYPE: PRT
<213> ORGANISM: human

<400> SEQUENCE: 1090

Cys Thr Asn Gly Ile Leu Leu Lys Lys
1               5

<210> SEQ ID NO 1091
<211> LENGTH: 6
<212> TYPE: PRT
<213> ORGANISM: human

<400> SEQUENCE: 1091

Cys Thr Gly Leu Leu Lys
1               5

<210> SEQ ID NO 1092
<211> LENGTH: 9
<212> TYPE: PRT
<213> ORGANISM: human

<400> SEQUENCE: 1092

Cys Thr Thr Gly Val Leu Leu Arg Lys
1               5

<210> SEQ ID NO 1093
<211> LENGTH: 30
<212> TYPE: PRT
<213> ORGANISM: human

<400> SEQUENCE: 1093

His Ser His Ile Ser Asn Arg Lys Thr Thr Asn Gly Tyr Leu Glu Val
1               5                   10                  15

Ala Pro Thr Trp Lys Gly Lys Ala Gly Gln Gly Phe Gly His

-continued

```
                    20                  25                  30
```

<210> SEQ ID NO 1094
<211> LENGTH: 10
<212> TYPE: PRT
<213> ORGANISM: human

<400> SEQUENCE: 1094

```
Trp Lys Gly Lys Ala Gly Gln Gly Phe Gly
1               5                   10
```

<210> SEQ ID NO 1095
<211> LENGTH: 8
<212> TYPE: PRT
<213> ORGANISM: human

<400> SEQUENCE: 1095

```
Trp Gly Ala Gly Gln Gly Phe Gly
1               5
```

<210> SEQ ID NO 1096
<211> LENGTH: 10
<212> TYPE: PRT
<213> ORGANISM: human

<400> SEQUENCE: 1096

```
Trp Arg Gly Arg Ala Gly Gln Gly Phe Gly
1               5                   10
```

<210> SEQ ID NO 1097
<211> LENGTH: 17
<212> TYPE: PRT
<213> ORGANISM: human

<400> SEQUENCE: 1097

```
Ile Ser Asn Arg Lys Thr Thr Asn Gly Tyr Leu Glu Val Ala Pro Thr
1               5                   10                  15

Trp
```

<210> SEQ ID NO 1098
<211> LENGTH: 12
<212> TYPE: PRT
<213> ORGANISM: human

<400> SEQUENCE: 1098

```
Ile Ser Arg Lys Thr Thr Gly Glu Val Ala Pro Trp
1               5                   10
```

<210> SEQ ID NO 1099
<211> LENGTH: 17
<212> TYPE: PRT
<213> ORGANISM: human

<400> SEQUENCE: 1099

```
Ile Ser Ala Arg Lys Pro Phe Thr Leu Gly Glu Val Ala Pro Val
1               5                   10                  15

Trp
```

<210> SEQ ID NO 1100
<211> LENGTH: 15
<212> TYPE: PRT
<213> ORGANISM: human

<400> SEQUENCE: 1100

```
Arg Lys Thr Thr Asn Gly Tyr Leu Glu Val Ala Pro Thr Trp Lys
1               5                   10                  15

<210> SEQ ID NO 1101
<211> LENGTH: 9
<212> TYPE: PRT
<213> ORGANISM: human

<400> SEQUENCE: 1101

Arg Lys Thr Thr Tyr Val Pro Trp Lys
1               5

<210> SEQ ID NO 1102
<211> LENGTH: 15
<212> TYPE: PRT
<213> ORGANISM: human

<400> SEQUENCE: 1102

Arg Lys Thr Thr Leu Tyr Asp Met Asp Val Glu Pro Ser Trp Lys
1               5                   10                  15

<210> SEQ ID NO 1103
<211> LENGTH: 7
<212> TYPE: PRT
<213> ORGANISM: human

<400> SEQUENCE: 1103

Tyr Arg Leu Met Glu Glu Asn
1               5

<210> SEQ ID NO 1104
<211> LENGTH: 6
<212> TYPE: PRT
<213> ORGANISM: human

<400> SEQUENCE: 1104

Arg Leu Met Glu Glu Asn
1               5

<210> SEQ ID NO 1105
<211> LENGTH: 6
<212> TYPE: PRT
<213> ORGANISM: human

<400> SEQUENCE: 1105

Arg Leu Met Glu Glu Asn
1               5

<210> SEQ ID NO 1106
<211> LENGTH: 6
<212> TYPE: PRT
<213> ORGANISM: human

<400> SEQUENCE: 1106

Arg Leu Met Glu Glu Asn
1               5

<210> SEQ ID NO 1107
<211> LENGTH: 7
<212> TYPE: PRT
<213> ORGANISM: human

<400> SEQUENCE: 1107

Tyr Arg Leu Met Glu Glu Asn
```

-continued

```
1               5

<210> SEQ ID NO 1108
<211> LENGTH: 7
<212> TYPE: PRT
<213> ORGANISM: human

<400> SEQUENCE: 1108

Tyr Arg Leu Met Glu Glu Asn
1               5

<210> SEQ ID NO 1109
<211> LENGTH: 8
<212> TYPE: PRT
<213> ORGANISM: human

<400> SEQUENCE: 1109

Tyr Arg Leu Glu Met Glu Glu Asn
1               5

<210> SEQ ID NO 1110
<211> LENGTH: 5
<212> TYPE: PRT
<213> ORGANISM: human

<400> SEQUENCE: 1110

Arg Leu Met Glu Glu
1               5

<210> SEQ ID NO 1111
<211> LENGTH: 4
<212> TYPE: PRT
<213> ORGANISM: human

<400> SEQUENCE: 1111

Arg Leu Met Glu
1

<210> SEQ ID NO 1112
<211> LENGTH: 5
<212> TYPE: PRT
<213> ORGANISM: human

<400> SEQUENCE: 1112

Arg Leu Met Asp Glu
1               5

<210> SEQ ID NO 1113
<211> LENGTH: 7
<212> TYPE: PRT
<213> ORGANISM: human

<400> SEQUENCE: 1113

Tyr Arg Leu Met Glu Glu Asn
1               5

<210> SEQ ID NO 1114
<211> LENGTH: 7
<212> TYPE: PRT
<213> ORGANISM: human

<400> SEQUENCE: 1114

Tyr Arg Leu Met Glu Glu Asn
1               5
```

<210> SEQ ID NO 1115
<211> LENGTH: 8
<212> TYPE: PRT
<213> ORGANISM: human

<400> SEQUENCE: 1115

Tyr Arg Leu Glu Met Glu Glu Asn
1               5

<210> SEQ ID NO 1116
<211> LENGTH: 5
<212> TYPE: PRT
<213> ORGANISM: human

<400> SEQUENCE: 1116

Arg Leu Met Glu Glu
1               5

<210> SEQ ID NO 1117
<211> LENGTH: 4
<212> TYPE: PRT
<213> ORGANISM: human

<400> SEQUENCE: 1117

Arg Leu Met Glu
1

<210> SEQ ID NO 1118
<211> LENGTH: 5
<212> TYPE: PRT
<213> ORGANISM: human

<400> SEQUENCE: 1118

Arg Leu Met Asp Glu
1               5

<210> SEQ ID NO 1119
<211> LENGTH: 13
<212> TYPE: PRT
<213> ORGANISM: human

<400> SEQUENCE: 1119

Lys Ser Phe Lys Tyr Asn Ile Ser Leu Met Phe Cys Lys
1               5                   10

<210> SEQ ID NO 1120
<211> LENGTH: 12
<212> TYPE: PRT
<213> ORGANISM: human

<400> SEQUENCE: 1120

Ser Phe Lys Tyr Asn Ile Ser Leu Met Phe Cys Lys
1               5                   10

<210> SEQ ID NO 1121
<211> LENGTH: 9
<212> TYPE: PRT
<213> ORGANISM: human

<400> SEQUENCE: 1121

Ser Tyr Ile Ser Leu Met Phe Cys Lys
1               5

<210> SEQ ID NO 1122

```
<211> LENGTH: 20
<212> TYPE: PRT
<213> ORGANISM: human

<400> SEQUENCE: 1122

Ser Tyr Met Tyr Gln Ile Ser Leu Gln Gln Ala Phe Cys Thr Val Ile
1               5                   10                  15

Met Phe Cys Lys
            20

<210> SEQ ID NO 1123
<211> LENGTH: 8
<212> TYPE: PRT
<213> ORGANISM: human

<400> SEQUENCE: 1123

Tyr Asn Ile Ser Leu Met Phe Cys
1               5

<210> SEQ ID NO 1124
<211> LENGTH: 7
<212> TYPE: PRT
<213> ORGANISM: human

<400> SEQUENCE: 1124

Tyr Asn Ile Leu Met Phe Cys
1               5

<210> SEQ ID NO 1125
<211> LENGTH: 7
<212> TYPE: PRT
<213> ORGANISM: human

<400> SEQUENCE: 1125

Tyr Asn Ile Leu Met Phe Cys
1               5

<210> SEQ ID NO 1126
<211> LENGTH: 10
<212> TYPE: PRT
<213> ORGANISM: human

<400> SEQUENCE: 1126

Lys Ser Phe Lys Tyr Asn Ile Ser Leu Met
1               5                   10

<210> SEQ ID NO 1127
<211> LENGTH: 8
<212> TYPE: PRT
<213> ORGANISM: human

<400> SEQUENCE: 1127

Lys Ser Phe Lys Tyr Asn Ser Leu
1               5

<210> SEQ ID NO 1128
<211> LENGTH: 9
<212> TYPE: PRT
<213> ORGANISM: human

<400> SEQUENCE: 1128

Lys Ser Phe Lys Tyr Asn Ser Leu Leu
1               5
```

```
<210> SEQ ID NO 1129
<211> LENGTH: 6
<212> TYPE: PRT
<213> ORGANISM: human

<400> SEQUENCE: 1129

Gly Ile Ser Thr Leu Lys
1               5

<210> SEQ ID NO 1130
<211> LENGTH: 6
<212> TYPE: PRT
<213> ORGANISM: human

<400> SEQUENCE: 1130

Gly Ile Ser Thr Leu Lys
1               5

<210> SEQ ID NO 1131
<211> LENGTH: 6
<212> TYPE: PRT
<213> ORGANISM: human
<220> FEATURE:
<221> NAME/KEY: misc_feature
<222> LOCATION: (6)..(9)
<223> OTHER INFORMATION: Xaa can be any naturally occurring amino acid

<400> SEQUENCE: 1131

Gly Ile Ser Thr Leu Lys
1               5

<210> SEQ ID NO 1132
<211> LENGTH: 6
<212> TYPE: PRT
<213> ORGANISM: human

<400> SEQUENCE: 1132

Gly Ile Ser Thr Leu Lys
1               5

<210> SEQ ID NO 1133
<211> LENGTH: 10
<212> TYPE: PRT
<213> ORGANISM: human
<220> FEATURE:
<221> NAME/KEY: misc_feature
<222> LOCATION: (6)..(9)
<223> OTHER INFORMATION: Xaa can be any naturally occurring amino acid

<400> SEQUENCE: 1133

Ile Ser Thr Leu Lys Xaa Xaa Xaa Xaa Lys
1               5                   10

<210> SEQ ID NO 1134
<211> LENGTH: 6
<212> TYPE: PRT
<213> ORGANISM: human
<220> FEATURE:
<221> NAME/KEY: misc_feature
<222> LOCATION: (5)..(8)
<223> OTHER INFORMATION: Xaa can be any naturally occurring amino acid

<400> SEQUENCE: 1134

Ile Ser Thr Leu Lys Lys
1               5

<210> SEQ ID NO 1135
```

```
<211> LENGTH: 10
<212> TYPE: PRT
<213> ORGANISM: human

<400> SEQUENCE: 1135

Ile Ser Thr Leu Lys Lys Lys Thr Asn Lys
1               5                   10

<210> SEQ ID NO 1136
<211> LENGTH: 10
<212> TYPE: PRT
<213> ORGANISM: human
<220> FEATURE:
<221> NAME/KEY: misc_feature
<222> LOCATION: (5)..(8)
<223> OTHER INFORMATION: Xaa can be any naturally occurring amino acid

<400> SEQUENCE: 1136

Ser Thr Leu Lys Xaa Xaa Xaa Xaa Lys Leu
1               5                   10

<210> SEQ ID NO 1137
<211> LENGTH: 6
<212> TYPE: PRT
<213> ORGANISM: human

<400> SEQUENCE: 1137

Ser Thr Leu Lys Lys Leu
1               5

<210> SEQ ID NO 1138
<211> LENGTH: 10
<212> TYPE: PRT
<213> ORGANISM: human

<400> SEQUENCE: 1138

Ser Thr Leu Lys Gln Leu Glu Glu Lys Leu
1               5                   10

<210> SEQ ID NO 1139
<211> LENGTH: 5
<212> TYPE: PRT
<213> ORGANISM: human

<400> SEQUENCE: 1139

Gly Asp Pro Asn Ser
1               5

<210> SEQ ID NO 1140
<211> LENGTH: 5
<212> TYPE: PRT
<213> ORGANISM: human

<400> SEQUENCE: 1140

Gly Asp Pro Asn Ser
1               5

<210> SEQ ID NO 1141
<211> LENGTH: 5
<212> TYPE: PRT
<213> ORGANISM: human

<400> SEQUENCE: 1141

Gly Asp Pro Asn Ser
1               5
```

```
<210> SEQ ID NO 1142
<211> LENGTH: 5
<212> TYPE: PRT
<213> ORGANISM: human

<400> SEQUENCE: 1142

Gly Asp Pro Asn Ser
1               5

<210> SEQ ID NO 1143

<400> SEQUENCE: 1143

000

<210> SEQ ID NO 1144

<400> SEQUENCE: 1144

000

<210> SEQ ID NO 1145

<400> SEQUENCE: 1145

000

<210> SEQ ID NO 1146

<400> SEQUENCE: 1146

000

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149

000

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152
```

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

-continued

```
<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000
```

NEOEPITOPE DETECTION OF DISEASE USING PROTEIN ARRAYS

CROSS-REFERENCE TO RELATED APPLICATIONS

This Continuation-In-Part Application claims priority to U.S. Continuation-In-Part patent application Ser. No. 11/060,867, filed Feb. 17, 2005, issued as U.S. Pat. No. 7,964,536 and U.S. Continuation-In-Part patent application Ser. No. 10/004,587, filed Dec. 4, 2001, issued as U.S. Pat. No. 7,863,004, which is incorporated herein by reference.

GRANT INFORMATION

Research in this application was supported in part by a grant from the National Institute of Health (NIH Grant No. IR21CA100740-01) and a grant from MEDC (Grant No. MLSC 558). The Government has certain rights in the invention.

STATEMENT REGARDING SEQUENCE LISTING

The sequence listing associated with this application is provided in electronic text format and is hereby incorporated by reference into the specification. The name of the text file containing the sequence listing is: 0788 5 AMEND SqncListAsEfiled111610.txt. The file is 208 KB and was created on Nov. 16, 2010.

BACKGROUND OF THE INVENTION

1. Technical Field

The present invention relates to an assay and method for diagnosing disease. More specifically, the present invention relates to an immunoassay for use in diagnosing cancer.

2. Background Art

It is commonly known in the art that genetic mutations can be used for detecting cancer. For example, the tumorigenic process leading to colorectal carcinoma formation involves multiple genetic alterations (Fearon, et al. (1990) Cell 61, 759-767). Tumor suppressor genes such as p53, DCC and APC are frequently inactivated in colorectal carcinomas, typically by a combination of genetic deletion of one allele and point mutation of the second allele (Baker, et al. (1989) Science 244, 217-221; Fearon, et al. (1990) Science 247, 49-56; Nishisho, et al. (1991) Science 253, 665-669; and Groden, et al. (1991) Cell 66, 589-600). Mutation of two mismatch repair genes that regulate genetic stability was associated with a form of familial colon cancer (Fishel, et al. (1993) Cell 75, 1027-1038; Leach, et al. (1993) Cell 75, 1215-1225; Papadopoulos, et al. (1994) Science 263, 1625-1629; and Bronner, et al. (1994) Nature 368, 258-261). Proto-oncogenes such as myc and ras are altered in colorectal carcinomas, with c-myc RNA being overexpressed in as many as 65% of carcinomas (Erisman, et al. (1985) Mol. Cell. Biol. 5, 1969-1976), and ras activation by point mutation occurring in as many as 50% of carcinomas (Bos, et al. (1987) Nature 327, 293-297; and Forrester, et al. (1987) Nature 327, 298-303). Other proto-oncogenes, such as myb and neu are activated with a much lower frequency (Alitalo, et al. (1984) Proc. Natl. Acad. Sci. USA 81, 4534-4538; and D'Emilia, et al. (1989) Oncogene 4, 1233-1239). No common series of genetic alterations is found in all colorectal tumors, suggesting that a variety of such combinations can be able to generate these tumors.

Increased tyrosine phosphorylation is a common element in signaling pathways that control cell proliferation. The deregulation of protein tyrosine kinases (PTKS) through overexpression or mutation has been recognized as an important step in cell transformation and tumorigenesis, and many oncogenes encode PTKs (Hunter (1989) in oncogenes and the Molecular Origins of Cancer, ed. Weinberg (Cold Spring Harbor Laboratory Press, Cold Spring Harbor, N.Y.), pp. 147-173). Numerous studies have addressed the involvement of PTKs in human tumorigenesis. Activated PTKs associated with colorectal carcinoma include c-neu (amplification), trk (rearrangement), and c-src and c-yes (mechanism unknown) (D'Emilia, et al. (1989), ibid; Martin-Zanca, et al. (1986) Nature 3, 743-748; Bolen, et al. (1987) Proc. Natl. Acad. Sci. USA 84, 2251-2255; Cartwright, et al. (1989) J. Clin. Invest. 83, 2025-2033; Cartwright, et al. (1990) Proc. Natl. Acad. Sci. USA 87, 558-562; Talamonti, et al. (1993) J. Clin. Invest. 91, 53-60; and Park, et al. (1993) Oncogene 8, 2627-2635).

Mutations, such as those disclosed above can be useful in detecting cancer. However, there have been few advancements which can repeatably be used in diagnosing cancer prior to the existence of a tumor. Approximately 40,500 new cases of head and neck squamous cell carcinoma (HNSCC) will be diagnosed in the United States and 11,170 Americans will die from this disease in the year 2006. Worldwide, HNSCC is the sixth most common malignancy with incidence of 644,000 new cases a year. Despite progress in diagnostic and treatment modalities in the past 30 years, long-term survival for patients affected by HNSCC has not significantly improved. One major impediment to improving survival in this patient population is the failure to detect this cancer at an early stage. More than two-thirds of patients with HNSCC are diagnosed at an advanced stage when the five-year survival is less than 40%. In many cases, these patients are offered radical treatments that often result in significant physical disfigurement as well as dysfunction of speech, breathing, and swallowing. The plight of these patients with advanced stage disease is in distinct contrast to that of patients who are diagnosed early. Early stage HNSCC patients have an excellent five-year survival rate of more than 80% and experience significantly less impact on their quality of life after treatment with single modality therapy. This dramatic difference in survival and quality of life underlies the importance of early detection in this disease.

Early detection can be achieved by screening patients at high risk for development of cancer. Although the American Cancer Society has issued guidelines for screening of breast, colon, prostate, and uterine cancers, no such guideline exists for HNSCC. This is especially unfortunate given that patients at increased risk for development of HNSCC can be easily identified (history of excess alcohol and/or tobacco use) and targeted for screening. Early detection can also be improved by reducing diagnostic delays, reported to be between 3 to 5.6 months. Misdiagnosis at initial presentation to primary care physicians is common (44% to 63%) and may be due to the nonspecific nature of presenting symptoms (sore throat, hoarseness, ear pain, etc) as well as the technical difficulty of examination in the head and neck region. The delay in diagnosis and referral to specialist has a significant negative impact on patient outcome and survival. Thus, there exists a need for a simple, noninvasive, and inexpensive test, widely accessible to physicians in the primary care setting, which can be used to screen (in asymptomatic patients) and diagnose (in symptomatic patients) HNSCC in high risk population to improve early detection.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art that allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of cancer evaluation, the use of conventional or needle biopsy samples for cancer marker assays is often undesirable, because a primary goal of such assays is to detect the cancer before it progresses to a palpable or detectable tumor stage. Prior to this stage, biopsies are generally contraindicated, making early screening and low risk monitoring procedures employing such samples untenable. Therefore, there is a general need in the art to obtain samples for cancer marker assays by less invasive means than biopsy, for example, by serum withdrawal.

Efforts to utilize serum samples for cancer marker assays have met with limited success, largely because the targeted markers are either not detectable in serum, or because telltale changes in the levels or activity of the markers cannot be monitored in serum. In addition, the presence of cancer markers in serum probably occurs at the time of micro-metastasis, making serum assays less useful for detecting pre-metastatic disease. Serological analysis of recombinant cDNA expression libraries (SEREX) of tumors with autologous serum is a well established technique which has been used successfully to identify many relevant tumor antigens. However, many of the SEREX antigens identified from a specific cancer patient reacted only with autologous serum antibodies from that particular patient and tend to recognize antibodies only at a low frequency in sera from other cancer patients. Thus, clinical tests based on these SEREX antigens that are patient-specific rather than cancer-specific are insufficient for early detection of cancer.

In view of the above, an important need exists in the art for more widely applicable, non-invasive methods and materials to obtain biological samples for use in evaluating, diagnosing and managing breast and other diseases including cancer, particularly for screening early stage, nonpalpable tumors. A related need exists for methods and materials that utilize such readily obtained biological samples to evaluate, diagnose and manage disease, particularly by detecting or measuring selected cancer markers, or panels of cancer markers, to provide highly specific, cancer prognostic and/or treatment-related information, and to diagnose and manage pre-cancerous conditions, cancer susceptibility, bacterial and other infections, and other diseases.

Autoantibodies against cancer-specific antigens have been identified in cancers of the colon, breast, kidney, lung, ovarian, and head and neck. Immune response with antibody production may be elicited due to the over-expression of cellular proteins such as Her2, the expression of mutated forms of cellular protein such as mutated p53, or the aberrant expression of tissue-restricted gene products such as cancer-testis antigens by cancer cells. Because these autoantibodies are raised against specific antigens from the cancer cells, the detection of these antibodies in a patient's serum can be exploited as diagnostic biomarkers of cancer in that particular patient. Further, the immune system is especially well adapted for the early detection of cancer since it can respond to even low levels of an antigen by mounting a very specific and sensitive antibody response. Thus, the use of immune response as a biosensor for early detection of cancer through serum-based assay holds great potential as an ideal screening and diagnostic tool.

With specific regard to such assays, specific antibodies can only be measured by detecting binding to their antigen or a mimic thereof. Although certain classes of immunoglobulins containing the antibodies of interest can, in some cases, be separated from the sample prior to the assay (Decker, et al., EP 0,168,689 A2), in all assays, at least some portion of the sample immunoglobulins are contacted with antigen. For example, in assays for specific IgM, a portion of the total IgM can be adsorbed to a surface and the sample removed prior to detection of the specific IgM by contacting with antigen. Binding is then measured by detection of the bound antibody, detection of the bound antigen or detection of the free antigen.

For detection of bound antibody, a labeled anti-human immunoglobulin or labeled antigen is normally allowed to bind antibodies that have been specifically adsorbed from the sample onto a surface coated with the antigen, Bolz, et al., U.S. Pat. No. 4,020,151. Excess reagent is washed away and the label that remains bound to the surface is detected. This is the procedure in the most frequently used assays, or example, for hepatitis and human immunodeficiency virus and for numerous immunohistochemical tests, Nakamura, et al., Arch Pathol Lab Med 1122:869-877 (1988). Although this method is relatively sensitive, it is subject to interference from non-specific binding to the surface by non-specific immunoglobulins that can not be differentiated from the specific immunoglobulins.

Another method of detecting bound antibodies involves combining the sample and a competing labeled antibody, with a support-bound antigen, Schuurs, et al., U.S. Pat. No. 3,654,090. This method has its limitations because antibodies in sera bind numerous epitopes, making competition inefficient.

For detection of bound antigen, the antigen can be used in excess of the maximum amount of antibody that is present in the sample or in an amount that is less than the amount of antibody. For example, radioimmunoprecipitation ("RIP") assays for GAD autoantibodies have been developed and are currently in use, Atkinson, et al., Lancet 335:1357-1360 (1990). However, attempts to convert this assay to an enzyme linked immunosorbent assay ("ELISA") format have not been successful. The RIP assay is based on precipitation of immunoglobulins in human sera, and led to the development of a radioimmunoassay ("RIA") for GAD autoantibodies. In both the RIP and the RIA, the antigen is added in excess and the bound antigen:antibody complex is precipitated with protein A-Sepharose. The complex is then washed or further separated by electrophoresis and the antigen in the complex is detected.

Other precipitating agents can be used such as rheumatoid factor or C1q, Masson, et al., U.S. Pat. No. 4,062,935; polyethylene glycol, Soeldner, et al., U.S. Pat. No. 4,855, 242; and protein A, Ito, et al., EP 0,410,893 A2. The precipitated antigen can be measured to indicate the amount of antibody in the sample; the amount of antigen remaining in solution can be measured; or both the precipitated antigen and the soluble antigen can be measured to correct for any labeled antigen that is non-specifically precipitated. These methods, while quite sensitive, are all difficult to carry out because of the need for rigorous separation of the free antigen from the bound complex, which requires at a minimum filtration or centrifugation and multiple washing of the precipitate.

Alternatively, detection of the bound antigen can be employed when the amount of antigen is less than the maximum amount of antibody. Normally, that is carried out using particles such as latex particles or erythrocytes that are coated with the antigen, Cambiaso, et al., U.S. Pat. No. 4,184,849 and Uchida, et al., EP 0,070,527 A1. Antibodies can specifically agglutinate these particles and can then be detected by light scattering or other methods. It is necessary in these assays to use a precise amount of antigen as too little antigen provides an assay response that is biphasic and high antibody titers can be read as negative, while too much antigen adversely affects the sensitivity. It is therefore necessary to carry out sequential dilutions of the sample to assure that positive samples are not missed. Further, these assays tend to detect only antibodies with relatively high affinities and the sensitivity of the method is compromised by the tendency for all of the binding sites of each antibody to bind to the antigen on the particle to which it first binds, leaving no sites for binding to the other particle.

For assays in which the free antigen is detected, the antigen can also be added in excess or in a limited amount although only the former has been reported. Assays of this type have been described where an excess of antigen is added to the sample, the immunoglobulins are precipitated, and the antigen remaining in the solution is measured, Masson, et al., supra and Soeldner, et al., supra. These assays are relatively insensitive because only a small percentage change in the amount of free antigen occurs with low amounts of antibody, and this small percentage is difficult to measure accurately.

Practical assays in which the free antigen is detected and the antigen is not present in excess of the maximum amount of antibody expected in a sample have not been described. However, in van Erp, et al., Journal of Immunoassay 12(3): 425-443 (1991), a fixed concentration of monoclonal antibody was incubated with a concentration dilution series of antigen, and free antigen was then measured using a gold sol particle agglutination immunoassay to determine antibody affinity constants.

There has been much research in the area of evaluating useful markers for determining the risk factor for patients developing IDDM. These include insulin autoantibodies, Soeldner, et al., supra and circulating autoantibodies to glutamic acid decarboxylase ("GAD"), Atkinson, et al., PCT/US89/05570 and Tobin, et al., PCT/US91/06872. In addition, Rabin, et al., U.S. Pat. No. 5,200,318 describes numerous assay formats for the detection of GAD and pancreatic islet cell antigen autoantibodies. GAD autoantibodies are of particular diagnostic importance because they occur in preclinical stages of the disease, which can make therapeutic intervention possible. However, the use of GAD autoantibodies as a diagnostic marker has been impeded by the lack of a convenient, nonisotopic assay.

One assay method involves incubating a support-bound antigen with the sample, then adding a labeled anti-human immunoglobulin. This is the basis for numerous commercially available assay kits for antibodies such as the Syn ELISA kit which assays for autoantibodies to GAD65, and is described in product literature entitled "Syn$^{ELISA}$ GAD II-Antibodies" (Elias USA, Inc.). Substantial dilution of the sample is required because the method is subject to high background signals from adsorption of non-specific human immunoglobulins to the support.

Many of the assays described above involve detection of antibody that becomes bound to an immobilized antigen. This can have an adverse affect on the sensitivity of the assay due to difficulty in distinguishing between specific immunoglobulins and other immunoglobulins in the sample, which bind non-specifically to the immobilized antigen. There is not only a need to develop an assay that avoids non-specific detection of immunoglobulins, but there is also the need for an improved method of detecting antibodies that combines the sensitivity advantage of immunoprecipitation assays with a simplified protocol. Finally, assays that can help evaluate the risk of developing diseases are medically and economically very important. The present invention addresses these needs.

SUMMARY OF THE INVENTION

The present invention provides for a diagnostic device for use in detecting the presence of HNSCC in a patient including a detector device for detecting a presence of at least one marker indicative of HNSCC, the detector device including a panel of markers for HNSCC.

The present invention also provides for a diagnostic device for use in staging HNSCC in a patient including a detector device for detecting a presence of at least one marker indicative of stages of HNSCC, the detector device including a panel of markers for HNSCC.

Markers for HNSCC are provided selected from the markers listed in Table 5.

A method of diagnosing HNSCC is provided, including the steps of detecting markers in the serum of a patient indicative of the presence of HNSCC, and diagnosing the patient with HNSCC.

A method of staging HNSCC is provided, including the steps of detecting markers in the serum of a patient indicative of a stage of HNSCC, and determining the stage of HNSCC. A method of staging cancer is also similarly provided.

Further provided is a method of personalized immunotherapy, including the steps of detecting markers in the serum of a patient with the above diagnostic device, analyzing reactivity of markers in the serum to markers in the panel, identifying markers in the serum with the highest reactivity, and using the markers identified as immunotherapeutic agents personalized to the immunoprofile of the patient. A method of personalized targeted therapy is similarly provided.

A method of making a personalized anti-cancer vaccine is provided, including the steps of detecting markers in the serum of a patient with the above diagnostic device, analyzing reactivity of markers in the serum to markers in the panel, identifying markers in the serum with the highest reactivity, and formulating an anti-cancer vaccine using the identified markers.

Also provided is a method of predicting a clinical outcome in a HNSCC patient, including the steps of analyzing a pattern of reactivity of a patient's serum with a panel of HNSCC markers, and predicting a clinical outcome.

A method of making a panel of head and neck squamous cell carcinoma markers is provided, including the steps of creating HNSCC cDNA libraries, replicating the HNSCC cDNA libraries, performing differential biopanning, selecting clones to be arrayed on a protein microarray, immunoreacting the microarray against HNSCC patient serum, and selecting highly reactive clones for placement on a panel.

DESCRIPTION OF THE DRAWINGS

Other advantages of the present invention are readily appreciated as the same becomes better understood by reference to the following detailed description when considered in connection with the accompanying drawings wherein:

FIG. 1 shows the matrix of reactivity between sets of clones coming from patients 1-12 (in rows) and sera from same patients (in columns). At this point (step 2 of Procedure 2), the matrix contains the results of the self-reactions: patients 1-10 have a specific self-reaction whereas patients 11 and 12 do not, and patients 11 and 12 are eliminated from the clone selection procedure;

FIG. 2 shows a matrix of reactivity between sources of clones and different sera ordered by reactivity; the clones from patient 2 react with sera from self (column 2) and patients 4 and 8; the clones from patient 3 react with sera from self (column 3) and patients 6 and 10, etc. Note that the union of the set of clones coming from patients 2, 3, 5, 7 and 1 ensures that the chip made with these clones reacts with all patients;

FIGS. 4A and 4B are photographs showing phage clones spotted in replication of six in an ordered array onto nitrocellulose coated glass slides;

DETAILED DESCRIPTION OF THE INVENTION

Figure 3:
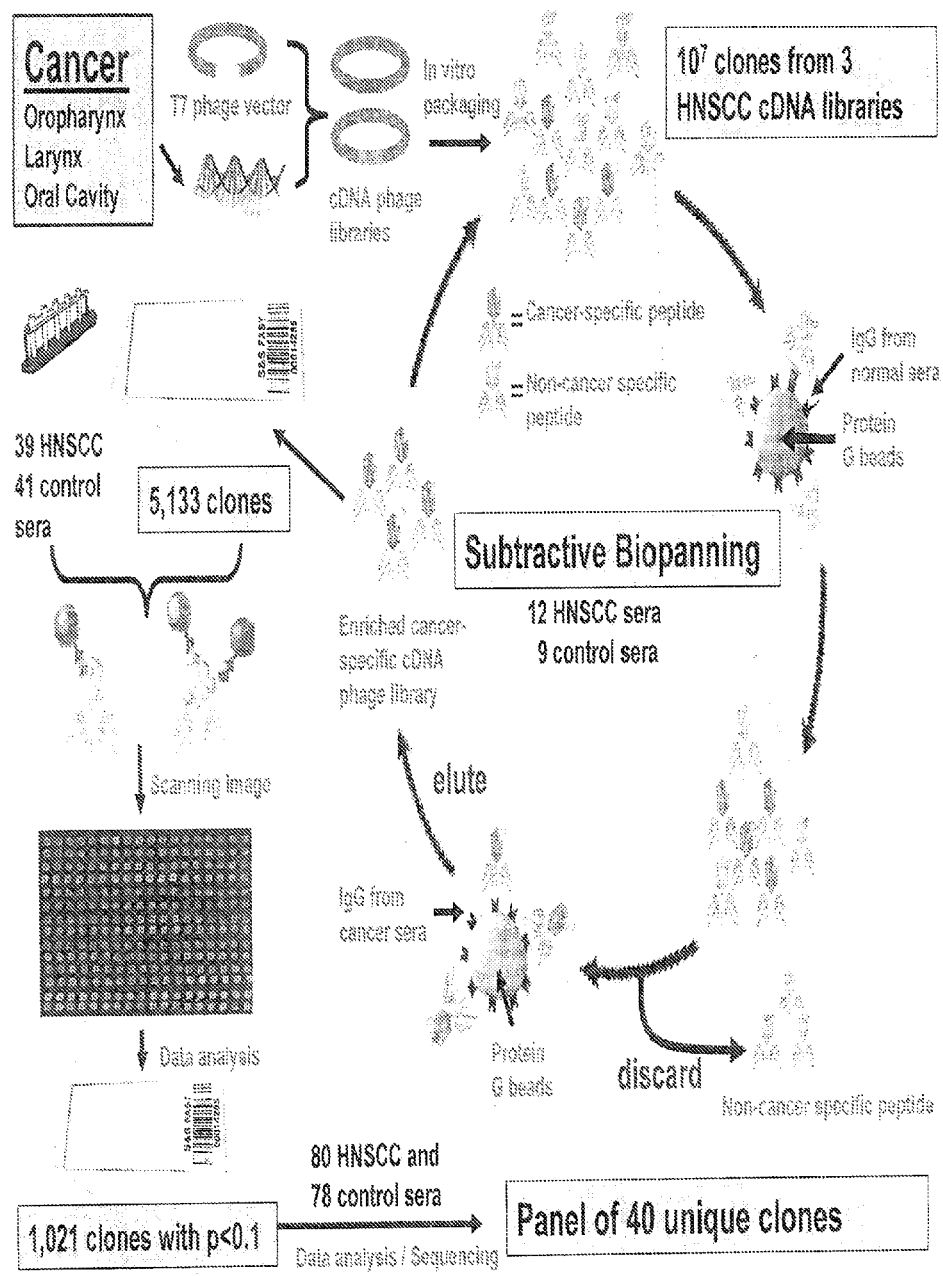
FIG. 3 is a schema showing the process of the present invention.

Generally, the present invention provides a method and markers for use in detecting disease and stages of disease. In other words, the markers can be used to determine the presence of disease without requiring the presence of symptoms. Particularly, the present invention provides a method and markers for use in detecting HNSCC and stages of HNSCC, as well as various other diagnostic methods, which are further described below.

The present invention can further be understood in light of the following terms and definitions.

By "bodily fluid" as used herein it is meant any bodily fluid known to those of skill in the art to contain antibodies therein. Examples include, but are not limited to, blood, saliva, tears, spinal fluid, serum, and other fluids known to those of skill in the art to contain antibodies.

By "biopanning", it is meant a selection process for use in screening a library (Parmley and Smith, Gene, 73:308 (1988); Noren, C. J., NEB Transcript, 8(1); 1 (1996)). Biopanning is carried out by incubating phages encoding the peptides with a plate coated with the proteins, washing away the unbound phage, eluting, and amplifying the specifically bound phage. Those skilled in the art readily recognize other immobilization schemes that can provide equivalent technology, such as but not limited to binding the proteins or other targets to beads.

By "staging" the disease, as for example in cancer, it is intended to include determining the extent of a cancer, especially whether the disease has spread from the original site to other parts of the body. The stages can range from 0 to 5 with 0 being the presence of cancerous cells and 5 being the spread of the cancer cells to other parts of the body including the lymph nodes. Further, the staging can indicate the stage of a borderline histology. A borderline histology is a less malignant form of disease. Additionally, staging can indicate a relapse of disease, in other words the reoccurrence of disease.

The term "marker" as used herein is intended to include, but is not limited to, a gene or a piece of a gene which codes for a protein, a protein such as a fusion protein, open reading frames such as ESTs, epitopes, mimotopes, antigens, and any other indicator of immune response. Each of these terms is used interchangeably to refer to a marker. The marker can also be used as a predictor of disease or the recurrence of disease.

"Mimotope" refers to a random peptide epitope that mimics a natural antigenic epitope during epitope presentation, which is further included in the invention. Such mimotopes are useful in the applications and methods discussed below. Also included in the present invention is a method of identifying a random peptide epitope. In the method, a library of random peptide epitopes is generated or selected. The library is contacted with an anti-antibody. Mimotopes are identified that are specifically immunoreactive with the antibody. Sera (containing anti antibodies) or antibodies generated by the methods of the present invention can be used. Random peptide libraries can, for example, be displayed on phage (phagotopes) or generated as combinatorial libraries.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the various immunoglobulin diversity/joining/variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$ 1 by a disulfide bond. The F(ab)'$_2$ can be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill can appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al., Nature 348:552-554 (1990)).

For preparation of monoclonal or polyclonal antibodies, any technique known in the art can be used (see, e.g., Kohler & Milstein, Nature 256:495-497 (1975); Kozbor, et al., Immunology Today 4: 72 (1983); Cole, et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, can be used to express humanized antibodies. Alternatively, phage display technology can be used to identify antibodies and heteromeric Fab fragments that specifically bind to selected antigens (see, e.g., McCafferty, et al., Nature 348:552-554 (1990); Marks, et al., Biotechnology 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay wherein an antibody specifically binds to an antigen. The immunoassay is characterized by the use of specific binding properties of a particular antibody to isolate, target, and/or quantify the antigen. In addition, an antigen can be used to capture or specifically bind an antibody.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions can require an antibody that is selected for its specificity for a particular protein. For example, polyclonal antibodies raised to modified β-tubulin from specific species such as rat, mouse, or human can be selected to obtain only those polyclonal antibodies that are specifically immunoreactive, e.g., with β-tubulin modified at cysteine 239 and not with other proteins. This selection can be achieved by subtracting out antibodies that cross-react with other molecules. Monoclonal antibodies raised against modified β-tubulin can also be used. A variety of immunoassay formats can be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction can be at least twice background signal or noise and more typically more than 10 to 100 times background.

A "label" or a "detectable moiety" is a composition detectable by spectroscopic, photochemical, biochemical, immunochemical, or chemical means. For example, useful labels include $^{32}$P, fluorescent dyes, iodine, electron-dense reagents, enzymes (e.g., as commonly used in an ELISA), biotin, digoxigenin, or haptens and proteins for which antisera or monoclonal antibodies are available, e.g., by incorporating a radiolabel into the peptide, or any other label known to those of skill in the art.

A "labeled antibody or probe" is one that is bound, either covalently, through a linker or a chemical bond, or noncovalently, through ionic, van der Waals, electrostatic, or hydrogen bonds to a label such that the presence of the antibody or probe can be detected by detecting the presence of the label bound to the antibody or probe.

The terms "isolated" "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "support or surface" as used herein, the term is intended to include, but is not limited to a solid phase which is typically a support or surface, which is a porous or non-porous water insoluble material that can have any one of a number of shapes, such as strip, rod, particle, including beads and the like. Suitable materials are well known in the art and are described in, for example, U.S. Pat. No. 5,185, 243 to Ullman, et al., columns 10-11, U.S. Pat. No. 4,868,104 to Kurn, et al., column 6, lines 2142 and U.S. Pat. No. 4,959,303 to Milburn, et al., column 6, lines 14-31, which are incorporated herein by reference. Binding of ligands and receptors to the support or surface can be accomplished by well-known techniques, readily available in the literature. See, for example, "Immobilized Enzymes," Ichiro Chibata, Halsted Press, New York (1978) and Cuatrecasas, J. Biol. Chem. 245:3059 (1970). Whatever type of solid support is used, it must be treated so as to have bound to its surface either a receptor or ligand that directly or indirectly binds the antigen. Typical receptors include antibodies, intrinsic factor, specifically reactive chemical agents such as sulfhydryl groups that can react with a group on the antigen, and the like. For example, avidin or streptavidin can be covalently bound to spherical glass beads of 0.5-1.5 mm and used to capture a biotinylated antigen.

Signal producing system ("sps") includes one or more components, at least one component being a label, which generates a detectable signal that relates to the amount of bound and/or unbound label, i.e. the amount of label bound or not bound to the compound being detected. The label is any molecule that produces or can be induced to produce a signal, such as a fluorescer, enzyme, chemiluminescer, or photosensitizer. Thus, the signal is detected and/or measured by detecting enzyme activity, luminescence, or light absorbance.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as Q-beta replicase; promoters; dyes; fluorescers such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; photosensitizers; particles such as latex or carbon particles; suspendable particles; metal sol; crystallite; liposomes; cells, etc., which can be further labeled with a dye, catalyst, or other detectable group. Suitable enzymes and coenzymes are disclosed in U.S. Pat. No. 4,275,149 to Litman, et al., columns 19-28, and U.S. Pat. No. 4,318,980 to Boguslaski, et al., columns 10-14; suitable fluorescers and chemiluminescers are disclosed in U.S. Pat. No. 4,275,149 to Litman, et al., at columns 30 and 31; which are incorporated herein by reference. Preferably, at least one sps member is selected from the group consisting of fluorescers, enzymes, chemiluminescers, photosensitizers, and suspendable particles.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps can then include all the components required to produce a measurable signal, which can include substrates, coenzymes, enhancers, additional enzymes, substances that react with enzymatic products, catalysts, activators, cofactors, inhibitors, scavengers, metal ions, specific binding substance required for binding of signal generating substances, and the like. A detailed discussion of suitable signal producing systems can be found in U.S. Pat. No. 5,185,243 to Ullman, et al., columns 11-13, which is incorporated herein by reference.

The label is bound to a specific binding pair (hereinafter "sbp") member which is the antigen, or is capable of directly or indirectly binding the antigen, or is a receptor for the antigen, and includes, without limitation, the antigen; a ligand for a receptor bound to the antigen; a receptor for a ligand bound to the antigen; an antibody that binds the antigen; a receptor for an antibody that binds the antigen; a receptor for a molecule conjugated to an antibody to the antigen; an antigen surrogate capable of binding a receptor for the antigen; a ligand that binds the antigen, etc. Binding of the label to the sbp member can be accomplished by means of non-covalent bonding, for example, by formation of a complex of the label with an antibody to the label, or by means of covalent bonding, for example, by chemical reactions which result in replacing a hydrogen atom of the label with a bond to the sbp member or can include a linking group between the label and the sbp member. Such methods of conjugation are well known in the art. See for example, U.S. Pat. No. 3,817,837 to Rubenstein, et al., which is incorporated herein by reference. Other sps members can also be bound covalently to sbp members. For example, in U.S. Pat. No. 3,996,345 to Ullman, et al., two sps members such as a fluorescer and quencher can be bound respectively to two sbp members that both bind the analyte, thus forming a fluorescer-$sbp_1$:analyte:$sbp_2$-quencher complex. Formation of the complex brings the fluorescer and quencher in close proximity, thus permitting the quencher to interact with the fluorescer to produce a signal. This is a fluorescent excitation transfer immunoassay. Another concept is described in, EP 0,515,194 A2 to Ullman, et al., which uses a chemiluminescent compound and a photosensitizer as the sps members. This is referred to as a luminescent oxygen channeling immunoassay. Both the aforementioned references are incorporated herein by reference.

The method and markers of the present invention can be used to diagnose the presence of a disease or a disease stage in a patient, as well as in other diagnostic methods as mentioned above. Specifically, a diagnostic device for use in detecting the presence of HNSCC in a patient is provided and includes a detector device for detecting the presence of at least one marker in the serum of the patient.

The detector includes, but is not limited to, an assay, a slide, a filter, a microarray, a macroarray, computer software implementing data analysis methods, and any combinations thereof. For example, the detector can be an immunoassay such as ELISA. The detector can also include a two-color detection system or other detector system known to those of skill in the art.

The detector also includes a panel of markers that are indicative of the presence of disease. The panel of markers can include markers that are known to those of skill in the art and markers determined utilizing the methodology disclosed herein. Examples of diseases that the markers detect include, but are not limited to, gynecological sickness such as endometriosis, ovarian cancer, breast cancer, cervical cancer, HNSCC, and primary peritoneal carcinoma. The method can also be used to identify overexpressed or mutated proteins in tumor cells. That such proteins are mutated or overexpressed presumably is the basis for the immune reaction to these proteins. Therefore, markers identified using these methods could provide markers for molecular pathology as diagnostic or prognostic markers. In the present invention, the markers are preferably used to detect HNSCC. Preferably, the markers are selected from those listed in Table 5.

A method of making a panel of head and neck squamous cell carcinoma markers is provided, including the steps of creating HNSCC cDNA libraries, replicating the HNSCC cDNA libraries, performing differential biopanning, selecting clones to be arrayed on a protein microarray, immunoreacting the microarray against HNSCC patient serum, and selecting highly reactive clones for placement on a panel. The method of making the detector and panel are further described in the examples below as well.

This diagnostic device can be used to diagnose HNSCC by detecting markers in the serum of a patient indicative of the presence of HNSCC, and diagnosing the patient with HNSCC. As further described below, the serum of the patient is compared to the panel of markers in the detector device, and based on the reactivity of the serum with the panel, a diagnosis is made.

The present invention also provides for a diagnostic device for use in staging HNSCC in a patient including a detector device for detecting a presence of at least one marker indicative of stages of HNSCC, wherein the detection device includes a panel of markers for HNSCC. The detector is essentially the same as described above; however, the detector is created to determine the stage of HNSCC. Relevant markers are selected according to each stage of HNSCC desired in order to make the panel of HNSCC markers. This panel can then be used in the diagnostic device to test a patient's serum in order to determine the stage of their HNSCC. Knowing the stage of HNSCC can aid in selecting appropriate treatments.

The present invention also provides for a more general method of staging cancer, by detecting RNA or protein levels of markers that are overexpressed or altered due to mutation in the serum of a patient indicative of a stage of cancer with the diagnostic device, and determining the stage of the cancer.

A method of personalized immunotherapy is provided, including the steps of detecting markers in the serum of a patient with the diagnostic device as described above, analyzing reactivity of markers in the serum to markers in the panel of the diagnostic device, identifying markers in the serum with the highest reactivity, and using the markers identified as immunotherapeutic agents personalized to the immunoprofile of the patient. Thus, the immunotherapy is targeted to a person's immunoprofile based on the panel of markers.

According to the present invention, the immunotherapeutic agents are preferably immunotherapeutic agents for HNSCC; however, the immunotherapeutic agents can also be directed to other diseases such as, but not limited to, those mentioned above. For personalized immunotherapy, the reactivity to particular epitope clones can be correlated using sera from patients having cancer. Using a comprehensive panel of epitope markers that can accurately detect early stage HNSCC, one can utilize these antigens as immunotherapeutic agents personalized to the immunoprofile of each patient. When T-cells from the patient recognize antigen biomarkers, the T-cells are stimulated, activated and therefore produce an immune-response. Such reactivity demonstrates the potential of each antigen as a component of a vaccine to induce a T cell-mediated immune response essential for generation of cancer vaccines. Individuals scoring positive in the presymptomatic testing for HNSCC are then offered an anti-cancer vaccine tailored to their immunoprofile against a panel of tumor antigens.

Like the method of personalize immunotherapy, the present invention also provides for a method of personalized targeted therapy by detecting markers that are overexpressed or altered due to mutation in the serum of a patient with the diagnostic device as described above, analyzing reactivity of markers in the serum to markers in the panel of the diagnostic device, identifying markers in the serum with the highest reactivity, and using the markers identified as therapeutic targets personalized to the patient. In other words, this method is directed to different types of therapy and not just immunotherapy.

Treatment of a patient can be altered based upon the markers detected. For example, the treatment can be specifically designed based upon the markers identified. In other words, the therapy can be altered to most suitably treat the identified markers, such that the treatment is designed to most efficiently treat the identified marker. Thus, the treatment is personalized according to the patient's needs. The ability to adjust the therapy enables the treatment to be tailored to the needs of the person being treated. The treatments that can be used range from vaccines to chemotherapy.

The present invention therefore also provides for a method of making a personalized anti-cancer vaccine, including the steps of detecting markers in the serum of a patient with the diagnostic device as described above, analyzing reactivity of markers in the serum to markers in the panel of the diagnostic device, identifying markers in the serum with the highest reactivity, and formulating an anti-cancer vaccine using the identified markers. Preferably, the anti-cancer vaccine is an anti-HNSCC vaccine.

As further described in the examples below, a method is also provided of predicting a clinical outcome in a HNSCC patient, including the steps of analyzing a pattern of reactivity of a patient's serum with a panel of HNSCC markers, and predicting a clinical outcome. The detector device including the panel as described above can be used to analyze the patient's serum. Further, the clinical outcome predicted includes, but is not limited to, a response to a particular therapeutic intervention or chemotherapeutic drug, survival, and development of neck or distant metastasis.

Explanations as well as examples are provided below detailing the methods and devices of the present invention.

The analysis of mRNA expression in tumors does not necessarily reveal the status of protein levels in the cancer cells. Other factors such as protein half-life and mutation can be altered without an effect on mRNA levels thus masking significant molecular changes at the protein level. Serum antibody reactivity to cellular proteins occurs in cancer patients due to presentation of mutated forms of proteins from the tumor cells or overexpression of proteins in the tumor cells. The host immune system can direct individuals to molecular events critical to the genesis of the disease. Using a candidate gene approach, experience has shown that the frequency of serum positivity to any single protein is low. Therefore, to increase the identification of such autoantigens, a more global approach is employed to exploit immunoreactivity to identify large numbers of cDNAs coding for proteins that are mutated or upregulated in cancer cells.

In order to develop an effective screening test for early detection of HNSCC cancer, cDNA phage display libraries are used to isolate cDNAs coding for epitopes reacting with antibodies present specifically in the sera of patients with HNSCC cancer. The methods of the present invention detect various antibodies that are produced by patients in reaction to proteins overexpressed in their HNSCC tumors. This is achievable by differential biopanning technology using human sera collected both from normal individuals and patients having HNSCC cancer and phage display libraries expressing cDNAs of genes expressed in HNSCC tumors and cell lines. Serum reactivity toward a cellular protein can occur because of the presentation to the immune system of a mutated form of the protein from the tumor cells or overexpression of the protein in the tumor cells. The strategy provides for the identification of epitope-bearing phage clones (phagotopes) displaying reactivity with antibodies present in sera of patients having HNSCC cancer but not in control sera from unaffected individuals. This strategy leads to the identification of novel disease-related epitopes for diseases including, but not limited to, HNSCC cancer, that have prognostic/diagnostic value with additional potential for therapeutic vaccines and medical imaging reagents. This also creates a database that can be used to determine both the presence of disease and the stage of the disease.

The series of experiments disclosed herein provide direct evidence that biopanning a T7 coat protein fusion library can isolate epitopes for antibodies present in polyclonal sera. This also showed that the technology can be applied to direct microarray screening of large numbers of selected phage against numerous patient and control sera. This approach provides a large number of biomarkers for early detection of disease.

More specifically, the methods of the present invention provide four to five cycles of affinity selection and biopanning which are carried out with biological amplification of the phage after each biopanning, meaning growth of the biological vector of the cDNA expression clone in a biological host. Examples of biological amplification include, but are not limited to, growth of a lytic or lysogenic bacteriophage in host bacteria or transformation of bacterial host with selected DNA of the cDNA expression vector. The number of biopanning cycles generally determines the extent of the enrichment for phage that binds to the sera of patient with HNSCC cancer. This strategy allows for one cycle of biopanning to be performed in a single day. Someone skilled in the art can establish different schedules of biopanning that provide the same essential features of the procedure described above.

Two biopanning experiments are performed with each library differentially selecting clones between control and disease patient sera. The first selection is to isolate phagotope clones that do not bind to control sera pooled from control individuals but do bind to a pool of disease patient serum. This set of phagotope clones represent epitopes that are indicative of the presence of disease as recognized by the host immune system. The second type of screening is performed to isolate phagotope clones that did not bind to a pool of control sera but do bind to an individual patient's serum. Those sets of phagotope clones represent epitopes that are indicative of the presence of disease.

Subsequent to the biopanning, the clones so isolated can be used to contact antibodies in sera by spotting the clones or peptide sequences of amino acids containing those encoded by the clones. After spotting on a solid support, the arrays are rinsed briefly in a 1% BSA/PBS to remove unbound phage, then transferred immediately to a 1% BSA/PBS blocking solution and allowed to sit for one hour at room temperature. The excess BSA is rinsed off from the slides using PBS. This step insures that the elution step of antibodies is more effective. The use of PBS elutes all of the antibodies without harming the binding of the antibody. Antibody detection of reaction with the clones or peptides on the array is carried out by labeling of the serum antibodies or through the use of a labeled secondary antibody that reacts with the patient's antibodies. A second control reaction to every spot allows for greater accuracy of the quantitation of reactivity and increases sensitivity of detection.

The slides are subsequently processed to quantify the reaction of each phagotopes. Such processing is specific to the label used. For instance, if fluorophore cy3-cy5 labels are used, this processing is done in a laser scanner that captures an image of the slide for each fluorophore used. Subsequent image processing familiar to those skilled in the art can provide intensity values for each phagotope. The data analysis can be divided into the following steps:

1. Pre-processing and normalization.
2. Identifying the most informative markers
3. Building a predictor for molecular diagnosis of HNSCC cancer and validating the results.

The purpose of the first step is to cleanse the data from artifacts and prepare it for the subsequent steps. Such artifacts are usually introduced in the laboratory and include: slide contamination, differential dye incorporation, scanning and image processing problems (e.g. different average intensities from one slide to another), imperfect spots due to imperfect arraying, washing, drying, etc. The purpose of the second step is to select the most informative phages that can be used for diagnostic purposes. The purpose of the third step is to use a software classifier able to diagnose cancer based on the antibody reactivity values of the selected phages. The last step also includes the validation of this classifier and the assessment of its performance using various measures such as specificity, sensitivity, positive predictive value and negative predictive value. The computation of such measures can be done on cases not used during the design of the chip in order to assess the real-world performance of the diagnosis tool obtained.

The pre-processing and normalization step is performed for arrays using two channels such as Cy5 for the human IgG and Cy3 for the T7 control, the spots are segmented, and the mean intensity is calculated for each spot. A mean intensity value is calculated for the background, as well. A background corrected value is calculated by subtracting the background from the signal. If necessary, non-linear dye effects can be eliminated by performing an exponential normalization (Houts, 2000) and/or LOESS normalization of the data and/or a piecewise linear normalization. The values obtained from each channel are subsequently divided by their mean of the intensities over the whole array. Subsequently, the ratio between the IgG and the T7 channels was calculated. The values coming from replicate spots (spots printed in quadruplicates) are combined by calculating mean and standard deviation. Outliers (outside+/−two standard deviations) are flagged for manual inspection). Single channel arrays are pre-processed in a similar way but without taking the ratios. This preprocessing sequence was shown to provide good results for all preliminary data analyzed.

The step of selecting the most informative markers is used to identify the most informative phages out of the large set of phages started with. The better the selection, the better is the expected accuracy of the diagnosis tool.

A first test is necessary to determine whether a specific epitope is suitable for inclusion in the final set to be spotted. The selection methods to be applied follow the principles of the methods successfully applied in (Golub et al., 1999; Alizadeh et al., 2000) and can be briefly described in the following.

Procedure 1

The procedure is initiated defining a template for the cancer case. Unlike gene expression experiments where the expression level of a gene can be either up or down in cancer vs. healthy subjects, here the presence of antibodies specific to cancer are tested for. Therefore, epitopes with high reactivity in controls and low reactivity in patients are not expected and the profile is sufficient. Each epitope can have a profile across the given set of patients. The profile of each epitope is compared with the templates using a correlation-based distance. Those skilled in the art can recognize that other distances can be used without essentially changing the procedure.

The epitopes are then prioritized based on the similarity between the reference profile and their actual profile. For example, as detailed in U.S. Ser. No. 11/060,867 (incorporated herein by reference), 46 epitopes were found to be informative for a correlation threshold of 0.8. The final cutoff threshold is calculated by doing 1000 random permutations once the whole data set become available. Each such permutation moves randomly the subjects between the 'patient' and 'control' categories. Calculating the score of each epitope profile for such permutations allows for the establishment of a suitable threshold for the similarity (Golub et. al. 1999).

The technique follows closely the one used in (Golub, 1999). However, the technique can be further improved as follows. Firstly, this technique was shown to provide good results if most controls are consistent by providing the same type of reactivity. However, preliminary data showed that there are control subjects that show a non-specific reactivity with all clones, while still clearly different from patients. Such control subjects with a high non-specific reaction introduces spikes in the clone profile in the area corresponding to the control subjects. These spikes decrease the score of the relevant clones making them more difficult to distinguish from the irrelevant ones. In order to reduce this effect, all control subjects with a non-specific response (i.e. a unimodal distribution) were eliminated from the analysis leading to the epitope selection.

A second essential modification is related to the set of epitopes selected. There are rare patients who might react only to a small number of very specific epitopes. If the selection of the epitopes is done on statistical grounds alone, such very specific epitopes can be missed if the set of patients available contains only few such rare patients. In order to maximize the sensitivity of the penultimate test resulted from this work, every effort was made to include epitopes which might be the only ones reacting to rare patients. In order to do this, the information content of the set of epitopes is maximized while trying to minimize the number of epitopes used using the following procedure.

Procedure 2

It is assumed that there are m patients and k controls. n random patients are selected from the m available. For each of the n patients used for epitope selection, amplification is performed (n×4 biopannings) as well as self-reactions. Those patients/epitopes that do not react to themselves are eliminated.

A chip is made with all available, self-reacting epitopes printed in quadruplicates. This chip is reacted with all patients and controls (n+k antibody reactions). Controls are eliminated with a non-specific reactivity. For the set of epitopes coming from a single patient, Procedure 1 is applied to order the epitopes in the order of their informational content and the ones that can be used to differentiate patients from controls are selected.

The epitopes are ordered by their reactivity in decreasing order of the number of patients they react to. This list is scanned from the top down, and epitopes are moved from this list to the final set. Every time a set of epitopes from a patient x is added to the final set, the patient x and all other patients that these epitopes react to are represented in the current set of epitopes. This is repeated until all patients are represented in the current set of epitopes.

This procedure minimizes the number of epitopes used while maximizing the number of patients that react to the chip containing the selected epitopes.

The following example shows how this procedure works using a simple example. The matrix in FIG. 1 contains a row i for the clones coming from patient i and a column j for the serum coming from patient j. A serum is said to react specifically with a set of clones if the histogram of the ratios is bimodal. A serum is said to react non-specifically if the histogram of the ratio is unimodal. Furthermore, a serum might not react at all with a set of clones. If the serum from patient j reacts specifically with the clones from patient i, the matrix can contain a value of 1 at the position (i, j). The element at position (i, j) is left blank if the there is no reaction or the reaction is non-specific.

Each set of epitopes corresponding to a row of the matrix is pruned by sub-selecting epitopes according to Procedure 1. The rows are now sorted in decreasing reactivity (number of patients other than self that the clones react to). For instance, in FIG. 2, the clones from patient 2 react with sera from self (column 2) and patients 4 and 8. The clones from patient 3 react with sera from self (column 3) and patients 6 and 10, etc. The final set of clones was obtained from patients 2, 3, 5, 7 and 1 (reading top-down in column 1). Clones coming from patients 8, 9 and 10 are not included since these patients already react to clones coming from other patients. This set ensures that the chip made with these clones reacts with all patients in this example.

Procedure 3

Arrays using two channels such as Cy5 for the human IgG and Cy3 for the T7 control are processed as follows. The spots are segmented and the mean intensity is calculated for each spot. A mean intensity value is calculated for the background, as well. A background corrected value is calculated by subtracting the background from the signal. The values coming from each channel are normalized by dividing by their mean. Subsequently, the ratio between the IgG and the T7 channels are calculated and a logarithmic function is applied. The values coming from replicate spots (spots printed in quadruplicates) are combined by calculating mean and standard deviation. Outliers (outside+/−two standard deviations) are flagged for manual inspection. Someone skilled in the art can recognize that various combinations and permutations of the steps above or similar could replace the normalization procedure above without substantially changing rest of the data analysis process. Such similar steps include without limitation taking the median instead of the mean, using logarithmic functions in various bases, etc.

The histogram of the average log ratio is calculated. If the histogram is unimodal there is no specific response. If the histogram is clearly bimodal, there is a specific response. All subjects analyzed fell in one of these two categories or had no response at all. A mixed probability model is used in less clear cases to fit two normal distributions as in (Lee, 2000). If the two distributions found under the maximum likelihood assumption are separated by a distance d of more than 2 standard deviations (corresponding to a p-value of approximately 0.05), there is a specific response. If the distance is less than 2 standard deviations, the response can be considered as not specific. The preliminary data analyzed so far showed a very good separation of the distributions for the patients.

Once the chosen clones are spotted on the final version of the array, a number of sera coming from both patients and controls can be tested. These sera come from subjects not used in any of the phases that lead to the fabrication of the array (i.e. not involved in clone selection, not used as controls, etc.). Each test was evaluated using Procedure 3 above. The performance on this validation data can be reported in terms of PPV, NPV, specificity and sensitivity. Since these performance indicators are calculated on data not previously used, they provide a good indication of the performance of the test for screening purposes for the various categories of patients envisaged in the general population.

The present invention also provides a kit including all of the technology for performing the above analysis. This is included in a container of a size sufficient to hold all of the required pieces for analyzing sera, as well as a digital medium such as a floppy disk or CDROM containing the software necessary to interpret the results of the analysis. These components include the array of clones or peptides spotted onto a solid support, prewashing buffers, a detection reagent for identifying reactivity of the patients' serum antibodies to the spotted clones or peptides, post-reaction washing buffers, primary and secondary antibodies to quantify reactivity of the patients' serum antibodies with the spotted array and methods to analyze the reactivity so as to establish an interpretation of the serum reactivity.

A biochip, otherwise known as a biosensor, for detecting the presence of the disease state in a patient's sera is provided by the present invention. The biochip has a detector contained within the biochip for detecting antibodies in a patient's sera. This allows a patient's sera to be tested for the presence of a multitude of diseases or reaction to disease markers using a single sample and the analysis can be conducted and analyzed on a single chip. By utilizing such a chip, the time required for the detection of disease is lowered while also enabling a doctor to determine the level of disease spread or infection. The chip, or other informatics system can be altered to weigh the results. In other words, the informatics can be altered to adjust the levels of sensitivity and/or specificity of the chip.

The above discussion provides a factual basis for the use of the combination of markers and method of making the combination. The methods used with a utility of the present invention can be shown by the following non-limiting examples and accompanying figures.

Example 1

Combining phage display technology with protein microarray technology, 5,133 selectively cloned tumor antigens were screened and ranked using a feature selection method based on receiver-operator characteristic curves for neural network classifiers. A model was built using the top-ranked 40 biomarkers. The entire modeling strategy, both feature selection and model development, was validated by bootstrapping on an independent set of 80 cancer and 78 control sera. Estimated accuracy of this modeling strategy was 82.9% (95% CI 77.2-87.9) with sensitivity of 83.2% (95% CI 74.0-91.6) and specificity of 82.7% (95% CI 74.5-93.6). The accuracy of this novel diagnostic platform represents a significant improvement over current diagnostic accuracy of 37% to 56% in the primary care setting. Further, the diagnostic test described can be easily translated into assays such as enzyme linked immunosorbent assay that is already widely available in clinical practice and familiar to clinical laboratories. This facilitates wide-spread application of this assay as a simple tool to screen (in asymptomatic patients) and diagnose (in symptomatic patients) HNSCC in high risk population.

Methods

HNSCC and control patients were recruited from the otolaryngology clinic population.

Construction of T7 phage display cDNA libraries. HNSCC specimens were obtained at the time of surgical extirpation and poly-A RNA extracted and purified. The construction of T7 phage cDNA display libraries was performed using Novagen's OrientExpress cDNA Synthesis (Random primer system) and Cloning System as per manufacturer's suggestions.

Differential biopanning of HNSCC phage display cDNA libraries. Differential biopannings using sera from control and HNSCC patients were performed as per the manufacturer's protocol (T7Select System, TB178).

Protein microarray immunoreaction. Individual clones were picked and arrayed in replicates of 6 onto FAST™ slides (Schleicher & Schuell) using a robotic microarrayer Prosys 5510TL (Cartesian Technologies).

Microarray data analysis. Following immunoreaction, the microarrays were scanned with an Axon Laboratories 4100A scanner (Axon Laboratories) using 635 nm and 532 nm lasers to produce a red (AlexaFluor647) and green (AlexaFluor532) composite image. Using the ImaGene™ 6.0 (Biodiscovery) image analysis software, the binding of each of the cancer-specific peptides with IgGs in each serum was then analyzed and expressed as a ratio of red to green fluorescent intensities. The microarray data were further processed by a sequence of transformations including background correction, omission of poor quality spots, log-transformation, normalization by subtracting the global median (in log scale), then combining of 6 spot replicates to yield a mean value for each marker.

Sequencing of phage cDNA clones. Individual phage clones were PCR amplified using forward primer 5'GTTC-TATCCGCAACGTTATGG3' (SEQ ID NO: 1) and reverse primer 5'GGAGGAAAGTCGTTTTTTGGGG3' (SEQ ID NO: 2) and sequenced using forward primer by Wayne State University Sequencing Core Facility.

Serum samples. Blood samples from HNSCC patients (Stages I-IV) and control patients were obtained after informed consent. Both HNSCC and control patients were recruited from the otolaryngology clinic population. All enrolled HNSCC patients have cancer confirmed on pathology. Control patients underwent thorough head and neck examination and imaging to rule out the presence of cancer after they initially presented with nonspecific head and neck symptoms such as sore throat, hoarseness, dysphagia, coughing, choking and gasping, neck mass, and otalgia. Blood samples were centrifuged at 2,500 rpm at 4° C. for 15 minutes and supernatants were stored at −70° C.

Construction of T7 phage display cDNA libraries. Head and neck cancer specimens were obtained at the time of surgical extirpation and immediately placed in RNA later solution (Ambion). Total RNA extraction was performed using TRIZOL reagent (Invitrogen Corporation) per the manufacturer's protocol. After extraction, poly-A RNAs were purified twice using Straight A mRNA Isolation System (EMD Biosciences) per protocols from the manufacturer. The construction of T7 phage cDNA display libraries was performed using Novagen's OrientExpress cDNA Synthesis (Random primer system) and Cloning System as per the manufacturer's suggestions (Novagen)

Differential biopanning of HNSCC phage display cDNA libraries. Differential biopannings using sera from normal healthy patients and HNSCC patients were performed as per manufacturer's protocol (Novagen: T7Select System, TB178). Protein G Plus-agarose beads were used for serum immunoglobulins (IgGs) immobilization. Three to five rounds of biopanning were performed using serum from each of the 12 HNSCC patients. Each cycle of biopanning consisted of passing the entire phage library through protein-G beads coated with IgGs from pooled sera of healthy controls, passage through beads coated with IgGs from individual serum from HNSCC patients, followed by final elution of bound phage clones from the beads.

Protein microarray immunoreaction. Individual clones were picked and arrayed in replicates of six onto FAST™ slides (Schleicher & Schuell) using a robotic microarrayer Prosys 5510TL (Cartesian Technologies) with 32 Micro-Spotting Pins (TeleChem). Protein microarrays were blocked with 4% milk in 1×PBS for one hour at room temperature followed by another hour of incubation with primary antibodies consisting of human serum at a dilution of 1:300 in PBS, mouse anti-T7 capsid antibodies (0.15 µg/ml) (EMD Biosciences, Madison, Wis.), and BL21 E. coli cell lysates (5 µg/ml). The microarrays were then washed three times in PBS/0.1% Tween-20 solution four minutes each at room temperature and then incubated with AlexaFluor647 (red fluorescent dye)-labeled goat anti-human IgG antibodies (1 µg/ml) and AlexaFluor532 (green fluorescent dye)-labeled goat anti-mouse IgG antibodies (0.05 µg/ml) (Molecular Probes, Eugene, Oreg.) for one hour in the dark. Finally, the microarrays were washed three times in PBS/0.1% Tween-20 four minutes each, then twice in PBS for two minutes each and air dried.

Results

Differential biopanning results in enrichment of T7 phage HNSCC cDNA display libraries. T7 phage cDNA display libraries were constructed from three HNSCC specimens (floor of mouth, base of tongue, and larynx). The insertion of foreign HNSCC cDNAs into the T7 phage capsid genes results in the production of fusion capsid proteins. Foreign peptides displayed in this fashion have been shown to fold in their native conformations, thus exposing both linear and conformational antigens on the surface of the bacteriophage where they are accessible for selection and analysis.

A potential limitation of the T7 phage display system, however, is the absence of post-translational modifications such as glycosylation, sulfation, and phosphorylation which can influence the folding and binding of these peptides. Each of these three cDNA phage libraries was found to contain between $10^6$ and $10^7$ primary recombinants. Since the majority of the clones in the HNSCC cDNA libraries carried normal self-proteins, differential biopanning was performed in order to enrich the cDNA libraries with clones expressing the HNSCC-specific peptides (FIG. 3). The technique relied on specific antigen-antibody reactions to remove clones binding to immunoglobulins present in control sera from non-cancer patients while retaining clones with peptides of interest (HNSCC-specific antigens) binding to antibodies in HNSCC sera that serve as the bait. In order to increase the diversity of HNSCC-specific peptides, the cDNA libraries were biopanned against sera from 12 HNSCC patients with tumors representing different subsites of head and neck (Table 1a and 1b).

FIG. 3 depicts a schema showing the process of combining phage-display technology, protein microarrays, and bioinformatics tools to profile and select a panel of 40 unique clones from an initial 107 clones in the three HNSCC cDNA phage display libraries. Three cDNA libraries were constructed from HNSCC specimens. Because the majority of the clones in the HNSCC cDNA libraries carried normal self-proteins, subtractive biopanning was performed in order to enrich the cDNA libraries with clones expressing the HNSCC-specific peptides. The technique relied on specific antigen-antibody reactions to remove clones binding to immunoglobulins (IgGs) from control sera while retain clones with peptides of interest (HNSCC-specific antigens) using antibodies in HNSCC sera as bait. Protein G Plus-agarose beads were used for serum IgGs immobilization. Three to five rounds of biopanning were performed using serum from each of the 12 HNSCC patients. Each cycle of biopanning consisted of passing the entire phage library through protein-G beads coated with IgGs from pooled sera of healthy controls, passage through beads coated with IgGs from individual serum from HNSCC patients, followed by final elution of bound phage clones from the column. Following biopanning, a total of 5,133 clones were randomly chosen from the 12 highly enriched pools of T7 phage cDNA libraries. These clones were arrayed and immunoreacted against serum samples from 39 HNSCC and 41 control patients. The binding of arrayed HNSCC-specific peptides with antibodies in sera was quantified with the AlexaFluor647 (red-fluorescent dye)-labeled anti-human antibody. Any small variation in the amount of phage particles spotted throughout the microarray was quantified by measuring the amount of mouse anti-T7 capsid antibodies bound using AlexaFluor532 (green fluorescent dye)-labeled goat anti-mouse IgG antibody. Following immunoreaction, the microarray data was analyzed and processed by a sequence of transformations. To reduce the number of clones for further analysis, one-tailed t-test was used to select 1,021 clones (from the original 5,133 clones) with increased reactivity to cancer sera compared to control sera ($p<0.1$). Sera from 80 cancer and 78 non-cancer controls, not previously used for biopanning or selection of clones, were immunoreacted against the previously selected 1,021 HNSCC-specific peptides. The reactivity of each of the 1,021 cancer-specific peptides with each of these 158 sera was then analyzed. Following data normalization and transformation, the top 100 clones based on one-tailed t-test were selected. Subsequently these 100 clones were re-ranked based on their performance in a neural network model. The performance measure used was the area under the curve (AUC) taken as an average over 200 bootstrap trials. These clones were then sequenced and analyzed for homology to mRNA and genomic entries in the GenBank databases using BLASTn. A classifier, based on a three-layer feed-forward neural network, was then built using the top unique biomarkers. Several models were created using the increasing number of features from the top ranked clones. An input set size of 40 clones was found to be a good compromise between the performance and complexity of the classifier.

High throughput protein microarray immunoscreening for selection of informative HNSCC-specific biomarkers. A total of 5,133 clones were randomly chosen from the 12 highly enriched pools of T7 phage clones from these cDNA libraries. These clones were arrayed and immunoreacted against serum samples from 39 HNSCC patients (Table 2a) and 41 controls (Table 2b). The binding of arrayed HNSCC-specific peptides with antibodies in sera was quantified with the AlexaFluor647 (red-fluorescent dye)-labeled anti-human antibody. The amount of phage particles spotted throughout the microarray was quantified by measuring the amount of phage at each spot using a mouse monoclonal antibody to the T7 capsid protein quantified using AlexaFluor532 (green fluorescent dye)-labeled goat anti-mouse IgG antibody. The ratio of AlexFluor647 intensity over AlexaFluor532 intensity was then calculated in order to account for any small variation in the serum antibody binding to antigens due to different amounts of phage particles spotted on the microarray (FIG. 4).

FIG. 4 shows phage clones that were spotted in replication of six in an ordered array onto FAST™ nitrocellulose coated glass slides. The reactivity of each clone with each serum sample was analyzed and expressed as a ratio of red fluorescent intensity to green fluorescent intensity. The binding of arrayed HNSCC-specific peptides with antibodies in sera was detected with the AlexaFluor647 (red-fluorescent dye)-labeled anti-human antibody. The use of mouse anti-T7 capsid antibodies, detected with the use of AlexaFluor532 (green fluorescent dye)-labeled goat anti-mouse IgG antibody, was necessary in order to normalize for any small variation in the amount of phage particles spotted throughout the microarray chip.

Following immunoreaction, the microarray data was processed by a sequence of transformations and then analyzed. To reduce the number of clones for further analysis, one-tailed t-tests under the R environment (v2.3.0) were used to select clones with increased binding to immunoglobulins present in cancer sera compared to control sera using the criterion of p<0.10; 1021 clones met the criterion. In general, the visually positive clones (yellow or orange spots) that reacted with cancer sera but not control sera (FIG. 5) corresponded to those for which the t-test was statistically significant.

Figure 5B:
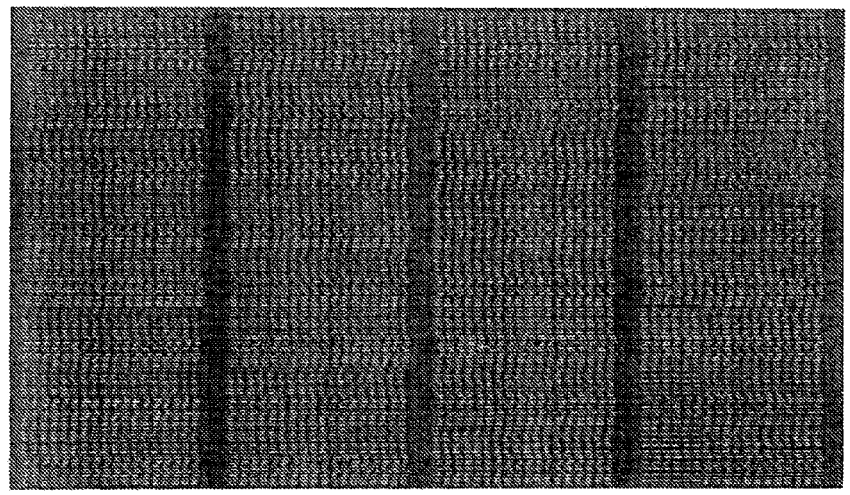
FIGS. 5A and 5B are photographs showing protein microarrays immunoreacted against a serum sample from HNSCC patient (FIG. 5A) and serum from a control patient (FIG. 5B)
Figure 5A:
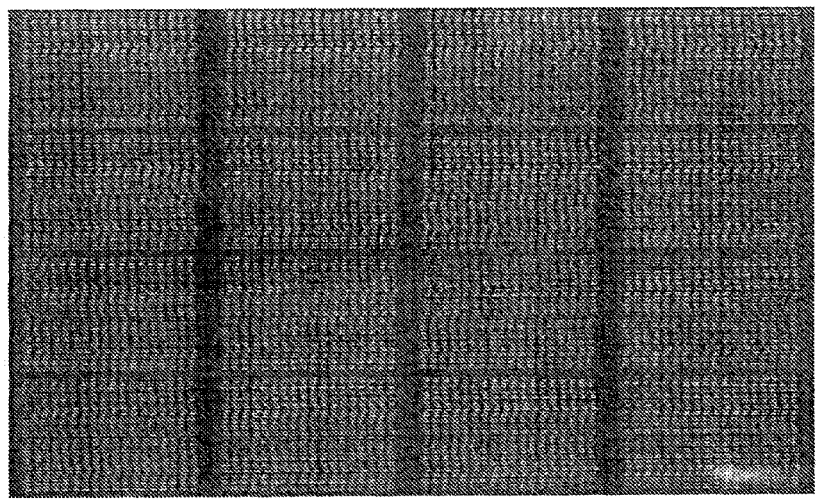

FIG. 5 shows the protein microarrays immunoreacted against a serum sample from HNSCC patient (left panel) and serum from control patient (right panel). The visually positive clones are represented by yellow or orange spots in replication of six. These visually positive clones corresponded to the statistically significant clones selected based on the t-test.

Ranking of top clones based on protein microarray immunoreaction. Sera from 80 HNSCC patients and 78 controls, not previously used for biopanning or selection of clones, were immunoreacted against the previously selected 1,021 HNSCC-specific peptides. Of the 80 HNSCC patients, 18 had early stage (I and II) and 62 had advanced stage (III and IV) disease. The distribution of early and late stage disease reflects the distribution of HNSCC in clinical practice. HNSCC from almost all subsites of head and neck were represented (Table 3a). Cases and controls are similar in age, race, and gender (Table 3b). The reactivity of each of the 1,021 cancer-specific peptides with each of these 158 sera was then analyzed. Following data normalization and transformation, clones were ranked on the basis of the attained significance levels from the one-tailed t-tests and the top 100 clones were selected. Subsequently these 100 clones were re-ranked based on their performance in a neural network model using area under the ROC curve (AUC) averaged over 200 bootstrap trials. These 100 clones were then sequenced and analyzed for homology to mRNA and genomic entries in the GenBank databases using BLASTn. The predicted amino acids were also determined in-frame with the T7 gene 10 capsid protein. A list of unique clones was generated by eliminating duplicate clones as well as those clones containing truncated peptides with fewer than 5 amino acids.

Figure 6:
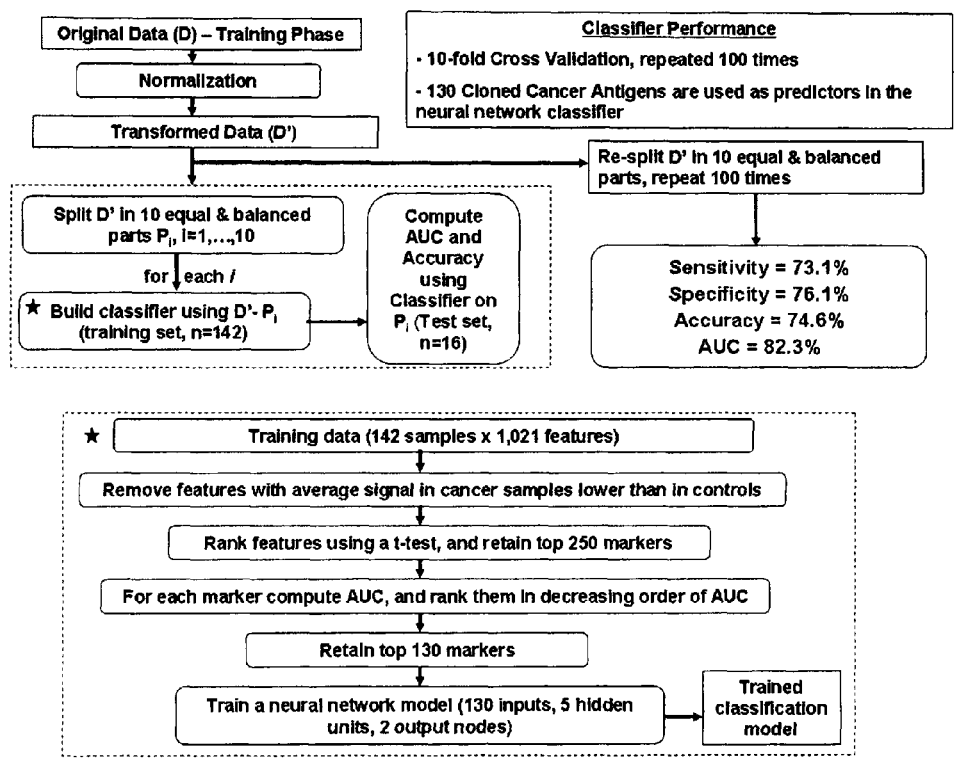
FIG. 6 is a schema showing the process of calculating the real accuracy of the process of the present invention.
Figure 7A:
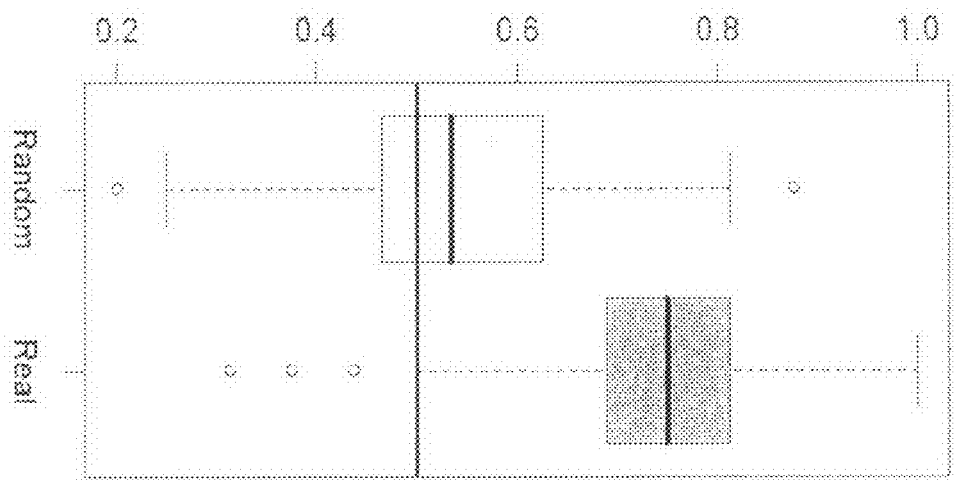
FIGS. 7A and 7B are graphs showing the link between the immunoreaction level of the different clones and the class membership of the samples (cancer versus healthy).
Figure 7B:
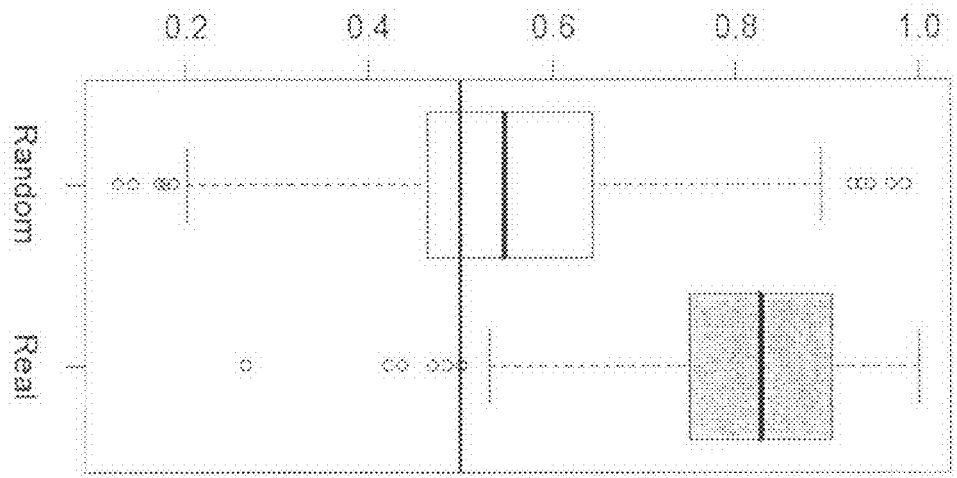

Validation of modeling strategy. A classifier, based on a three-layer feed-forward neural network, was then built using the top unique biomarkers, using the nnet package under the R environment (v2.3.0). Several models were created using increasing numbers of features from the top ranked clones. An input set size of 40 clones was found to be a good compromise between the performance and complexity of the classifier. Special attention was paid to avoid data overfitting by using a reduced number of hidden nodes (n=4) as well as using a training method (Broyden-Fletcher-Goldfarb-Shanno) that included regularization, as implemented in the nnet package. The performance of the classifier was estimated by averaging over 100 bootstrap samples from the original data set (80 cancer and 78 control sera) to obtain an accuracy of 82.9% (95% CI 77.2-87.9) with sensitivity of 83.2% (95% CI 74.0-91.6) and specificity of 82.7% (95% CI 74.5-93.6) (FIG. 6). The classifier was able to detect early stage HNSCC at least as well as late stage cancers. In fact, the accuracy on early stage cancers (86.7%) was slightly better than the accuracy on late stage cancers (82.9%). The performance of this classifier in detecting cancer from different subsites of head and neck region was 85% (glottis), 86.2% (supraglottis), 90% (hypopharynx), 83.5% (oropharynx), 95% (nasopharynx), and 78.6% (oral cavity).

Of the top 40 unique clones, there were five clones that contained known gene products in the reading frame of the T7 gene 10 capsid protein. These included ubiquinone-binding protein, NADH dehydrogenase subunit 1, pp 21 homolog (transcription elongation factor A (SII)-like 7), multiple myeloma overexpression gene 2, and C10 protein (Table 4). The remaining 35 clones contained peptides that were different from the original proteins coded by the inserted gene fragments. This occurred because the inserted gene fragments were out of frame with the open reading frame of the T7 10B gene (n=14) (Table 5a), represented untranslated region of known genes (n=11) (Table 5b), or contained sequences from unknown genes (n=10) (Table 5c). It is likely that the recombinant gene products of these clones mimic some other natural antigens, and hence can be termed mimotopes. BLASTp search of the SWISSPROT database for homology to each in-frame mimotope revealed that many of these gene products mimic known cancer proteins and as such represent putative tumor antigens.

FIG. 6 shows the schema used to calculate the real accuracy from apparent accuracy and optimism. A classifier (C), based on the top 40 clones, was trained and tested using 80 cancer and 78 control samples. The resulting accuracy (96.2%) is called the apparent accuracy and is an optimistic estimate of the true accuracy. Estimation of the real-world performance of the classifier methodology (feature selection and model training) was evaluated by averaging over 100 bootstrap samples. Each bootstrap run involved resampling by drawing from the original dataset with replacement. For every bootstrap sample, a set of 40 features was selected which performed best on this new arrangement of the data and a classifier (C') was trained based on that data and these features. The classifier C' was subsequently applied to both the original data and bootstrap datasets. The difference between the accuracies on these two data sets provided a measure of the "optimism" embedded in the apparent accuracy. The expected real-world performance (82.9%) was obtained by subtracting the mean values of the optimism (13.3%) from the apparent accuracy parameter (96.2%). The confidence intervals of the estimated performance indices were determined from the empirical distribution of the optimism value.

Evaluation of neural network classifier performance using 10-fold cross validation. Sera from 80 HNSCC patients and 78 controls, not previously used for biopanning or selection of clones, were immunoreacted against the previously selected 1,021 HNSCC-specific peptides. Of the 80 HNSCC patients, 18 had early stage (I and II) and 62 had advanced stage (III and IV) disease, reflecting the distribution of HNSCC in clinical practice. HNSCC from almost all subsites of head and neck were represented (Table 3a). In order to reflect the target screening population, control sera used were taken from patients who presented with symptoms or exams similar to that of head and neck cancer patients. Many of these control patients also have history of moderate to excessive tobacco and/or alcohol use. Cases and controls are similar in age, race, and gender (Table 3b).

A ten-fold cross-validation procedure was used to assess the performance of neural network model for cancer classification based of patterns of serum immunoreactivity against a panel of biomarkers. In this scheme, the data was split into 10 equal parts, balanced with respect to the cancer and control groups. Both the clone (feature) selection and model training were based on $9/10^{th}$ of the data and the model was tested on the remaining $1/10^{th}$ of the dataset. Feature selection based on training data (142 samples) included several steps. First, clones that immunoreacted, on average, less with sera from cancer patients than controls were discarded. The remaining clones were then ranked using the p-value from a t-test and the top 250 clones were used individually to derive a ROC curve. Finally, the top 130 clones ranked in decreasing order of area under the ROC curve (AUC) were retained to build a classification model, based on a three-layer feed-forward neural network, using the nnet package[32] under the R environment (v2.3.0). Special attention was paid to avoid data overfitting by using a reduced number of hidden nodes (n=5) as well as using a training method (Broyden-Fletcher-Goldfarb-Shanno) which included regularization, as implemented in the nnet package. The resulting classifier was then tested against the independent test set of 16 samples. The entire 10-fold cross-validation was repeated 100 times in order to minimize any potential bias due to random partition of training and test sets (FIG. 2).

The classification method yields an average accuracy of 74.6% (95% CI, 52.5% to 96.7%) with AUC of 82.3%, sensitivity of 73.1%, and specificity of 76.1%. Notably this classifier was able to detect early stage HNSCC (72.8%) at least as well as late stage cancers (73.2%). The sensitivity of this classifier in detecting cancer from different subsites of head and neck region was 73.9% (glottis), 72.6% (supraglottis), 83.7% (hypopharynx), 74.9% (oropharynx), 87.5% (nasopharynx), 67.3% (oral cavity), and 60% (unknown primary). To further verify that there is a true link between the immunoreaction level of the different clones and the class membership of the samples (cancer vs. healthy), the class identifiers were randomly permuted among the patients and recalculated the cross-validation procedure with the permuted data. As expected, the estimate of accuracy and AUC obtained in these permuted cases were around 50% and are statistically significantly different (p<1e-15) from the accuracy (74.6%) and AUC (82.3%) obtained using the actual class identifiers (FIG. 3).

Characterization of the panel of 130 biomarker panel. Clones were ranked based on the number of times they were selected and used in the 130 biomarker panel out of 1,000 possible reiterations (10-fold×100 different partitions) (Table 4). The top 130 markers were sequenced and analyzed for homology to mRNA and genomic entries in the GenBank databases using BLASTn. The predicted amino acids were also determined in-frame with the phage T7 gene 10 capsid protein. Of the top 130 clones, there were 8 clones that contained known gene products in the reading frame of the T7 gene 10 capsid protein. These included multiple myeloma overexpression gene 2, ubiquinone binding protein, NADH dehydrogenase subunit 1, C10 protein, and a hypothetical protein LOC400242 (Table 5). The remaining 122 clones contained peptides that were different from the original proteins coded by the inserted gene fragments. This occurred because the inserted gene fragments were out of frame with the open reading frame of the T7 10B gene (n=61) (Table 6a), represented untranslated region of known genes (n=18) (Table 6b), or contained sequences from unknown genes (n=43) (Table 6c). It is likely that the recombinant gene products of these clones mimic some other natural antigens, and hence can be termed mimotopes. BLASTp search of the SWISSPROT database for homology to each in-frame mimotope revealed that many of these gene products mimic known cancer proteins and as such represent putative tumor antigens.

Discussion

Protein microarray technology was used for high throughput quantitative analysis of the antibody-antigen reaction between 238 serum samples and 5,133 cloned cancer antigens pre-selected via biopanning. Using specialized bioinformatics, the massive dataset was mined to identify a panel of top 130 cancer biomarkers (FIG. 1). Many of these markers represent or mimic known cancer antigens. Based on this panel of 130 cancer biomarkers, a trained neural network classifier has a sensitivity of 73.1% and specificity of 76.1% in discriminating cancer from noncancer serum samples in an independent test set. The performance of this classifier represents a significant improvement over current diagnostic accuracy in the primary care setting with reported sensitivity of 37% to 46% and specificity of 24%.

The results presented in this study indicate the potential of a new platform for cancer detection based on analysis of pattern of serum immunoreactivity against a panel of cancer antigens. The pattern of immunoreactivity is highly reproducible. In addition, serum IgGs were found to be extremely stable, which should minimize interlaboratory variations in clinical diagnostics setting. A significant advantage of the approach is the potential to translate this technology into simple assay systems, such the enzyme-linked immunosorbent assay (ELISA), which is already widely available in clinical practice and familiar to clinical laboratories. This facilitates the wide-spread application of this assay as a simple tool in the primary care setting to screen (in asymptomatic patients) and diagnose (in symptomatic patients) HNSCC in high risk population.

Finally, the pattern of reactivity of biomarkers with serum samples from HNSCC can be analyzed to develop other classifiers capable of predicting clinical outcome and thereby guiding the most optimal therapeutic treatments. For example, the clinical outcomes that can be predicted include, but are not limited to, response to a particular therapeutic intervention or chemotherapeutic drug, survival, and development of neck or distant metastasis. These biomarkers also have utility in post-treatment monitoring of HNSCC patients and provide new targets for therapeutic interventions or diagnostic imaging in future clinical trials. Because the host immune system can reveal molecular events (overexpression or mutation) critical to the genesis of HNSCC, this proteomics technology can also identify genes with mechanistic involvement in the etiology of the disease.

In conclusion, using a novel technology based on a combination of high throughput antigen selection using microarray-based serological profiling and specialized bioinformatics identified a panel of antigen biomarkers that can provide sufficient accuracy for a clinically relevant, serum-based cancer detection test based on the pattern of serum immunoglobulin binding.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE 1a

Tumor subsites and stages of the 12 HNSCC sera used in the subtractive biopanning.

| Subsites | Stage I | Stage II | Stage III | Stage IV | Total |
|---|---|---|---|---|---|
| Supraglottis | 0 | 0 | 0 | 3 | 3 |
| Glottis | 1 | 0 | 0 | 1 | 2 |
| Nasopharynx | 0 | 0 | 0 | 0 | 0 |
| Oropharynx | 0 | 0 | 0 | 3 | 3 |
| Hypopharynx | 0 | 0 | 0 | 0 | 0 |
| Oral Cavity | 0 | 0 | 0 | 3 | 3 |
| Unknown | 0 | 0 | 0 | 1 | 1 |
| Total | 1 | 0 | 0 | 11 | 12 |

TABLE 1b

Patient characteristics of the 12 HNSCC patients and 9 control patients whose sera were used in the subtractive biopanning.

| | HNSCC | Control |
|---|---|---|
| Number of patients | 12 | 9 |
| Mean Age (range) | 61.6 (46-87) | 38 (22-56) |
| Race | | |
| African American | 6 | 5 |
| Caucasian | 6 | 3 |
| Hispanics | 0 | 1 |
| Gender | | |
| Male | 11 | 5 |
| Female | 1 | 4 |

TABLE 2a

Tumor subsites and stages of the 39 HNSCC sera used for immunoscreening of the original 5,134 clones.

| Subsites | Stage I | Stage II | Stage III | Stage IV | Total |
|---|---|---|---|---|---|
| Supraglottis | 1 | 2 | 1 | 5 | 9 |
| Glottis | 4 | 0 | 2 | 1 | 7 |
| Nasopharynx | 1 | 0 | 0 | 0 | 1 |
| Oropharynx | 1 | 1 | 0 | 8 | 10 |
| Hypopharynx | 0 | 0 | 1 | 0 | 1 |
| Oral Cavity | 1 | 2 | 0 | 5 | 8 |
| Cervical Esophagus | 0 | 0 | 0 | 1 | 1 |
| Unknown | 0 | 0 | 0 | 2 | 2 |
| Total | 8 | 5 | 4 | 22 | 39 |

TABLE 2b

Patient characteristics of the 39 HNSCC patients and 41 control patients whose sera were used for immunoscreening of the original 5,134 clones.

| | HNSCC | Control |
|---|---|---|
| Number of patients | 39 | 41 |
| Mean Age (range) | 60 (26-87) | 47 (20-76) |
| African American | 22 | 27 |
| Caucasian | 17 | 13 |
| Hispanics | 0 | 1 |
| Gender | | |
| Male | 35 | 27 |
| Female | 4 | 14 |

TABLE 3a

Tumor subsites and stages of the 80 HNSCC sera used for immunoscreening of the 1,021 clones arrayed on the master protein microchips.

| Subsites | Stage I | Stage II | Stage III | Stage IV | Total |
|---|---|---|---|---|---|
| Supraglottis | 2 | 1 | 5 | 2 | 10 |
| Glottis | 2 | 1 | 3 | 8 | 14 |
| Nasopharynx | 1 | 1 | 0 | 2 | 4 |
| Oropharynx | 1 | 1 | 0 | 14 | 16 |
| Hypopharynx | 0 | 1 | 3 | 5 | 9 |
| Oral Cavity | 2 | 5 | 1 | 13 | 21 |
| Cervical Esophagus | 0 | 0 | 0 | 1 | 1 |
| Unknown | 0 | 0 | 0 | 5 | 5 |
| Total | 8 | 10 | 12 | 50 | 80 |

TABLE 3b

Patient characteristics of the 80 HNSCC patients and 78 control patients whose sera were used for immunoscreening of the 1,021 clones arrayed on the final protein microchips.

| | HNSCC | Control |
|---|---|---|
| Number of patients | 80 | 78 |
| Mean Age (range) | 60 (27-81) | 51 (19-74) |
| Race | | |
| African American | 45 | 45 |
| Caucasian | 35 | 33 |
| Gender | | |
| Male | 59 | 57 |
| Female | 21 | 21 |

TABLE 4

Ranking of clones based on the number of times out of 1,000 possible rankings they were selected in the 130 biomarker panel used to build the neural network classifier.

| Name | Rank | Number of times selected out of 1000 possibile times |
|---|---|---|
| 1_H3 | 1 | 1000 |
| 1_H8 | 2 | 1000 |
| 10_C3 | 3 | 1000 |
| 10_F12 | 4 | 1000 |
| 10_G8 | 5 | 1000 |
| 10_H6 | 6 | 1000 |
| 2_D4 | 7 | 1000 |
| 2_D8 | 8 | 1000 |
| 2_G11 | 9 | 1000 |

TABLE 4-continued

Ranking of clones based on the number of times out of 1,000 possible rankings they were selected in the 130 biomarker panel used to build the neural network classifier.

| Name | Rank | Number of times selected out of 1000 possibile times |
|---|---|---|
| 2_G8 | 10 | 1000 |
| 2_H4 | 11 | 1000 |
| 5_C8 | 12 | 1000 |
| 6_C8 | 13 | 1000 |
| 6_D4 | 14 | 1000 |
| 6_G11 | 15 | 1000 |
| 6_G12 | 16 | 1000 |
| 7_C11 | 17 | 1000 |
| 7_C4 | 18 | 1000 |
| 7_G4 | 19 | 1000 |
| 10_B11 | 20 | 999 |
| 10_G11 | 21 | 999 |
| 11_C4 | 22 | 999 |
| 2_D3 | 23 | 999 |
| 3_D4 | 24 | 999 |
| 9_C4 | 25 | 999 |
| 1_D7 | 26 | 998 |
| 10_C9 | 27 | 998 |
| 7_C3 | 28 | 998 |
| 9_G4 | 29 | 998 |
| 9_G8 | 30 | 998 |
| 11_B12 | 31 | 997 |
| 2_C10 | 32 | 996 |
| 2_G4 | 33 | 996 |
| 9_G12 | 34 | 995 |
| 11_C8 | 35 | 994 |
| 5_G3 | 36 | 994 |
| 8_C4 | 37 | 994 |
| 10_C4 | 38 | 993 |
| 10_G5 | 39 | 993 |
| 10_G7 | 40 | 993 |
| 5_C11 | 41 | 991 |
| 1_D12 | 42 | 990 |
| 10_D6 | 43 | 985 |
| 10_D12 | 44 | 982 |
| 4_G8 | 45 | 982 |
| 1_D11 | 46 | 980 |
| 5_H8 | 47 | 979 |
| 8_G11 | 48 | 979 |
| 1_D2 | 49 | 978 |
| 6_H8 | 50 | 976 |
| 9_C12 | 51 | 976 |
| 11_B8 | 52 | 974 |
| 9_F12 | 53 | 972 |
| 10_B12 | 54 | 969 |
| 2_G7 | 55 | 965 |
| 1_G4 | 56 | 954 |
| 5_C4 | 57 | 954 |
| 4_G7 | 58 | 953 |
| 1_H2 | 59 | 952 |
| 9_G7 | 60 | 949 |
| 10_H8 | 61 | 947 |
| 11_C7 | 62 | 947 |
| 2_G3 | 63 | 946 |
| 2_D6 | 64 | 943 |
| 10_F10 | 65 | 942 |
| 10_G12 | 66 | 934 |
| 8_G3 | 67 | 933 |
| 1_H7 | 68 | 931 |
| 2_C8 | 69 | 919 |
| 12_D10 | 70 | 907 |
| 9_H4 | 71 | 904 |
| 10_H11 | 72 | 889 |
| 2_H3 | 73 | 877 |
| 2_C12 | 74 | 871 |
| 1_G3 | 75 | 868 |
| 11_B10 | 76 | 866 |
| 5_C3 | 77 | 864 |
| 2_C11 | 78 | 857 |
| 11_C9 | 79 | 847 |
| 5_H4 | 80 | 845 |
| 1_C12 | 81 | 843 |
| 10_D7 | 82 | 840 |
| 2_H7 | 83 | 830 |
| 10_E12 | 84 | 819 |
| 9_C3 | 85 | 810 |
| 11_C3 | 86 | 809 |
| 2_C2 | 87 | 809 |
| 5_C7 | 88 | 807 |
| 11_A1 | 89 | 796 |
| 10_F11 | 90 | 795 |
| 2_F3 | 91 | 787 |
| 2_H8 | 92 | 785 |
| 2_G2 | 93 | 782 |
| 10_F8 | 94 | 775 |
| 10_H3 | 95 | 774 |
| 11_C1 | 96 | 761 |
| 9_C2 | 97 | 759 |
| 2_C3 | 98 | 728 |
| 6_C12 | 99 | 728 |
| 10_B10 | 100 | 710 |
| 12_C4 | 101 | 697 |
| 2_C7 | 102 | 669 |
| 8_B12 | 103 | 659 |
| 5_D4 | 104 | 653 |
| 5_G4 | 105 | 652 |
| 8_D4 | 106 | 644 |
| 1_H4 | 107 | 634 |
| 1_D6 | 108 | 598 |
| 4_G4 | 109 | 587 |
| 10_B4 | 110 | 581 |
| 11_A2 | 111 | 571 |
| 10_E8 | 112 | 570 |
| 10_C1 | 113 | 558 |
| 8_H10 | 114 | 558 |
| 6_G8 | 115 | 551 |
| 9_C6 | 116 | 541 |
| 1_D4 | 117 | 538 |
| 6_C4 | 118 | 528 |
| 6_G3 | 119 | 498 |
| 12_C12 | 120 | 495 |
| 1_D8 | 121 | 489 |
| 5_C6 | 122 | 479 |
| 12_D2 | 123 | 453 |
| 6_F4 | 124 | 453 |
| 1_G8 | 125 | 442 |
| 8_G8 | 126 | 431 |
| 9_H7 | 127 | 424 |
| 9_D11 | 128 | 418 |
| 6_C3 | 129 | 417 |
| 10_D3 | 130 | 408 |
| 11_D4 | 131 | 406 |
| 2_F4 | 132 | 405 |
| 10_C8 | 133 | 403 |
| 4_B3 | 134 | 401 |
| 4_F8 | 135 | 400 |
| 9_B12 | 136 | 389 |
| 2_D2 | 137 | 374 |
| 11_B6 | 138 | 373 |
| 4_C8 | 139 | 360 |
| 2_C1 | 140 | 349 |
| 5_G6 | 141 | 348 |
| 11_C6 | 142 | 344 |
| 11_B2 | 143 | 326 |
| 3_C4 | 144 | 325 |
| 1_G7 | 145 | 320 |
| 11_D8 | 146 | 317 |
| 1_C8 | 147 | 312 |
| 9_G10 | 148 | 306 |
| 8_B4 | 149 | 302 |
| 8_C8 | 150 | 293 |
| 12_D6 | 151 | 292 |
| 10_F6 | 152 | 287 |
| 7_G1 | 153 | 287 |
| 7_G3 | 154 | 286 |
| 2_G10 | 155 | 284 |

TABLE 4-continued

Ranking of clones based on the number of times out of 1,000 possible rankings they were selected in the 130 biomarker panel used to build the neural network classifier.

| Name | Rank | Number of times selected out of 1000 possibile times |
|---|---|---|
| 8_B3 | 156 | 281 |
| 10_B8 | 157 | 276 |
| 3_C8 | 158 | 272 |
| 1_G2 | 159 | 270 |
| 1_D3 | 160 | 269 |
| 9_F10 | 161 | 267 |
| 8_D8 | 162 | 261 |
| 9_G11 | 163 | 251 |
| 5_C12 | 164 | 236 |
| 11_C11 | 165 | 233 |
| 4_C4 | 166 | 232 |
| 7_G2 | 167 | 223 |
| 7_H4 | 168 | 217 |
| 6_A10 | 169 | 213 |
| 9_H5 | 170 | 210 |
| 11_A11 | 171 | 207 |
| 11_A3 | 172 | 193 |
| 6_B4 | 173 | 183 |
| 10_G4 | 174 | 180 |
| 10_H9 | 175 | 176 |
| 2_H1 | 176 | 174 |
| 11_D5 | 177 | 172 |
| 2_B11 | 178 | 163 |
| 8_F2 | 179 | 158 |
| 11_B9 | 180 | 150 |
| 11_B1 | 181 | 149 |
| 1_G12 | 182 | 146 |
| 12_C7 | 183 | 145 |
| 9_B8 | 184 | 145 |
| 6_D11 | 185 | 143 |
| 4_C3 | 186 | 138 |
| 7_G8 | 187 | 130 |
| 9_C1 | 188 | 121 |
| 10_B3 | 189 | 120 |
| 2_G12 | 190 | 119 |
| 11_D10 | 191 | 114 |
| 10_H7 | 192 | 113 |
| 5_F8 | 193 | 112 |
| 11_C10 | 194 | 111 |
| 8_B7 | 195 | 111 |
| 2_C9 | 196 | 110 |
| 1_H11 | 197 | 109 |
| 11_B4 | 198 | 109 |
| 10_F7 | 199 | 104 |
| 8_F3 | 200 | 104 |
| 9_H6 | 201 | 100 |
| 4_G3 | 202 | 98 |
| 5_G8 | 203 | 98 |
| 7_C9 | 204 | 93 |
| 1_G6 | 205 | 92 |
| 11_C12 | 206 | 89 |
| 11_D3 | 207 | 88 |
| 2_C4 | 208 | 84 |
| 5_G2 | 209 | 83 |
| 1_C4 | 210 | 80 |
| 5_G10 | 211 | 79 |
| 1_C10 | 212 | 78 |
| 11_A4 | 213 | 75 |
| 3_G7 | 214 | 74 |
| 12_D11 | 215 | 73 |
| 7_G6 | 216 | 73 |
| 8_C11 | 217 | 73 |
| 11_B3 | 218 | 71 |
| 6_F8 | 219 | 70 |
| 9_C10 | 220 | 68 |
| 1_B10 | 221 | 67 |
| 1_C11 | 222 | 67 |
| 5_H9 | 223 | 67 |
| 9_B4 | 224 | 66 |
| 11_D7 | 225 | 65 |
| 2_G1 | 226 | 64 |
| 10_C11 | 227 | 60 |
| 12_D12 | 228 | 58 |
| 9_G2 | 229 | 56 |
| 4_D7 | 230 | 55 |
| 1_H6 | 231 | 54 |
| 8_H6 | 232 | 52 |
| 10_H10 | 233 | 49 |
| 5_D8 | 234 | 49 |
| 12_D4 | 235 | 48 |
| 12_C9 | 236 | 47 |
| 2_F7 | 237 | 47 |
| 9_F1 | 238 | 45 |
| 1_H10 | 239 | 43 |
| 8_G5 | 240 | 42 |
| 6_C7 | 241 | 41 |
| 2_G6 | 242 | 37 |
| 8_H11 | 243 | 36 |
| 12_D9 | 244 | 32 |
| 2_F11 | 245 | 32 |
| 12_C8 | 246 | 31 |
| 5_G11 | 247 | 31 |
| 11_C5 | 248 | 30 |
| 11_D9 | 249 | 30 |
| 2_D11 | 250 | 30 |
| 9_F8 | 251 | 29 |
| 10_B9 | 252 | 28 |
| 4_D10 | 253 | 28 |
| 6_B10 | 254 | 28 |
| 5_C10 | 255 | 27 |
| 10_F4 | 256 | 26 |
| 5_D12 | 257 | 26 |
| 9_G3 | 258 | 26 |
| 2_D1 | 259 | 25 |
| 5_H11 | 260 | 25 |
| 9_C11 | 261 | 25 |
| 2_B6 | 262 | 23 |
| 8_G4 | 263 | 23 |
| 9_B3 | 264 | 21 |
| 11_B11 | 265 | 19 |
| 6_B8 | 266 | 19 |
| 6_F2 | 267 | 19 |
| 7_D4 | 268 | 19 |
| 7_H1 | 269 | 19 |
| 2_B8 | 270 | 18 |
| 3_D2 | 271 | 18 |
| 8_D10 | 272 | 18 |
| 6_F7 | 273 | 17 |
| 8_G12 | 274 | 17 |
| 9_C9 | 275 | 17 |
| 11_A12 | 276 | 15 |
| 12_B4 | 277 | 15 |
| 2_C6 | 278 | 15 |
| 6_D7 | 279 | 15 |
| 10_H4 | 280 | 14 |
| 2_H2 | 281 | 14 |
| 6_F3 | 282 | 14 |
| 11_C2 | 283 | 13 |
| 2_F8 | 284 | 13 |
| 10_G6 | 285 | 12 |
| 2_B2 | 286 | 12 |
| 1_F4 | 287 | 11 |
| 10_H5 | 288 | 11 |
| 12_D8 | 289 | 11 |
| 4_H1 | 290 | 11 |
| 7_G11 | 291 | 11 |
| 8_C12 | 292 | 11 |
| 9_H8 | 293 | 11 |
| 11_A5 | 294 | 10 |
| 3_C3 | 295 | 10 |
| 5_F11 | 296 | 10 |
| 10_C12 | 297 | 9 |
| 3_H8 | 298 | 9 |
| 4_B4 | 299 | 9 |
| 8_H3 | 300 | 9 |
| 10_B7 | 301 | 8 |

TABLE 4-continued

Ranking of clones based on the number of times out of 1,000 possible rankings they were selected in the 130 biomarker panel used to build the neural network classifier.

| Name | Rank | Number of times selected out of 1000 possibile times |
|---|---|---|
| 10_C7 | 302 | 8 |
| 11_A6 | 303 | 8 |
| 11_D11 | 304 | 8 |
| 11_D2 | 305 | 8 |
| 2_F2 | 306 | 8 |
| 6_B6 | 307 | 8 |
| 6_B9 | 308 | 8 |
| 7_C8 | 309 | 8 |
| 10_A12 | 310 | 7 |
| 10_D8 | 311 | 7 |
| 11_D1 | 312 | 7 |
| 12_A9 | 313 | 7 |
| 12_C11 | 314 | 7 |
| 2_B3 | 315 | 7 |
| 4_H4 | 316 | 7 |
| 6_B11 | 317 | 7 |
| 6_B3 | 318 | 7 |
| 9_B11 | 319 | 7 |
| 12_A1 | 320 | 6 |
| 12_A11 | 321 | 6 |
| 3_G8 | 322 | 6 |
| 11_A10 | 323 | 5 |
| 2_G5 | 324 | 5 |
| 3_D3 | 325 | 5 |
| 8_G7 | 326 | 5 |
| 1_C7 | 327 | 4 |
| 1_D10 | 328 | 4 |
| 10_H2 | 329 | 4 |
| 12_C3 | 330 | 4 |
| 2_B10 | 331 | 4 |
| 2_D7 | 332 | 4 |
| 2_H6 | 333 | 4 |
| 5_F4 | 334 | 4 |
| 5_G12 | 335 | 4 |
| 6_D6 | 336 | 4 |
| 7_B12 | 337 | 4 |
| 8_D2 | 338 | 4 |
| 9_D6 | 339 | 4 |
| 1_A6 | 340 | 3 |
| 1_C6 | 341 | 3 |
| 12_B5 | 342 | 3 |
| 3_H2 | 343 | 3 |
| 6_G7 | 344 | 3 |
| 7_A1 | 345 | 3 |
| 7_D3 | 346 | 3 |
| 7_H3 | 347 | 3 |
| 9_C7 | 348 | 3 |
| 9_E2 | 349 | 3 |
| 9_F3 | 350 | 3 |
| 1_C3 | 351 | 2 |
| 1_F3 | 352 | 2 |
| 1_G11 | 353 | 2 |
| 3_D12 | 354 | 2 |
| 3_H5 | 355 | 2 |
| 5_B8 | 356 | 2 |
| 6_A9 | 357 | 2 |
| 7_E1 | 358 | 2 |
| 8_H2 | 359 | 2 |
| 9_D2 | 360 | 2 |
| 9_E12 | 361 | 2 |
| 9_E5 | 362 | 2 |
| 9_E9 | 363 | 2 |
| 1_D9 | 364 | 1 |
| 1_G9 | 365 | 1 |
| 10_D4 | 366 | 1 |
| 10_E11 | 367 | 1 |
| 10_E3 | 368 | 1 |
| 10_E4 | 369 | 1 |
| 10_E5 | 370 | 1 |
| 11_B7 | 371 | 1 |
| 12_B8 | 372 | 1 |
| 12_B9 | 373 | 1 |
| 12_D3 | 374 | 1 |
| 12_D7 | 375 | 1 |
| 2_F6 | 376 | 1 |
| 3_C2 | 377 | 1 |
| 3_G6 | 378 | 1 |
| 5_A9 | 379 | 1 |
| 5_B3 | 380 | 1 |
| 6_B12 | 381 | 1 |
| 7_F4 | 382 | 1 |
| 8_B8 | 383 | 1 |
| 8_C3 | 384 | 1 |
| 8_G6 | 385 | 1 |
| 9_B9 | 386 | 1 |
| 9_E1 | 387 | 1 |
| 9_E10 | 388 | 1 |
| 9_H10 | 389 | 1 |

TABLE 5

Eight of the 130 top clones represented epitopes. These clones contained gene fragments in the reading frame of the T7 gene 10 capsid gene and thus expressed the same original peptides coded by the inserted gene fragments.

| Rank | Clone | Description of the genes that are in-frame with T7 10B gene | Peptide sequences of Mimotopes in-frame with T7 10B gene | Size of peptide | Description of sequences that are in-frame with T7 10B gene |
|---|---|---|---|---|---|
| 4 | 10_F12 | gi\|19717685\|gb\|AF487338.1\| H sapiens multiple myeloma overexpression gene 2 (MYEOV2) mRNA Length = 452, Score = 698 bits(352) Expect = 0 Id = 363/368 (98%) Gaps = 0/368(0%) | AEMFPEG AGPYVDL DEAGGST GLLMDLA ANEKAVH ADFFNDF EDLFDDD DIQ | 51 | gi\|20503274\|gb\|AAL96264.2\| Multiple myeloma overexpression gene 2 |
| 12 | 5_C8 | gi\|190805\|gb\|M37387.1\|HUMQBPIC Human mitochondrial ubiquinone-binding protein | LVSRPFQ HQASGW MVFENGI | 20 | gi\|190806\|gb\|AAA60361.1\| Ubiquinone binding protein |

TABLE 5-continued

| | | | | | |
|---|---|---|---|---|---|
| | | (HQPI) gene, exon 2<br>Length = 75<br>Score = 131 bits(66)<br>Expect = 2e-28<br>Id = 73/74(98%)<br>Gaps = 1/74(1%) | TMLQDSI<br>NWG | | |
| 19 | 7_G4 | gi\|78499271\|gb\|DQ246833.1\|<br>H sapiens isolate IND23<br>mitochondrion, complete<br>genome,<br>Length = 16320<br>Score = 218 bits (110)<br>Expect = 2e-54<br>Id = 118/121(97%)<br>Gaps = 0/121 (0%)<br>Product = NADH dehydrogenase<br>subunit 1 | PPWSPIVE<br>LLDAQVA<br>ADPDKLV<br>ERFELAV<br>DALSPEV<br>YTTYFVT<br>KTLLLTS<br>LFL | 27 | gi\|29690911\|gb\|AAQ88761.1\|<br>NADH<br>dehydrogenase<br>subunit 1 |
| 40 | 10_G7 | gi\|19717685\|gb\|AF487338.1\|<br>H sapiens multiple myeloma<br>overexpression gene 2<br>(MYEOV2) mRNA<br>Length = 452,<br>Score = 698 bits(352)<br>Expect = 0<br>Id = 363/368 (98%)<br>Gaps = 0/368(0%) | AEMFPEG<br>AGPYVDL<br>DEAGGST<br>GLLMDLA<br>ANEKAVH<br>ADFFNDF<br>EDLFDDD<br>DIQ | 51 | gi\|20503274\|gb\|AAL96264.2\|<br>Multiple myeloma<br>overexpression<br>gene 2 |
| 41 | 5_C11 | gi\|190805\|gb\|M37387.1\|HUMQBPIC<br>Human mitochondrial<br>ubiquinone-binding protein<br>(HQPI) gene, exon 2<br>Length = 75<br>Score = 131 bits(66)<br>Expect = 2e-28<br>Id = 73/74(98%)<br>Gaps = 1/74(1%) | LVSRPFQ<br>HQASGW<br>MVFENGI<br>TMLQDSI<br>NWG | 20 | gi\|190806\|gb\|AAA60361.1\|<br>Ubiquinone<br>binding protein |
| 66 | 10_G12 | gi\|1633547\|gb\|U47924.1\|HSU47924<br>Human chromosome 12p13<br>sequence, complete sequence<br>Length = 222930<br>Features in this part of subject<br>sequence: C10<br>Score = 430 bits (217)<br>Expect = 8e-118<br>Id = 224/227 (98%)<br>Gaps = 0/227 (0%) | GRKGLEF<br>ARLVKSY<br>EAQDPEI<br>ASLSGKL<br>KALFLPP<br>MTLPPHG<br>PAAGGSV<br>AAS | 48 | gi\|19923951\|ref\|NP612434.1\|<br>C10 protein |
| 81 | 1_C12 | gi\|5360992\|emb\|AL023494.12\|HS366L4<br>Human DNA sequence from<br>clone RP3-366L4 on<br>chromosome 22q11.23-12.2,<br>Length = 37658<br>Score = 309 Bits (156)<br>Expect = 6e-82<br>Id = 156/156 (100%)<br>Gaps = 0/156 (0%)<br>Strand = Plus/Minus | GWSAMA<br>QSWLTAT<br>STSRVQVI<br>LLPQPPE | 28 | gi\|46409510\|ref\|NP997326.1\|<br>hypothetical<br>protein<br>LOC400242 |
| 111 | 11_A2 | gi\|19717685\|gb\|AF487338.1\|<br>H sapiens multiple myeloma<br>overexpression gene 2<br>(MYEOV2) mRNA<br>Length = 452<br>Score = 698 bits(352)<br>Expect = 0<br>Id = 363/368 (98%)<br>Gaps = 0/368(0%) | AEMFPEG<br>AGPYVDL<br>DEAGGST<br>GLLMDLA<br>ANEKAVH<br>ADFFNDF<br>EDLFDDD<br>DIQ | 51 | gi\|20503274\|gb\|AAL96264.2\|<br>Multiple myeloma<br>overexpression<br>gene 2 |

| Rank | Region of similarity of peptide |
|---|---|
| 4 | Score = 168 bits (389), Expect = 3e-42<br>Id = 51/51 (100%), Pos = 51/51 (100%)<br>Gaps = 0/51 (0%)<br>Query2 EMFPEGAGPYVDLDEAGGSTGLLMDLAANEKAVHADFFNDFEDLFDDDDIQ<br>       EMFPEGAGPYVDLDEAGGSTGLLMDLAANEKAVHADFFNDFEDLFDDDDIQ<br>Sbjct7 EMFPEGAGPYVDLDEAGGSTGLLMDLAANEKAVHADFFNDFEDLFDDDDIQ |

TABLE 5-continued

```
12  Score = 72.7 bits (164)
    Expect = 6e-14
    Id = 20/20 (100%)
    Pos = 20/20 (100%)
    Gaps = 0/20 (0%)
    Query  10 ASGWMVFENGITMLQDSINW 29
              ASGWMVFENGITMLQDSINW
    Sbjct   4 ASGWMVFENGITMLQDSINW 23

19  Score = 49.3 bits (116)
    Expect = 5e-05
    Id = 23/27 (85%)
    Pos = 25/27 (92%)
    Gaps = 0/27 (0%)
    Query  27 LAVDALSPEVYTTYFVTKTLLLTSLFL   53
              +   DALSPE+YTTYFVTKTLLLTSLFL
    Sbjct 245 MTYDALSPELYTTYFVTKTLLLTSLFL  271

40  Score = 168 bits (389)
    Expect = 3e-42
    Id = 51/51 (100%)
    Pos = 51/51 (100%)
    Gaps = 0/51 (0%)
    Query2 EMFPEGAGPYVDLDEAGGSTGLLMDLAANEKAVHADFFNDFEDLFDDDDIQ
           EMFPEGAGPYVDLDEAGGSTGLLMDLAANEKAVHADFFNDFEDLFDDDDIQ
    Sbjct7 EMFPEGAGPYVDLDEAGGSTGLLMDLAANEKAVHADFFNDFEDLFDDDDIQ 41  Score = 72.7 bits (164)
    Expect = 6e-14
    Id = 20/20 (100%)
    Pos = 20/20 (100%)
    Gaps = 0/20 (0%)
    Query  10 ASGWMVFENGITMLQDSINW 29
              ASGWMVFENGITMLQDSINW
    Sbjct   4 ASGWMVFENGITMLQDSINW 23

66  Score = 144 bits (333)
    Expect = 7e-35,
    Id = 47/48 (97%)
    Positives = 48/48 (100%)
    Gaps = 0/48 (0%)
    Q  11 LEFARLVKSYEAQDPEIASLSGKLGALFLPPMTLPPHGPAAGGSVAAS   58
          L+FARLVKSYEAQDPEIASLSGKLGALFLPPMTLPPHGPAAGGSVAAS
    S  79 LKFARLVKSYEAQDPEIASLSGKLGALFLPPMTLPPHGPAAGGSVAAS  126

81  Score = 82.5 bits (187)
    Expect = 7e-17
    Id = 25/28 (89%)
    Positives = 26/28 (92%)
    Gaps = 0/28 (0%)
    Query   1 GWSAMAQSWLTATSTSRVQVILLPQPPE 28
              GWASAMAQSWLT TS S+VQVILLPQPPE
    Sbjct 121 GWSAMAQSWLTATSTSRVQVILLPQPPE 148

111 Score = 168 bits (389)
    Expect = 3e-42
    Id = 51/51 (100%)
    Pos = 51/51 (100%)
    Gaps = 0/51 (0%)
    Query2 EMFPEGAGPYVDLDEAGGSTGLLMDLAANEKAVHADFFNDFEDLFDDDDIQ
           EMFPEGAGPYVDLDEAGGSTGLLMDLAANEKAVHADFFNDFEDLFDDDDIQ
    Sbjct7 EMFPEGAGPYVDLDEAGGSTGLLMDLAANEKAVHADFFNDFEDLFDDDDIQ
```

Table 6. One hundred twenty-two of the top 130 clones contained peptides which were different from the original proteins coded by the inserted gene fragments. This occurred because a) the inserted gene fragment was out of frame with the open reading frame of the T7 10B gene (n=61), b) the inserted gene fragment represented untranslated region of known gene (n=18), or c) the inserted gene fragment represented sequences from unknown gene (n=43).

TABLE 6a

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| 1 | 1_H3 | gi\|13097209\|gb\|BC00337 0.1\| *Homo sapiens* cystatin B (stefin B) (cDNA clone MGC: 17497 IMAGE: 3453675), complete cds Length = 613 Score = 517 bits (261) Expect = 1e-144 Id = 265/267 (99%) Gaps = 0/267 (0%) Strand = Plus/Plus | KLLHQGAR RRRGLRTP ASVPISPS | 24 | gi\|2135396\|pir\|S71548 Homeotic protein pG2 gi\|85726204\|gb\|ABC79623.1\| cytokeratin associated protein gi\|4505037\|ref\|NP_003564.1\| Latent transforming growth factor beta binding protein 4 gi\|56206067\|emb\|CAI23573.1 Myc target 1 gi\|1703642\|gb\|AAB37683.1\| p65 Net1 proto-oncogene protein | Score = 28.6 bits (60), Expect = 1.1 Id = 12/22 (54%), Positives = 14/22 (63%) Gaps = 3/22 (13%) Query 4 LHQGARRRRGLRTPASVPISPS 25 L QG RRR L  +SVP +PS Sbjct 228 LQQGGRPRGDL---SVVPTAPS 246 Score = 26.1 bits (54), Expect = 9.3 Identities = 9/11 (81%), Positives = 9/11 (81%), Gaps = 1/11 (9%) Query 7 ARRRRGLRTPA 17 ARRRA LRT A Sbjct 292 ARRRR-LRTAA 301 Score = 24.4 bits (50), Expect = 21 Id = 9/15 (60%), Positives = 9/15 (60%), Gaps = 5/15 (33%) Query 9 RRRRGLRTPASVPIS 23 RRRR      AS PIS Sbjct 95 RRRR----ASAPIS 104 |
| 2 | 1_H8 | gi\|20357564\|ref\|NM_0001 00.2\| *Homo sapiens* cystatin B (stefin B) (CSTB), mRNA cystatin B (liver thiol proteinase inhibitor) Length = 674 Score = 424 bits (214) Expect = 6e-116 Id = 214/214 (100%) Gaps = 0/214 (0%) Strand = Plus/Plus | VIQEPG GRGDKL LHQGAR RRRCLR TPASVPI SPS | 34 | gi\|28892\|emb\|CAA35582.1\| Unnamed protein product gi\|2135396\|pir\|S71548 Homeotic protein pG2 gi\|48422276\|sp\|O43432\|IF4G 3_HUMAN Eukaryotic translation initiation factor 4 gamma3 (eIF-4-gamma3) (eIF-4-gamma II) gi\|2829451\|sp\|P56182\|NNP1 HUMAN NNP-1 protein (Novel nuclear protein 1) (Nucleolar protein Nop52) gi\|2190402\|emb\|CAA73944.1\| latent TGF-beta binding protein-4 gi\|56206067\|emb\|CAI23573.1 myc target 1 | Score = 30.3 bits (64), Expect = 0.34 Id = 12/22 (54%), Positives = 14/22 (63%) Gaps = 3/22 (13%) Query 9 LHQGARRRRXGLRTPASVPISPS 30 L QG RRR L  +SVP +PS Sbjct 227 LQQGGRPRGDL---SVVPTAPS 245 Score = 26.9 bits (56), Expect = 4.6 Id = 15/28 (53%), Positives = 17/28 (60%) Gaps = 7/28 (25%) Query 1 GRVIQEPGGRGDKLLHQGARR----RR 23 GR  Q PGGRG  LL+ G+RR      RR Sb 880 GR-QTPGGRGVPLLNVGSRSQPGQRR 905 Score = 25.2 bits (52), Expect = 28 Id = 11/20 (55%), Positives = 13/20 (65%), Gaps = 6/20 (30%) |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | | | | gi\|34098712\|sp\|Q9H0U9\|TSY L1_HUMAN Testis-specific Y-encoded-like protein 1 gi\|1703642\|gb\|AAB37683.1\| p65 Net1 proto-oncogene protein | Query 15 GRGDKLLHQGARRRGLRTP 34 GRG +GAR+RR RTP Sbjct 424 GRG----QRGARQRR--RTP 437 |
| 6 | 10_H 6 | gi\|75905883\|gb\|AY96358 5.2\| Homo sapiens isolate 14_LoF (Tor65) mitochondrion Length = 16569 Score = 232 bits (117) Expect = 2e-58 Id = 119/120 (99%) Gaps = 0/120 (0%) Strand = Plus/Minus | NSSVD | 5 | gi\|123291744\|emb\|CA114853. 2\| ADAMTS-like gi\|119617528\|gb\|EAW97122. 1\| SLIT-ROBO Rho GTPase activating protein 1, isoform CRA_a gi\|119591326\|gb\|EAW70920. 1\|SP140 nuclear body protein, isoform CRA_a gi\|119620377\|gb\|EAW99971. 1\| EH domain binding protein 1, isoform CRA_c | Score = 18.0 bits (35), Expect = 1284 Id = 5/5 (100%), Positives 5/5 (100%), Gaps = 0/5 (0%) Query 1 NSSVD 5 NSSVD Sbjct 541 NSSVD 545 |
| 10 | 2_G8 | gi\|39992414\|gb\|BC06441 8.1\| Homo sapiens FK506 binding protein 9, 63 kDa, mRNA (cDNA cloneIMAGE: 5750487), partial cds Length = 2421 Score = 486 bits (245) Expect = 1e-134 Id = 259/264 (98%) Gaps = 0/264 (0%) Strand = Plus/Minus | GSGKIKKSV LWDRKVGI RKN | 20 | gi\|56202484\|emb\|CAI21939.1 HBxAg transactivated protein 2 (XTP2) gi\|119611307\|gb\|EAW90901. 1\|BAT2 domain containing 1, isoform CRA_d gi\|29427863\|sp\|Q8WUM0\|N U133_HUMAN Nuclear pore complex protein Nup133 (Nucleoporin Nup133) (133 kDa nucleoporin) gi\|61216828\|sp\|Q96HF1\|SFR P2_HUMAN Secreted apoptosis - related protein 1 gi\|12803735\|gb\|AAH02704.1 Signal transducer and activator of transcription 1 gi\|29337296\|ref\|NP_803881.1 Melanoma antigen family D, 4 isoform 2 gi\|57012811\|sp\|Q7Z419\|IBR D2_HUMAN E3 ubiquitin ligase IBRDC2 (p53 - inducible RING finger protein) | Score = 24.0 bits (49), Expect = 29 Id = 9/13 (69%), Positives = 9/13 (69%), Gaps = 0/13 (0%) Query 2 SGKIKKSVIMDRK 14 SG IKK VL D K Sbjct 83 SGPIKKPVLRDMK 95 Score = 24.0 bits (49), Expect = 41 Id = 6/6 (100%), Positives = 6/6 (100%), Gaps = 0/6 (0%) Query 8 SVLWDR 13 SVLWDR Sbjct 101 SVLWDR 106 Score = 23.1 bits (47), Expect = 73 Id = 6/6 (100%), Positives = 6/6 (100%), Gaps = 0/6 (0%) Query 6 KKSVLW 11 KKSVLW Sbjct 233 KKSVLW 238 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 11 | 2_H4 | gi\|39992414\|gb\|BC064418.1\| Homo sapiens FK506 binding protein 9, 63 kDa, mRNA (cDNA cloneIMAGE: 5750487), partial cds Length = 2421 Score = 307 bits (155) Expect = 3e-81 Id = 158/159 (99%) Gaps = 0/159 (0%) Strand = Plus/Minus | GSRKIXWT ALWETKVG LCLkLKMD EPCLSHAC YPNTLGGQ GGRITRXR LRPSWPTQ | 56 | Gi\|4758932\|ref\|NP_004563.1\| Plakophilin 2 isoform 2b gi\|15929032\|gb\|AAH14974.1\| VIF1B protein gi\|15341934\|gb\|AAH13155.1\| CRYZL1 protein gi\|6932986\|ref\|NP_0010193 86.1\| filamin-binding LIM protein-1 isoform b gi\|386941\|gb\|AAA59814.1\| MHC HLA-DR-beta-1 chain gi\|11038659\|ref\|NP_067610.1 ADAM metallopeptidase with tlironibospondin type 1 gi\|62088182\|dbj\|BAD92538.1 SLC2A11 protein variant gi\|33356179\|ref\|NP_031370.2 transcription termination factor, RNA polymerase 1 gi\|7416053\|dbj\|BAA93676.1\| survivin-beta gi\|3335138\|gb\|AAC39892.1\| RNA polyinerase 1 40 kD gi\|522145\|gb\|AAB02649.1\| B-cell growth factor | Score = 48.1 bits (106), Expect = 5e-06 Id = 15/17 (88%), Positives = 16/17 (94%), Gaps = 0/17 (0%) Query 30 HACYPNTLGGQGGRITR 46 HAC P+TLGGQGGRITR Sbjct 477 HACNPSTLGGQGGRITR 493 Score = 43.9 bits (96), Expect = 9e-05 Id = 14/17 (82%), Positives = 16/17 (94%), Gaps = 0/17 (0%) Query 30 HACYPNTLGGQGGRITR 46 HAC P+TLGG+GGRITR Sbjct 270 HACNPSTLGGRGGRITR 286 Score = 41.4 bits (90), Expect = 5e-04 Id = 13/16 (81%), Positives = 14/16 (87%), Gaps = 0/16 (0%) Query 30 HACYPNTLGGQGGRIT 45 H C P+TLGGQGGRIT Sbjct 98 HVCNPSTLGGQGGRIT 113 |
| 15 | 6_G1 1 | gi\|33876180\|gb\|BC00141 0.2\| Homo sapiens S100 calcium binding protein A11 (calgizzarin), mRNA (cDNA clone MGC: 2149 IMAGE: 3140092), complete cds Length = 568 Score 844 bits (426) Expect = 0.0 Id = 430/432 (99%) Gaps = 0/432 (0%) Strand = Plus/Plus /gene = "100A11" | LAQLQHGK NLQPYRD | 15 | gi\|38372397\|sp\|Q9ULK0\|GR1 D1_HUMAN Glutamate receptor delta-1 subunit precursor (GluR delta-1) gi\|2499758\|sp\|Q92729\|PTPR U_HUMAN Receptor type tyrosine protein phosphatase U precursor (Pancreatic carcinoma phosphatase 2) (PCP-2) gi\|2441904\|jgb\|AAL65133.2 Ovarian cancer related tumor marker CA125 gi\|30060232\|gb\|AAP13073.1 E3 ligase for inhibin receptor gi\|5053128\|gb\|AAD33053.2 | Score = 23.5 bits (48), Expect = 54 Id = 8/12 (66%), Positives = 8/12 (66%), Gaps = 3/12 (25%) Query 4 LQHGKNLQPYRD 15 LQHG PYRD Sbjct 774 LQHGS---PYRD 782 Score = 22.3 bits (45), Expect = 95 Id = 6/8 (75%), Positives = 7/8 (87%), Gaps = 0/8 (0%) Query 8 KNLQPYRD 15 KNL PYR+ Sbjct 451 KNLLPYRN 458 Score = 22.3 bits (45), Expect = 95 Id = 9/14 (64%), Positives = 10/14 (71%), |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | | | | Scar2 gi\|59800456\|sp\|Q9Y6W5\|WA SF2_HUMAN Wiskott-Aldrich syndrome protein family member 2 (WASP-family protein member2) (WAVE-2 protein) | Gaps = 1/14 (7%)<br>Query 1 LAQLQHG-KNLQPY 13<br>L+QL HG K L PY<br>Sbjct 13105 LSQLTHGIKELGPY 13118<br>Score 22.3 bits (45), Expect = 95<br>Id = 9/14 (64%), Positives = 10/14 (71%),<br>Gaps = 1/14 (7%)<br>Query 1 LAQLQHG-KNLQPY 13<br>L+QL HG K L PY<br>Sbct 14041 LSQLTHGIKELGPY 14054<br>Score = 19.7 bits (39), Expect = 556<br>Id = 10/19 (52%), Positives = 11/19 (57%),<br>Gaps = 4/19 (21%)<br>Query 1 LAQLQHG-KNLQPY---RD 15<br>L+QL HG L PY RD<br>Sbjct 20748 LSQLTHGITELGPYTLDRD 20766<br>Score = 18.0 bits (35), Expect = 1802<br>Id = 8/14 (57%), Positives = 9/14 (64%),<br>Gaps = 1/14 (7%)<br>Query 1 LAQLQHG-KNLQPY 13<br>L+QL HG L PY<br>Sbjct 15291 LSQLTHGITELGPY 15304 |
| 21 | 10_G 11 | gi\|17390908\|gb\|BC01838 6.1\| Homo sapiens cytochrome c oxidase subunit VIIb, mRNA (cDNA clone MGC: 9065 IMAGE: 3861730) Length = 454 Score = 549 bits (277), Expect = e-153 Id = 316/328 (96%), Gaps = 3/328 (0%) Strand = Plus/Plus tissue_type = "Ovary, adenocarcinoma" /gene = "COX7B" | NSSL | 4 | gi\|125987841\|sp\|Q99102\|MU C4_HUMAN Pancreatic adenocarcinoma mucin gi\|125863935\|sp\|Q8N584\|CR 017_HUMAN TPR repeat-containing protein C18orf17 gi\|121944808\|emb\|CAK5073 5.1\| immunoglobulin A heavy chain variable region gi\|120431468\|gb\|ABM21709. 1\| env protein gi\|119943116\|ref\|NP_001073 328.1\| G protein-coupled | Score = 14.6 bits (27), Expect = 10793<br>Id = 4/4 (100%), Positives = 4/4 (100%),<br>Gaps = 0/4 (0%)<br>Query 1 NSSL 4<br>NSSL<br>Sbjct 44 NSSL 47 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | /product = "cytochrome c oxidase subunit VIIb, precursor" | | | receptor 64 isoform 2 | |
| 22 | 11_C4 | gi\|4503528\|ref\|NM_001416.1\| Eukaryotic translation initiation factor 4A, isoform I (EIF4A1) mRNA Length = 1383 Score = 371 bits(187) Expect = 5e-100 Id = 199/205 (97%) Gaps = 0/205 (0%) Strand = Plus/Plus | VDSRTRSM TYSKSSTAT PR | 19 | gi\|47458813\|ref\|NP_006242.4 Protein kinase, AMP-activated, a-1 catalytic subunit isoform 1 (PRKAA1) gi\|47605556\|sp\|Q9NYF8\|BCL F1_HUMAN Bcl-2 associated transcriptional factor (Btl) gi\|8039798\|sp\|P30414\|NKCR_HUMAN NK-tumor recognition protein gi\|5870841\|gb\|AAA35734.2\| cyclophilin-related protein gi\|24419041\|gb\|AAL65133.2\| Ovarian cancer related tumor marker CA125 gi\|45768720\|gb\|AAH67812.1\| Cyclin L1 | Score = 28.6 bits (60), Expect = 1.1 Id = 14/27 (51%), Pos = 16/27 (59%), Gaps = 9/27 (33%) Query 1 VDSRT-----RSM----TYSKSSTATP 18 VDSRT RS+ T +KS TATP Sbjct471 VDSRTYLLDSRSIDDEITEAKSGTATP 497 Score = 25.7 bits (53), Expect = 9.0 Id = 8/11 (72%), Pos = 10/11 (90%), Gaps = 0/11 (0%) Query 3 SRTRSMTYSKS 13 SR+RS TYS+S Sbjct 36 SRSRSRTYSRS 46 Score = 23.5 bits (48), Expect = 52 Id = 9/18 (50%), Pos = 12/18 (66%), Gaps = 6/18 (33%) Query 10 RTRSMTY-------SK SST 21 RTRS++Y S+ SST Sbjct 1328 RTRSVSYSHSRSRSRSST 1345 |
| 26 | 1_D7 | gi\|57165047\|gb\|AY86482 4.1\| Homo sapiens CDC37 cell division cycle 37 homolog (S. cerevisiae) (CDC37) gene, complete cds Length = 16460 Score = 333 bits (168) Expect = 4e-89 Id = 168/168 (100%) Gaps = 0/168 (0%) Strand = Plus/Plus | LPRVQAQG GRVPEETE GAGGGRGR QGRAGAPA GRGTAAAQ GGAELGAE AGGDAQEG SLRPHSSN | 64 | gi\|148429165\|sp\|Q86V8\|THO C4_HUMAN THO complex subunit 4 (Tho4) (Transcriptional coactivator Aly/REF) gi\|47117879\|sp\|P83369\|LSM1 1_HUMAN U7 snRNA-associated Sm-like protein LSm11 gi\|62087836\|dbj\|BAD92365.1 serum response factor (c-fos serum response element-binding transcriptional factor) variant gi\|46397045\|sp\|Q9NQ03\|SCR T2_HUMAN | Score = 36.7 bits (79), Expect = 0.016 Id = 19/37 (51%), Positives = 21/37 (56%), Gaps = 14/37 (37%) Query 8 GGRVPETEGAGGGRGRQGRAGAPAGRGTAAAQGGAE 44 GGR GGGCR GRAG+ GRG GGA+ Sbjct 21 GGR------GGGRGR-GRAGSQGGRG----GGAQ 43 Score = 35.0 bits (75), Expect = 0.069 Identities = 17/24 (70%), Positives = 17/24 (70%), Gaps = 2/24 (8%) Query 19 GGGRGRQGRA-GAPAGRGTAAAQG 41 GGGRGR GRA GA AG G AA G Sbjct 69 GGGRGR-GRARGAAAGSGVPAAPG 91 Score = 28.6 bits (60), Expect = 4.3 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 27 | 10_C9 | gi\|31107\|emb\|Z11692.1\|H SEF2MR H.sapiens mRNA for elongation factor 2<br>Length = 3080<br>Score = 848 bits (428)<br>Expect = 0.0<br>Id = 430/431 (99%)<br>Gaps = 0/431 (0%)<br>Strand = Plus/Plus | QTTPGDCP DTATLP | 14 | Transcriptional repressor scratch 2 | Identities = 24/58 (41%), Positives = 24/58 (41%), Gaps = 17/58 (29%)<br>Q6<br>AQGGRVPEETEGAGGRGRQRAGAPAGRGTAAAQGGA--------ELGAE 48<br>A GGRVP GAG G GR R A A T A GA ELGAE<br>S49 ANGGRVPG-NGAGLGPGRLEREAAAAATTPAPTAGALYSGSEGDSESGEEEELGAE 104 |
| | | gi\|135959\|sp\|P19438\|TNR1A_HUMAN Tumor necrosis factor receptor superfamily member 1A precursor (p60) (TNF-R1) (TNFR-1) (p55) (CD120a antigen) | | | | Score = 24.0 bits (49), Expect = 41<br>Id = 6/7 (85%), Positives = 7/7 (100%),<br>Gaps = 0/7 (0%)<br>Query 3 TPGDCPD 9<br>TPGDCP+<br>Sbjct 300 TPGDCPN 306 |
| | | Tumor necrosis factor-binding protein 1 (TBP1) gi\|119587880\|gb\|EAW67476.1\| Cas-Br-M (murine) ecotropic retroviral transforming sequence gi\|119574887\|gb\|EAW54502.1\| ubiquitin specific peptidase 54 | | | | Score = 23.1 bits (47), Expect = 74<br>Id = 6/6 (100%), Positives = 6/6 (100%),<br>Gaps = 0/6 (0%)<br>Query 3 TPGDCP 8<br>TPGDCP<br>Sbjct 514 TPGDCP 519 |
| | | gi\|115855\|sp\|P22681\|CBL_HUMAN E3 ubiquitin-protein ligase (Proto-oncogene c-CBL) (Casitas B-lineage lymphoma proto-oncogene) | | | | Score = 23.1 bits (47), Expect = 74<br>Id = 11/17 (64%), Positives = 11/17 (64%),<br>Gaps = 5/17 (29%)<br>Query 2 TTPGDC-PD---TATLP 14<br>TTPG C P TATLP<br>Sbjct 1375 TTPG-CNPQLYTATLP 1390 |
| 29 | 9_G4 | gi\|71482588\|ref\|NM_0010 20.4\| Homo sapiens ribosomal protein S16 (RPS16), mRNA<br>Length = 603<br>Score = 260 bits (131)<br>Expect = 4e-67<br>Id = 131/131 (100%)<br>Gaps = 0/131 (0%)<br>Strand = Plus/Plus | NSSV | 4 | gi\|126215737\|sp\|Q15Z9\|LO NF2_HUMAN Neuroblastoma apoptosis-related protease gi\|120587027\|ref\|NP_065769.3\| ubiquitin specific peptidase 31 gi\|119626680\|gb\|EAX06275.1\| alpha-kinase 1 gi\|119620124\|gb\|EAW99718.1\| dual specificity phosphatase 11 | Score = 14.6 bits (27), Expect = 10793<br>Id = 4/4 (100%), Positives = 4/4 (100%),<br>Gaps = 0/4 (0%)<br>Query 1 NSSV 4<br>NSSV<br>Sbjct 206 NSSV 209 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 31 | 11_B 12 | gi\|74027260\|ref\|NM_0068 46.2\| Homo sapiens serine peptidase inhibitor, Kazal type 5 (SPINK5), mRNA Length = 3610 Score = 216 bits (109), Expect = 1e-53 Id = 109/109 (100%), Gaps = 0/109 (0%) Strand = Plus/Plus | ERGKKRKI REMLQDM VPVVVEEE TLRTNVLSI GNK | 35 | gi\|57863277\|ref\|NP_0010099 21.1\| hypothetical protein LOC23355 isoform a gi\|14042300\|dbj\|BAB55190.1\| unnamed protein product gi\|50083293\|ref\|NP_116205.3 hypothetical protein LOC84902 gi\|2815622\|gb\|AAC39562.1\| kinesin-related protein gi\|2407245\|gb\|AAB70531.1\| putative transcription factor CR53 gi\|38605529\|sp\|Q9Y4A5\|TRR AP_HUMAN Transformation/transcription domain-associated protein (350/400 kDa PCAF-associated factor) gi\|14589891\|ref\|NP_001784.2 cadherin 3, type 1 preproprotein gi\|226518\|prf\|\|1516312A gi\|4099609\|gb\|AAD00657.1\| Ca dependent cell adhesion protein cell division control-related protein 2b | Score = 29.9 bits (63), Expect = 0.55 Id = 10/18 (55%), Positives = 13/18 (72%), Gaps = 3/18 (16%) Query 7 KIREM--LQDMVPVVVE 21 KI+ M  QDMVPV+V+ Sbjct 569 KIQVMEQHFQDMVPVIVD 586 Score = 29.1 bits (61), Expect = 0.98 Id = 12/25 (48%), Positives = 14/25 (56%), Gaps = 0/25 (0%) Query 6 RKIREMLQDMVPVVVEEETL-RTNV 29 R+IRE+LQD        TL RT V Sbjct730 RRIRELLQD--------TLTRTGV 745 Score = 28.6 bits (60), Expect = 1.3 Id = 12/24 (50%), Positives = 17/24 (70%), Gaps = 4/24 (16%) Query 5 KRKIREMLQDMVPVVVEEET--LR 26 KR+ REM Q+M ++ +EET  LR Sbjct 1 KRRERMQQEM--MLRDEETMELR 22 |
| 32 | 2_C1 0 | gi\|14506788\|ref\|NM_00297 0.1\| Homo sapiens spermidine/spermine N1-acetyltransferase (SAT), mRNA Length = 1060 Score = 1031 bits (520) Expect = 0.0 Id = 520/520 (100%), Gaps = 0/520 (0%) Strand = Plus/Plus | RKGKKKSKR RKWLNS | 14 | gi\|57209583\|emb\|CAI41374.1 Sarcoma antigen 1 gi\|8216987\|emb\|CAB92443.1\| Putative tumor antigen gi\|23396625\|sp\|Q9NQT8\|K11 3B_HUMAN Kinesin-like protein KIF13B (Kinesin-like protein GAKIN) gi\|7227890\|sp\|O24175\|FL_O RYSA Putative transcription factor FL (RFL) gi\|51701343\|sp\|Q8TD10\|CHD 5_HUMAN Chromodomain helicase-DNA-binding protein | Score = 25.7 bits (53), Expect = 9.1 Identities = 10/20 (50%), Positives = 12/20 (60%), Gaps = 7/20 (35%) Query 1 RKGKK---SKRRK---WLN 13 RK K+   SKRRK    WL+ Sbjct 51 RKSKRHSSSKRRKSMSSWLD 70 Score = 24.8 bits (51), Expect = 22 Id = 6/6 (100%), Positives = 6/6 (100%), Gaps = 0/6 (0%) Query 8 RRKWLN 13 RRKWLN Sbjct 1092 RRKWLN 1097 Score = 24.4 bits (50), Expect = 30 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | | | | 5 (CHD-5) gi\|126178\|sp\|P14151\|LYAM1_HUMAN L-selectin precursor (Lymph node homing receptor) (Leukocyte surface antigen Leu-8) (TQ1) (gp90-MEL) (Leukocyte-endothelial cell adhesion molecule 1) (LECAM1) (CD62L antigen) | Id = 7/10 (70%), Positives = 10/10 (100%), Gaps = 0/10 (0%) Query 1 RKGKKSKRRK 10 RKGKK++R+K Sbjct 172 RKGKKARRKK 181 |
| 35 | 11_C8 | gi\|45359854\|ref\|NM_0020 78.3\| Homo sapiens golgi autoantigen, golgin subfamily a, 4 (GOLGA4), mRNA Length = 7717 Score = 270 bits (136) Expect = 1e-69 Id = 138/139 (99%) Gaps = 0/139 (0%) Strand = Plus/Minus | TKAK | 4 | gi\|54607086\|ref\|NP_068756.2 elongation factor for selenoprotein translation gi\|57863304\|ref\|NP_056340.2 inhibitor of Bruton's tyrosine kinase gi\|52548190\|gb\|AAU82085.1\| tumor amplified and TRAK 321 overexpressed sequence 2 gi\|20800447\|gb\|AAF23433.3\| breast cancer-associated antigen BRCA1 | Score = 14.6 bits (27), Expect = 7683 Id = 4/4 (100%), Positives = 4/4 (100%), Gaps = 0/4 (0%) Query 1 TKAK 4 TKAK Sbjct 318 |
| 37 | 8_C4 | gi\|92443613\|gb\|BC01555 9.1\| Homo sapiens ribosomal protein S24, mRNA (cDNA clone IMAGE: 3635225), Length = 3566 Score = 680 bits (343) Expect = 0.0 Id = 343/343 (100%) Gaps = 0/343 (0%) Strand = Plus/Plus | PNSG | 4 | gi\|124001556\|ref\|NP_001028 685.2\|G protein-coupled receptor 34 isoform 2 gi\|122892256\|gb\|ABM67195.1\| immunoglobulin heavy chain variable region gi\|122939151\|ref\|NP_001073 626.1\| Rho GTPase activating protein 9 isoform 2 | Score = 15.1 bits (28), Expect = 8044 Id = 4/4 (100%), Positives = 4/4 (100%), Gaps = 0/4 (0%) Query 1 PNSG 4 PNSG Sbjct 225 PNSG 228 |
| 38 | 10_C4 | >gi\|19913404\|ref\|NM_00 3286.2\| Homo sapiens topoisomerase (DNA) I (TOP1) Score = 1003 bits (506) Expect = 0.0 | NSSA | 4 | gi\|124001558\|ref\|NP_689799.3\| ubiquitin specific protease gi\|122892053\|gb\|ABM67094.1\| mutant lipase H gi\|120660404\|gb\|AAI30523.1\| Receptor tyrosine kinase- | Score = 14.2 bits (26), Expect = 14482 Id = 4/4 (100%), Positives = 4/4 (100%), 54 Gaps = 0/4 (0%) Query 1 NSSA 4 NSSA Sbjct 2051 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | Id = 561/585 (95%)<br>Gaps = 1/585 (0%)<br>Strand = Plus/Plus | | | like orphan receptor 2<br>gi\|120660344\|gb\|AAI30362.1\| BRCC2<br>gi\|114432132\|gb\|AB174674.1\| breast and ovarian cancer susceptibility protein 2 truncated variant | NSSA 2054 |
| 39 | 10_G5 | gi\|62897624\|dbj\|AK222303 2.1\|<br>Homo sapiens mRNA for beta actin variant, clone: JTH03396<br>Length = 1820<br>Score = 309 bits (156)<br>Expect = 4e-82<br>Id = 156/156 (100%)<br>Gaps = 0/156 (0%)<br>Strand = Plus/Minus | RRLKKFCIT | 9 | gi\|60549585\|gb\|AAX24102.1\| cation-transporting P5-ATPase<br>gi\|33469249\|gb\|AAQ19673.1\| general transcription factor II i repeat domain 2<br>gi\|57209558\|emb\|CAI41998.1\| melanoma associated antigen (mutated) 1-like 1<br>gi\|37932158\|gb\|AAP72185.1\| migration-inducing protein 3<br>gi\|13477103\|gb\|AAH05005.1\| Lung cancer-related protein 8<br>gi\|6919941\|sp\|Q15113\|PCOLC_HUMAN Procollagen C-proteinase enhancer protein precursor<br>gi\|6196767\|ref\|NP_001013682.1\| stromal cell derived factor receptor 2 homolog<br>gi\|74759724\|sp\|Q8IYT8\|ULK2_HUMAN Serine/threonine-protein kinase ULK2 | Score = 25.2 bits (52), Expect = 11<br>Id = 8/11 (72%), Positives = 8/11 (72%),<br>Gaps = 3/11 (27%)<br>Query 1 RRLKK---FCI 8<br>RRLKK   FCI<br>Sbjct 459 RRLKKRGIFCI 469<br>Score = 23.5 bits (48), Expect = 36<br>Id = 6/6 (100%), Positives = 6/6 (100%),<br>Gaps = 0/6 (0%)<br>Query 3 LKKFCI 8<br>LKKFCI<br>Sbjct 603 LKKFCI 608<br>Score = 22.7 bits (46), Expect = 65<br>Id = 6/6 (100%), Positives = 6/6 (100%),<br>Gaps = 0/6 (0%)<br>Query 1 RRLKKF 6<br>RRLKKF<br>Sbjct 441 RRLKKF 446 |
| 42 | 1_D12 | gi\|13097335\|gb\|BC003418.1\|<br>Homo sapiens cyclic AMP phosphoprotein, 19 kD, mRNA (cDNA clone MGC: 5468 IMAGE: 3451558), complete cds<br>Length = 1228<br>Score = 335 bits (169)<br>Expect = 4e-89<br>Id = 169/169(100%) | IFAGGGGP AGPGRAGT GGGRVASA TR | 26 | gi\|18204601\|gb\|AAH21228.1\| FLJ10700 protein<br>gi\|12644292\|sp\|P49840\|GSK3A_HUMAN Glycogen synthase kinase-3 alpha (GSK-3 alpha)<br>gi\|6291532\|dbj\|BAA86298.1\| Cbl-c<br>gi\|46397888\|sp\|Q9ULV8\|CBLC_HUMAN Signal transduction protein CBL-C<br>gi\|20149596\|ref\|NP_036248.2 | Score = 31.6 bits (67), Expect = 2.9<br>Id = 18/32 (56%), Positives = 18/32 (56%),<br>Gaps = 10/32 (31%)<br>Query 2 FAGG----GGP----AGPG---RAGTGGGRVAS 23<br>F GG    G P   A PG   RAGTGGG VAS<br>Sbjct475 FHGGQPTGAPLDCAAAPGAHYRAGTGGGPVAS 506<br>Score = 29.1 bits (61), Expect = 1.1<br>Id = 15/24 (62%), Positives = 17/24 (70%),<br>Gaps = 7/24 (29%)<br>Query 10 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | Gaps = 0/169(0%) Strand = Plus/Plus | | | Cas-Br-M (murine) ecotropic retroviral transforming sequence c gi\|56206355\|emb\|CAI18503.1 HLA-B associated transcript 3 gi\|5453736\|ref\|NP_005351.2\| v-maf musculoaponeurotic fibrosarcoma oncogene homolog isoform a gi\|21759253\|sp\|O75444\|MAF_HUMAN Transcription factor Maf (Proto-oncogene c-mat) gi\|47078300\|ref\|NP_542159.2 apoptosis related protein 3 isoform b gi\|6932999\|ref\|NP_006276.2 testis-specific protein kinase 1 gi\|2499660\|sp\|Q15569\|TESK1_HUMAN Dual-specificity testis-specific protein kinase 1 | GGGGP----AGPGRAGTGGGRVAS 29 GGGGP       +GPG  GTGGG+ AS Sbjct 32 GGGGPGGSASGPG--GTGGGK-AS 52 Score = 27.4 bits (57), Expect = 2.7 Id = 11/15 (73%), Positives = 12/15 (80%) Gaps = 2/15 (13%) Query 3 AGGGPAGPGRAGTG 17 AGGGP GPG  G+G Sbjct 65 AGGGPGGPG--GSG 77 |
| 44 | 10_D 12 | gi\|3329373\|gb\|AF038952.1\|AF038952 Homo sapiens cofactor A protein mRNA, complete cds Length = 574 Score = 392 bits (198) Expect = 2e-106 Id = 202/204 (99%) Gaps = 0/204 (0%) Strand = Plus/Plus | VKIMTLKS RQRSYKNP G | 17 | gi\|56417662\|emb\|CAI19057.1 Novel protein gi\|16923934\|gb\|AAL31642.1\| NOV1 gi\|40675561\|gb\|AAH64981.1\| Putative NFkB activating protein gi\|51701611\|sp\|Q9BX67\|JAM3_HUMAN Junctional adhesion molecule c precursor (JAM-C) gi\|38570359\|gb\|AAR24620.1\| Migration-inducing gene 13 Deoxyhypusine synthase | Score = 23.1 bits (47), Expect = 53 Id = 7/8 (87%), Positives = 7/8 (87%), Gaps = 0/8 (0%) Query 5 TLKSRQRS 12 TLK RQRS Sbjct 152 TLKERQRS 159 Score = 23.1 bits (47), Expect = 53 Id = 9/15 (60%), Positives = 12/15 (80%), Gaps = 1/15 (6%) Query 1 VKIMTLKSRQRSYKN 15 VK++TLK R+ S KN Sbjct 39 VKLLTLKPRETS-KN 52 Score = 23.1 bits (47), Expect = 53 Id = 7/9 (77%), Positives = 8/9 (88%), Gaps = 0/9 (0%) Query 6 LKSRQRSYK 14 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| 45 | 4_G8 | gi\|56788032\|gb\|AY69246 4.1\| Growth-ihibiting gene 46 mRNA Length = 1715 Score = 823 bits (415) Expect = 0.0 Id = 415/415 (100%) Gaps = 0/415 (0%) Strand = Plus/Minus | RPARSRRM MAWGKA | 14 | gi\|57163116\|emb\|CAI39857.1 Protein (peptidyl-prolyl cis/trans isomerase) NIMA-interacting, 4 (parvulin) gi\|32171215\|ref\|NP_859066.1 Transducer of regulated cAMP response element binding protein gi\|37574639\|gb\|AAQ93056.1\| Antigen MLAA-10 gi\|59800455\|sp\|Q9UPY6\|WA SF3_HUMAN Wiskott-Aldrich syndrome protein family member 3 (WASP-family protein member 3) gi\|17368482\|sp\|Q15773\|MLF 2_HUMAN Myeloid leukemia factor 2 gi\|10720185\|sp\|Q9Y4L1\|OXR P_HUMAN 150 kDa oxygen-regulated protein precursor (Orp150) (Hypoxia up-regulated 1) | L+SRQR YK Sbjct 260 LQSRQRDYK 268 Score = 26.5 bits (55), Expect = 5.1 Id = 7/8 (87%), Positives = 7/8 (87%), Gaps = 0/8 (0%) Query 1 RPARSRRM 8 RP RSRPM Sbjct 14 RPERSRRM 21 Score = 23.5 bits (48), Expect = 40 Id = 6/7 (85%), Positives = 6/7 (85%), Gaps = 0/7 (0%) Query 6 RRMMAWG 12 RR MAWG Sbjct 144 RRTMAWG 150 Score = 23.1 bits (47), Expect = 53 Id = 8/12 (66%), Positives = 9/12 (75%), Gaps = 2/12 (16%) Query 2 PARSR-RMM-AW 11 PA+R RMM AW Sbjct 46 PAQPRHRMMSAW 57 |
| 47 | 5_H8 | gi\|33342277\|ref\|NM_0252 04.2\| Hypothetical protein PP2447, mRNA Score = 232 bits (117) Expect = 3e-58, Id = 117/117 (100%) Strand = Plus/Plus | DWRVPR PAPHHR LGARRL PNLHAA PGRAAP RAASGL | 36 | gi\|3647275\|emb\|CAA12110.1 Matrilin-3 gi\|3252872\|gb\|AAC24200.1\| BRCA1-associated protein 2 gi\|60390212\|sp\|Q969P8\|KISS R_HUMAN KiSS-1 receptor (KiSS-1R) (Metastin receptor) gi\|21265064\|ref\|NP_620688.1 ADAM metallopeptidase with thrombospondin type 1 motif, 17 preproprotein gi\|51094804\|gb\|EAL24050.1\| cAMP responsive element binding protein 3-like 2 Basic transcriptional factor 2 | Score = 30.8 bits (65), Expect = 0.31 Id = 11/17 (64%), Positives = 11/17 (64%), Gaps = 5/17 (29%) Query 5 PRPAPHHRLGARRLPNL 21 PRPAP ARRLP L Sbjct 2 PRPAP-----ARRLPGL 13 Score = 30.3 bits (64), Expect = 0.41 Id = 18/40 (45%), Positives = 18/40 (45%), Gaps = 16/40 (40%) 2 WRVPRPAPHHRLGARRLPNLHAA-----PGRAAPRAASGL 36 W PRP R LP L A PGRAA R AS L 566 W--PRP-------RALP-LRGAVGSCPPGRAAARGASDL 594 Score = 29.9 bits (63), Expect = 0.59 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| 48 | 8_G1 1 | Homo sapiens prothymosin, alpha (gene sequence 28), mRNA (cDNA clone MGC: 45641 IMAGE: 4335961), complete cds Length = 1213 Score = 97.6 bits (49), Expect = 6e-18 Identities = 49/49 (100%) Gaps = 0/49 (0%) Strand = Plus/Minus | NSSCSE | 6 | gi\|119629922\|gb\|EAX09517.1 PBX/knotted 1 homeobox 1, isoform CRA_a gi\|91992160\|ref\|NP_055196. mutL homolog 3 isoform 2- gi\|6689928\|gb\|AAF23904.1\|A F195657_1 DNA mismatch repair protein gi\|119623371\|gb\|EAX02966.1 scavenger receptor class F, member 2, isoform CRA gi\|6648106\|sp\|Q05086\|UBE3 A_HUMAN Ubiquitin-protein ligase E3A (Renal carcinoma antigen NY-REN-54) gi\|11385658\|gb\|AAG34910.1\| AF273050_1 CTCL tumor antigen se37-2 gi\|1872514\|gb\|AAB49301.1\| E6-associated protein E6-AP\|ubiquitin-protein ligase | Id = 19/41 (46%), Positives = 19/41 (46%), Gaps = 17/41 (41%) WRVPRPAPHHRLGARRLPNLHAAPG-R-------AAPRA 32 WRV RP  H     LP L AAPG  R         AAPRA 41 WRV-RPDDVH------LPPLPAAPGPRRRRRPRTPPAAPRA 74 Score = 19.3 bits (38), Expect = 638 Id = 5/6 (83%), Positives = 6/6 (100%), Gaps = 0/6 (0%) Query 1     NSSCSE 6 +SSCSE Sbjct 323   DSSCSE 328 Score = 19.3 bits (38), Expect = 638 Id = 5/6 (83%), Positives = 6/6 (100%), b Gaps = 0/6 (0%) Query 1     NSSCSE 6 NS+CSE Sbjct 83    NSTCSE 88 Score = 19.3 bits (38), Expect = 638 Id = 5/6 (83%), Positives = 6/6 (100%), Gaps = 0/6 (0%) Query 1     NSSCSE 6 N+SCSE Sbjct 102   NNSCSE 107 |
| 49 | 1_D2 | gi\|20357564\|ref\|NM_0001 00.2\| Homo sapiens cystatin B (stefin B) (CSTB), mRNA Length = 674 Score = 232 bits (117) Expect = 9e-59 Id = 117/117 (100%) Gaps = 0/117 (0%) Strand = Plus/Plus | RGDKLLHQ GARRRRGL RTPASVPIS PS | 27 | gi\|28892\|emb\|CAA35582.1\| unnamed protein product gi\|2135396\|pir\|\|S71548 homeotic protein pG2-human gi\|38648796\|gb\|AAH63316.1\| FBXL17 protein LQQGRRRGDL---SSVPTAPS 246 Score = 28.2 bits (59), Expect = 2.1 Id = 11/18 (61%), Positives = 11/18 (61%), | Score = 28.6 bits (60), Expect = 1.6 Id = 12/22 (54%), Positives = 14/22 (63%), Gaps = 3/22 (13%) Query 6    LHQGARRRGLRTPASVPISPS 27              L QG RRR L   +SVP+ PS Sbjct 228                               Gaps = 5/18 (27%) |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 52 | 11_B8 | gi\|110624286\|dbj\|AK258 50.1\| Homo sapiens mRNA for E1B-55 kDa-associated protein 5 isoform a variant, clone: FCC125H07 Length = 3447 Score = 307 bits (155) Expect = 2e-81 Id = 158/159 (99%) Gaps = 0/159 (0%) Strand = Plus/Plus | RCSSXNRX GREGCPRS CGLRNESQ LHVARCWG LPG | 35 | gi\|3184264\|gb\|AAC19917.1\| F02569_2 gi\|113426694\|ref\|XP_001130 029.1\| PREDICTED: hypothetical protein gi\|34533723\|dbj\|BAC86786.1\| unnamed protein product gi\|119568019\|gb\|EAW47634. 1\| fibronectin type III domain containing 1 Gaps = 5/22 (22%) Query 7 | Query 11 RRRRGL----RTPASVP 23 RRRR L   RTPA VP Sbjct 25 RRRRPLLRLPRRTPAKVP 42<br><br>Score = 30.8 bits (65), Expect = 0.42 ID = 11/16 (68%), Positives = 13/16 (81%), Gaps = 3/16 (18%) Query 8 QG--REGCPRSCGLRNE 22 QG  REGCP  CGLR++ Sbjct 179 QGAREGCP---CGLRHQ 192 Score = 28.2 bits (59), Expect = 2.5 Identities = 14/22 (63%), Positives = 15/22 (68%)<br><br>RQG-REGCPRSCGLRNESQLHV 27 R G REGCPR C  R +S LHV Sbjct 33 RPGLPREGCPR-C--R-QSVLHV 50 Score = 27.8 bits (58), Expect = 3.3 Id = 9/12 (75%), Positives = 10/12 (83%), Gaps = 1/12 (8%) Query 7 RQGREG-CPRSC 17 RQGREG C R+C Sbjct 1234 RQGREGACHRAC 1245 |
| 55 | 2_G7 | gi\|48734768\|gb\|BC07192 8.1\| Homo sapiens ribosomal protein S17, mRNA (cDNA clone MGC: 88613 IMAGE: 5090053), complete cds Length = 488 Score = 476 bits(240) Expect = 7e-132 Id = 268/270 (99%) Gaps = 1/270 (0%) Strand = Plus/Plus | ERPSKRYL HQAAGGGE RKERQLCS | 24 | gi\|51476730\|emb\|CAH18336. 1\| hypothetical protein gi\|30354570\|gb\|AAH51765.1\| Nuclear factor kappa-B, subunit 1 gi\|23271363\|gcb\|AAH35512.1\| WD repeat domain 49 gi\|31621301\|ref\|NP_853550.1 regulator of G-protein signalling like 1 gi\|40254949\|ref\|NP_065960.2 erythrocyte membrane protein band 4.1 like 5 gi\|14917040\|sp\|Q15127\|SCA | Score = 25.2 bits (52), Expect = 12 Id = 12/23 (52%), Positives = 13/23 (56%), Gaps = 9/23 (39%) Query 7 YLHQAGGGER------KE-RQ 21 YL QA GGG+R      KE  RQ Sbjct 177 YL-QABGGGDRQLGDREKELTRQ 198 Score = 25.2 bits (52), Expect = 12 Id = 12/23 (52%), Positives = 13/23 (56%), Gaps = 9/23 (39%) Query 7 YLHQAGGGER------KE-RQ 21 YL QA GGG+R      KE  RQ |

TABLE 6a-continued

| Rank | Clone | Description of the genes that are in Mimotope clones | Peptide sequences of Mimotopes, in-frame with T7 10B gene | Size of peptide | Description of the sequences that Mimotopes mimic | Region of similarity of peptide (only the top 3 sequences are shown) |
|---|---|---|---|---|---|---|
| | | | | | M2_HUMAN Secretory carrier-associated membrane protein 2 | Sbjct 177 YL-QAEGGDRQLGDREKELTRQ 198 Score = 24.0 bits (49), Expect = 29 Id = 8/16 (50%), Positives = 9/16 (56%), Gaps = 5/16 (31%) Query 8 LHQAGGGERKERQLC 23 LH ERK +QLC Sbjct 675 LHH----ERKAKQLC 685 |
| 58 | 4_G7 | gi\|71559137\|ref\|NM_0010 29.3\| Homo sapiens ribosomal protein S26 (RPS26), mRNA Length = 699 Score = 367 bits (185) Expect = 1e-98 Id = 202/210 (96%) Gaps = 0/210 (0%) Strand = Plus/Plus | SSQGHF | 6 | gi\|21753429\|dbj\|BAC04343.1\| unnamed protein product Roquin (RING finger and C3H zinc finger protein 1) gi\|55960182\|emb\|CAI17337.1 G protein-coupled receptor 123 gi\|22749391\|ref\|NP_689910.1 solute carrier family 44, member 5 gi\|55960275\|emb\|CAI14751.1 novel MAM domain containing protein gi\|73918937\|sp\|Q8NCS7\|CTL 5_HUMAN Choline transporter-like protein Ribosomal protein S6 kinase 2 (S6K2) (Serine/threonine-protein kinase 14 beta) gi\|55664933\|emb\|CAH71148. 1\| colony stimulating factor 1 (macrophage) | Score = 21.8 bits (44), Expect = 78 Id = 6/6 (100%), Positives = 6/6 (100%), Gaps = 0/6 (0%) Query 1 SSQGHF Sbjct 74 SSQGHF Score = 19.3 bits (38), Expect = 619 Id = 5/5 (100%), Positives = 5/5 (100%), Gaps = 0/5 (0%) Query 2 SQGHF Sbjct 74 SQGHF Score = 18.0 bits (35), Expect = 1097 Id = 5/5 (100%), Positives = 5/5 (100%), Gaps = 0/5 (0%) Query 1 SSQGH Sbjct 189 SSQGH 193 |
| 59 | 1_H2 | gi\|39992414\|gb\|BC06441 8.1\| Homo sapiens FK506 binding protein 9, 63 kDa, mRNA (cDNA clone IMAGE: 5750487), partial cds Length = 2421 Score = 486 bits (245) Expect = 1e-134 Id = 259/264 (98%) | GSGKIKKSV LWDRKVGI RKN | 20 | gi\|19923432\|ref\|NP_054876.2 coiled-coil domain containing 113 gi\|12053083\|emb\|CAB66719. 1\| hypothetical protein gi\|115298682\|ref\|NP_055987. 2\| HBxAg transactivated protein 2 gi\|119594637\|gb\|EAW74231. 1\| phospholipase C, beta 3 (phosphatidylinositol- | Score = 28.2 bits (59), Expect = 2.1 Id = 8/12 (66%), Positives = 11/12 (91%), Gaps = 1/12 (8%) Query 7 KSV-LNDRKVEI 17 KS+ +W+RKVEI Sbjct 336 KSIRMWERKVEI 347 Score = 24.8 bits (51), Expect = 23 Id = 10/15 (66%), Positives = 10/15 (66%), Gaps = 0/15 (0%), |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | Gaps = 0/264 (0%)<br>Strand = Plus/Minus | | | specific)<br>gi\|119590306\|gb\|EAW69900.<br>1\| nucleoporin 133 kDa | Query 2<br>SGKIKKSVLWDRKVE 16<br>SG IKK VL D K E<br>Sbjct 1013<br>SGPIKKPVLRDMKEE 1027<br>Score = 22.7 bits (46), Expect = 98<br>Id = 7/8 (87%), Positives = 7/8 (87%)<br>Gaps = 0/8 (0%)<br>Query 10<br>LWDRKVGI 17<br>L DRKVGI<br>Sbjct 671<br>LSDRKVGI 678 |
| 60 | 9_G7 | gi\|119380763\|gb\|EF17744<br>7.1\|<br>Homo sapiens isolate<br>TA23 mitochondrion,<br>complete genome<br>Length = 16569<br>Score = 424 bits (214)<br>Expect = 2e-116<br>Id = 214/214 (100%)<br>Gaps = 0/214 (0%)<br>Strand = Plus/Plus | ARRWSRST<br>LCRSICL | 15 | gi\|10732604\|gb\|AAG22468.1\|<br>AF193040_1 uknown<br>gi\|119584289\|gb\|EAW63885.<br>1\| tRNA nucleotidyl<br>transferase, CCA-adding, 1,<br>isoform CRA_a<br>gi\|68566213\|sp\|Q8NFZ6\|VN1<br>R2_HUMAN<br>Vomeronasal type-1<br>receptor 2<br>(V1r-like receptor 2)<br>(hGPCR25)<br>Putative G-protein coupled<br>receptor | Score = 24.8 bits (51), Expect = 23<br>Id = 7/8 (87%), Positives = 7/8 (87%),<br>Gaps = 0/8 (0%)<br>Query 2<br>RRWSRSTL 9<br>RRWS STL<br>Sbjct 187<br>RRWSPSTL 194<br>Score = 24.0 bits (49), Expect = 41<br>Id = 7/9 (77%), Positives = 7/9 (77%),<br>Gaps = 2/9 (22%)<br>Score = 22.3 bits (45), Expect = 133<br>Id = 8/10 (80%), Positives = 8/10 (80%),<br>Gaps = 1/10 (10%)<br>Query 5<br>SRSTLCRSIC 14<br>SRS LC SIC<br>Sbjct 373<br>SRSRLC-SIC 381 |
| 61 | 10_H<br>8 | gi\|37704380\|ref\|NM_0040<br>48.2\|<br>Homo sapiens beta-2-<br>microglobulin (B2M),<br>mRNA<br>Length = 987<br>Score = 246 bits (124)<br>Expect = 2e-62<br>Id = 124/124 (100%)<br>Gaps = 0/124 (0%)<br>Strand = Plus/Plus | LIQHQHLG<br>QI | 10 | Zinc finger protein 566<br>gi\|32470620\|sp\|Q9Y6K5\|QAS<br>3_HUMAN<br>2'-5'-oligoadenylate<br>synthetase 3 (p100 OAS)<br>gi\|73620903\|sp\|Q5SZK8\|FRE<br>M2_HUMAN<br>FRAS1-related extracellular<br>matrix protein 2 precursor<br>gi\|21263627\|sp\|Q9NQ28\|ZNF<br>71_HUMAN<br>Endothelial zinc finger | Score = 23.1 bits (47), Expect = 74<br>Id = 6/7 (85%), Positives = 7/7 (100%).<br>Gaps = 0/7 (0%)<br>Query 1<br>LIQHQHL 7<br>LIQHQ+L<br>Sbjct 410<br>LIQHQNL 416<br>Score = 22.7 bits (46), Expect = 99<br>Id = 7/8 (87%), Positives 7/8 (87%),<br>Gaps = 1/8 (12%)<br>Query 1 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | | | | protein induced by tumor necrosis factor alpha (Zinc finger protein 71) | LIQ-HQHL 7<br>LIQ HQHL<br>Sbjct 258<br>LIQQHQHL 265<br>Score = 21.4 bits (43), Expect = 174<br>Id = 7/9 (77%), Positives = 8/9 (88%)<br>Gaps = 0/9 (0%) |
| | | | | | Probable ATP-dependent helicase DDX41 | Query 1<br>LIQHQHLGQ 9<br>LIQ+ HLGQ<br>Sbjct 1379<br>LIQYVHLGQ 1367 |
| | | | | | DEAD-box protein 41 | |
| 64 | 2_D6 | Homo sapiens actin, gamma 1, mRNA (cDNA clone IMAGE: 3461395)<br>Score = 172 bits (87)<br>Expect = 2e-40<br>Identities = 87/87 (100%) | RPHCEL<br>WGMLAP<br>TDCCHL<br>HRSSF | 23 | gi|119533|sp|P04626|ERBB2_HUMAN Receptor tyrosine-protein kinase erbB-2 precursor (p185erbB2) (C-erbB-2) (NEU proto-oncogene) | Score = 25.2 bits (52) Expect = 15<br>Identities = 6/6 (100%)<br>Positives = 6/6 (100%)<br>Query 14<br>PTDCCH 19<br>PTDCCH<br>Sbjct: 232<br>PTDCCH 237 |
| | | | | | gi|20139132|sp|Q9BZF2|OSR7_HUMAN Oxysterol binding protein-related protein 7 | Score = 15.9 bits (30) Expect = 9714,<br>Identities = 5/6 (63%),<br>Positives = 5/6 (63%)<br>Query: 19<br>HLHRSS 24<br>H HRSS<br>Sbjct: 1045<br>HRHRSS 1050 |
| | | | | | gi|13633990|sp|Q9NQE7|TSSP_HUMAN Thymus-specific serine protease precursor | Score = 24.0 bits (49), Expect = 38<br>Id = 8/12 (66%), Pos = 8/12 (66%),<br>Gaps = 0/12 (0%)<br>Query 10<br>LAPTDCCHLHRS 21<br>L PTD HL RS<br>Sbjct 291<br>LPPTDYAHLQRS 302 |
| | | | | | gi|29428029|sp|Q9NW08|RPC2_HUMAN DNA-directed RNA polymerase III subunit 127.6 kDa polypeptide | Score = 23.5 bits (48), Expect = 51<br>Id = 6/7 (85%), Positives = 7/7 (100%),<br>Gaps = 0/7 (0%)<br>Query 6<br>LWGMLAP 12<br>LWG+LAP<br>Sbjct 17<br>LWGLLAP 23 |
| | | | | | gi|2811086|sp|P00533|EGFR_HUMAN Epidermal growth factor receptor precursor (Receptor tyrosine-protein kinase ErbB-1) | |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| 67 | 8_G3 | gi|71373270|gb|DO13740 8.1| Homo sapiens isolate UV122 mitochondrion, complete genome Length = 16568 Score = 496 bits (250) Expect = 2e-137 Id = 250/250 (100%) Gaps = 0/250 (0%) Strand = Plus/Plus /gene = "COX1" /product = "cytochrome c oxidase subunit 1" | PHNTFSAYP ECPDVTRT TPMHTPHE TSYHL | 30 | gi|24419041|gb|AAL65133.2| ovarian cancer related tumor marker CA 125 | Score = 27.4 bits (57), Expect = 2.7 Id = 12/24 (50%), Positives = 15/24 (62%), Gaps = 6/24 (25%) Query 2        HNTFSAYPE----CPDVTRTTPM 20               H+T SAYPE        P+VT T+ M Sbjct 4847     HSTVSAYPEPSKVTSPNVT-TSTM 4869 Score = 22.3 bits (45), Expect = 91 Id 10/18 (55%), Positives = 11/18 (61%) Gaps = 5/18 (27%) Query 13       DVTRTTPMHTPH--ETSY 28               DVT T+P  P   ETSY Sbjct 4440     DVTWTSP---PSVAETSY 4454 |
| | | | | | gi|68566146.sp.Q9NQW7|XP P1_HUMAN Xaa-Pro aminopeptidase 1 (Soluble aminopeptidase P) | Score = 20.6 bits (41), Expect = 296 Id = 9/16 (56%), Positives = 10/16 (62%), Gaps = 2/16 (12%) Query 7        AYPECPDVTRTTPMH 22               AY E P V  T+PM T Sbjct 6614     AYSEPPRV-TSPMVT 6627 |
| | | | | | gi|32699681|sp|Q9H4B6|SAV 1_HUMAN Salvador hoinolog 1 protein (45 kDa WW domain protein) (hWW45) | Score = 26.9 bits (56), Expect = 4.9 Id = 11/18 (61%), Positives = 12/18 (66%), Gaps = 6/18 (33%) Query 13       DVTRTTPMH--TPHETSY 28               DVTRT MH  TP T+Y Sbjct 426      DVTRT--MHFGTP--TAY 439 Score = 26.1 bits (54), Expect = 11 Id = 16/36 (44%), Positives = 19/36 (52%), Gaps = 11/36 (30%) Query 3        PNSSPHNTFSAYPECPDV-TRT----TPMH-TPHE 31               P+SSP N FS       DV +R      TP+ TPHE Sbjct 53       PDSSP-NAFST---SGDVVSRNQSFLRTPIQRTPHE 84 Score = 26.1 bits (54), Expect = 11 Id = 10/15 (66%), Positives = 11/15 (73%), Gaps = 1/15 (6%) Query 12       SAYPECPDVTRT-TP 25               SAY  CPD+T T TP |
| | | | | | gi|2230414|sp|O15067|PUR4_HUMAN Phosphoribosylformylglycin amidine synthase (FGAM synthase) | |
| | | | | | gi|39793978|gb|AAH63538.1| PFAS protein | |
| | | | | | gi|8134719|sp|Q92966|SNPC 3_HUMAN snRNA activating protein complex 50 kDa subunit (Proximal sequence element-binding transcription factor beta subunit) (PSE-binding factor beta subunit) (PTF beta subunit) | |
| | | | | | gi|55960781|emb|CAI16349.1 hepatoma-derived growth factor (high-mobility group protein 1-like) | |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | | | | | Sbjct 826 SAYAVCPDITATVTP 840<br>Score = 17.6 bits (34), Expect = 2315<br>Id = 9/21 (42%), Positives = 10/21 (47%),<br>Gaps = 8/21 (38%)<br>Query 10<br>ECPDVTRT-------TPMHTP 23<br>ECP V R  TP+ TP<br>Sbjct 15<br>ECP-VRRNGQGDAPPTPLPTP 34 |
| 68 | 1_H7 | gi\|30584378\|gb\|BT00777 0.1\| Synthetic construct Homo sapiens cystatin B (stefin B) mRNA<br>Score = 280 bit(141)<br>Expect = 1e-72<br>Id = 141/141 (100%)<br>Strand = Plus/Plus | GRVIQE PGGRGD KLLHQG ARRRRG LRTPAS VPISPS | 36 | gi\|28892\|emb\|CAA35582.1\| unnamed protein product<br>gi\|2135396\|pir\|\|S71548 homeotic protein pG2-human<br>gi\|48428276\|sp\|O43432\|IF4G 3_HUMAN Eukaryotic translation initiation factor 4 gamma 3 (eIF-4-gamma 3) (eIF-4G 3) (eIF-4-gamma II) (eIF4GII)<br>gi\|2190402\|emb\|CAA73944.1\| latent TCF-beta binding protein-4 | Score = 28.6 bits (60), Expect = 1.4<br>Identities = 12/22 (54%), Positives = 14/22 (63%)<br>Gaps = 3/22 (13%)<br>Query 15<br>LHQGARRRRGLRTPASVPISPS 36<br>L QG RRR L  +SVP +PS<br>Sbjct 227<br>LQQGRRRGDL--SSVPTAPS 245<br>Score = 28.6 bits (60), Expect = 1.3<br>Identities = 12/22 (54%), Positives = 14/22 (63%),<br>Gaps = 3/22 (13%)<br>Query: 15<br>LHQGARRRRGLRTPASVPISPS 36<br>L QG RRR L  +SVP +PS<br>Sbjct: 228<br>LQQGRRRGDL--SSVPTAPS 246<br>Score = 26.9 bits (56), Expect = 4.3<br>Identities = 15/28 (53%), Positives = 17/28 (60%)<br>Gaps = 7/28 (25%)<br>Query: 1<br>GRVIQEPGGRGDKLLHQGARR-------RR 23<br>GR  Q  PGGRG LL+ G+RR        RR<br>Sbjct: 685<br>GR---QTPGGRGVPLLNVGSRRSQPGQRR 710 |
| 69 | 2_C8 | gi\|39992414\|gb\|BC06441 8.1\| Homo sapiens FK506 binding protein 9,63 kDa, mRNA (cDNACloneIMAGE: 575 0487), partial cds<br>Length = 2421<br>Score = 486 bits (245)<br>Expect = 1e-134<br>Id = 259/264 (98%) | GSGKIKKSV LWDRKVGI RKN | 20 | gi\|56202484\|emb\|CAI21939.1 HBxAg transactivated protein 2 (XTP2)<br>gi\|119611307\|gb\|EAW90901. 1\| BAT2 domain containing 1, isoform CRA_d<br>gi\|29427863\|sp\|Q8WUM0\|N U133_HUMAN Nuclear pore complex protein Nup133 | Score = 24.0 bits (49), Expect = 29<br>Id = 9/13 (69%), Positives = 9/13 (69%),<br>Gaps = 0/13 (0%)<br>Query 2<br>SGKIKKSVLWDRK 14<br>SG IKK VL D K<br>Sbjct 83<br>SGPIKPVLRDMK 95<br>Score = 24.0 bits (49), Expect = 41<br>Id = 6/6 (100%), Positives = 6/6 (100%), |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | Gaps = 0/264 (0%)<br>Strand = Plus/Minus | | | gi\|6121682B\|sp\|Q96HF1\|SFR<br>P2_HUMAN<br>Secreted apoptosis - related protein 1<br>gi\|12803735\|gb\|AAH02704.1\|<br>Signal transducer and activator of transcription 1<br>gi\|29337296\|ref\|NP_803881.1\|<br>Melanoma antigen family D, 4 isoform 2<br>gi\|57012811\|sp\|Q7Z4I9\|IBR<br>D2_HUMAN<br>E3 ubiquitin ligase IBRDC2 (p53- inducible RING finger protein)<br>Phospholipase C beta 3 | Gaps = 0/6 (0%)<br>Query 8<br>SVLWDR 13<br>SVLWDR<br>Sbjct 101<br>SVLWDR 106<br>Score = 23.1 bits (47), Expect = 73<br>Id = 6/6 (100%), Positives = 6/6 (100%),<br>Gaps = 0/6 (0%)<br>Query 6<br>KKSVLW 11<br>KKSVLW<br>Sbjct 233<br>KKSVLW 238 |
| 70 | 12_D | gi\|24430161\|ref\|NM_0003<br>04.2\| Homo sapiens peripheral myelin protein 22 (PMP22), transcript variant 1, mRNA<br>Length = 1828<br>Score = 357 bits (180),<br>Expect = 3e-96<br>Id = 208/219 (94%)<br>Gaps = 1/219 (0%)<br>Strand = Plus/Minus | TQLV | 4 | gi\|38569484\|ref\|NP_060111.2<br>kinesin family member 21A<br>gi\|21265037\|ref\|NP_055058.1<br>ADAM metallopeptidase with throinbospondin type I motif, 3 proprotein<br>gi\|57209716\|emb\|CAI40838.1<br>cadherin related 23<br>gi\|56204273\|emb\|CAI19274.1<br>retinoblastoina-associated factor 600 (RBAF600)<br>gi\|55962143\|emb\|CAI15704.1<br>calsyntenin 1<br>gi\|42525235\|gb\|AAS18317.1<br>CDK5 regulatory subunit associated protein 1 transcript variant 3 | Score = 15.5 bits (29), Expect = 4278<br>Identities = 4/4 (100%), Positives = 4/4 (100%),<br>Gaps = 0/4 (0%)<br>Query 1<br>TQLV 4<br>TQLV<br>Sbjct 78<br>TQLV 81 |
| 73 | 2_H3 | gi\|125541850\|gb\|EF40865<br>6.1\| Homo sapiens haplotype H7 mitochondrion, complete genoine<br>Length = 16569<br>Score = 1199 bits (605),<br>Expect = 0.0<br>Id = 665/677 (98%)<br>Gaps = 0/677 (0%)<br>Strand = Plus/Minus | GVSVNEAS<br>YDGKYSSY | 16 | gi\|58202610\|gb\|AAW67356.1<br>random intestinal-homing antibody heavy chain variable region<br>gi\|60326824\|gb\|AAX18924.1<br>anti-TARP (novel breast and prostate tumor-associated antigen) immnnoglobnlin heavy chain<br>gi\|13161090\|gb\|AAK13479.1 | Score = 27.8 bits (58), Expect = 2.9<br>Id = 9/14 (64%), Positives = 10/14 (71%),<br>Gaps = 0/14 (0%)<br>Query 3<br>WVNEASYDGKYSSY 16<br>WV SYDGKY +Y<br>Sbjct 49<br>WVAVISYDGKYENY 62<br>Score = 25.2 bits (52), Expect = 17<br>Id = 8/11 (72%), Positives 8/11 (72%),<br>Gaps = 0/11 (0%), |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | /product = "NADH dehydrogenase subunit 1" | | | AF332227_1 heat shock transcription factor 2-like protein gi\|119602637\|gb\|EAW82231. 1\| eukaryotic translation elongation factor 1 delta gi\|10719919\|sp\|Q15326\|ZMY 11_HUMAN (Adenovirus 5 E1A-binding protein) | Query 3 WVNEASYDGKY 13 WV SYDGKY Sbjct 47 WVAVISYDGKY 57 Score = 24.4 bits (50), Expect = 31 Id = 7/8 (87%), Positives = 7/8 (87%), Gaps = 0/8 (0%) Query 2 VSVNEASY 9 VSVNEA Y Sbjct 352 VSVNEAPY 359 |
| 75 | 1_G3 | gi\|71483115\|ref\|NM_0010 24.3\| Homo sapiens ribosomal protein S21 (RPS21), mRNA Length = 418 Score = 383 bits (193) Expect = 6e-14 Id = 202/206 (98%) Gaps = 0/206 (0%) Strand = Plus/Plus /product = "ribosomal protein S21" | GAAQPR NAERRR RVRGPV RAAEML R | 28 | gi\|34526547\|dbj\|BAC85151.1\| FLJ00336 protein gi\|37590807\|gb\|AAH59399.1\| Solute carrier family 27 (fatty acid transporter) gi\|3139079\|gb\|AAC36682.1\| cullin 3 gi\|51095155\|gb\|EAL24398.1\| hypothetical protein FLJ36031 gi\|7018298\|emb\|0AB75612.1\| c394H11.1 (similar to SOX (SRY (sex determining region Y))) gi\|22261792\|sp\|O60312\|AT10 A_HUMAN Probable phospholipid-transporting ATPase VA gi\|14009443\|dbj\|BAB47392.1\| putative aminophospholipid translocase gi\|26986715\|gb\|AAN86723.1\| gi\|54673563\|gb\|AAH37322.3\| Transcription factor MLR1 gi\|1169723\|sp\|P41439\|FOLR3 _HUMAN Folate receptor gamma precursor (FR-gamma) gi\|55957252\|emb\|CAI12668. pancreas specific transcription factor, 1a gi\|11493712\|gb\|AAG35617.1\| | Score = 29.9 bits (63), Expect = 0.47 Id = 10/13 (76%), Positives 10/13 (76%) Gaps = 1/13 (7%) Query 7 QP-RNAERRRVR 18 QP R AERR RVR Sbjct 347 QPVREAERRHRVR 359 Score = 29.5 bits (62), Expect = 0.63 Id = 11/18 (61%), Positives = 13/18 (72%) Gaps = 1/18 (5%) Query 11 AERRRAVRGPVRAA-EML 27 AERA R RG +R A +ML Sbjct 173 AERRSRSRGAIRNACQML 190 Score = 28.6 bits (60), Expect = 1.1 Id = 12/17 (70%), Positives = 12/17 (70%) Gaps = 2/17 (11%) Query 8 PRNAERRRRVRGPVRAA 24 PR A RRRR RG RAA Sbjct 122 PRAAARRRR-RG-ARAA 136 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | | | | homeobox transcription factor gi\|57242761\|ref\|NP_003795.2 receptor (TNFRSF)-interacting serine-threonine kinase 1 gi\|60393639\|sp\|Q3546\|RIPK 1_HUMAN Receptor-interacting serine threonine-protein kinase 2 (Cell death protein RIP) | |
| 76 | 11_B 10 | gi\|18808464\|gb\|BC02116 7.1\| Homo sapiens prostaglandin E synthase 3 (cytosolic), mRNA (cDNA clone IMAGE: 3683159), partial cds Length = 1057 Score = 420 bits (212) Expect = 3e-115 Id = 212/212(100%) Gaps = 0/2 12(0%) Strand = Plus/Plus | NSSHH | 5 | gi\|119616592\|gb\|EAW96186. 1\| killer cell lectin-like receptor subfamily C, member 3, isoform CRA_c gi\|119618016\|gb\|EAW97610. 1\| apoptotic peptidase activating factor gi\|119630109\|gb\|EAX09704.1 dual-specificity tyrosine-(Y)-phosphorylation regulated kinase 1A, isoform CRA_c gi\|119580009\|gb\|EAW59605. 1\| SW1/SNF related, matrix associated, actin dependent regulator of chromatin | Score = 19.3 bits (38), Expect = 532 Id = 5/5(100%), Positives = 5/5(100%), Gaps = 0/5(0%) Query 1 NSSHH 5 NSSHH Sbjct 137 NSSHH 141 |
| 77 | 5_C3 | gi\|98162806\|ref\|NM_0174 32.3\| Homo sapiens prostate tumor overexpressed gene 1 (PTOV1), mRNA Length = 1884 Score = 206 bits (104), Expect = 5e-51 Id = 104/104(100%), Gaps = 0/104(0%) Strand = Plus/Plus | LGTSTAQQ HGGWCPEA SKDGPHPST FPQ | 28 | gi\|119592169\|gb\|EAW71763. 1\| hCG1794614, isoform gi\|21750918\|dbj\|BAC03866.1\| unnamed protein product gi\|4877793\|gb\|AAD31434.1\| DNA methyltransferase 3 beta 5 gi\|62898391\|dbj\|BAD97135.1 BCL2-like 14 isoform 1 gi\|56748611\|sp\|Q9BZR8\|B2L 14_HUMAN Apoptosis facilitator Bcl-2-like 14 protein gi\|118572673\|sp\|O14513\|NA P5_HUMAN Nck-associated protein 5 (Peripheral clock protein) | Score = 27.4 bits (57), Expect = 3.8 Id = 15/26 (57%), Positives = 16/26 (61%), Gaps = 9/26 (34%) Query 8 QHGGWCPEASKD--GPHP---STFPQ 28 QHGG CP +K GPHP ST PQ Sbjct 13 QHGG-CP--AKALPGPHPGVVST-PQ 34 Score = 27.4 bits (57), Expect = 3.8 Id = 7/7 (100%), Positives = 7/7 (100%), Gaps = 0/7 (0%) Query 11 GWCPEAS 17 GWCPEAS Sbjct 131 GWCPEAS 137 Score = 25.2 bits (52), Expect = 16 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 79 | 11_C9 | gi\|18008638\|gb\|BC020889.1\| Homo sapiens cDNA clone IMAGE: 4692359 Length = 1436 Score = 466 bits (235), Expect = 4e-129 Id = 247/253 (97%), Gaps = 0/253 (0%) | DCSC | 4 | gi\|13633942\|sp\|Q9UM82\|SPAT2_HUMAN Spermatogenesis-associated protein 2 | Id = 8/10 (80%), Positives = 8/10 (80%), Gaps = 1/10 (10%) Query 8 QHGGWW-PEA 16 QHG WC PEA Sbjct 145 QHGPWCPPEA 154 |
|  |  |  |  |  | gi\|119615430\|gb\|EAW95024.1\| EPH receptor B2 | Score = 17.6 bits (34), Expect = 1378 Id = 4/4 (100%), Positives = 4/4 (100%) Gaps = 0/4 (0%) Query 1 DCSC 4 DCSC Sbjct 216 DCSC 219 |
|  |  |  |  |  | gi\|119599812\|gb\|EAW79406.1\| integrin, beta 5 gi\|119583687\|gb\|EAW63283.1\| ADAM metallopeptidase domain 9 (meltrin gamma) gi\|115502238\|sp\|Q9Y2K2\|QSK_HUMAN Serine threonine -protein kinase QSK gi\|119603107\|gb\|EAW82701.1\| phosphorylase kinase, beta, isoform CRA_b |  |
| 80 | 5_H4 | gi\|34304330\|ref\|NM_183063.1\| Homo sapiens ring finger protein 7 (RNF7), transcript variant 2, mRNA Length = 1880 Score = 708 bits (357) Expect = 0.0 Id = 365/369 (98%) Gaps = 0/369 (0%) Strand = Plus/Plus | NRSRWICG PLGLIKALV | 17 | gi\|13124092\|sp\|Q9UBT3\|DKK4_HUMAN Dikkopf-related protein 4 precursor (Dkk-4) (24) gi\|51477372\|ref\|XP_293360.4 PREDICTED: Similar to Ubiquitin ligase SIAH1 seven in absentia homolog 1-like gi\|48146981\|emb\|CAG33713.1\| NOV [Homo sapiens] gi\|1352515\|sp\|P48745\|NOV_HUMAN NOV protein homolog precursor (NovH) (Nephroblastoma overexpressed gene protein homolog) gi\|55925626\|ref\|NP_001007254.1\| endogenous retroviral sequence 3 gi\|44887883\|sp\|Q14264\|ENR1_HUMAN HERV-R_7q21.2 provirus ancestral | Score = 24.0 bits (49), Expect = 29 Id = 8/13 (61%), Positives = 9/13 (69%) Gaps = 3/13 (23%) Query 5 WICGPLGLIKALV 17 W+C PLG ALV Sbjct 11 WLCSPLG--ALV 20 Score = 22.3 bits (45), Expect = 95 Id = 7/9 (77%), Positives = 8/9 (88%) Gaps = 0/9 (0%) Query 8 GPLGLIKAL 16 GPLGLI+ L Sbjct 72 GPLGLIRNL 80 Score = 22.3 bits (45), Expect = 129 Id = 5/5 (100%), Positives = 5/5 (100%), Gaps = 0/5 (0%) Query 5 WICGP 9 WICGP Sbjct 419 WICGP 423 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | | | | Env polyprotein precursor (Envelope polyprotein) | |
| 83 | 2_H7 | gi\|4506788\|ref\|NM_00297 0.1\| Homo sapiens spermidine/spermine N1-acetyltransferase (SAT), mRNA Length = 1060 Score = 1031 bits (520) Expect = 0.0 Id = 520/520 (100%) Gaps = 0/520 (0%) Strand = Plus/Plus | RKGKKSKR RKWLNS | 14 | gi\|8924242\|ref\|NP_061136.1\| sarcoma antigen 1 | Score = 25.7 bits (53), Expect = 9.1 Id = 10/20 (50%), Positives = 12/20 (60%), Gaps = 7/20 (35%) Query 1   RKGKK---SKRRK---WLN 13 RK K+   SKRRK    WL+ Sbjct 51  RKSKRHSSSKRRKSMSSWLD 70 |
| | | | | | gi\|8216987\|emb\|CAB92443.1\| putative tumor antigen | Score = 25.2 bits (52), Expect = 12 Id = 7/9 (77%), Positives = 8/9 (88%), Gaps = 0/9 (0%) Query 4   KKSKRRKWL 12 KK K+RKWL Sbjct 22  KK K+RKWL |
| | | | | | gi\|51458801\|ref\|XP_089384.7 \|PREDICTED: similar to RIKEN cDNA A430025D11 3B_HUMAN Kinesin-like protein KIF13B | Score = 24.4 bits (50), Expect = 30 Id = 7/7 (100%), Positives = 7/7 (100%), Gaps = 0/7 (0%) Query 4   KKSKRRK 10 KKSKRRK Sbjct 60  KKSKRRK 66 |
| | | | | | gi\|23396625\|sp\|Q9NQT8\|K11 gi\|57013078\|sp\|Q7Z699\|SPR E1_HUMAN Sprouty-related, EVH1 domain containing protein 1 | Score = 24.8 bits (51), Expect = 22 Id = 6/6 (100%), Positives = 6/6 (100%), Gaps = 0/6 (0%) Query 8   RRKWLN 13 RRKWLN Sbjct 1092 RRKWLN 1097 |
| | | | | | gi\|31565770\|gb\|AAH53600.1\| Transmembrane and coiled-coil domains 4 | |
| | | | | | gi\|56202682\|emb\|CAI20092.1 \| novel protein | |
| | | | | | gi\|7227890\|sp\|O24175\|FL_O RYSA Putative transcription factor FL | |
| | | | | | gi\|51701343\|sp\|Q8TD10\|CHD 5_HUMAN Chromodomain helicase-DNA-binding protein 5 (CHD-5) | Score = 24.4 bits (50), Expect = 22 Id = 8/11 (72%), Positives = 8/11 (72%), Gaps = 1/11 (9%) Query 1   RKGKKSKRRKW 11 RK KK  RRKW Sbjct 178 RKKKENRRKW 187 |
| | | | | | gi\|126178\|sp\|P14151\|LYAM1 _HUMAN L-selectin precursor (Lymph node homing receptor) (Leukocyte adhesion molecule 1) (gp90-MEL) | |
| | | | | | gi\|18378735\|ref\|NP_055625.2 centrosome-associated protein 350 | |
| 85 | 9_C3 | gi\|92444107\|gb\|BC01388 7.1\| Homo sapiens | GDPNSS | 6 | gi\|119615660\|gb\|EAW95254. 1\| cytoplasmic linker | Score = 18.5 bits (36), Expect = 1148 Id = 5/5 (100%), Positives = 5/5 (100%), |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | mRNA similar to mouse double minute 2, human homolog of; p53-binding protein (cDNA clone IMAGE: 3841679) Length = 3865 Score = 835 bits (421) Expect = 0.0 Id = 423/424 (99%) Gaps = 0/424 (0%) Strand = Plus/Plus | | | associated gi\|119607399\|gb\|EAW86993. 1\| telomeric repeat binding factor (NIMA-interacting) 1 gi\|119588279\|gb\|EAW67873. 1\| protein tyrosine phosphatase, receptor typeJ gi\|119626399\|gb\|EAX05994.1 dentin sialophosphoprotein gi\|119613825\|gb\|EAW93419. 1\| TNF receptor-associated factor 5 gi\|116242829\|sp\|Q9Y4A5\|TR RAP_HUMANTransformation transcription domain-associated protein | Gaps = 0/5 (0%) Query 1 GDPNS 5 GDPNS Sbjct 177 GDPNS 181 Score = 18.5 bits (36), Expect = 1148 Id = 5/5 (100%), Positives = 5/5 (100%), Gaps = 0/5 (0%) Query 2 DPNSS 6 DPNSS Sbjct 2031 DPNSS 2035 |
| 87 | 2_C2 | gi\|30584378\|gb\|BT00777 0.1\| Synthetic construct Homo sapiens cystatin B (stefin B) mnRNA Score = 280 bit (141) Expect = 1e-72 Id = 141/141 (100%) Strand = Plus/Plus | GRVIQE PGGRGD KLLHQC ARRRG LRTPAS VPISPS | 36 | gi\|28892\|emb\|CAA35582.1\| unnamed protein product gi\|2135396\|pir\|\|S71548 homeotic protein pG2 gi\|48428276\|sp\|O43432\|IF4G 3_HUMAN Eukaryotic translation initiation factor 4 gamma 3 (eIF-4-gamma II) (eIF4GII) gi\|2190402\|emb\|CAA73944.1\| latent TGF-beta binding protein-4 | Score = 28.6 bits (60), Expect = 1.4 Identities = 12/22 (54%), Positives = 14/22 (63%), Gaps = 3/22 (13%) Query 15 LHQGARRRRGLRTPASVPISPS 36 L QG RRR L   +SVP +PS Sbjct 227 LQQGGRRGDL--SSVPTAPS 245 Score = 28.6 bits (60), Expect = 1.3 Identities = 12/22 (54%), Positives = 14/22 (63%), Gaps = 3/22 (13%) Query 15 LHQGARRRRGLRTPASVPISPS 36 L QG RRR L   +SVP +PS Sbjct: 228 LQQGGRRRGDL--SSVPTAPS 246 Score = 26.9 bits (56), Expect = 4.3 Identities 15/26 (53%) Positives = 17/28 (60%), Gaps = 7/28 (25%) Query: 1 GRVIQEPGGRGDKLLHQGARR-----RR 23 GR Q PGGRG  LL+ G+RR    RR Sbjct: 685 GR--QTPGGRGVPLLNVGSRRSQPGQRR 710 |
| 90 | 10_F 11 | gi\|125656973\|gb\|EF06115 0.1\| Homo sapiens isolate UV0758 mitochondrion, | VGNGEG RLEVL | 11 | gi\|20177960\|sp\|Q96JB6\|LOX L4_HUMAN Lysyl oxidase homolog 4 gi\|4826914\|ref\|NP_005081.1\| | Score = 24.8 bits (51), Expect = 21 Id = 7/7 (100%), Positives = 7/7 (100%) Gaps = 0/7 (0%) Query 11 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | complete genome Length = 16573 Score = 208 bits (105) Expect = 3e-51 Id = 112/115 (97%) Gaps = 0/115 (0%) Strand = Plus/Minus /product = "NADH dehydrogenase subunit 1" | | | phospholipase A2, group IVB gi\|3811347\|gb\|AAC78836.1\| cytosolic phospholipase A2 gi\|2745961\|gb\|AAB94793.1\| Bcd orf2 gi\|5453978\|ref\|NP_006250.1\| protein kinase, cGMP-dependent type II gi\|51473081\|ref\|XP_372641.2 Spermatogenesis associated protein PD1 gi\|157282312\|emb\|CAD43180. 3\| interleukin-1 receptor associated kinase-2 gi\|20177834\|sp\|O43866\|CD5 L_HUMAN CD5 antigen-like precursor (SP-alpha) (IgM-associated peptide) | EGRLEVL 17 EGRLEVL Sbjct 43 EGRLEVL 49 Score = 24.4 bits (50), Expect = 22 Id = 7/7 (100%), Positives = 7/7 (100%), Gaps = 0/7 (0%) Query 4 GEGRLEV 10 GEGRLEV Sbjct 349 GEGRLEV 355 Score = 22.3 bits (45), Expect = 97 Id = 6/8 (75%), Positives = 8/8 (100%), Gaps = 0/8 (0%) Query 4 GEGRLEVL 11 G+GRLE+L Sbjct 152 GQGRLEIL 159 |
| 93 | 2_G2 | gi\|6706619\|emb\|AJ25197 3.1\|HSA251973 Homo sapiens partial steerin-1 gene Length = 200033 Features in this part of subject sequence: steerin-1 protein Score = 662 bits (334) Expect = 0.0 Id = 370/380 (97%) Gaps = 2/380 (0%) Strand = Plus/Minus | GSRVRMSG KKKERK | 14 | gi\|11322769\|emb\|CAC16957. 1\| gap junction protein, alpha 3, 46 kDa (connexin 46) gi\|119607339\|gb\|EAW86933. 1\| centrosome and spindle pole associated protein 1, isoform 1 gi\|119578900\|gb\|EAW58496. nucleolar protein) family 6 (RNA-associated), isoform gi\|20141241\|sp\|P50454\|SERP H_HUMANSerpin H1 precursor (Collagen-binding protein) (Proliferation-inducing gene 14 protein) gi\|30583027\|gb\|AAP35758.1\| serine (or cysteine) proteinase inhibitor, clade H (heat shock protein 47), member 2 | Score = 26.5 bits (55), Expect = 7.1 Id = 8/10 (80%), Positives = 8/10 (80%), Gaps = 0/10 (0%) Query 4 VRMSGKKKER 13 VRM KKKER Sbjct 100 VRMEKKKER 109 Score = 24.4 bits (50), Expect = 31 Id = 7/8 (87%), Positives = 8/8 (100%), Gaps = 0/8 (0%) Query 6 MSGKKKER 13 +SGKKKER sbjct 5 LSGKKKER 12 Score = 24.0 bits (49), Expect = 41 Id = 7/10 (70%), Positives = 9/10 (90%), Gaps = 0/10 (0%) Query 4 VRMSGKKKER 13 VR+S KKK+R Sbjct 95 VRLSEKKKDR 104 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 94 | 10_F 8 | gi\|21411332\|gb\|BC03101 2.1\| Homo sapiens eukaryotic translation elongation factor 1 gamma, mRNA (cDNA clone MGC: 32765 IMAGE: 4654721), complete cds Length = 1441 Score = 965 bits (487) Expect = 0.0 Id = 529/550 (96%) Gaps = 0/550 (0%) Strand = Plus/Plus | NSSVS | 5 | gi\|119626680\|gb\|EAX06275.1 alpha-kinase 1, isoform ectonucleotide pyrophosphatase/phospho-diesterase 4 gi\|119597572\|gb\|EAW77166. 1\| AT hook containing transcription factor 1 gi\|119583836\|gb\|EAW63432. 1\| testis expressed sequence 15, isoform CRA_a gi\|118572823\|sp\|Q96QP1\|AL PK1_HUMAN Lymphocyte alpha-protein kinase gi\|91208166\|sp\|Q96Q15\|SMG 1_HUMAN Serine/threonine-protein kinase SMG1 | Score = 17.2 bits (33), Expect = 2312 Id = 5/5 (100%), Positives = 5/5 (100%), Gaps = 0/5 (0%) Query 1 NSSVS 5 NSSVS Sbjct 3340 NSSVS 3344 |
| 95 | 10_H 3 | gi\|33869450\|gb\|BC01719 4.2\| Homo sapiens E74-like factor 4 (ets domain transcription factor), mRNA (cDNA clone MGC: 1755 IMAGE: 3138355), complete cds Length = 4121 Score = 904 bits (456), Expect = 0.0 Id = 464/467 (99%) Gaps = 0/467 (0%) Strand = Plus/Plus | SICA | 4 | gi\|119621016\|gb\|EAX00611.1 solute carrier family 30 (zinc transporter), member 3 gi\|119629012\|gb\|EAX08607. FRAS1 related extracellular matrix protein 2 gci\|119590121\|gb\|EAW69715. 1\| nuclear VCP-like gi\|110282976\|sp\|P46020\|KPB 1_HUMAN Phosphorylase b kinase regulatory subunit alpha, skeletal muscle isoform gi\|62087778\|dbj\|BAD92336. rearranged L-myc fusion sequence variant | Score = 15.9 bits (30), Expect = 4455 Id = 4/4 (100%), Positives = 4/4 (100%), Gaps = 0/4 (0%) Query 1 SICA 4 SICA Sbjct 741 SICA 744 |
| 96 | 11_C 1 | gi\|109148511\|ref\|NR_003 089.1\| Homo sapiens OTU domain, ubiquitin aldehyde binding 1 (OTUB1), transcript variant 2, transcribed RNA Length = 2518 Score = 829 bits (418) Expect = 0.0 | QLRISTTRS WT | 11 | gi\|119628939\|gb\|EAX08534.1 hCG2042156 gi\|116496611\|eb\|AAI26137.1\| DNASE2B protein gi\|46395921\|sp\|Q8WZ79\|DN S2B_HUMAN Deoxyribonuclease-2-beta gi\|17066106\|emb\|CAD12457. 1\| Novex-3 Titin Isoform gi\|119610438\|gb\|EAW90032. | Score = 24.0 bits (49), Expect = 41 Id = 7/10 (70%), Positives = 8/10 (80%), Gaps = 0/10 (0%) Query 1 QLRISTTRSW 10 QLR ST R+W Sbjct 88 QLRDSTARAW 97 Score = 23.1 bits (47), Expect = 75 Id = 6/6 (100%), Positives = 6/6 (100%), |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | Id = 425/428 (99%)<br>Gaps = 0/428 (0%)<br>Strand = Plus/Plus | | | 1\| netrin 1<br>gi\|119582311\|gb\|EAW61907.<br>1\| centaurin, delta 3,<br>gi\|47779175\|gb\|AAT38470.1\|<br>immunoglobulin heavy<br>chain<br>gi\|5456914\|gb\|AAD43707.1\|<br>protocadherin alpha 5<br>gi\|4502681\|ref\|NP_001772.1\|<br>CD69 antigen (p60, early T-<br>cell activation antigen)<br>gi\|584906\|sp\|Q07108\|CD69_<br>HUMAN Early activation<br>antigen CD69<br>(Early T-cell activation<br>antigen p60) | Gaps = 0/6 (0%)<br>Query 5<br>STTRSW 10<br>STTRSW<br>Sbjct 68<br>STTRSW 73<br>Score = 22.3 bits (45), Expect = 134<br>Id = 6/8 (75%), Positives = 7/8 (87%),<br>Gaps = 0/8 (0%)<br>Query 3<br>RISTTRSW 10<br>RIS+T SW<br>Sbjct 3491<br>RISSTSSW 3498<br>Score = 16.8 bits (32), Expect = 6145<br>Id = 6/9 (66%), Positives = 7/9 (77%),<br>Gaps = 2/9 (22%)<br>Query 3<br>RISTT--RS 9<br>RIST+ RS<br>Sbjct 312<br>RISTSPIRS 320 |
| 98 | 2_C3 | gi\|30584378\|gb\|BT00777<br>0.1\| Synthetic construct<br>Homo sapiens cystatin B<br>(stefin B) mRNA<br>Score = 280 bit (141)<br>Expect = 1e-72<br>Id = 141/141 (100%)<br>Strand = Plus/Plus | GRVIQE<br>PGGRGD<br>KLLHQG<br>ARRRRG<br>LRTPAS<br>VPISPS | 36 | gi\|28892\|emb\|CAA35582.1\|<br>unnamed protein product<br>gi\|2135396\|pir\|\|S71548<br>homeotic protein pG2-<br>human<br>gi\|48428276\|sp\|O43432\|IF4G<br>3_HUMAN<br>Eukaryotic translation<br>initiation factor 4 gamma 3<br>(eIF-4-gamma II)<br>gi\|2190402\|emb\|CAA73944.1\|<br>latent TGF-beta binding<br>protein-4 | Score = 28.6 bits (60), Expect = 1.4<br>Identities = 12/22 (54%), Positives = 14/22 (63%),<br>Gaps = 3/22 (13%)<br>Query 15<br>LHQGARRRRGLRTPASVPISPS 36<br>L QG RRR L  +SVP +PS<br>Sbjct 227<br>LQQGGRRRGDL---SSVPTAPS 245<br>Score = 28.6 bits (60), Expect = 1.3<br>Identities = 12/22 (54%), Positives = 14/22 (63%),<br>Gaps = 3/22 (13%)<br>Query: 15<br>LHQGARRRRGLRTPASVPISPS 36<br>L QG RRR L  +SVP +PS<br>Sbjct: 228<br>LQQGGRRRGDL---SSVPTAPS 246<br>Score = 26.9 bits (56), Expect = 4.3<br>Identities = 15/28 (53%), Positives = 17/28 (60%),<br>Gaps = 7/28 (25%)<br>Query: 1<br>GRVIQEPGGRGDKLLHQGARR-----RR 23 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| 10 6 | 8_D4 | gi\|7779425\|gb\|BC10604 6.1\| Homo sapiens pre-B-cell colony enhancing factor 1, transcript variant 1, mRNA (cDNA clone MGC: 117256 IMAGE: 6161081), complete cds Length = 2144 Score = 256 bits (129) Expect = 3e-65 Id = 144/151 (95%) Gaps = 0/151 (0%) Strand = Plus/Plus | DMSYK | 5 | gi\|59798440\|sp\|Q9UNA4\|PO L1_HUMAN DNA polymerase iota (RAD30 homolog B) (Eta2) gi\|56757695\|sp\|Q9ULC6\|PA DI1_HUMAN Protein-arginine deiminase type I (Peptidylarginine deiminase I) gi\|3122589\|sp\|O15355\|PP2C G_HUMAN Protein phosphatase 2C gamma isoform gi\|68067549\|sp\|P07858\|CAT B_HUMAN Cathepsin B precursor (Cathepsin B1) gi\|12585368\|sp\|Q16890\|TPD5 3_HUMAN Tumor protein D53 (hD53) gi\|52000845\|sp\|Q9UL12\|SAR H_HUMAN Sarcosine dehydrogenase, mitochondrial precursor (SarDH) (BPR-2) gi\|1711371\|sp\|P54764\|EPHA4 _HUMAN Ephrin type-A receptor 4 precursor (Tyrosine-protein kinase receptor SEK) gi\|17380181\|sp\|O60508\|PR17 HUMAN Pre-mRNA splicing factor PRP17 (hPRP17) (Cell division cycle 40 homolog) (EH-binding protein 3) gi\|62087974\|dbj\|BAD92434. protein phosphatase 1G variant | GR Q PGGRG LL+G+RR RR Sbjct: 685 GR--QTPGGRGVPLLNVGSRRSQPGQRR 710 Score = 18.5 bits (36), Expect = 933 Id = 4/5 (80%), Positives = 5/5 (100%), Gaps = 0/5 (0%) Query 1 DMSYK 5 +MSYK Sbjct 104 EMSYK 108 Score = 18.0 bits (35), Expect = 914 Id = 4/4 (100%), Positives = 4/4 (100%), Gaps = 0/4 (0%) Query 1 DMSY 4 DMSY Sbjct 162 DMSY 165 |
| 10 8 | 1_D6 | gi\|20357564\|ref\|NM_0001 00.2\| Homo sapiens cystatin B (stefin B) | RGDKLLHQ GARRRRGL RTPASVPIS | 27 | gi\|28892\|emb\|CAA35821\| unnamed protein product gi\|2135396\|pir\|\|S71548 | Score = 28.6 bits (60), Expect = 1.6 Id = 12/22 (54%), Positives = 14/22 (63%) Gaps = 3/22 (13%) |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 10 | | (CSTB), mRNA Length = 674 Score = 232 bits (117) Expect = 9e-59 Id = 117/117 (100%) Gaps = 0/117 (0%) Strand = Plus/Plus | PS | | homeotic protein pG2-human gi\|38648796\|gb\|AAH63316.1\| FBXL17 protein | Query 6 LHQGARRRRGLRTPASVPISPS 27 L QG RRR L +SVP +PS Sbjct 228 LQQGGRRGDL---SSVPTAPS 246 Score = 28.2 bits (59), Expect = 2.1 Id = 11/18 (61%), Positives = 11/18 (61%), Gaps = 5/18 (27%) Query 11 RRRRGL----RTPASVP 23 RRRR L RTPA VP Sbjct 25 RRRPLLRLPRRTPAKVP 42 |
| 9 | 4_G4 | gi\|56788032\|gb\|AY692464.1\| Homo sapiens growth-inhibiting gene 46 mRNA, complete cds Length = 1715 Score = 825 bits (416) Expect = 0.0 Id = 416/416 (100%) Gaps = 0/4 16 (0%) Strand = Plus/Minus | RPARSR RMMAW GKA | 14 | gi\|57163116\|emb\|CAI39857.1\| protein (peptidyl-prolyl cis/trans isomerase) NIMA-interacting, 4 (parvulin) gi\|32171215\|ref\|NP_859066.1\| transducer of regulated cAMP response element-binding protein (CREB) 2 gi\|59800455\|sp\|Q9UPY6\|WA SF3_HUMAN Wiskott-Aldrich syndrome protein family member 3 (WASP-family protein member 3) gi\|4927214\|gb\|AAD33054.1\| scar3 gi\|57013057\|gb\|Q6STE5\|SMR D3_HUMAN SWI/SNF-related matrix-associated actin-dependent regulator of chromatin subfamily D member 3 gi\|19421557\|gb\|AAK56405.1\| chromodomain helicase DNA binding protein 5 gi\|1399745\|gb\|AAB08988.1\| myelodysplasia/myeloid leukemia factor 2 gi\|73921220\|sp\|Q86WB0\|NIP A_HUMAN Nuclear-interacting partner of anaplastic lymphoma | Score = 26.5 bits (55), Expect = 5.0 Id = 7/8 (87%), Positives = 7/8 (87%), Gaps = 0/8 (0%) Query 1 RPARSRRM 8 RP RSRRM Sbjct 14 RPERSRRM 21 Score = 23.5 bits (48), Expect = 40 Id = 6/7 (85%), Positives = 6/7 (85%), Gaps = 0/7 (0%) Query 6 RRMMAWG 12 RR MAWG Sbjct = 144 RRTMAWG 150 Score = 23.1 bits (47), Expect = 53 Id = 8/14 (57%), Positives = 9/14 (64%), Gaps = 4/14 (28%) Query 1 RPARSRR----MMA 10 R AR+RR MMA Sbjct 149 RKARNRRQEWNMMA 162 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| | | | | | kinase) (hNIPA) gi\|41019490\|sp\|P49736\|MCM 2_HUMAN DNA replication licensing factor MCM2 (Nuclear protein DM28) gi\|1706888\|sp\|P53539\|FOSB_HUMAN Protein fosB (G0/G1 switch regulatory protein 3) | |
| 112 | 10_E8 | gi\|123998528\|gb\|D08959 40.2\| Synthetic construct Homo sapiens clone IMAGE: 3938260; FLH191546.01L; RZPD0839E0667D ribosomal protein L7a (RPL7A) gene, encodes complete protein Length = 841 Score = 678 bits (342) Expect = 0.0 Id = 342/342 (100%) Gaps = 0/342 (0%) Strand = Plus/Plus | AETVGP GREEGC WQRGRP NEETTC PSSRS | 29 | gi\|113422952\|ref\|XP_001129 208.1\| PREDICTED: hypothetical protein gi\|34785506\|gb\|AAH57760.1\| MORN repeat containing 3 gi\|119622706\|gb\|EAX02301.1 proprotein covertase subtilisin/kexin type 6, isoformn CRA_a | Score = 26.5 bits (55), Expect = 6.8 Id = 11/16 (68%), Positives = 11/16 (68%), Gaps = 5/16 (31%) Query 5 GPGREEGC--W-QRGR 17 GPGR GC W QRGR sbjct 101 GPGR--GCGGWVQRGR 114 Score = 25.2 bits (52), Expect = 16 Id = 6/7 (85%), Positives = 7/7 (100%), Gaps = 0/7 (0%) Query 10 EGCWQRG 16 EGCW+RG Sbjct 161 EGCWERG 167 Score = 24.8 bits (51), Expect = 22 Id = 7/7 (100%), Positives = 7/7 (100%), Gaps = 0/7 (0%) Query 4 VGPGREE 10 VGPGREE sbjct 620 VGPGREE 626 |
| 114 | 8_H10 | gi\|114520617\|ref\|NM_021 130.3\| Homo sapiens peptidylprolyl isomerase A (cyclophilin A) (PPIA), mRNA Length = 2276 Score = 436 bits (220) Expect = 5e-120 Id = 223/224 (99%) | PIDGLATSA IMACEVTT LTHKPWNN SVKAGTLIT KSFLSSAQS TKIFCCLW DLVCKQLK GDAAQGLA VDGNVKEQ | 94 | gi\|119623272\|gb\|EAX02867.1 hCG1792883, isoform gi\|119623270\|gb\|EAX02865.1 hCG1792883, isoform gi\|119624576\|gb\|EAX04171.1 solute carrier family 22 gi\|119577790\|gb\|EAW57386. 1\| dystrophia myotonica-containing WD repeat | Score = 65.1 bits (146), Expect = 1e-10 Id = 23/35 (65%), Positives = 27/35 (77%), Gaps = 1/35 (2%) Query41 AQSTKIFCCLWDLVCKQLKGDAAQGLAVDGNVKEQ 75 AQS KIFCCLW+ V KQL DAAQGL + G+V+E Sbjct56 AQSMKIFCCLWNFVYKQL-EDAAQGLTMGGDVEEH 89 Score = 58.3 bits (130), Expect = 1e-08 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| | | Gaps = 0/224 (0%) Strand = Plus/Minus | SIHKLHNTA RXSLRPHSS N | | motif, isoform CRA_a gi|119570084|gb|EAW49699. 1| F-box and leucine-rich repeat protein 15 gi|119570183|gb|EAW49798. 1| mitochondrial ribosomal protein L43, isoform CRA_c gi|3216558|gb|AAP72126.1| G protein-coupled receptor 120 | Id = 20/31 (64%), Positives = 24/31 (77%), Gaps = 1/31 (3%) Query 45 KIFCCLWDLVCKQLKGDAAQGLAVDGNVKEQ 75 KIFCCLW+ V KQL DAAQGL + G+V+E Sbjct 2 KIFCCLWNFVVKQL-EDAAQGLTMGDVEEH 31 Score = 27.4 bits (57), Expect = 25 Id = 10/15 (66%), Positives = 11/15 (73%), Gaps = 4/15 (26%) Query 49 CL--WDLVCKQLKG 60 CL  WDLVC+Q KG Sbjct 136 CLSLQWDLVCEQ-KG 149 |
| 11 5 | 6_G8 | gi|30584378|gb|BT00777 0.1| Synthetic construct Homo sapiens cystatin B (stefin B) mRNA Score = 280 bit(141) Expect = 1e-72 Id = 141/141 (100%) Strand = Plus/Plus | GRVIQE PGGRGD KLLHQC ARRRRG LRTPAS VPISPS | 36 | gi|28892|emb|CAA35582.1| unnamed protein product gi|2135396|pir||S71548 hoemotic protein pG2 gi|48428276|sp|O43432|IF4G 3_HUMAN Eukaryotic translation initiation factor 4 gamma 3 (eIF-4-gamma 3) (eIF-4-gamma II) gi|2190402|emb|CAA73944.1| latent TGF-beta binding protein-4 | Score = 28.6 bits (60), Expect = 1.4 Identities = 12/22 (54%), Positives = 14/22 (63%), Gaps = 3/22 (13%) Query 15 LHQGARRRRGLRTPASVPISPS 36 L QG RRR L  +SVP +PS Sbjct 227 LQQGGRRRGDL---SSVPTAPS 245 Score = 28.6 bits (60), Expect = 1.3 Identities = 12/22 (54%), Positives = 14/22 (63%), Gaps = 3/22 (13%) Query: 15 LHQGARRRRGLRTPASVPISPS 36 L QG RRR L  +SVP +PS Sbjct: 228 LQQGGRRRGDL---SSVPTAPS 246 Score = 26.9 bits (56), Expect = 4.3 Identities = 15/28 (53%), Positives = 17/28 (60%), Gaps = 7/28 (25%) Query: 1 GRVIQEPGGRGDKLLHQGARR----RR 23 GR Q PGGRG LL+ G+RR    RR Sbjct: 685 GR--QTPGGRGVPLLNVGSRSQPGQRR 710 |
| 11 7 | 1_D4 | gi|20357564|ref|NM_0001 00.2| Homo sapiens cystatin B (stefin B) (CSTB) cystatin B (liver thiol proteinase | GRVIQE PGGRGD KLLHQG ARRRRG LRIPAS | 34 | gi|28892|emb|CAA35582.1| unnamed protein product gi|2135396|pir||S71548 hoemotic protein pG2 gi|48428276|sp|O43432|IF4G | Score = 28.6 bits (60), Expect = 1.4 Identities = 12/22 (54%), Positives = 14/22 (63%), Gaps = 3/22 (13%) Query 15 LHQGARRRRGLRTPASVPISPS 36 |

TABLE 6a-continued

| Rank | Clone | Description of the genes that are in Mimotope clones | Peptide sequences of Mimotopes, in-frame with T7 10 B gene | Size of peptide that Mimotopes mimic | Description of the sequences | Region of similarity of peptide (only the top 3 sequences are shown) |
|---|---|---|---|---|---|---|
| 11 | 6_C4 | gi\|71559137\|ref\|NM_0010 29.3\| Homo sapiens ribosomal protein S26 (RPS26), mRNA Length = 699 Score = 367 bits (185) Expect = 1e-98 Id = 202/210 (96%) Gaps = 0/210 (0%) Strand = Plus/Plus | VPISPS | 3_HUMAN Eukaryotic translation initiation factor 4 gamma 3 (eIF-4-gamma 3) (eIF-4-gamma II) gi\|2190402\|emb\|CAA73944.1\| latent TGF-beta binding protein-4 | L QG RRR L   +SVP +PS<br>Sbjct 227 LQQGGRRRGDL--SSVPTAPS 245<br>Score = 28.6 bits (60), Expect = 1.3<br>Identities = 12/22 (54%), Positives = 14/22 (63%),<br>Gaps = 3/22 (13%)<br>Query: 15 LHQGARRRRGLRTPASVPISPS 36<br>L QG RRR L   +SVP +PS<br>Sbjct 228 LQQGGRRRGDL--SSVPTAPS 246<br>Score = 26.9 bits (56), Expect = 4.3<br>Identities = 15/28 (53%), Positives = 17/28 (60%),<br>Gaps = 7/28 (25%)<br>Query: 1 GRVIQEPGGRGDKLLHQGARR----RR 23<br>GR  Q PGGRG   LL+ G+RR      RR<br>Sbjct: 685 GR--QTPGGRGVPLLNVGSRRSQPGQRR 710 |
| 8 | | gi\|21753429\|dbj\|BAC04343.1 Unnamed protein product gi\|12643872\|sp\|Q9UBS0\|KS6 B2_HUMAN Ribosomal protein S6 kinase 2 (S6K2) (70 kDa ribosomal protein S6 kinase-related kinase) (Serine/threonine-protein kinase 14 beta) Colony stimulating factor 1 Roquin (RING finger and C3H zinc finger protein 1) G protein coupled receptor 123 Solute carrier family 44, member 5 Choline transporter-like protien 5 | SSQGHF | 6 | Score = 21.8 bits (44), Expect = 78<br>Id = 6/6 (100%), Pos = 6/6 (100%),<br>Gaps = 0/6 (0%)<br>Query 1 SSQGHF 6<br>SSQGHF<br>Sbjct 74 SSQGHF 79<br>Score = 18.0 bits (35), Expect = 1097<br>Id = 5/5 (100%), Pos = 5/5 (100%),<br>Gaps = 0/5 (0%)<br>Query 1 SSQGH 5<br>SSQGH<br>Sbjct 189 SSQGH 193 |
| 12 | 1_D8 | gi\|123997386\|gb\|DQ8953 69.2\| Synthetic construct Homo sapiens clone IMAGE: 3505011; FLH183687.01L; | LPRVQAQG GRVPEETE GAGGGRGR QGRAGAPA GRGTAAAQ GGAELGAE | 64 | gi\|48429165\|sp\|Q86V81\|THO C4_HUMAN THO complex subunit 4 (Tho4) (Ally of AML-1 and LEF-1) (Transcriptional coactivator Aly/REF) (bZIP | Score = 36.7 bits (79), Expect = 0.016<br>Id = 19/37 (51%), Positives = 21/37 (56%),<br>Gaps = 14/37 (37%)<br>Query8 GGRVPEETEGAGGGRGRQGRAGAPAGRGTAAAQGGAE 44<br>GGR   PE EG  GGR GR GRAGAPAGRGT  A QGGAE<br>GGR       GGGRGR GRAG+   GRG       GGA+ |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 12 | 5_C6 | RZPD0839F06141D CDC37 cell division cycle 37 homolog (S. cerevisiae) (CDC37) gene, encodes complete protein<br>Length = 1177<br>Score = 333 bits (168)<br>Expect = 2e-88<br>Id = 168/168 (100%)<br>Gaps = 0/168 (0%)<br>Strand = Plus/Plus | AGGDAQEG SLRPHSSN | | enhancing factor BEF) gi\|47117879\|sp\|P83369\|LSM1 1_HUMAN U7 snRNA-associated Sm-like protein Lsm11 gi\|30802096\|gb\|AAH51353.1\| LSM11 protein | SbJct21<br>GGR------GGGRGR-GRAGSQGGRG----GGAQ 43<br>Score = 21.0 bits (42), Expect = 848<br>Id = 10/16 (62%), Positives = 10/16 (62%),<br>Gaps = 4/16 (25%)<br>Query 19<br>GGGRGRQGRAGAPAGR 34<br>GG RGR GR     AGR<br>Sbjct 221<br>GGARCR-GRG---AGR 232<br>Score = 35.0 bits (75), Expect = 0.052<br>Id = 17/24 (70%), Positives = 17/24 (70%),<br>Gaps = 2/24 (8%)<br>Query 19<br>GGGRGRQGRA-GAPAGRGTAAAQG 41<br>GGGRGR GRA GA AG G  AA G<br>Sbjct 69<br>GGGRGR-GRARGAAAGSGVPAAPG 91 |
| 2 | | gi\|75992939\|ref\|NM_0046 51.3\| Homo sapiens ubiquitin specific peptidase 11 (USP11), mRNA<br>Length = 3300<br>Score = 446 bits (225)<br>Expect = 5e-123<br>Id = 225/225(100%)<br>Gaps = 0/225(0%)<br>Strand = Plus/Plus | VVSPPSSAR PACVCPSSS DPPF | 22 | gi\|119592058\|gb\|EAW71652 1\| hCG2006056, isoform CRA_d gi\|119618258\|gb\|EAW97852. 1\| acetyl-Coenzyme A carboxylase beta, isoform gi\|14589876\|ref\|NP_115835.1 embryonal Fyn-associated substrate isoform 2; Efs2 -- gi\|29336893\|sp\|Q96DN6\|MB D6_HUMAN Methyl-CpG-binding domain protein 6 gi\|5146429\|ref\|XP_380018.2 similar to Ankyrin repeat and IBR domain-containing protein 1; ANK1B1 protein gi\|88943889\|sp\|Q70EK8\|UBP 53_HUMAN Inactive ubiquitin carboxyl-terminal hydrolase 53 | Score = 29.1 bits (61), Expect = 1.2<br>Id = 11/17 (64%), Positives = 12/17 (70%),<br>Gaps = 4/17 (23%)<br>Query 5<br>PSSARPACVCPSS--SD 19<br>PS  RP+CVCP  S   SD<br>Sbjct 66<br>PS--RPSCVCPCSARSD 80<br>Score = 27.4 bits (57), Expect = 3.8<br>Id = 10/19 (52%), Positives = 11/19 (57%),<br>Gaps = 8/19 (42%)<br>Query 4<br>PPSSARPACVCPSSSDPPF 22<br>PPSSARPA           PP+<br>Sbjct 254<br>PPSSARPA-------PPY 264<br>Score = 26.5 bits (55), Expect = 6.9<br>Id = 12/21 (57%), Positives = 13/21 (61%),<br>Gaps = 6/21 (28%)<br>Query 1<br>VVSPPSSARPACVCPSSSDPP 21<br>VV PP  ARP   CP+S   PP<br>Sbjct 9<br>VVPPP--ARP---CPTSC-PP 23 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|
| 124 | 6_F4 | gi\|17426141\|gb\|AF325326.1\|F325326S0\| Homo sapiens macrophin 1 isoforms (MACF1) gene, exon 3<br>Length = 2486<br>Score = 803 bits (405)<br>Expect = 0.0<br>Id = 405/405 (100%)<br>Gaps = 0/405 (0%)<br>Strand = Plus/Plus | NSSKE | 4 | gi\|119626370\|gb\|EAX05965.1 protein tyrosine phosphatase, non-receptor type 13<br>gi\|119617338\|gb\|EAW96932.1\| ubiquitin specific peptidase 52, isoform CRA_e<br>gi\|119585128\|gb\|EAW64724.1\| kinesin family member 15<br>gi\|62087388\|dbj\|BAD92141.1 protein tyrosine phosphatase, non-receptor type 13 | Score = 18.0 bits (35), Expect = 1284<br>Id = 5/5 (100%), Positives = 5/5 (100%),<br>Gaps = 0/5 (0%)<br>Query 1 NSSKE 5<br>     NSSKE<br>Sbjct 916 NSSKE 920 |
| 125 | 1_G8 | gi\|51317362\|ref\|NM_002473.3\| Homo sapiens myosin, heavy chain 9 non-muscle (MYH9), mRNA<br>Length = 7474<br>Score = 626 bits (316)<br>Expect = 4e-177<br>Id = 335/342 (97%)<br>Gaps = 1/342 (0%)<br>Strand = Plus/Plus | AMRASRRR<br>FSSNARAPG<br>GXHRPAGG<br>GAGGGAGQ<br>HGADQRPA<br>EEGQPADR<br>PDQHRPE<br>PGAQPRPE<br>ERECSAAA<br>GTPEQGA | 79 | gi\|4502919\|ref\|NP_001288.1\| cyclic nucleotide gated channel beta 1<br>gi\|45476939\|sp\|Q8IX07\|FOG1_HUMAN Zinc finger protein ZFPM1 (Friend of GATA protein 1)<br>gi\|4210366\|emb\|CAA10317.1\| APC2 protein<br>gi\|5031587\|ref\|NP_005874.1\| adenomatosis polyposis coli 2<br>gi\|21360802\|gb\|AAM49715.1\| hepatoma-derived growth factor-HGDF5<br>gi\|21263499\|sp\|Q9BZ76\|CNTP3_HUMAN Contactin-associated protein-like 3 precursor (Cell recognition molecule Caspr3)<br>gi\|6002605\|gb\|AAF00055.1\| transcription factor TBLyM<br>gi\|7341310\|gb\|AAF61243.1\| T-cell-specific T-box transcription factor T-bet<br>gi\|42490771\|gb\|AAH66122.1\| BCR protein<br>gi\|82546843\|ref\|NP_004318. breakpoint cluster region isoform 1 | Score = 35.4 bits (76), Expect = 0.056<br>Id = 20/43 (46%), Positives = 23/43 (53%),<br>Gaps = 16/43 (37%)<br>Query 39 RPA--EEGQPADRPDQH--R------PEPGAQ----PRPEERE 67<br>  RP    EEG PA+ P++H R    PEPG Q    PEERE<br>Sbjct 1201 RPEGEEG-PAE-PEEHSVRICMSPGPGEQILSVKMPEERE 1241<br>Score = 24.0 bits (49), Expect = 157<br>Id = 17/49 (35%), Positives = 18/48 (37%),<br>Gaps = 27/48 (56%)<br>Query 42 EEGQPADRPDQH---------------R--PE-PGAQP---------RPE 64<br>  EEG  A  PDQH        R  PE PG+ P    RPE<br>Sbjct 1158 EEGSAA--PDQHTHPREAATDPPAPRTPPEPPGSPPSSPPPASLCRPE 1203<br>Score = 32.5 bits (69), Expect = 0.44<br>Id = 21/41 (51%), Positives = 22/41 (53%),<br>Gaps = 14/41 (34%)<br>Query 44 GQPADRPDQHR--PEPGAQPRPEERECSAAAG---TPEQGA 79<br>  GQPA+ PD  R  P PGA  R EE    AG    TPE GA<br>Sbjct 625 GQPAE-PDAPRSSPGPGA--R-EE----GAGGAATPEDGA 656<br>Score = 32.0 bits (68), Expect = 0.59<br>Id = 26/57 (45%), Positives = 28/57 (49%),<br>Gaps 19/57 (33%)<br>Query 24 GGGAGGGAGQHGADQRFAEEGQPADRPDQHRPEP-GAQPR----PE-E--RECSAAA 72 |

TABLE 6a-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide (only the top 3 sequences are shown) |
|---|---|---|---|---|---|---|

GGGAGG AG H A R   EEG           P P G++PR       E E REC   AA
Sbjct 1305
GGGAG-AGLHFAGHRRRREEG--------PAPTGSRPRGAADQELELLRECLGAA 1350
Score = 19.7 bits (39), Expect = 2966
Id = 5/6 (83%), Positives = 6/6 (100%),
Gaps = 0/6 (0%)
Query 37
DQRPAE 42
D+RPAE
Sbjct 1658
DERPAE 1663
Score = 18.9 bits (37), Expect = 5340
Id = 10/16 (62%), Positives = 10/16 (62%),
Gaps = 4/16 (25%)
Query 13
ARAPGXHRPAGGGAG 28
AR  GG  P GGGAG
Sbjct 390
ARD-GG---PEGGGAG 401
Score = 17.6 bits (34), Expect = 12900
Id = 7/9 (77%), Positives = 7/9 (77%),
Gaps = 0/9 (0%)
Query 24
GGQAGGGAG 32
GG  GGGAG
Sbjct 393
GGPEGGGAG 401

TABLE 6b

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 7 | 2_D4 | gi\|37790795\| gb\|AY42221 1.1\| *Homo sapiens* cholesteryl ester transfer protein, plasma (CETP) gene, complete cds Lengh = 25612 Score = 99.6 bits (50) Expect = 2e-18 Id = 50/50 (100%) Gaps = 0/50 (0%) Strand = Plus/Minus | WDCATACQ PGSQRDSVS KKKKKKGG XGKN | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM 2_HUMAN Initiation factor 2 associated 67 kDa glycoprotein (p67) (p67eIF2) gi\|29337146\|sp\|Q9NQB0\|TF7 L2_HUMAN Transcription factor 7-like 2 gi\|71153825\|sp\|Q9BQG0\|MB B1A_HUMAN Myb-binding protein 1A E2F-associated phosphoprotein (EAPP) gi\|12644154\|sp\|P20042\|IF2B_HUMAN Eukaryotic translation initiation factor 2 subunit 2 Metastasis adhesion protein (Metadherin) Programmed cell death protein 11 (T cell-specific transcription factor 1-alpha) (TCF1-alpha) gi\|2822161\|gb\|AAB97937.1\| rab3 effector-like | Score = 37.5 bits (81), Expect = 0.003 Id = 14/25 (56%), Positives = 16/25 (64%), Gaps = 9/25 (36%) Query 8 QPGS           QRDSVSKKKKKK 23 +PGS           +RDSVSKKKKKK Sbjct 127 EPGSCHSTPAWATERDSVSKKKKKK 151 Score = 16.8 bits (32), Expect = 5786 Id = 6/11 (54%), Positives = 7/11 (63%), Gaps = 0/11 (0%) Query 13 RDSVSKKKKKK 23 R+ VS K   KK Sbjct 85 RNPVSTKSTKK 95 |
| 8 | 2_D8 | gi\|37790795\| gb\|AY42221 1.1\| *Homo sapiens* cholesteryl ester transfer protein, plasma (CETP) gene, complete cds Length = 25612 Score = 99.6 bits (50) Expect = 2e-18 Id = 50/50 (100%) Gaps = 0/50 (0%) Strand = Plus/Minus | WDCATA CQPGSQ RDSVSK KKKKKR G | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM 2_HUMAN Initiation factor 2 associated 67 kDa glycoprotein (p67) (p67eIF2) gi\|29337146\|sp\|Q9NQB0\|TF7 L2_HUMAN Transcription factor 7-like 2 gi\|71153825\|sp\|Q9BQG0\|MB B1A_HUMAN Myb-binding protein 1A E2F-associated phosphoprotein (EAPP) gi\|12644154\|sp\|P20042\|IF2B_HUMAN Eukaryotic translation initiation factor 2 subunit 2 Metastasis adhesion protein (Metadherin) Programmed cell death protein 11 (T cell-specific transcription factor 1-alpha) (TCF1-alpha) gi\|2822161\|gb\|AAB97937.1\| rab3 effector-like | Score = 37.5 bits (81), Expect = 0.003 Id = 14/25 (56%), Positives = 16/25 (64%), Gaps = 9/25 (36%) Query 8 QPGS           QRDSVSKKKKKK 23 +PGS           +RDSVSKKKKKK Sbjct 127 EPGSCHSTPAWATERDSVSKKKKKK 151 Score = 16.8 bits (32), Expect = 5786 Id = 6/11 (54%), Positives = 7/11 (63%), Gaps = 0/11 (0%) Query 13 RDSVSKKKKKK 23 R+ VS K   KK Sbjct 85 RNPVSTKSTKK 95 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 9 | 2_G 11 | gi\|37790795\| gb\|AY42221 1.1\| *Homo sapiens* cholesteryl ester transfer protein, plasma (CETP) gene, complete cds Lengh = 25612 Score = 99.6 bits (50) Expect = 2e-18 Id = 50/50 (100%) Gaps = 0/50 (0%) Strand = Plus/Minus | WDCATA CQPGSQ RDSVSK KKKKKR G | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM 2_HUMAN Initiation factor 2 associated 67 kDa glycoprotein (p67) (p67eIF2) gi\|29337146\|sp\|Q9NQB0\|TF7 L2_HUMAN Transcription factor 7-like 2 gi\|71153825\|sp\|Q9BQG0\|MB B1A_HUMAN Myb-binding protein 1A E2F-associated phosphoprotein (EAPP) gi\|12644154\|sp\|P20042\|IF2B_HUMAN Eukaryotic translation initiation factor 2 subunit 2 Metastasis adhesion protein (Metadherin) Programmed cell death protein 11 (T cell-specific transcription factor 1-alpha) (TCF1-alpha) gi\|2822161\|gb\|AAB97937.1\| rab3 effector-like | Score = 37.5 bits (81), Expect = 0.003 Id = 14/25 (56%), Positives = 16/25 (64%), Gaps = 9/25 (36%) Query 8 QPGS          QRDSVSKKKKKK 23 +PGS          +RDSVSKKKKKK Sbjct 127 EPGSCHSTPAWATERDSVSKKKKKK 151 Score = 16.8 bits (32), Expect = 5786 Id = 6/11 (54%), Positives = 7/11 (63%), Gaps = 0/11 (0%) Query 13 RDSVSKKKKK 23 R+ VS K   KK Sbjct 85 RNPVSTKSTKK 95 |
| 16 | 6_G 12 | gi\|12584762\| emb\|AL3910 01.12\| Human DNA sequence from clone RP11-477H21 on chromosome 1 Contains part of the PBX1 gene for pre-B-cell leukemia transcription factor 1 Length = 196730 Score = 65.9 bits (33) Expect = 2e-08 Id = 59/71 (83%) Gaps = 0/71 (0%) Strand = Plus/Plus /gene = "PBX1" /product = "pre-B-cell leukemia transcription factor 1" | NSSGV | 5 | gi\|119630243\|gb\|EAX09838.1\| interferon (alpha, beta and omega) receptor 1, isoform gi\|119609949\|gb\|EAW89543. 1\| lectin, galactoside-binding, soluble, 3 binding protein, isoform CRA_a gi\|119593835\|gb\|EAW73429. 1\| cadherin, EGF LAG seven-pass G-type receptor 1 (flamingo homolog, Drosophila), isoformCRA_b gi\|56203586\|emb\|CA119162.1\| tripartite motif-containing 67 | Score = 17.2 bits (33), Expect = 2312 Id = 5/5 (100%), Positives = 5/5 (100%), Gaps = 0/5 (0%) Query 1 NSSGV 5 NSSGV Sbjct 154 NSSGV 158 |

TABLE 6b-continued

| Rank | Clone | Description of the genes that are in Mimotope clones | Peptide sequences of Mimo- topes, in-frame with T7 10 B gene | Size of pep- tide | Description of the sequences that Mimotopes mimic | Region of similarity of peptide |
|---|---|---|---|---|---|---|
| 17 | 7_C1 | gi\|18072476\| emb\|AL3566 08.23\| Human DNA sequence from clone RP11-724N1 on chromosome 10 Contains the 5' end of the CNNM2 gene for cyclin M2 and a CpG is- land, com- plete se- quence Length = 161053 Score = 971 bits (490) Expect = 0.0 Id = 490/490 (100%), Gaps = 0/490 (0%) Strand = Plus/Minus | GRGGGGGR GGGGRIRR RKPQEPEK QRAEVQIQ G | 33 | gi\|56566042\|gb\|AAV98357.1\| nucleolar protein family A member 1 gi\|119615069\|gb\|EAW94663. 1\| CEBP-induced protein Heterogeneous nuclear ribonucleoprotein U-like protein 1 (Adenovirus early region 1B-associated protein 5) (E1B-55 kDa-associated protein 5) (E1B-AP5) | Score = 37.1 bits (80), Expect = 0.004 Id = 16/19 (84%), Positives = 16/19 (84%), Gaps = 2/19 (10%) Query 1 GRGG-GGGRGGGGGI-GGR 17 GRGG GGGRGGGGG GCR Sbjct 172 GRGGRGGGRGGGGGFRGGR 190 Score = 32.5 bits (69), Expect = 0.11 Id = 13/19 (68%), Positives = 14/19 (73%), Gaps = 3/19 (15%) Query 1 GRGGGG---GRGGGGGIRR 16 GRGGG     GRGG GG+RR Sbjct 8 GRGGGAWGPGRGGAGGLRR 26 |
| 18 | 7_C4 | gi\|77744392\| gb\|DQ23098 8.1\| SW1/SNF related, matrix assoc- iated, actin dependent regulator of chromatin, subfamily b, member 1 gene Length = 50890 Score = 125 bits (63) Expect = 7e- 27 Id = 63/63 (100%) Gaps = 0/63 (0%) Strand = Plus/Plus | ADHKVRSL RPA | 11 | gi\|55961387\|emb\|CA117418.1\| cAMP responsive element binding protein-like 1 (24.4) gi\|1705471\|sp\|P55107\|BMP3 B_HUMAN Bone morphogenetic protein 3b precursor (BMP-3b) Growth/differentiation factor 10 (GDF-10) (23.5) (Bone inducing protein) gi\|12643326\|sp\|Q9ULV3\|CIZ 1_HUMAN Cip1-interacting zinc finger protein (Nuclear protein NP94) gi\|62087674\|dbj\|BAD92284.1 ELK1, member of ETS oncogene family variant Ubiquitin specific protease 42 Chondroitin-4-O- sulfotransferase-3 | Score = 24.4 bits (50), Expect = 22 Id = 7/7 (100%), Pos = 7/7 (100%), Gaps = 0/7 (0%) Query 5 VRSLRPA 11 VRSLRPA Sbjct 151 VRSLRPA 157 Score = 23.5 bits (48), Expect = 54 Id = 9/15 (60%), Pos = 11/15 (73%), Gaps = 2/15 (13%) Query 3 PNSSADHKVRSLRPA 17 PN+SAD +VR  R A Sbjct 280 PNNSADPRVR--RAA 292 Score = 21.0 bits (42), Expect = 233 Id = 7/11 (63%), Positives = 9/11 (81%), Gaps = 2/11 (18%) Query 2 DHKV--RSLRP 10 DHK+  +SLRP Sbjct 27 DHKIAKQSLRP 37 |
| 23 | 2_D3 | gi\|37552371\| ref\|NT_0112 55.14\| Hs19_11412 *Homo sapiens* chromosome 19 genomic con- tig, refer- ence assembly Length = 7286004 Features in this part of | NSSLF | 5 | gi\|119623720\|gb\|EAX03315.1\| DEAH (Asp-Glu-Ala-His) box polypeptide 16, isoform CRA_d gi\|119618562\|gb\|EAW98156. 1\| citron (rho-interacting, serine/threonine kinase 21), isoform CRA_b gi\|5833114\|gb\|AAD53401.1\|A F107840_1 nuclear pore- associated protein gi\|119581856\|gb\|EAW61452. 1\| T-cell leukemia homeobox | Score = 18.5 bits (36), Expect = 957 Id = 5/5 (100%), Positives = 5/5 (100%), Gaps = 0/5 (0%) Query 1 NSSLF 5 NSSLF Sbjct 265 NSSLF 269 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | subject sequence: adenomatosis polyposis coli 2 Score = 793 bits (400) Expect = 0.0 Id = 411/416 (98%) Gaps = 0/416 (0%) Strand = Plus/Minus | | 3 | | |
| 24 | 3_D4 | gi\|555853\|gb\|U13369.1\|HSU13369 Human ribosomal DNA complete repeating unit Length = 42999 Score = 850 bits (429) Expect = 0.0 Id = 431/432 (99%) Gaps = 0/432 (0%) Strand = Plus/Plus | PRQSFTLVA | 9 | gi\|21749258\|dbj\|BAC03563.1\| Unnamed protein product gi\|14043145\|gb\|AAH07560.1\| LASP1 protein LIM and SH3 domain protein 1 (LASP-1) (MLN 50) gi\|46937163\|emb\|CAE45323.1\|LIM-nebulette alpha-1,3-glucosyltransferase ALG8 isoform b Carbohydrate sulfotransferase 6 Sortilin-related receptor precursor Novel protein similar to mouse meiosis defective 1 gene Erythroid differentiation-related factor 1 (EDRF1) | Score = 25.2 bits (52), Expect = 11 Id = 7/7 (100%), Pos = 7/7 (100%), Gaps = 0/7 (0%) Query 2 RQSFTLV 8 RQSFTLV Sbjct 25 RQSFTLV 31 Score = 25.2 bits (52), Expect = 17 Id = 7/9 (77%), Pos = 9/9 (100%), Gaps = 0/9 (0%) Query 7 PRQSFTLVA 15 P+QSFT+VA Sbjct 58 PKQSFTMVA 66 |
| 30 | 9_G8 | gi\|17907166\|emb\|AL133351.34\| Human DNA sequence from clone RP1-90J20 on chromosome 6p24.1-25.3 Contains the 5' end of a putative novel gene, the SERPINB9 gene for serine (or cysteine) proteinase inhibitor clade B (ovalbumin) member 9, a novel gene, the SERPINB6 gene for serine (or cysteine) proteinase inhibitor clade B (ovalbumin) member 6, three putative novel genes, the gene for | RVGRKVQ | 7 | gi\|8134304\|sp\|Q92667\|AKAP1_HUMAN A kinase anchor protein 1 (Protein kinase A anchoring protein 1) (22.3) (Spermatid A-kinase anchor protein 84)(S-AKAP84) gi\|22261\|sp\|P13765\|2DOB_HUMAN HLA class II histocompatibility antigen, DO beta chain precursor gi\|57209707\|emb\|CA141975.1\| Protein phosphatase 2 regulatory subunit B, beta Dual specificity A-kinase anchoring protein 1 Solute carrier family 2 | Score = 22.3 bits (45), Expect = 131 Id = 7/8 (87%), Positives = 7/8 (87%), Gaps = 0/8 (0%) Query 6 SRVGRKVQ 13 SRV RKVQ Sbjct 172 SRVPRKVQ 179 Score = 21.4 bits (43), Expect = 235 Id = 6/6 (100%), Positives = 6/6 (100%), Gaps = 0/6 (0%) Query 8 VGRKVQ 13 VGRKVQ Sbjct 117 VGRKVQ 122 Score = 18.5 bits (36), Expect = 954 Id = 5/5 (100%), Positives = 5/5 (100%), Gaps = 0/5 (0%) Query 3 GRKVQ 7 GRKVQ Sbjct 335 GRKVQ 339 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | NAD(P)H dehydrogenase quinone 2 (NQO2) and eight predicted CpG islands, complete sequence Length = 173670 Score = 559 bits (282) Expect = 3e-156 Id = 314/320 (98%) Gaps = 4/320 (1%) Strand = Plus/Plus | | | | |
| 33 | 2_G4 | gi\|14336700\| gb\|AE006464.1\| *Homo sapiens* 16p13.3 sequence section 3 of 8 Length = 256073 Features in this part of subject sequence: RAR (RAS like GTPase) like Score = 103 bits (52) Expect = 8e-20 Id = 73/81 (90%) Gaps = 0/81 (0%) Strand = Plus/Plus | LQPGRQSET PSQKKKKK NLGGMGTG AHPFDPSTL GS | 36 | gi\|34528883\|dbj\|BAC85594.1\| Phsophorylase kinase alpha/beta gi\|33415049\|gb\|AAQ18032.1\| Transformation-related protein 10 gi\|34528883\|dbj\|BAC85594.1\| unnamed protein product Phsophorylase kinase alpha/beta Putative nucleolar trafficking phosphoprotein SLC2A11 protein variant CLL associated antigen KW-2 Ras-related protein H-Ras BCL2-associated athanogene isoform 1L (BAG-1) Lung cancer metastasis-related protein (LCMRP1) | Score = 55.4 bits (123), Expect = 2e-07 Id = 17/17 (100%), Positives = 17/17 (100%), Gaps = 0/17 (0%) Query 1 LQPGRQSETPSQKKKKK 17 LQPGRQSETPSQKKKKK Sbjct 19 LQPGRQSETPSQKKKKK 35 Score = 44.3 bits (97), Expect = 4e-04 Id = 15/17 (88%), Positives = 15/17 (88%), Gaps = 0/17 (0%) Query 1 LQPGRQSETPSQKKKKK 17 LQPG QSETPSQRK KK Sbjct 37 LQPGLQSETPSQKKTKK 53 |
| 36 | 5_G3 | gi\|119380763\| gb\|EF177447.1\| *Homo sapiens* isolate TA23 mitochondrion, complete genome Length = 16569 Score = 105 bits (53) Expect = 1e-20 Id = 53/53 (100%) Gaps = 0/53 (0%) Strand = Plus/Minus | HRGSPSNVG AFRIGRESV KESLFY | 24 | gi\|4837879\|gb\|AAD30731.1\| immunoglobulin heavy chain variable region gi\|30060232\|gb\|AAP13073.1\| E3 ligase for inhibin receptor gi\|85682779\|sp\|Q9ULT8\|HECD1_HUMAN E3 ubiquitin-protein ligase HECTD1 (HECT domain-containing protein 1) (E3 ligase for inhibin receptor) (EULIR) | Score = 25.7 bits (53), Expect = 12 Id = 8/13 (61%), Positives = 10/13 (76%), Gaps = 0/13 (0%) Query 11 FRIGRESVKESLF 23 P I R++VK SLF Sbjct 64 FTISRDNVKNSLF 76 Score = 25.2 bits (52), Expect = 17 Id = 11/21 (52%), Positives = 12/21 (57%), Gaps = 7/21 (33%) Query 9 GAFRIGR----ESVK----ESL 22 G FR+GR E VK ESL Sbjct 2123 GEFRVGRLKHERVKVPRGESL 2143 Score = 15.1 bits (28), Expect = 19195 Id = 4/4 (100%), Positives = 4/4 (100%), |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | | Gaps = 0/4 (0%)<br>Query 2<br>RGSP 5<br>RGSP<br>Sbjct 288<br>RGSP 291<br>Score = 25.2 bits (52),<br>Expect = 17<br>Id = 11/21 (52%),<br>Positives = 12/21 (57%),<br>Gaps = 7/21 (33%)<br>Query 9<br>GAFRIGR---ESVK----ESL 22<br>G FR+GR  E VK   ESL<br>Sbjct 2123<br>GEFRVGRLKHERVKVPRGESL 2143 |
| 43 | 10_D6 | gi\|119380763\|gb\|EF177447.1\| *Homo sapiens* isolate TA23 mitochondrion, complete genome<br>Length = 16569<br>Score = 446 bits (225),<br>Expect = 4e-123<br>Id = 261/261 (100%),<br>Gaps = 0/261 (0%)<br>Strand = Plus/Minus | NSSVGC | 6 | gi\|55960173\|emb\|CA114537.1\| HIV type I enhancer binding protein 3<br>gi\|119617590\|gb\|EAW97184.1\| Mdm4, transformed 3T3 cell double minute 1, p53 binding protein (mouse), isoform CRA_b<br>gi\|119604594\|gb\|EAW84188.1\| IVRAB3D, member RAS oncogene family, isoform CRA_a | Score = 17.2 bits (33),<br>Expect = 2774<br>Id = 5/5 (100%),<br>Positives = 5/5 (100%),<br>Gaps = 0/5 (0%)<br>Query 1<br>NSSVG 5<br>NSSVG<br>Sbjct 30<br>NSSVG 34 |
| 56 | 1_G4 | gi\|37790795\|gb\|AY422211.1\| *Homo sapiens* cholesteryl ester transfer protein, plasma (CETP) gene, complete cds<br>Length = 25612<br>Score = 99.6 bits (50)<br>Expect = 1e-18<br>Id = 50/50 (100%)<br>Gaps = 0/50 (0%)<br>Strand = Plus/Minus | WDCATACQ PGSQRDSVS KKKKKKGG XEKXXGXG XFFXXXKX XXXFXRXF XPXFXXK | 56 | gi\|34535600\|dbj\|BAC87373.1\| Unnamed protein product<br>gi\|1350799\|sp\|P49646\|YYY1 HUMAN Very very hypothetical protein RMSA-1<br>gi\|537530\|gb\|AAB68050.1\| chromnosomal protein Lymphoid enhancer binding factor 1 (LEF-1) (T cell-specific transcription factor 1-alpha) (TCF1-alpha)<br>Methionine aminopeptidase 2 (MetAP 2) (Initiation factor 2 associated 67 kDa glycoprotein) (p67) (p67eIF2) | Score = 37.5 bits (81),<br>Expect = 0.019<br>Id = 14/25 (56%),<br>Positives = 16/25 (64%),<br>Gaps = 9/25 (36%)<br>Query 8<br>QPGS---------QRDSVSKKKKKK 23<br>+PGS---------+RDSVSKKKKKK<br>Sbjct 127<br>EPGSCHSTPAWATERDSVSKKKKKK 151<br>Score = 27.4 bits (57),<br>Expect = 22<br>Id = 8/10 (80%),<br>Positives = 10/10 (100%),<br>Gaps = 0/10 (0%)<br>Query 14<br>DSVSKKKKKK 23<br>++VSKKKKKK<br>Sbjct 265<br>ETVSKKKKKK 274 |
| 72 | 10_H11 | gi\|14329907\|emb\|AL162431.17\| Human DNA sequence fr clone RP11-46A10 on chromosome 1q25.2-31.1 Contains 3' end of XPR1 gene for xen- | ARQVF | 5 | gi\|57162452\|emb\|CA140479.1\| BRCA2 (Breast cancer 2, early onset) (19.3)<br>gi\|4502451\|ref\|NP_000050.1\| Breast cancer 2, early onset<br>gi\|13540359\|gb\|AAK9432.1\| Mutant early onset breast cancer susceptibility protein<br>gi\|21361458\|ref\|NP_055601.2 | Score = 19.3 bits (38),<br>Expect = 378<br>Id = 5/5 (100%),<br>Positives = 5/5 (100%),<br>Gaps = 0/5 (0%)<br>Query 1<br>ARQVF 5<br>ARQVF<br>Sbjct 329<br>ARQVF 333 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | otropic and polytropic retrovirus receptor Length = 139006 Score = 170 bits(86) Expect = 7e-40 Id = 117/122 (95%) Gaps = 0/122 (0%) Strand = Plus/Minus | | | Rho guanine nucleotide exchange factor (GEF) 17 gi\|15987489\|gb\|AAL11991.1\| Tumor endothelial marker 4 gi\|51477779\|ref\|XP_067076.3 PREDICTED: similar to testis specific protein, Y-linked 2 Crn (crooked neck-like 1) Inhibitor of Bruton's tyrosine kinase (16.8) | |
| 74 | 2_C1 2 | gi\|37790795\| gb\|AY42221 1.1\|*Homo sapiens* cholesteryl ester transfer protein, plasma (CETP) gene, complete cds Length = 25612 Score = 99.6 bits (50) Expect = 2e-18 Id = 50/50 (100%) Gaps = 0/50 (0%) Strand = Plus/Minus | WDCATA CQPGSQ RDSVSK KKKKKR G | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM 2_HUMAN Initiation factor 2 associated 67 kDa glycoprotein (p67) (p67eIF2) gi\|29337146\|sp\|Q9NQB0\|TF7 L2_HUMAN Transcription factor 7-like 2 gi\|71153825\|sp\|Q9BQG0\|MB B1A_HUMAN Myb-binding protein 1A E2F-associated phosphoprotein (EAPP) gi\|12644154\|sp\|P20042\|IF2B_HUMAN Eukaryotic translation initiation factor 2 subunit 2 Metastasis adhesion protein (Metadherin) Programmed cell death protein 11 (T cell-specific transcription factor 1-alpha) (TCF1-alpha) Methionine aminopeptidase 2 (MetAP 2) (Peptidase M 2) (Initiation factor 2 associated 67 kDa glycoprotein) (p67) (p67eIF2) gi\|2822161\|gb\|AAB97937.1\| rab3 effector-like | Score = 37.5 bits (81), Expect = 0.003 Id = 14/25 (56%), Positives = 16/25 (64%), Gaps = 9/25 (36%) Query 8 QPGS---------QRDSVSKKKKKK 23 +PGS        +RDSVSKKKKKK Sbjct 127 EPGSCHSTPAWATERDSVSKKKKKK 151 Score = 16.8 bits (32), Expect = 5786 Id = 6/11 (54%), Positives = 7/11 (63%), Gaps = 0/11 (0%) Query 13 RDSVSKKKKKK 23 R+ VS K  KK Sbjct 85 RNPVSTKSTKK 95 |
| 91 | 2_F3 2 | gi\|37790795\| gb\|AY42221 1.1\|*Homo sapiens* cholesteryl ester transfer protein, plasma (CETP) gene, complete cds Length = 25612 | WDCATA CQPGSQ RDSVSK KKKKKR G | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM 2_HUMAN Initiation factor 2 associated 67 kDa glycoprotein | Score = 37.5 bits (81), Expect = 0.003 Id = 14/25 (56%), Positives = 16/25 (64%), Gaps = 9/25 (36%) Query 8 QPGS---------QRDSVSKKKKKK 23 +PGS        +RDSVSKKKKKK Sbjct 127 EPGSCHSTPAWATERDSVSKKKKKK 151 Score = 16.8 bits (32), Expect = 5786 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | Score = 99.6 bits (50) Expect = 2e-18 Id = 50/50 (100%) Gaps = 0/50 (0%) Strand = Plus/Minus | | | (p67) (p67eIF2) gi\|29337146\|sp\|Q9NQB0\|TF7L2_HUMAN Transcription factor 7-like 2 gi\|71153825\|sp\|Q9BQG0\|MBB1A_HUMAN Myb-binding protein 1A E2F-associated phosphoprotein (EAPP) gi\|12644154\|sp\|P20042\|IF2B_HUMAN Eukaryotic translation initiation factor 2 subunit 2 Metastasis adhesion protein (Metadherin) Programmed cell death protein 11 (T cell-specific transcription factor 1-alpha) (TCF1-alpha) Methionine aminopeptidase 2 (MetAP 2) (Peptidase M 2) gi\|2822161\|gb\|AAB97937.1\| rab3 effector-like | Id = 6/11 (54%), Positives = 7/11 (63%), Gaps = 0/11 (0%) Query 13 RDSVSKKKKKK 23 R+ VS K  KK Sbjct 85 RNPVSTKSTKK 95 |
| 92 | 2_H2 | gi\|37790795\|gb\|AY422211.1\|Homo sapiens cholesteryl ester transfer protein, plasma (CETP) gene, complete cds Length = 25612 Score = 99.6 bits (50) Expect = 2e-18 Id = 50/50 (100%) Gaps = 0/50 (0%) Strand = Plus/Minus | WDCATACQPGSQRDSVSKKKKKRG | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM2_HUMAN Initiation factor 2 associated 67 kDa glycoprotein (p67) (p67eIF2) gi\|29337146\|sp\|Q9NQB0\|TF7L2_HUMAN Transcription factor 7-like 2 gi\|71153825\|sp\|Q9BQG0\|MBB1A_HUMAN Myb-binding protein 1A E2F-associated phosphoprotein (EAPP) gi\|12644154\|sp\|P20042\|IF2B_HUMAN Eukaryotic translation initiation factor 2 subunit 2 Metastasis adhesion protein (Metadherin) Programmed cell death protein 11 (T cell-specific transcription factor 1-alpha) (TCF1-alpha) Methionine aminopeptidase 2 (MetAP 2) (Peptidase M 2) gi\|2822161\|gb\|AAB97937.1\| rab3 effector-like | Score = 37.5 bits (81), Expect = 0.003 Id = 14/25 (56%), Positives = 16/25 (64%), Gaps = 9/25 (36%) Query 8 QPGS---------QRDSVSKKKKKK 23 +PGS          +RDSVSKKKKKK Sbjct 127 EPGSCHSTPAWATERDSVSKKKKKK 151 Score = 16.8 bits (32), Expect = 5786 Id = 6/11 (54%), Positives = 7/11 (63%), Gaps = 0/11 (0%) Query 13 RDSVSKKKKKK 23 R+ VS K  KK Sbjct 85 RNPVSTKSTKK 95 |
| 104 | 5_D4 | gi\|16306514\|gb\|AC009967.8\|Homo sapiens BAC clone RP11-401O19 | YKQRRRVKREHPNRKQLKDILLASHGGPSP | 30 | gi\|16741704\|gb\|AAH16648.1\| Fos-related antigen 1 (FOS-like antigen 1) (28.2) gi\|29792148\|gb\|AAH50283.1\| WASF3 protein (27.8) gi\|59798973\|sp\|Q9H0K1\|SN1 | Score = 28.2 bits (59), Expect = 2.0 Id = 13/31 (41%), Pos = 16/31 (51%), Gaps = 11/31 (35%) Query3 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | from 2 Length = 176206 Score = 694 bits (350) Expect = 0.0 Id = 350/350 (100%) Gaps = 0/350 (0%) Strand = Plus/Minus | | | L2_HUMAN Serine/threonine protein kinase SNF1-like kinase 2 gi\|7380440\|sp\|P46100\|ATRX _HUMAN Transcriptional regulator ATRX (X-linked helicase II) (X-linked nuclear protein) Fonconi anemia group A Protein (25.7) E2F dimerization partner 2 Dehydrogenase/reductase SDR family member 7 Retinal short chain dehydrogenase/reductase 4 | QRRRVKREHPN---------RKQLKDILLA 23 +RRRV+RE N       RK+L D L A Sbjct106 ERRRVRRER-NKLAAAKCRNRRKELTDFLQA 135 Score = 27.8 bits (58), Expect = 2.0 Id = 10/19 (52%), Pos = 13/19 (68%), Gaps = 4/19 (21%) Query 2 KQRRRVKRE----HPNRKQ 16 K++RR KRE    +PNR Q Sbjct 174 KEKRRQKREKHKLNPNRNQ 192 Score = 26.9 bits (56), Expect = 4.9 Id = 9/14 (64%), Pos = 11/14 (78%), Gaps = 2/14 (14%) Query 17 LKDILLASHGGPSP 30 LKDI+LA+   PSP Sbjct 535 LKDIMLANQ--PSP 546 |
| 7 | 2_D4 | gi\|37790795\| gb\|AY42221 1.1\|Homo sapiens cholesteryl ester trans- fer protein, plasma (CETP) gene, com- plete cds Length = 25612 Score = 99.6 bits (50) Expect = 2e-18 Id = 50/50 (100%) Gaps = 0/50 (0%) Strand = Plus/Minus | WDCATACQ PGSQRDSVS KKKKKKGG XGKN | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) gi\|1703273\|sp\|P50579\|AMPM 2_HUMAN Initiation factor 2 assoc- iated 67 kDa glycoprotein (p67) (p67eIF2) gi\|29337146\|sp\|Q9NQB0\|TF7 L2_HUMAN Transcription factor 7- like 2 gi\|71153825\|sp\|Q9BQG0\|MB B1A_HUMAN Myb-binding protein 1A E2F-associated phosphoprotein (EAPP) gi\|12644154\|sp\|P20042\|IF2B_ HUMAN (Metadherin) Programmed cell death protein 11 (T cell-specific transcrip- tion factor 1-alpha) (TCF1- alpha) Methionine aminopeptidase 2 (MetAP 2) (Peptidase M 2) (Iniation factor 2 associated 67 kDa glycoprotein) (p67) (p67eIF2) gi\|2822161\|gb\|AAB97937.1\| rab3 effector-like | Score = 37.5 bits (81), Expect = 0.003 Id = 14/25 (56%), Positives = 16/25 (64%), Gaps = 9/25 (36%) Query 8 QPGS---------QRDSVSKKKKKK 23 +PGS         +RDSVSKKKKKK Sbjct 127 EPGSCHSTPAWATERDSVSKKKKKK 151 Score = 16.8 bits (32), Expect = 5786 Id = 6/11 (54%), Positives = 7/11 (63%), Gaps = 0/11 (0%) Query 13 RDSVSKKKKKK 23 R+ VS K  KK Sbjct 85 RNPVSTKSTKK 95 |
| 8 | 2_D8 | gi\|37790795\| gb\|AY42221 1.1\|Homo sapiens cholesteryl ester trans- fer protein, plasma (CETP) | WDCATA CQPGSQ RDSVSK KKKKKR G | 29 | gi\|34535600\|dbj\|BAC87373.1\| Unnamed protein product gi\|1350799\|sp\|P49646\|YYY1 Very very hypothetical protein RMSA-1 gi\|8928194\|sp\|Q9UJU2\|LEF1 Lymphoid enhancer binding factor 1 (LEF-1) | Score = 37.5 bits (81), Expect = 0.003 Id = 14/25 (56%), Positives = 16/25 (64%), Gaps = 9/25 (36%) Query 8 QPGS---------QRDSVSKKKKKK 23 +PGS         +RDSVSKKKKKK |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | gene, complete cds<br>Length = 25612<br>Score = 99.6 bits (50)<br>Expect = 2e-18<br>Id = 50/50 (100%)<br>Gaps = 0/50 (0%)<br>Strand = Plus/Minus | | | gi\|1703273\|sp\|P50579\|AMPM 2_HUMAN<br>Initiation factor 2 associated 67 kDa glycoprotein (p67) (p67eIF2)<br>gi\|29337146\|sp\|Q9NQB0\|TF7 L2_HUMAN<br>Transcription factor 7-like 2<br>gi\|71153825\|sp\|Q9BQG0\|MB B1A_HUMAN<br>Myb-binding protein 1A<br>E2F-associated phosphoprotein (EAPP)<br>gi\|12644154\|sp\|P20042\|IF2B_HUMAN<br>Eukaryotic translation initiation factor 2 subunit 2<br>Metastasis adhesion protein (Metadherin)<br>Programmed cell death protein 11<br>(T cell-specific transcription factor 1-alpha) (TCF1-alpha)<br>Methionine aminopeptidase 2 (MetAP 2) (Peptidase M 2) (Iniation factor 2 associated 67 kDa glycoprotein) (p67) (p67eIF2)<br>gi\|2822161\|gb\|AAB97937.1\|<br>rab3 effector-like | Sbjct 127<br>EPGSCHSTPAWATERDSVSKKKKKK 151<br>Score = 16.8 bits (32),<br>Expect = 5786<br>Id = 6/11 (54%),<br>Positives = 7/11 (63%),<br>Gaps = 0/11 (0%)<br>Query 13<br>RDSVSKKKKKK 23<br>R+ VS K  KK<br>Sbjct 85<br>RNPVSTKSTKK 95 |

TABLE 6b

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 3 | 10_C 3 | gi\|19807899\|gb\|AC11076 9.2\|*Homo sapiens* BAC clone RP11-141B14 from 2, complete sequence<br>Length = 134317<br>Score = 599 bits (302)<br>Expect = 2e-168<br>Id = 312/317 (98%)<br>Gaps = 0/317 (0%)<br>Strand = Plus/Plus | EMKRHIST LRWKTCLN ANMKELLE IKVTGKIRY NQGL | 37 | gi\|585487\|sp\|Q07325\|SCYB9_HUMAN<br>Small inducible cytokine B9 precursor (CXCL9)<br>Gamma interferon induced monokine (MIG) (27.8)<br>gi\|62898822\|dbj\|BAD97265.1<br>Serologically defined colon cancer antigen 33 variant Antigen NY-CO-33 (26.1)<br>gi\|31077164\|sp\|O95757\|HS74_L_HUMAN<br>Heat shock 70 kDa protein 4L<br>gi\|21315086\|gb\|AAH30792.1\|<br>Cyclin-dependent kinase 5, regulatory subunit 1 | Score = 27.8 bits (58), Expect = 5.1<br>Id = 14/28 (50%), Pos = 17/28 (60%)<br>Gaps = 11/28 (39%)<br>Query 12<br>ISTLRWK----TCLN---ANMKELLEIK 32<br>I+TL  K     TCLN   A++ KEL IK<br>Sbjct 64<br>IATL--KNGVQTCLNPDSADVKEL--IK 87<br>Score = 26.1 bits (54), Expect = 9.0<br>Id = 9/13 (69%), Pos = 12/13 (92%),<br>Gaps = 1/13 (7%)<br>Query 19<br>MKELLEIKVTGKI 31<br>M+EL+E KVTGK+<br>Sbjct 270<br>MEELVE-KVTGKV 281<br>Score = 24.0 bits (49), Expect = 39<br>Id = 6/6 (100%), Pos = 6/6 (100%),<br>Gaps = 0/6 (0%)<br>Query 8<br>TLRWKT 13<br>TLRWKT<br>Sbjct 403<br>TLRWKT 408 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | Transient receptor potential cation channel subfamily V member 3 Vanilloid receptor-like 3 (VRL-3) Dehydrodolichyl diphosphate synthase Tyrosyl-tRNA synthetase Putative mitochondrial outer membrane protein import receptor | |
| 5 | 10_G 8 | gi\|21686938\| gb\|AC11605 0.3\|*Homo sapiens* BAC clone RP11-427F2 from 2, complete sequence Length = 165225 Score = 343 bits (173) Expect = 3e-92 Id = 179/182 (98%) Gaps = 0/182 (0%) Strand = Plus/Plus | CINMDSPPK QC | 11 | gi\|57208724\|emb\| CAI42568.1 GNAS complex locus (OTTHUMP-00000031737) Guanine nucleotide binding protein, alpha stimulating activity polypeptide 1 (24.8) gi\|68565390\|sp\| Q14676\|MDC1_HUMAN Mediator of DNA damage checkpoint protein 1 (Nuclear factor with BRCT domains 1) gi\|50400452\|sp\| Q7Z569\|BRAP HUMAN BRCA1-associated protein (Impedes mitogenic signal propagation)(IMP) gi\|739072\|prf\| 12002263A E1A-assoc protein gp130 Retinoblastoma-like protein 2 gi\|55957867\|emb\| CA113220.1 E74-like factor 1 (ets domain transcription factor) RUN and SH3 domain containing protein 2 Ezrin-radixin-moesin binding phosphoprotein 50 Impedes mitogenic signal propagation (IMP) Membrane-associated nucleic acid binding protein E1A-associated protein gp130 | Score = 24.8 bits (51), Expect = 338 Id = 6/7 (85%), Pos = 7/7 (100%), Gaps = 0/7 (0%) Query 2 INMDSPP 8 +NMDSPP Sbjct 195 VNMDSPP 201 Score = 22.3 bits (45), Expect = 131 Id = 7/9 (77%), Pos = 7/9 (77%), Gaps = 2/9 (22%) Query 4 MDSPP--KQ 10 MDSPP  KQ Sbjct 1818 MDSPPHQKQ 1826 Score = 22.3 bits (45), Expect = 131 Id = 8/12 (66%), Pos = 8/12 (66%), Gaps = 2/12 (16%) Query 1 CINM--DSPPKQ 10 CIN   DSP KQ Sbjct 110 CINAAPDSPSKQ 121 |
| 13 | 6_C8 | gi\|21263318\| gb\|AC10444 1.2\|*Homo sapiens* chromosome 3 clone RP11- | GAGWEWV | 7 | gi\|18089035\|gb\| AAH20586.1\| SERS14 protein (23.1) gi\|49256613\|gb\| AAH73912.1\| | Score = 23.1 bits (47), Expect = 38 Id = 5/5 (100%), Pos = 5/5 (100%), Gaps = 0/5 (0%) Query 3 GWEWV 7 GWEWV |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | 901H12, complete sequence Length = 177320 Score = 262 bits (132) Expect = 4e-67 Id = 160/171 (93%) Gaps = 1/171 (0%) Strand = Plus/Minus | | | ACCN4 protein (22.7) Regenerating islet derived protein 3 alpha precursor Pancreatitis associated protein 1 (PAP) (21.8) ELAM-1 ligand fucosyltransferase Mitochondrial ribosomal protein bMRP64 | Sbjct 946 GWEWV 950 Score = 22.7 bits (46), Expect = 50 Id = 5/5 (100%), Positives = 5/5 (100%), Gaps = 0/5 (0%) Query 2 AGWEW 6 AGWEW Sbjct 255 AGWEW 259 |
| 14 | 6_D4 | gi\|15004913\| gb\|AC00947 5.5\|*Homo sapiens* BAC clone RP11-285F23 from 2, complete sequence Score = 835 bits(421) Expect = 0.0 Id = 424/425 (99%) Gaps = 0/425 (0%) Strand = Plus/Minus | PLCLASLLS FIVCLFHFR YLPTILLPP ILKHKCNDR MHLTCFGS AKALMYSL SNNRC | 57 | gi\|57209194\|emb\| CA141407.1 Dedicator of cytokinesis 11(32.9) DOCK11 protein Cdc42-associated guanine nucleotide exchange factor ACG\|DOCK11 (32.9) gi\|13634012\|sp\| Q15884\|CI61_HUMAN Protein C9orf61 (Protein X123) (30.3) Probable G-protein coupled receptor 113 precursor (G-protein coupled receptor PGR23) (29.5) Seven transmembrane helix receptor (26.9) Taste receptor type 2 member 7 (T2R7) (26.5) Wingless-type MMTV integration site family (26.5) | Score = 32.9 bits (70), Expect = 0.19 Id = 8/9 (88%), Positives = 9/9 (100%), Gaps = 0/9 (0%) Query 12 VCLFHFRYL 20 VCLFHFRY+ Sbjct 1319 VCLFHFRYM 1327 Score = 30.3 bits (64), Expect = 1.7 Id = 14/44 (31%), Pos = 20/44 (45%), Gaps = 21/44 (47%) 6 SPLCLA-------SLLSFIVCLFHFR-------------YLPT 28 S +C+A    S+LSF+VC F +R        +LPT 37 SRMCMAISICQMLSMLSFVVCAFRYRHMFKRGWPMGTCCLFLPT 80 |
| 20 | 10_B 11 | gi\|21747795\| gb\|AC12486 4.3\| *Homo sapiens* BAC clone RP11-570J4 from 4, complete sequence Length = 166797 Score = 224 bits (113) Expect = 4e-56 Id = 113/113 (100%) Gaps = 0/113 (0%) Strand = Plus/Plus | NSFHN | 5 | gi\|119626686\|gb\| EAX06281.1\| hCG21296, isoform CRA_c gi\|119615394\|gb\| EAW94988.1 ubiquitin specific peptidase 48, isoform CRA_b gi\|119584494\|gb\| EAW64090.1 solute carrier family 6 (neurotransmitter transporter, GABA), member 1, isoform CRA_a | Score = 20.2 bits (40), Expect = 295 Id = 5/5 (100%), Positives = 5/5 (100%), Gaps = 0/5 (0%) Query 1 NSFHN 5 NSFHN Sbjct 310 NSFRN 314 |
| 25 | 9_C4 | gi\|22657585\| gb\|AC09156 4.12\|*Homo sapiens* chromosome | GITGSRPA WPTW | 12 | gi\|119623989\|gb\| EAX03584.1\| cAMP responsive element binding protein-like 1, | Score = 29.9 bits (63), Expect = 0.68 Id = 7/7 (100%), Positives = 7/7 (100%), Gaps = 0/7 (0%) Query 6 RPAWPTW 12 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | 11, clone RP11-732A19, complete sequence Length = 211735 Score = 317 bits (160) Expect = 4e-84 Id = 193/204 (94%) Gaps = 3/204 (1%) Strand = Plus/Plus | | | isoform CRA_d gi\|14250004\|gb\| AAH08394.1\| CREBL1 protein gi\|119629047\|gb\| EAX08642.1\| hCG1816309 gi\|119625915\|gb\| EAX05510.1\| homeodomain-only protein, isoform CRA_i gi\|24286115\|gb\| AAN46678.1\| hypothetical protein HGRHSV1 gi\|21751592\|dbj\| BAC03997.1\| unnamed protein product | RPAWPTW Sbjct 312 RPAWPTW 318 |
| 28 | 7_C3 | gi\|11493153\| emb\|AL1185 23.18\| HSJ1031J8 Human DNA sequence from clone RP5-1031J8 on chromosome 20 Contains a putative novel gene, complete sequence Length = 155213 Score = 1304 bits (658) Expect = 0.0 Id = 707/724 (97%) Gaps = 2/724 (0%) Strand = Plus/Plus | VRLVRTEE RLELRTRS WNWGLVQ | 23 | gi\|55859712\|emb\| CA110983.1 Glucosidase beta 2 (29.1) gi\|55663314\|emb\| CAH72550.1\|Asp (abnormal spindle)-like, microcephaly associate gi\|55663911\|emb\| CAH70187.1\|Ino-sitol 1,4,5-tris-phosphate 3-kinase B gi\|97536946\|sp\| Q9C0D0\|PHAR1_HUMAN Phosphatase and actin regulator 1 (26.1) gi\|37779178\|gb\| AAO73817.1\| HBeAg-binding pro-tein RPEL repeat containing 1 Neprilysin (Neutral endopeptidase) (NEP) (26.1) Selectin-like pro-tein Common acute lymphoblastic leu-kemia Ag precursor Ephrin type B re-ceptor 4 precursor (24.4) Tyrosine protein kinase receptor HTK Activated met onco-gene (24) Tpr (translocated promoter region to activated MET onco-gene) Serine/threonine protein phosphatase w/EF-hands-1 Sad1/unc-84-like protein 2 Rab5-interacting protein | Score = 29.1 bits (61), Expect = 0.89 Id = 7/7 (100%), Positives = 7/7 (100%), Gaps = 0/7 (0%) Query 15 RSWNWGL 21 RSWNWGL Sbjct 215 RSWNWGL 221 Score = 28.6 bits (60), Expect = 1.2 Id = 10/18 (55%), Pos = 14/18 (77%), Gaps = 3/18 (16%) Query 1 VRLVRTEERLELRTRSWN 18 VRLVRT  +EL T++W+ Sbjct 226 VRLVRT---MELLTQNWD 240 Score = 26.9 bits (56), Expect = 3.9 Id = 10/18 (55%), Pos = 12/18 (66%), Gaps = 6/18 (33%) Query 3 LV---RTEERLELRTRSW 17 LV  R+EER   RT+SW Sbjct 191 LVQGARSEER---RTKSW 205 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 34 | 9_G1 2 | gi\|15668084\| gb\|AC09257 3.2\|*Homo sapiens* BAC clone RP11-107 from 2, complete sequence Score = 281 bits (142) Expect = 4e-73 Id = 142/142 (100%) Gaps = 0/142 (0%) Strand = Plus/Plus | VFNCWF | 6 | gi\|41351160\|gb\| AAH65552.1\| IARS proteingi\|55957316\| emb\|CAI16202.1\| isoleucine-tRNA synthetase gi\|31874258\|emb\| CAD98022.1\| hypothetical protein gi\|32307152\|ref\| NP_000907.2\| oxytocin receptor | Score = 24.4 bits (50), Expect = 13 Id = 5/6 (83%), Positives = 6/6 (100%), Gaps = 0/6 (0%) Query 1 VFNCWF 6 VF+CWF Sbjct 413 VFDCWF 418 Score = 20.6 bits (41), Expect = 188 Id = 4/5 (80%), Positives = 5/5 (100%), Gaps = 0/5 (0%) Query 1 VFNCW 5 VF+CW Sbjct 184 VFDCW 188 |
| 46 | 1_D1 1 | gi\|34194579\| gb\|BC05296 3.21\|*Homo sapiens* Snf2-related CBP activator protein, mRNA (cDNA clone IMAGE: 5785548), complete cds Length = 4805 Score = 63.9 bits(32) Expect = 8e09 ld = 32/32 (100%) Gaps = 0/32 (0%) Strand = Plus/Minus | HLKKKKKK KRGTGXLR | 16 | gi\|119608512\|gb\| EAW88106.1 hCG2040846 gi\|12802996\|gb\| AAH01198.1\| Unknown (protein for IMAGE: 3355871) gi\|119586549\|gb\| EAW66145.1\| zinc finger homeo-box 2, isoform CRA_d gi\|1703273\|sp\| P50579\|AMPM 2_HUMAN Methionine amino-peptidase 2 (MetAP 2) (Peptidase M 2) (Initiation factor 2-associated 67 kDa glycoprotein) (P67) (p67eIF2) gi\|687243\|gb\| AAC63402.1\| eIF-2-associated p67 homolog gi\|49616863\|gb\| AAT67238.1\| ubiquitin specific protease 42 | Score = 30.8 bits (65), Expect = 0.37 Id = 9/9 (100%), Positives = 9/9 (100%), Gaps = 0/9 (0%) Query 1 HLKKKKKK 9 HLKKKKKK Sbjct 959 HLKKKKKK 967 Score 29.9 bits (63), Expect = 0.67 Id = 9/9 (100%), Positives = 9/9 (100%), Gaps = 0/9 (0%) Query 3 KKKKKKKRG 11 KKKKKKKRG Sbjct 100 KKKKKKKRG 108 Score = 29.5 bits (62), Expect = 0.90 Id = 9/10 (90%), Positives = 10/10 (100%), Gaps = 0/10 (0%) Query 2 LKKKKKKKRG 11 LKKKKKKK+G Sbjct 490 LKKKKKKKKG 499 |
| 50 | 6_H8 | gi\|4753288\| gb\|AC004828. 2\|AC004828 *Homo sapiens* clone DJ0514A23, complete sequence Length = 183249 Score = 670 bits (338), Expect = 0.0 Id = 351/357 (98%), Gaps = 0/357 (0%) Strand = Plus/Minus | TNSIFGSLE SY | 11 | gi\|29421174\|dbj\| BAA25472.2 KIAA0546 protein (27.4) gi\|34098393\|sp\| O95388\|WISP 1_HUMAN WNT1 inducible signaling pathway protein 1 precursor (WISP-1) (22.7) gi\|11055594\|gb\| AAG28165.1\| Paraneoplastic associated brain-testis-cancer antigen gi\|52782735\|sp\| Q7Z628\|ARH G8_HUMAN | Score = 27.4 bits (57), Expect = 2.8 Id = 8/10 (80%), Pos = 9/10 (90%), Gaps = 0/10 (0%) Query 1 TNSIFGSLES 10 TNS+FG LES Sbjct 736 TNSVFGGLES 745 Score = 22.7 bits (46), Expect = 98 Id = 7/10 (70%), Pos = 7/10 (70%), Gaps = 0/10 (0%) Query 2 NSIFGSLESY 11 N IF LESY Sbjct 350 NDIFADLESY 359 Score = 21.8 bits (44), Expect = 176 Id = 6/7 (85%), Positives = 7/7 (100%), Gaps = 0/7 (0%) Query 4 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | Neuroepithelial cell transforming gene 1 protein (p65 Net1 proto-oncogene) (Rho guanine nucleotide exchange factor 8) SET binding factor 2 (22.3) Sentrin-specific protease 7 Membrane-associated transporter protein Melanoma antigen AIM1 Solute carrier family 2 Sentrin-specific protease 7 (SUMO-1 specific protease 2) Nuclear pore complex protein Nup98-Nup96 precursor | IFGSLES 10 +FGSLES Sbjct 240 VFGSLES 246 |
| 51 | 9_C1 2 | gi\|13277000\| emb\|AL1387 04.12\| Human DNA sequence from clone RP11-417C20 on chromosome 13 Contains the 5' end of gene KIAA1016 and a CpG island, complete sequence Length = 165120 Score = 236 bits (119), Expect = 3e-59 Identities = 121/122 (99%), Gaps = 0/122 (0%) Strand = Plus/Minus | PVLSSHKNE ARDKGKCH P | 18 | gi\|41150972\|ref\| XP_371160.1\| PREDICTED: similar to 60S ribosomal protein L21 gi\|20140092\|sp\| Q92552\|RT27 _HUMAN Mitochondrial 28S ribosomal protein S27 (S27mt) (MRP-S27) gi\|62906888\|sp\| Q86T65\|DAA M2_HUMAN Dishevelled associated activator of morphogenesis 2 Adapter-related protein complex 4 mu 1 subunit Seven transmembrane helix receptor gi\|29164873\|gb\| AAO65168.1\| sarcoma antigen NY-SAR-27 gi\|739072\|prf\| 2002263A E1A-associated protein gp130 gi\|397148\|emb\| CAA52671.1\| Rb2\|p130 protein gi\|6686330\|sp\| Q08999\|RBL2_ HUMAN Retinoblastoma-like protein 2; Rb-related p130 protein Proteasome subunit beta type 4 precursor G1 to S phase transition protein | Score = 23.1 bits (47), Expect = 52 Id = 8/17 (47%), Positives = 10/17 (58%), Gaps = 5/17 (29%) Query 7 KNEARDKG-----KCHP 18 K EA++KG     KC P Sbjct 116 KKEAKEKGTWVQLKCQP 132 Score = 22.3 bits (45), Expect = 94 Id = 7/9 (77%), Positives = 8/9 (88%), Gaps = 0/9 (0%) Query 5 SHKNEARDK 13 SHK EAR+K Sbjct 37 SHKWEAREK 45 Score = 22.3 bits (45), Expect = 129 Id = 6/6 (100%), Positives = 6/6 (100%), Gaps = 0/6 (0%) Query 8 NEARDK 13 NEARDK Sbjct 932 NEARDK 937 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | 1 homolog Cytochrome p450 | |
| 53 | 9_FD1 2 | gi\|15055218\| gb\|AC06022 6.39\|*Homo sapiens* 12 BAC RP11- 101P14 (Roswell Park Cancer Institute Human BAC Library) complete sequence Length = 132604 Score = 36.2 bits (18) Expect = 5.6 Id = 18/18 (100%) Gaps = 0/18 (0%) Strand = Plus/Plus | PAGISRELV DKLAAALE | 17 | gi\|6636\|226\|pdb\| 1YX5\|B Chain B, Solution Structure Of S5a Uim-1UBIQUITIN COMPLEX gi\|118595723\|sp\| Q9P212\|PLC E1_HUMAN 1-phosphatidylino- sitol-4,5-bisphos- phate phosphodiesterase epsilon 1 (Phospho- lipase C-epsilon-1) (Phosphoinositide- specific phospho- lipase C epsilon-1) (Pancreas-enriched phospholipase C) gi\|119570428\|gb\| EAW50043. phospholipase C, epsilon 1, isoform CRA_b gi\|119620997\|gb\| EAX00592.1\| eukaryotic transla- tion initiation factor 2B, subunit 4 delta, 67kDa, isoform CRA_f gi\|90185247\|sp\| Q86W92\|L1PB 1_HUMAN Liprin-beta-1 (Pro- tein tyrosine phos- phatase receptor type f polypeptide- interacting pro- tein-binding pro- tein 1) (PTPRF-interacting protein-binding protein 1) (hSGT2) gi\|33337571\|gb\| AAQ13438.1\| AF057699_1 EIF-2B-delta-like protein | Score = 29.5 bits (62), Expect = 0.89 Id = 9/9 (100%), Positives = 9/9 (100%), Gaps = 0/9 (0%) Query 9 VDKLAAALE 17 VDKLAAALE 92 Sbjct 84 Score = 24.8 bits (51), Expect = 23 Id = 7/9 (77%), Positives = 9/9 (100%), Gaps = 0/9 (0%) Query 2 AGISRELVD 10 AGIS+EL+D AGISKELID 524 Sbjct 516 Score = 22.7 bits (46), Expect = 99 Id = 6/8 (75%), Positives = 8/8 (100%), Gaps = 0/8 (0%) Query 5 SRELVDKL 12 SR+LV+KL SRDLVNKL 291 Sbjct 284 |
| 54 | 10_B 12 | gi\|6449479\| gb\|AC009510. 9\| *Homo sapiens* 12p11-37.2- 54.4 BAC RP11- 1110J8 (Roswell Park Cancer In- stitute Human BAC Library) complete se- quence Length = 145859 Score = 676 bits (341) | HTQGCLPM ACAASDSPA CVVCSH | 23 | gi\|61214481\|sp\| Q81ZE3\|PACE 1_HUMAN Protein-associating with the carboxyl- terminal domain of ezrin (Ezrin-bind- ing protein PACE-1) (SCY1-like protein 3) gi\|41688566\|sp\| P60329\|KR124 _HUMAN Keratin-associated protein 12-4 (High sulfur kera- tin-associated protein 12.4) | Score = 31.2 bits (66), Expect = 0.27 Id = 9/10 (90%), Positives = 9/10 (90%), Gaps = 0/10 (0%) Query 14 DSPACVVCSH 23 DSP CVVCSH DSPMCVVCSH 447 Sbjct 438 Score = 26.5 bits (55), Expect = 6.7 Id = 11/19 (57%), Positives = 12/19 (63%), Gaps = 3/19 (15%) Query 1 HTQGCLPMACAASDSPACV 19 H+ GC PMAC   SP CV HSSGC-PMACPG--SPCCV 21 Sbjct 6 Score = 24.4 bits (50), Expect = 21 Id = 8/11 (72%), Positives = 9/11 (81%), |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | Expect = 0.0<br>Id = 358/366 (97%)<br>Gaps = 0/366 (0%)<br>Strand = Plus/Minus | | | gi\|51468842\|ref\|XP_374912.2\| PREDICTED: X-ray radiation resistance associated 1 TGF-beta resistance-associated protein TRAG gi\|73920974\|sp\|Q9Y4E6\|WDR 7_HUMAN WD-repeat protein 7 (TGF-beta resistance-associated protein TRAG) (Rabconacctin-3 beta) 6-phosphofructo-kinase type C Signal recognition particle 19 kDa Gastric mucin Contactin associated protein like 3 precursor Cell recognition molecule Caspr3 gi\|57015409\|sp\|Q8IWT3\|PARC_HUMAN p53-associated parkin-like cytoplasmic protein (UbcH7 associated protein 1) | Gaps = 1/11 (9%)<br>Query 6<br>LPMACAA-SDS 15<br>LPMAC A S+S<br>Sbjct 482<br>LPMACPALSES 492 |
| 57 | 5_C4 | gi\|14245766\|dbj\|AP00245 6.3\| *Homo sapiens* genomic DNA, chromosome 11q clone: RP11-956A8 complete sequence Length = 114109 Score = 961 bits(485) Expect = 0.0 Id = 485/485 (100%) Gaps = 0/485 (0%) Strand = Plus/Plus | VQKSGWGL A | 9 | gi\|33514905\|sp\|Q9P2R3\|ANF Y1_HUMAN Ankyrin repeat and FYVE domain protein 1 (21) gi\|22507380\|ref\|NP_683766.1 G protein-coupled receptor gi\|32171177\|ref\|NP_037529.2 Over-expressed breast tumor protein Adaptor-related protein complex (21) mRNA decapping enzyme 2 DCP2 decapping enzyme (Nudix motif 20) (20.2) Superoxide dismutase, mitochondrial precursor Sterol regulatory element binding protein cleavage activating protein Kallikrein 4 precursor (Prostase) | Score = 21.0 bits (42), Expect = 30<br>Id = 6/8 (75%), Pos = 6/8 (75%),<br>Gaps = 0/8 (0%)<br>Query 1<br>VQKSGWGL 8<br>V KSGW L<br>Sbjct 285<br>VDKSGWSL 292<br>Score = 21.0 bits (42), Expect = 210<br>Id = 5/6 (83%), Positives = 6/6 (100%),<br>Gaps = 0/6 (0%)<br>Query 1<br>VQKSGW 6<br>+QKSGW<br>Sbjct 203<br>IQKSGW 208 |
| 62 | 11_C 7 | gi\|18450186\|gb\|AC09316 8.3\| *Homo sapiens* BAC | KKKKKGV G | 8 | gi\|3264861\|gb\|AAC78729.1\| eukaryotic translation initiation | Score = 23.5 bits (48), Expect = 45<br>Id = 7/7 (100%), Positives = 7/7 (100%),<br>Gaps = 0/7 (0%)<br>Query 1 |

TABLE 6b-continued

| Rank | Clone | Description of the genes that are in Mimotope clones | Peptide sequences of Mimo- topes, in-frame with T7 10 B gene | Size of pep- tide | Description of the sequences that Mimotopes mimic | Region of similarity of peptide |
|---|---|---|---|---|---|---|
| | | clone RP11-148M21 from 7, complete sequence Length = 148689 Score = 58.0 bits (29) Expect = 1e-05 Id = 41/45 (91%) Gaps = 0/45 (0%) Strand = Plus/Minus | | | factor eIF3, p35 subunit gi\|119597676\|gb\| EAW77270.1 eukaryotic transla- tion initiation factor 3, subunit 1 alpha, 35 kDa, isoform gi\|119586121\|gb\| EAW65717. cyclin-dependent kinase-like 1 (CDC2-related kinase), isoform CRA_d gi\|18087335\|gb\| AAL58838.1\| AF390028_1 serine/threonine protein kinase kkialre- like 1 gi\|119625903\|gb\| EAX05498.1\| signal recognition particle 72 kDa, isoform CRA_c gi\|119618653I\|gb\| EAW98247.1 calcium/calmodulin- dependent protein kinase kinase 2, beta, isoform gi\|119609183\|gb\| EAW88777.1 chromodomain helicase DNA binding protein 4 Length = 1911 gi\|119589505\|gb\| EAW69099.1 general transcrip- tion factor IIF, polypeptide 1, 74 kDa, isoform CRA_b | KKKKKGV 7 KKKKKGV Sbjct 220 KKKKKGV 226 Score = 21.0 bits (42), Expect = 262 Id = 7/8 (87%), Positives = 7/8 (87%), Gaps = 0/8 (0%) Query 1 KKKKKGVG 8 KKKKKG G Sbjct 723 KKKKKGGG 730 Score = 20.6 bits (41), Expect = 351 Id = 6/6 (100%), Positives = 6/6 (100%), Gaps = 0/6 (0%) Query 1 KKKKKG 6 KKKKKG Sbjct 249 KKKKKG 254 |
| 63 | 2_G3 | gi\|9801555\| emb\|AL07933 5.29\|Human DNA sequence from clone RP1-132F21 on chromosome 20, complete sequence Length = 71117 Score = 196 bits (99) Expect = 4e-48 Identities = 99/99 (100%) Gaps = 0/99 (0%) Strand = Plus/Minus | LMLPGLSL PGTLGVRG SLSK | 20 | gi\|49522560\|gb\| AAH73937.1\| IGKC protein gi\|18676842\|dbj\| BAB85036.1\| unnamed protein product gi\|23111007\|ref\| NP_076957.3\| hypothetical protein LOC79018 gi\|73620594\|sp\| Q81VV7\|CQ03 9_HUMAN Uncharacterized protein C17orf39 gi\|27469499\|gb\| AAH41829.1\| Chromosome 17 open reading frame 39 gi\|119623763\|gb\| EAX03358.1\| | Score = 26.5 bits (55), Expect = 7.0 Id = 16/38 (42%), Positives = 16/38 (42%), Gaps = 19/38 (50%) Query1 LML--PG----------LSLPGTLG------VRGSLS 19 LML  PG          LSLP TLG       R SLS Sbjct11 LMLWVPGSSGDVVMTQSPLSLPVTLGQPASISCRSSLS 48 Score = 26.1 bits (54), Expect = 9.3 Id = 8/9 (88%), Positives = 8/9 (88%), Gaps = 0/9 (0%) Query 4 PGLSLPGTL 12 PGLSLP TL Sbjct 52 PGLSLPATL 60 Score = 25.7 bits (53), Expect = 13 Id = 9/12 (75%), Positives = 10/12 (83%), Gaps = 0/12 (0%) Query 1 LMLPGLSLPGTL 12 L+L GL LPGTL Sbjct 4 LLLAGLLLPGTL 15 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | corneodesmosin gi\|45477124\|sp\| Q86UW6\|N4B P2_HUMAN NEDD4-binding protein 2 (BCL-3-binding protein) | Score = 25.2 bits (52), Expect = 17 Id = 8/9 (88%), Positives = 8/9 (88%), Gaps = 0/9 (0%) Query 3 LPGLSLPGT 11 LPGL LPGT Sbjct 297 LPGLDLPGT 305 |
| 65 | 10_F 10 | gi\|18449730\| gb\|AC09269 4.6\|*Homo sapiens* 3q BAC RP11-172A10 (Roswell Park Cancer Institute Human BAC Library) complete sequence Length = 151549 Score = 444 bits (224) Expect = 2e-122 Id = 224/224 (100%) Gaps = 0/224 (0%) Strand = Plus/Minus | QIMRSG V | 7 | gi\|113420304\|ref\| XP_001127830.1\| PREDICTED: similar to piwi-like 2 gi\|98990269\|gb\| ABF60230.1\| SARP gi\|116241248\|sp\| Q8N9B4\|AN R42_HUMAN Ankyrin repeat domain-containing protein 42 gi\|119607118\|gb\| EAW86712.1 protein-L-isoaspartate (D-aspartate) O-methyltransferase domain containing 1, isoform gi\|119580466\|gb\| EAW60062.1 MCM5 minichromosome maintenance deficient 5, cell division cycle 46 (*S. cerevisiae*), isoform CRA_c gi\|27552808\|gb\| AAH42923.1\| Talin 1 gi\|546571\|gb\| AAB30677.1\| Wnt4 product [human, breast cell lines, Peptide Partial, 120 aa] | Score = 26.1 bits (54), Expect = 6.7 Id = 7/7 (100%), Positives = 7/7 (100%), Gaps = 0/7 (0%) Query 1 QIMRSGV 7 QIMRSGV Sbjct 548 QIMRSGV 554 Score = 21.8 bits (44), Expect = 128 Id = 7/8 (87%), Positives = 7/8 (87%), Gaps = 1/8 (12%) Query 1 QIM-RSGV 7 QIM RSGV Sbjct 115 QIMLRSGV 122 Score = 20.6 bits (41), Expect = 308 Id = 5/6 (83%), Positives = 6/6 (100%), Gaps = 0/6 (0%) Query 1 QIMRSG 6 QIMR+G Sbjct 21 QIMRTG 26 |
| 71 | 9_H4 | gi\|8748861\| gb\|AC019181. 4\|*Homo sapiens* BAC clone RP11-272E3 from 2, complete sequence Length = 190998 Score = 240 bits (121) Expect = 1e-60 Id = 121/121 (100%) Gaps = 0/121 (0%) Strand = Plus/Minus | SRYW | 4 | gi\|122892392\|gb\| ABM67263.1 immunoglobulin heavy chain variable region gi\|119608878\|gb\| EAW88472.1 G protein-coupled receptor 112, isoform CRA_b gi\|119599986\|gb\| EAW79580.1 immunoglobulin superfamily, member 11, isoform CRA_b gi\|119591313\|gb\| EAW70907.1 thyroid hormone receptor interactor 12, isoform CRA_l gi\|119588597\|gb\| EAW68191.1 F-box protein 3, isoform | Score = 18.9 bits (37), Expect = 571 Id = 4/4 (100%), Positives = 4/4 (100%), Gaps = 0/4 (0%) Query 1 SRYW 4 SRYW Sbjct 995 SRYW 998 |

TABLE 6b-continued

| Rank | Clone | Description of the genes that are in Mimotope clones | Peptide sequences of Mimo- topes, in-frame with T7 10 B gene | Size of pep- tide | Description of the sequences that Mimotopes mimic | Region of similarity of peptide |
|---|---|---|---|---|---|---|
| | | | | | gi\|110735406\|ref\| NP_573438.2\|pro- tein tyrosine phosphatase, receptor typeU | |
| 78 | 2_C1 1 | Homo sapiens chromosome 8, clone RP11-35G22, complete sequence Score = 40.1 bits (20) Expect = 0.99 Identities = 20/20 (100%) | TNGSKK EKKLXF LXXXXK | 11 | gi\|62906863\|sp\| P30084\|ECHM _HUMAN Enoyl-CoA hydratase, mito- chondrial precursor (Short chain enoyl- CoA hydratase) (SCEH) (Enoyl-CoA hydratase 1) gi\|51702191\|sp\| Q9H2Y7\|ZF10 6_HUMAN Zinc finger protein 106 homolog (Zfp-106) gi\|57284109\|emb\| CAI43036.1\| TAF7-Iike RNA polymerase II, TATA box binding protein (TBP)- associated factor, 50 kDa gi\|13603873\|gb\| AAK31974.1\| TBP-associated factor II Q gi\|401357\|sp\| Q02004\|VGLM_ DUGBV M polyprotein precursor /Contains: Glyco- protein G2; Non- structural protein NS-M; Glycoprotein G1\| gi\|6671334\|eb\| AAF23161.1\| disabled-2 gi\|1706487\|sp\| P98082\|DAB2_ HUMAN Disabled homolog 2 (Differentially expressed protein 2) (DOC-2) gi\|1706487\|sp\| P98082\|DAB2_ HUMAN Disabled homolog 2 (Differentially expressed protein 2) (DOC-2) gi\|1110539\|gb\| AAB19032.1\| mitogen-responsive phosphoprotein gi\|56202443\|emb\| CAI20904.1\| myeloidVlymphoid or mixed-lineage leukemia (trithorax homolog, Drosophila)\; | Score = 21.8 bits (44), Expect = 127 Identities = 8/10 (80%), Positives = 9/10 (90%), Gaps = 0/10 (0%) Query 1 TNGSKKEKKL 10 T GSKK+KKL Sbjct 1346 TRGSKKKKKL 1355 Score = 21.4 bits (43), Expect = 170 Identities = 6/6 (100%), Positives = 6/6 (100%), Gaps = 0/6 (0%) Query 5 KKEKKL 10 Sbjct 312 KKEKXL 317 Score = 21.4 bits (43), Expect = 170 Identities = 9/20 (45%), Positives = 9/20 (45%) Gaps = 11/20 (55%) Query 1 TNG----------SKKEKK 9 TNG         SKKEKK Sbjct 10 TNGQPDQQAAPKAPSKKEKK 29 Score = 21.0 bits (42), Expect = 229 Identities = 6/6 (100%), Positives = 6/6 (100%), Gaps = 0/6 (0%) Query 4 SKKEKK 9 Sbjct 185 SKKEKK 190 |

TABLE 6b-continued

| Rank | Clone | Description of the genes that are in Mimotope clones | Peptide sequences of Mimo- topes, in-frame with T7 10 B gene | Size of pep- tide | Description of the sequences that Mimotopes mimic | Region of similarity of peptide |
|---|---|---|---|---|---|---|
| | | | | | translocated to, 4 gi\|23306684\|gb\| AAN15215.1\| multiple myeloma transforming gene 2 | |
| 82 | 10_D 7 | gi\|18693518\| gb\|AC01591 1.8\|*Homo sapiens* chromosome gi\|18693518\| gb\|AC01591 1.8\|*Homo sapiens* chromosome 17, clone RPII-1094M14, complete se- quence Length = 181561 Score = 496 bits (250) Expect = 6e- 138 Id = 250/250 (100%) Gaps = 0/250 (0%) Strand = Plus/Plus | GETPELITT NTSQLNFR KQIVP | 22 | Similar to RIKEN cDNA 9130427A09 gene (24.8) gi\|23512334\|gb\| AAH38451.1\| Similar to RIKEN cDNA 9130427A09 gene gi\|60593095\|ref\| NP_001012660.1\| hypothetical protein LOC196996 gi\|31566169\|gb\| AAH53647.1\| Hypothetical protein LOC84978, isoform 1 gi\|22478057\|gb\| AAH36900.1\| ZWILCH protein gi\|38348727\|ref\| NP_071348.3\| thyroid adenoma associated isoform 1 gi\|34493758\|gb\| AAO46785.1\| death receptor in- teracting protein gi\|57162636\|emb\| CA139911.1\| solute carrier family 7 (cationic aa trans- porter, y+ system), member 1 gi\|13177667\|gb\| AAH03618.1\| Tara-like protein, isoform 1 gi\|20455324\|sp\| Q9H2D6\|TAR A_HUMAN TRIO and F-actin binding protein (Protein Tara) gi\|252582\|gb\| AAB22747.1\| IFN-tyk, tyk2 = interferon alpha\| beta signaling pathway-related protein tyrosine kinase gi\|56405328\|sp\| P29597\|TYK2 _HUMAN Non-receptor tyrosine-protein kinase TYK2 | Score = 24.8 bits (51), Expect = 16 Id = 7/7 (100%), Positives = 7/7 (100%), Gaps = 0/7 (0%) Query 7 ITTNTSQ 13 ITTNTSQ Sbjct 150 ITTNTSQ 156 Score = 24.0 bits (49), Expect = 29 Id = 10/19 (52%), Positives = 12/19 (63%), Gaps = 6/19 (31%) Query 1 GETPELITTNTSQLNF-RK 18 G+TP   TS+LNF RK Sbjct 185 GQTPA-----TSELNFLRK 198 Score = 24.0 bits (49), Expect = 29 Ids = 7/8 (87%), Positives = 7/8 (87%), Gaps = 0/8 (0%) Query 5 ELITTNTS 12 ELITTN S Sbjct 40 ELITTNNS 47 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 84 | 10_E 12 | gi\|11493153\| emb\|AL1185 23.18\| Human DNA sequence from clone RP5-1031J8 on chromosome 20, complete sequence Length = 155213 Score = 1449 bits (731) Expect = 0.0 Id = 767/777 (98%) Gaps = 0/777 (0%) Strand = Plus/Plus | PRMRWGX XXVAXWPV PSHW | 23 | gi\|119578750\|gb\| EAW58346.1\| glucosidase, beta (bile acid) 2, isoform CRA_b gi\|14042883\|dbj\| BAB55430.1\| unnamed protein product gi\|119611678\|gb\| EAW91272.1\| asp (abnormal spindle)-like, microcephaly associated gi\|62906885\|sp\| P27987\|IP3KB _HUMAN Inositol-trisphosphate 3-kinase_B gi\|21361517\|ref\| NP_056937.2\| SAPK substrate protein 1 gi\|54144631\|ref\| NP_112210.1\| phosphatase and actin regulator 1 gi\|70888311\|gb\| AAZ13758.1\| leukocyte specific transcript 1 gi\|37222213\|gb\| AAQ89957.1\| selectin-like protein gi\|68655017\|emb\| CAF04067.1\| SEL-OB protein gi\|119601416\|gb\| EAW81010.1\| splicing factor, arginine/serine-rich 5, isoform CRA_e | QScore = 29.1 bits (61), Expect = 1.2 Id = 7/7 (100%), Positives = 7/7 (100%), Gaps = 0/7 (0%) Query 15 RSWNWGL 21 RSWNWGL Sbjct 215 RSWHWGL 221 Score = 28.6 bits (60), Expect = 1.6 Id = 10/18 (55%), Positives = 14/18 (77%), Gaps = 3/18 (16%) Query 1 VRLVRTEERLELRTRSWN 18 VRLVRT +EL T++W+ Sbjct 241 VRLVRT---MELLTQNWD 255 Score = 26.9 bits (56), Expect = 5.1 Id = 10/18 (55%), Positives = 12/18 (66%), Gaps = 6/18 (33%) Query 3 LV---RTEERLELRTRSW 17 LV R+EER RT+SW Sbjct 191 LVQGARSEER---RTKSW 205 Score = 26.5 bits (55), Expect = 6.9 Id = 9/12 (75%), Positives = 9/12 (75%), Gaps = 2/12 (16%) Query 9 RLELRTRSWNWG 20 RLE RTR NWG Sbjct 286 RLETRTR--NWG 295 Score = 26.1 bits (54), Expect = 9.3 Id = 7/7 (100%), Positives = 7/7 (100%), Gaps = 0/7 (0%) Query 7 EERLELR 13 EERLELR Sbjct 449 EERLELR 455 Score = 26.1 bits (54), Expect = 9.3 Id = 8/11 (72%), Positives = 8/11 (72%), Gaps = 3/11 (27%) Query 7 EERLELRTRSW 17 EERLE RSW Sbjct 31 EERLE---RSW 38 |
| 86 | 11_C 3 | gi\|15808543\| gb\|AC09307 3.2\|*Homo sapiens* chromosome 19 clone LLNLR-275E5, complete sequence Length = 2616 Score = 319 bits (161) Expect = 2e-84 Id = 180/189 (95%) Gaps = 0/189 (0%) Strand = Plus/Minus | REMRLKNT KLQSDKRN NFGPGAVV HTCNPSTSG GXVGRIT | 40 | gi\|21756842\|dbj\| BAC04969.1\| unnamed protein product gi\|21389158\|gb\| AAM50513.1\| hypothetical protein gi\|20139105\|sp\| Q99959\|PKP2 _HUMAN Plakophilin-2 gi\|15929032\|gb\| AAH14974.1\| Yip1 interacting factor homolog B, isoform 1 gb\|2088182\|dbj\| BAD92538.1\| SLC2A11 piotein variant gi\|66932986\|ref\| | Score = 45.6 bits (100), Expect = 1e-05 Id = 17/22 (77%), Positives = 17/22 (77%), Gaps = 0/22 (0%) Query 19 GPGAVVHTCNPSTSGGXVGRIT 40 GPGAV H CNPST GG GRIT Sbjct 136 GPGAVAHACNPSTLGGRGGRIT 157 Score = 44.3 bits (97), Expect = 4e-05 Id = 16/21 (76%), Positives = 16/21 (76%), Gaps=0/21 (0%) Query 20 PGAVVHTCNPSTSGGXVGRIT 40 PG VVH CNPST GG GRIT Sbjct 17 PGTVVHACNPSTLGGQGGRIT 37 Score = 43.9 bits (96), Expect = 6e-05 Id = 19/27 (70%), Positives = 19/27 (70%), Gaps = 3/27 (11%) Query 15 RNNFG-PGAVVHTCNPSTSGGXVGRIT 40 RN G PGAV H CNPST GG GRIT |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | NP_001019386.1\|filamin-binding LIM protein-1 isoform b gi\|3335138\|gb\|AAC39892.1\| RNA polymerase 1 40 kD subunit gi\|7416053\|dbj\|BAA93676.1\| survivin-beta gi\|386941\|gb\|AAA59814.1\| MHC HLA-DR-beta-1 chain gi\|114849\|sp\|P20931\|YYY3_HUMAN Very very hypothetical B-cell growth factor (BCGF-12 kDa) gi\|48474670\|sp\|Q9NRR6\|1NP5_HUMAN (Phosphatidyl-inositol-4,5-bispHosphate 5-phosphatase) gi\|20455217\|sp\|O43353\|RIPK2_HUMAN Receptor-interacting serine/threonine-protein kinase 2 | Sbjct 468 RN--GWPGAVAHACNPSTLGGQGGRIT 492 |
| 88 | 5_C7 | gi\|22657585\|gb\|AC09156 4.12\|Homo sapiens chromosome 11, clone RP11-732A19, complete sequence Length = 211735 Score = 321 bits (162) Expect = 2e-85 Id = 194/204 (95%) Gaps = 3/204 (1%) Strand = Plus/Plus | GITGSRPA WPTW | 12 | gi\|119629047\|gb\|EAX08642.1\| hCG1816309 gi\|119625915\|gb\|EAX05510.1\| homeodomain-only protein, isoform CRA_i gi\|55961994\|emb\|CA118336.1\| cAMP responsive element binding protein-like 1 gi\|30046775\|gb\|AAH50548.1\| KIF4A protein gi\|119625748\|gb\|EAX05343.1\| kinesin family member 4A, isoform CRA_b gi\|119603999\|gb\|EAW83593.1\| NADH dehydrogenase (ubiquinone) 1 alpha subcomplex, 5, 13 kDa, isoform CRA_d | Score = 32.5 bits (69), Expect = 0.12 Id = 8/8 (100%), Positives = 8/8 (100%), Gaps = 0/8 (0%) Query 5 SRPAWPTW 12 SRPAWPTW Sbjct 18 SRPAWPTW 25 Score = 29.9 bits (63), Expect = 0.68 Id = 7/7 (100%), Positives = 7/7 (100%), Gaps = 0/7 (0%) Query 6 RPAWPTW 12 RPAWPTW Sbjct 312 RPAWPTW 318 Score = 28.2 bits (59), Expect = 2.2 Id = 7/8 (87%), Positives = 7/8 (87%), Gaps = 0/8 (0%) Query 5 SRPAWPTW 12 SRPAW TW Sbjct 1110 SRPAWATW 1117 |
| 89 | 11_A 1 | gi\|15789217\|gb\|AC08481 9.17\|Homo sapiens 12p BAC RPII-449P1 (Roswell Park | NSSA | 4 | gi\|125950975\|sp\|Q9Y4F3\|LKAP_HUMAN Limkain-b1 gi\|124001558\|ref\|NP_689799.3\| ubiquitin specific protease 54 | Score = 14.2 bits (26), Expect = 14482 Id = 4/4 (100%), Positives = 4/4 (100%), Gaps = 0/4 (0%) Query 1 NSSA 4 NSSA Sbjct 90 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | Cancer Institute Human BAC Library) complete sequence Length = 46530 Score = 418 bits (211) Expect = 1e-114 Id = 216/218 (99%) Gaps = 0/218 (0%) Strand = Plus/Minus | | | gi\|123242853\|emb\| CAI16881.2 quiescin Q6-like 1 gi\|120660404\|gb\| AAI30523.1\| Receptor tyrosine kinase-like orphan receptor 2 gi\|120659834\|gb\| AAI30364.1\| BRCC2 gi\|114432132\|gb\| AB174674.1\| breast and ovarian cancer susceptibility protein 2 truncated variant gi\|119628905\|gb\| EAX08500.1\| breast cancer 2, early onset, gi\|119625696\|gb\| EAX05291.1\| TAF1 RNA polymerase 11, TATA box binding protein (TBP)-associated factor, 250 kDa, isoform CRA_a gi\|119626158\|gb\| EAX05753.1\| protein phosphatase, EF-hand calcium binding domain 2, isoform gi\|119625726\|gb\| EAX05321.1\| myeloid/lymphoid or mixed-lineage leukemia (trithorax homolog, Drosophila); translocated to, 7, isoform | NSSA 93 |
| 97 | 9_C2 | gi\|11875985\| emb\|AL0968 68.15\|Human DNA sequence from clone RP3-493D19 on chromosome 6q14.3-16.1, complete sequence Length = 151761 Score = 757 bits (382) Expect = 0.0 Id = 385/386 (99%) Gaps = 0/386 (0%) Strand = Plus/Minus | NSNIY | 5 | gi\|119615275\|gb\| EAW94869.1\| zinc finger, UBR1 type 1, isoform CRA_c gi\|82659109\|ref\| NP_065816.2\| retinoblastoma-associated factor 600 gi\|19070472\|gb\| AAL83880.1\| AF348492_1 p600 gi\|33319488\|gb\| AAQ05647.1\| AF471472_1 Ig heavy chain variable region, VH3 family gi\|30046973\|gb\| AAH50539.1\| Solute carrier family 14 (urea transporter), member1 (Kidd blood group) | Score = 20.2 bits (40), Expect = 295 Id = 5/5 (100%), Positives = 5/5 (100%), Gaps = 0/5 (0%) Query 1 NSNIY 5 NSNIY Sbjct 356 NSNIY 360 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 99 | 6_C12 | gi\|20198509\| gb\|AC013452.0\|*Homo sapiens* chromosome 15 clone RP11-325E5 map 15q21.1, complete sequence Length = 204745 Score = 831 bits (419) Expect = 0.0 Id = 446/452 (98%) Gaps = 3/452 (0%) Strand = Plus/Minus | LTLRTKTT TVTV | 12 | gi\|89033971\|ref\| XP_931830.1 PREDICTED: Hypothetical protein XP_931830 gi\|55663026\|emb\| CAH172389.1\| Protocadherin 15 gi\|3070500\|gb\| AAH51787.1\| Death effector filament-forming Ced-4-like apoptosis protein gi\|1916615\|gb\| AAC51239.1\| Ribosomal RNA upstream binding transcription factor Polycystic kidney and hepatic disease 1 CCM2 protein PP10187 Caspase recruitment domain protein 7 | Score = 24.4 bits (50), Expect = 23 Id = 7/7 (100%), Pos = 7/7 (100%), Gaps = 0/7 (0%) Query 2 TLRTKTT 8 TLRTKTT Sbjct 134 TLRTKTT 140 Score = 23.1 bits (47), Expect = 56 Id = 8/9 (88%), Pos = 8/9 (88%), Gaps = 1/9 (11%) Query 2 TLRT-KTTT 9 TLRT KTTT Sbjct 610 TLRTSKTTT 618 Score = 22.3 bits (45), Expect = 96 Id = 7/9 (77%), Positives = 8/9 (88%), Gaps = 0/9 (0%) Query 4 RTKTTTVTV 12 RT TTT+TV Sbjct 245 RTTTTLTV 253 |
| 100 | 10_B10 | gi\|15705226\| emb\|AL390876.19\| Human DNA sequence from clone RP11-394D2 on chromosome 9, complete sequence Length = 185571 Score = 682 bits (344), Expect = 0.0 Ide = 365/365 (100%) Gaps = 0/365 (0%) Strand = Plus/Minus | TRGTKRSW VHSF | 12 | gi\|30983668\|gb\| AAP41104.1\| Cohen syndrome 1 protein splice variant 2 gi\|77416860\|sp\| Q92674\|FSHP 1_HUMAN Follicle-stimulating hormone primary response protein (FSH primary response protein 1) gi\|256180\|gb\| AAB23392.1\| cancer-associated retinopathy antigen gi\|464600\|sp\| P35243\|RECO_HUMAN Recoverin (Cancer associated retinopathy protein) (CAR protein) gi\|48428608\|sp\| Q12789\|TF3C 1_HUMAN General transcription factor 3C polypeptide 1 (Transcription factor IIIC-alpha subunit) (TF3C-alpha) (TFIIIC 220 kDa subunit) (TFIIIC220) (TFIIIC box B-binding subunit) gi\|18375626\|ref\| NP_542417.11 HLA-B associated transcript-2 isoform a gi\|4337110\|gb\| AAD18086.1\| BAT2 | Score = 25.2 bits (52), Expect = 12 Identities = 8/11 (72%), Positives = 9/11 (81%), Gaps = 1/11 (9%) Query 1 TRGTKRSWYHS 11 TR +KR WYHS Sbjct 18 TRTSKR-WYHS 27 Score = 24.4 bits (50), Expect = 377 Identities = 7/8 (87%), Positives = 7/8 (87%) Query: 2 GTKRSWYH 9 GT RSWYH Sbjct: 1098 GTVRSWYH 1105 Score = 22.3 bits (45), Expect = 96 Identities = 6/8 (75%), Positives = 6/8 (75%) Gaps = 0\|8 (0%) Query 2 RGTKRSWY 9 RG K SWY Sbjct 712 RGKKWSWY 719 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | gi\|55662017\|emb\|CAH70921.1\| v-abl Abelson murine leukemia viral oncogene homolog 2 | |
| 101 | 12_C4 | gi\|10440580\|gb\|AC01554 2.17\|Homo sapiens 3 BAC RP11-38B6 (Roswell Park Cancer Institute Human BAC Library) complete sequence, Length = 15150 Score = 252 bits (127) Expect = 1e-64 Id = 137/139 (98%) Gaps = 1/139 (0%) Strand = Plus/Plus | FFVFYLQS RIMTDTKI SPLH | 20 | gi\|12803135\|gb\|AAH0237.1\| Nipsnap homolog 1 (27.8) gi\|8216987\|emb\|CAB92443.1\| Putative tumor antigen Sarcoma antigen 1 gi\|24419041\|gb\|AAL65133.2\| Ovarian cancer related tumor marker CA125 | Score = 27.8 bits (58), Expect = 2.2 Id = 11/25 (44%), Pos = 14/25 (56%), Gaps = 7/25 (28%) Query 3 VFY-------LQSRIMTDTKISPLH 20 V+Y       ++SRIM   KISPL Sbjct 260 VYYTVPLVRHMESRIMIPLKISPLQ 284 Score = 26.5 bits (55), Expect = 5.3 Id = 9 12 (75%), Positives = 10 12 (83%), Gaps = 1/12 (8%) Query 9 RI-MTDTKISPL 19 RI MTDT ISP+ Sbjct 229 RINMTDTGISPM 240 Score = 23.5 bits (48), Expect = 41 Id = 8/10 (80%), Positives = 8/10 (80%), Gaps = 1/10 (10%) Query 10 IMTDT-KISP 18 IMTDT KI P Sbjct 9801 IMTDTEKIHP 9810 |
| 102 | 2_C7 | none | PCEMELESP HPAXCHL | 16 | gi\|119622175\|gb\|EAX01770.1\| hCG1986848 gi\|23396460\|sp\|O005121\|BCL9_HUMAN B-cell lymphoma 9 protein (Bcl-9) (Legless hoinolog) gi\|119569780\|gb\|EAW49395.1\| G protein-coupled receptor kinase 5, isoform CRA_b gi\|23822155\|sp\|Q9BX26\|SYCP2_HUMAN Synaptonemal complex protein 2 (SCP-2) gi\|98991767\|ref\|NP_690000.2\| mitogen-activated protein kinase kinase kinase 7 interacting protein 3 gi\|37538058\|gb\|AAQ92939.1\| NFkB activating protein 1 gi\|3182968\|sp\|O15528\|CP27B_HUMAN 25-hydroxyvitamin D-1 alpha hydroxylase, mitochondrial precursor (Cytochrome P450 subfamily XXVIIB polypeptide 1) (Cytochrome p450 | Score = 28.6 bits (60), Expect = 1.6 Id = 11/16 (68%), Positives = 12/16 (75%), Gaps = 4/16 (25%) Query 4 MELES-PH--PAXCHL 16 MELES PH  P+ CHL Sbjct 21 MELESMPHSVPS-CHL 35 Score = 25.7 bits (53), Expect = 13 Id = 8/11 (72%), Positives = 10/11 (90%), Gaps = 1/11 (9%) Query 3 EMEGPS-PHPA 12 EMEGP+ P+PA Sbjct 572 EMEGPNVPNPA 582 Score = 24.4 bits (50), Expect = 31 Id = 6/9 (66%), Positives = 8/9 (88%), Gaps = 0/9 (0%) Query 8 SPHPAXCHL 16 SPHP+ CH+ Sbjct 31 SPHPSLCHM 39 Score = 24.0 bits (49), Expect = 41 Id = 9/13 (69%), Positives = 9/13 (69%), Gaps = 4/13 (30%) Query 1 GC---EM-EGQSP 9 GC   EM EGQSP Sbjct 372 GCLIYEMIEGQSP 384 Score = 24.0 bits (49), Expect = 41 Id = 6/7 (85%), Positives = 7/7 (100%), Gaps = 0/7 0%) Query 4 MELESPH 10 ME+ESPH Sbjct 1230 MEIESPH 1236 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | 27B1) (Calcidiol 1-monooxygenase) (25-hydroxyvitamin D(3) 1-alpha-hydroxylase) (VD3 1A hydroxylase) (P450C1 alpha) (P450VD1-alpha) gi\|119620981\|gb\| EAX00576.1\| keratinocyte associated protein 3 | |
| 103 | 8_B12 | gi\|15789217\| gb\|AC08481 9.17\|Homo sapiens 12p BAC RP11-449P1 (Roswell Park Cancer Institute Human BAC Library) Length = 46530 Score = 480 bits (242) Expect = 1e-132 Id = 251/255 (98%) Gaps = 0/255 (0%) Strand = Plus/Minus | NSSA | 4 | gi\|124375836\|gb\| AAI32680.1\| Transmembrane channel-like 3 gi\|124001558\|ref\| NP_689799. ubiquitin specific protease54 gi\|120660404\|gb\| AAI30523.1\| Receptor tyrosine kinase-like orphan receptor 2 gi\|120660344\|gb\| AAI30362.1\| BRCC2 gi\|114432132\|gb\| ABI74674.1\| breast and ovarian cancer susceptibility protein 2 truncated variant gi\|119628905\|gb\| EAX08500.1\| breast cancer 2, early onset, isoform CRA_b gi\|119620918\|gb\| EAX00513.1\| restin-like 2, isoform CRA_e gi\|119625696\|gb\| EAX05291.1\| TAF1 RNA polymerase II, TATA box binding protein | Score = 14.2 bits (26), Expect = 14482 Identities = 4/4 (100%), Positives = 4/4 (100%) Gaps = 0/4 (0%) Query 1 NSSA 4 NSSA Sbjct 1178 NSSA 1181 |
| 105 | 5_G4 | gi\|2688799\| gb\|AC003681. 1\|AC003681 Human PAC clone RP3-394A18 from 22q12.1-qter, complete sequence Length = 88528 Score = 224 bits (113) Expect = 2e-56 Id = 119/121 (98%) Gaps = 0/121 (0%) Strand = Plus/Minus | GWQERRN KLTK | 11 | gi\|119600046\|gb\| EAW79640.1 WD repeat domain 52, isoform CRA_a gi\|112180716\|gb\| AAH30606.2 Coiled-coil domain containing 11 gi\|49176521\|gb\| AAT52215.1\| cell proliferation-inducing protein 53 gi\|1196104291\|gb\| EAW90023.1 hCG57025, isoform CRA_c gi\|110611170\|ref\| NP_620688.2\|ADAM metallopeptidase with thrombospondin type 1 motif, 17 preproprotein | Score = 23.1 bits (47), Expect = 75 Id = 6/7 (85%), Positives = 7/7 (100%), Gaps = 0/7 (0%) Query 3 QERRNKL 9 +ERRNKL Sbjct 704 EERRNKL 710 Score = 23.1 bits (47), Expect = 75 Id = 6/9 (66%), Positives = 8/9 (88%), Gaps = 0/9 (0%) Query 1 GWQERRNKL 9 GW+ERR+ L Sbjct 196 GWEERRDIL 204 Score = 22.7 bits (46), Expect = 100 Id = 6/6 (100%), Positives = 6/6 (100%), Gaps = 0/6 (0%) Query 4 ERRNKL 9 ERRNKL |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | gi\|74723116\|sp\|Q70EL4\|UBP43_HUMAN Ubiquitin carboxyl-terminal hydrolase 43 (Ubiquitin thioesterase 43) | Sbjct 25 ERRNKL 30 Score 22.7 bits (46), Expect = 100 Id = 7/11 (63%), Positives = 9/11 (81%), Gaps = 2/11 (18%) Query 2 WQERRN--KLT 10 W+ERRN +LT Sbjct 219 WRERRRAIRLT 229 |
| | | | | | gi\|119582112\|gb\|EAW61708. dynactin 4 (p62), | |
| | | | | | gi\|119581530\|gb\|EAW61126.1 polymerase (DNA directed), mu, isoform CRA_f | |
| | | | | | gi\|119614601\|gb\|EAW94195.1 SMAD specific E3 ubiquitin protein ligase | |
| | | | | | gi\|12018151\|gb\|AAG45422.1\| E3 ubiquitin ligase SMURF2 | |
| | | | | | gi\|81022914\|gb\|ABB55266.1\| rhabdomyosarcoma antigen MU-RMS-40.8 | |
| 107 | 1_H4 | gi\|12001748\|emb\|AL355052.3\|CNS05TC4 Human chromosome 14 DNA sequence BAC R-1070A8 of library RPC1-11 from chromosome 14 of *Homo sapiens* (Human), complete sequence Length = 179712 Score = 549 bits (277) Expect = 6e-154 Id = 277/277 (100%) Gaps = 0/277 (0%) Strand = Plus/Minus | VEGKVARC QSKSPGFED GLFGKF | 23 | gi\|51491211\|emb\|CAH18671.1\|hypothetical proteingi\|119598885\|gb\|EAW78479.1\|hCG2040711 gi\|119605408\|gb\|EAW85002.1 coagulation factor XII | Score = 25.2 bits (52), Expect = 17 Id = 7/10 (70%), Positives = 9/10 (90%), Gaps = 0/10 (0%) Query 8 CQSRSPGFED 17 CQSKSPG ++ Sbjct 409 CQSKSPGLDN 418 |
| | | | | | gi\|116242624\|sp\|Q12852\|M3K12_HUMAN Mitogen-activated protein kinase kinase kinase 12 (Mixed lineage kinase) | Score = 24.8 bits (51), Expect = 22 Id = 9/16 (56%), Positives = 9/16 (56%), Gaps = 5/16 (31%) Query 4 KVARCQSKSPGFEDGL 19 KV RC    GFED L Sbjct 69 KVGRC-----GFEDNL 79 |
| | | | | | gi\|561543\|gb\|AAA67343.1\| serine/threonine protein kinase | Score = 24.0 bits (49), Expect = 40 Id = 7/9 (77%), Positives = 7/9 (77%), Gaps = 0/9 (0%) Query 5 VARCQSKSP 13 VARCQ K P Sbjct 46 VARCQCKGP 54 |
| | | | | | gi\|4033480\|sp\|Q13595\|TRA2A_HUMAN Transformer-2 protein homolog (TRA-2 alpha) | |
| 110 | 10_B | | LTSKTQ RK | 8 | gi\|17368711\|sp\|Q9BZE4\|NOG1_HUMAN Nucleolar GTP-binding protein 1 (Chronic renal failure gene protein) (GTP-binding protein NGB) | Score = 23.1 bits (47), Expect = 70 Identities = 8/9 (88%), Positives = 8/9 (88%), Gaps = 1/9 (11%) Query 7 LT-SKTQRK 14 LT SKTQRK Sbjct 21 LTLSKTQRK 29 |
| | | | | | gi\|3153873\|gb\|AAC24364.1\| putative G-binding protein | Score = 23.1 bits (47), Expect = 43 Id = 8/9 (88%), Positives = 8/9 (88%), Gaps = 1/9 (11%) Query 1 LT-SKTQRK 8 LT SKTQRK |

TABLE 6b-continued

| Rank | Clone | Description of the genes that are in Mimotope clones | Peptide sequences of Mimo- topes, in-frame with T7 10 B gene | Size of pep- tide | Description of the sequences that Mimotopes mimic | Region of similarity of peptide |
|---|---|---|---|---|---|---|
| | | | | | gi\|27923746\|sp\| Q96P48\|CEN D2_HUMAN Centaurin delta 2 (Cnt-d2) gi\|51464006\|ref\| XP_497909.1\| similar to dual specificity phos- phatase 5; VH1-like phosphatase 3; serine/threonine specific protein phosphatase gi\|62089088\|dbj\| BAD92988.1\| Rho GTPase activat- ing protein 5 variant gi\|55859653\|emb\| CA110958.1\| nuclear receptor subfamily 5, group A, member 1 gi\|339550\|gb\| AAA50404.1\| transforming growth factor-beta-2 precursor gi\|62896709\|dbj\| BAD96295.1\| TATA binding protein interacting protein 49 kDa variant | Sbjct 5 LTLSKTQRK 13 Score = 23.1 bits (47), Expect = 43 Id = 8/9 (88%), Positives = 8/9 (88%), Gaps = 1/9 (11%) Query 1 LT-SKTQRK 8 LT SKTQRK Sbjct 19 LTLSKTQRK 27 Score = 21.4 bits (43), Expect = 228 Identities = 6/6 (100%), Positives = 6/6 (100%) Gaps = 0/6 (0%) Query 8 TSKTQR 13 TSKTQR Sbjct 684 TSKTQR 689 Score = 21.4 bits (43), Expect = 140 Id = 6/6 (100%), Positives = 6/6 (100%), Gaps = 0/6 (0%) Query 2 TSKTQR 7 TSKTQR Sbjct 119 TSKTQR 124 Score = 19.7 bits (39), Expect = 452 Id = 6/7 (85%), Positives = 7/7 (100%), Gaps = 0/7 (0%) Query 2 TSKTQRK 8 TSKT+RK Sbjct 820 TSKTKRK 826 Score = 18.9 bits (37), Expect = 814 Id = 5/5 (100%), Positives = 5/5 (100%), Gaps = 0/5 (0%) Query 4 KTQRK 8 KTQRK Sbjct 59 KTQRK 63 |
| 11 3 | 10_C 1 | gi\|55734203\| emb\|CR8614 77.1\|Human DNA sequence from clone XX-NCIH2171_ 4G20, com- plete sequence Length = 121004 Score = 577 bits (291) Expect = 2e- 162 Id = 315/315 (100%) Gaps = 0/315 (0%) Strand = Plus/Plus | GDPNSS | 6 | gi\|119588281\|gb\| EAW67875.1 protein tyrosine phosphatase, receptor typeJ gi\|11961566-\|gb\| EAW95254.1 cytoplasmic linker associated protein 1, isoform gi\|119607396\|gb\| EAW86990.1 telomeric repeat binding factor (NIMA-interacting) 1 gi\|119613827\|gb\| EAW93421.1 TNF receptor- associated factor 5, isoform CRA_a gi\|119597101\|gb\| EAW76695.1 transformation\| transcription domain-associated protein, gi\|119572538\|gb\| | Score = 18.5 bits (36), Expect = 1148 Id = 5/5 (100%), Positives = 5/5 (100%), Gaps = 0/5 (0%) Query 1 GDPNS 5 GDPNS Sbjct 177 GDPNS 181 Score = 18.5 bits (36), Expect = 1148 Id = 5/5 (100%), Positives = 5/5 (100%), Gaps = 0/5 (0%) Query 2 DPNSS 6 DPNSS Sbjct 2031 DPNSS 2035 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | EAW52153.1 protease, serine, 36, isoform gi\|116242829\|sp\| Q9Y4A5\|TR RAP_HUMAN Transformation\| transcription domain-associated protein (350/400 kDa PCAF-associated factor) gi\|119597105\|gb\| EAW76699.1 transformation\| transcription do main-associated protein, isoform CRA_g | |
| 116 | 9_C6 | gi\|18873821\| gb\|AC01027 9.5\|*Homo sapiens* chromosome 5 clone CTC-533D18, complete sequence Length = 125746 Score = 109 bits (55) Expect = 1e-21 Id = 63/67 (94%) Gaps = 0/67 (0%) Strand = Plus/Minus | GDPNSVY | 7 | gi\|62898359\|dbj\| BAD97119.1\| guanine monophos- phate synthetase variant | Score = 21.0 bits (42), Expect = 228 Id = 6/7 (85%), Positives = 6/7 (85%), Gaps = 0/7 (0%) Query = 1 GDPNSVY 7 G PNSVY Sbjct 171 GGPNSVY 177 |
| 119 | 6_G3 | gi\|244d18207\| gb\|AC08739 2.10\|*Homo sapiens* chromosome 17, clone RP11-676J12, complete sequence Length = 196772 Score = 1051 bits (530) Expect = 0.0 Id = 534/536 (99%) Gaps = 0/536 (0%) Strand = Plus/Minus | YVYRLPIRS LTGGAGGG GRQEAWM GT | 26 | gi\|4758412\|ref\| NP_004472.1\| Polypeptide N-acetylgalactosa-minyltransferase 2 Growth/differentia-tion factor-11 Ras and Rab interactor 3 | Score = 29.1 bits (61), Expect = 1.2 Id = 11/15 (73%), Positives = 12/15 (80%), Gaps = 1/15 (6%) Query 10 LTGGAGGG-CRQEAW 23 L GGAGGG GR+E W Sbjct 31 LAGGAGGGAGRKEDW 45 |
| 120 | 12_C12 | gi\|22002645\| emb\|AL1588 27.27\|Human DNA sequence from clone RP11-330M2 on chromosome 9, complete sequence | VWAA | 4 | gi\|31419318\|gb\| AAH52995.1\| SAPS2 protein gi\|32810412\|gb\| AAO65542.1\| UDP-glucuronosyl-transferase 2B7 gi\|13699834\|ref\| NP_085080.1\| | Score = 16.8 bits (32), Expect = 1771 Identities = 4/4 (100%), Positives = 4/4 (100%), Gaps = 0/4 (0%) Query 1 VWAA 4 VWAA Sbjct 684 VWAA 687 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | Length = 186108 Score = 531 bits (268) Expect = 1e-148 Id = 272/274 (99%) Gaps = 0/274 (0%) Strand = Plus/Plus | | | matrilin 4 isoform 2 gi\|55962492\|emb\| CAI17303.1\| receptor tyrosine kinase-like orphan receptor 2 gi\|57242755\|ref\| NP_055759.3\| calsyntenin 1 isoform 2 gi\|45767643\|gb\| AAH67427.1\| Cytochrome P450, family 1, sub-family A, poly-peptide 2 ATP-binding cassette Solute carrier family 26, member 11 | |
| 123 | 12_D2 | gi\|37694066\| ref\|NM_197955.1\|Homo sapiens chromosome 15 open reading frame 48 (C15orf48), transcript variant 1, mRNA Length = 815 Score = 214 bits (108) Expect = 1e-53 Id = 115/118 (97%) Gaps = 0/118 (0%) Strand = Plus/Minus | CTNGILLK KI | 10 | gi\|29568109\|ref\| NP_055520.2\| dedicator of cytokinesis 4 gi\|29335973\|gb\| AAO73565.1\| DOCK4 gi\|18089123\|gb\| AAH20733.1\| Sushi-repeat-containing protein, X-linked 2 gi\|22001626\|sp\| Q9UKD1\|GM EB2_HUMAN Glucocorticoid mod-ulatory element-binding protein 2 (GMEB-2) (Parvovirus initiation factor p79)(PIF p79) (DNA-binding protein p79PIF) 516.1\| nucleic acid hel-icase DDXx gi\|62897301\|dbj\| BAD96591.1\| Fanconi anemia, complemeatation group C variant gi\|16506130\|dbj\| BAB70696.1\| phosphatidylino-sitol 3-kinase-related protein kinase gi\|62087846\|dbj\| BAD92370.1\| ataxia telangi-ectasia mutated protein isoform 1 variant gi\|32483361\|ref\| NP_863658.1\| apoptotic protease activating factor isoform d | Score = 24.4 bits (50), Expect = 22 Id = 7/8 (87%), Positives = 7/8 (87%), Gaps = 0/8 (0%) Query 3 NGILLKKI 10 N ILLKKI Sbjct 1132 NSILLKKI 1139 Score = 23.1 bits (47), Expect = 54 Id = 6/7 (85%), Positives = 7/7 (100%), Gaps = 0/7 (0%) Query 1 CTNGILL 7 CTNG+LL Sbjct 135 CTNGVLL 141 Score = 22.3 bits (45), Expect = 98 Id = 6/8 (75%), Positives = 8/8 (100%), Gaps = 0/8 (0%) Query 3 NGILLKKI 10 NGI+L+KI Sbjct 149 NGIMLRKI 156 Score = 21.8 bits (44), Expect = 131 Id = 6/9 (66%), Positives = 8/9 (88%), Gaps = 0/9 (0%) Query 1 CTNGILLKK 9 CT G+LL+K Sbjct 678 CTTGVLLRK 686 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| 126 | 8_G8 | gi\|11544447\|emb\|AL139349.36\|Human DNA sequence from clone RP11-261P9 on chromosome 20 Length = 68754 Score = 1035 bits (522) Expect = 0.0 Id = 623/647 (96%) Gaps = 10/647 (1%) Strand = Plus/Minus | HSHISNRKT TNGYLEVA PTWKGKAG QGFGH | 30 | gi\|31874131\|emb\| CAD97974.1\| hypothetical protein gi\|15214067\|sp\| O95405\|ZFYV 9_HUMAN (Receptor activation anchor) Serine protease-like protein Smad anchor for receptor activation gi\|55741557\|ref\| NP_055809.1 Mitogen-activated protein kinase binding protein 1 gi\|182775\|gb\| AAA58487.1\| v-fos transformation effector protein Mothers against decapentaplegic homolog interacting protein (Madh-interacting protein) Novel serine protease Adapter related protein complex 3 beta 1 subunit Dickkopf-like protein 1 precursor | Score = 28.6 bits (60), Expect = 1.1 Id = 8/10 (80%), Pos = 10/10 (100%), Gaps = 0/10 (0%) Query 20 WKGKAGQGFG 29 W+G+AGQGFG Sbjct 5 WRGRAGQGFG 14 core = 26.5 bits (55), Expect = 4.8 Id = 12/19 (63%), Pos = 12/19 (63%), Gaps = 4/19 (21%) Query 4 ISNRK--TTNGYLEVAPTW 20 IS RK  TT G  EVAP W Sbjct 578 ISARKPFTTLG--EVAPVW 594 Score = 23.5 bits (48), Expect = 38 Id = 9/16 (56%), Pos = 12/16 (75%), Gaps = 2/16 (12%) Query 7 RKTTNGY-LEVAPTWK 21 RKTT   Y ++V P+WK Sbjct 609 RKTTL-YDMDVEPSWK 623 |
| 127 | 9_H7 | gi\|23268261\|gb\|AC129782.3\|*Homo sapiens* BAC clone RP111-2807 from UL, complete sequence Length = 66860 Score = 172 bits (87) Expect = 3e-41 Id = 92/94 (97%) Gaps = 0/94 (0%) Strand = Plus/Plus | YRLMEEN | 7 | gi\|119592213\|gb\| EAW71807.1 zona pellucida glycoprotein 3 (sperm receptor), isoform CRA_a gi\|113415975\|ref\| XP_001129178.1\|PREDICTED: similar to multiple coiled-coil GABABR1-binding protein gi\|28436730\|gb\| AAH47075.1\| Janus kinase and microtubule interacting protein 1 gi\|38641276\|gb\| AAR26235.1\| MARLIN1 gi\|119602807\|gb\| EAW82401.1 janus kinase and microtubule interacting protein 1, isoform CRA_a gi\|5817226\|emb\| CAB53703.1\| hypothetical protein gi\|11995070\|dbj\| BAB20049.1\| calmodulin-dependent phosphodiesterase | Score = 24.4 bits (50), Expect = 22 Id = 6/6 (100%), Positives = 6/6 (100%), Gaps = 0/6 (0%) Query 2 RLMEEN 7 RLMEEN Sbjct 124 RLMEEN 129 Score = 24.4 bits (50), Expect = 22 Id = 7/8 (87%), Positives = 7/8 (87%), Gaps = 1/8 (12%) Query 1 YRL-MEEN 7 YRL MEEN Sbjct 564 YRLEMEEN 571 Score = 18.5 bits (36), Expect = 1331 Id = 4/5 (80%), Positives = 5/5 (100%), Gaps = 0/5 (0%) Query 2 RLMEE 6 RLM+E Sbjct 207 RLMDE 211 Score = 24.4 bits (50), Expect = 22 Id = 7/8 (87%), Positives = 7/8 (87%), Gaps = 1/8 (12%) Query 1 YRL-MEEN 7 YRL MEEN Sbjct 571 YRLEMEEN 578 Score = 18.5 bits (36), Expect = 1331 Id = 4/5 (80%), Positives = 5/5 (100%), Gaps = 0/5 (0%) Query 2 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | | | | gi\|16151615\|emb\| CAC82208.1 3'5'-cyclic nucleotide phosphodiesterase 1A5 gi\|119631376\|gb\| EAX10971.\|1 phosphodiesterase 1A, calmodulin-dependent, isoform CRA_g gi\|1705942\|sp\| P54750\|PDE1A _HUMAN Calcium/calmodu-lin-dependent 3', 5'-cyclic nucleo-tide phosphodi-esterase 1A gi\|119604572\|gb\| EAW84166.1 SW1/SNF related, matrix associated, actin dependent regulator of chromatin, sub-family a, member 4 gi\|4056413\|gb\| AAC97987.1\| SN24_HUMAN; nuclear protein GRB1; home-otic gene regula-tor; SNF2-BETA gi\|738309\|prf\|\| 1924378A nucler protein GRB1 gi\|505088\|dbj\| BAA05143.1\| transcriptional activator hSNF2b gi\|109734817\|eb\| AAI17695.1\| DOCK4 protein gi\|40254834\|ref\| NP_006603.2\| kinesin family member 1C gi\|116242606\|sp\| O43896\|KIF1 C_HUMAN Kinesin-like pro-tein KIF1C gi\|109734809\|gb\| AA117689.1\| Dedicator of cytokinesis 4 | RLMEE 6 RLM+E Sbjct 207 RLMDE 211 |
| 12 8 | 9_D1 1 | gi\|20800377\| gb\|AC11661 8.4\|*Homo sapiens* BAC clone RP11-98L17 from 4, complete sequence Length = 153040 Score = 220 bits (111) Expect = 2e- | KSFKVNI SLMFCK | 13 | gi\|113415614\|ref\| XP_0011282 50.1\|PREDICTED: hypothetical protein gi\|119611411\|gb\| EAW91005. astrotactin, isoform CRA_a gi\|119602676\|gb\| EAW82270.1 hCG1995022 gi\|20270245\|ref\| | Score = 26.1 bits (54), Expect = 9.5 Id = 9/20(45%), Positives = 10/20 (50%), Query 2 SFKYNISL--------MFCK 13 S+ Y ISL      MFCK Sbjct 7 SYMYQISLQQAFCTVIMFCK 26 Score = 25.7 bits (53), Expect = 13 Id = 7/8 (87%), Positives = 7/8 (87%), Gaps = 1/8 (12%) Query 5 YNISLMFC 12 YNI LMFC |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | 55<br>Id = 113/114 (99%)<br>Gaps = 0/114 (0%)<br>Strand = Plus/Minus | | | NP_612474.1\|<br>GLI-Kruppel family member GLI4<br>gi\|33302619\|sp\|P10075\|GLI4_HUMAN<br>Zinc finger protein GLI4 (krueppel-related zinc finger protein 4) (Protein HKR4)<br>gi\|119576919\|gb\|EAW56515.1\|<br>CTTNBP2 N-terminal like,<br>gi\|119570340\|gb\|EAW49955.1\|<br>Rho GTPase activating protein 19, isoform CRA_d | Sbjct 686<br>YNI-LMFC 692<br>Score = 24.8 bits (51), Expect = 23<br>Id = 8/10 (80%), Positives = 9/10 (90%)<br>Gaps = 1/10 (10%)<br>Query 1<br>KSFKYNISLM 10<br>KSFKYN SL+<br>Sbjct 190<br>KSFKYN-SLL 198 |
| 129 | 6_C3 | none | GISTLK | 6 | gi\|119574273\|gb\|EAW53888.1\|<br>hCG2040542<br>gi\|119628905\|gb\|EAX08500.1\|<br>breast cancer 2, early onset, isoform CRA_b<br>gi\|55957538\|emb\|CA113195.1\|<br>BRCA2<br>gi\|14424438\|sp\|P51587\|BRCA2_HUMAN<br>Breast cancer type 2 susceptibility protein (Fanconi anemia group D1 protein)<br>gi\|42793995\|gb\|AAH66592.1\|<br>CUTL1 protein<br>gi\|119570613\|gb\|EAW50228.1\|<br>cut-like 1, CCAAT displacement protein (Drosophila), isoform<br>gi\|44887461\|gb\|AAS48058.1\|<br>T cell antigen receptor beta chain<br>gi\|1552504\|gb\|AAC80198.1\|<br>V segment translation product | Score = 20.6 bits (41), Expect = 426<br>Id = 6/6 (100%), Positives = 6/6 (100%),<br>Gaps = 0/6 (0%)<br>Query 1<br>GISTLK 6<br>GISTLK<br>Sbjct 170<br>GISTLK 175<br>Score = 19.3 bits (38), Expect = 1030<br>Id = 6/10 (60%), Positives = 6/10 (60%),<br>Gaps = 0/10 (0%)<br>Query 2<br>ISTLKXXXXK 11<br>ISTLK    K<br>Sbjct 580<br>ISTLKKKTNK 589<br>Score = 18.9 bits (37), Expect = 1381<br>Id = 6/10 (60%), Positives = 6/10 (60%),<br>Gaps = 0/10 (0%)<br>Query 3<br>STLKXXXXKL 12<br>STLK    KL<br>Sbjct 336<br>STLKQLEEKL 345 |
| 130 | 10_D3 | gi\|15451718\|gb\|AC022973.5\|Homo sapiens, clone RP11-47304, complete sequence<br>Length = 194367<br>Score = 180 bits (91)<br>Expect = 2e- | GDPNS | 5 | gi\|119615660\|gb\|EAW95254.1\|<br>cytoplasmic linker associated protein 1, isoform CRA_c<br>gi\|119607399\|gb\|EAW86993.1\|<br>telomeric repeat binding factor (NIMA-interacting) 1, isoform CRA_a<br>gi\|119612111\|gb\|EAW91705.1\| | Score = 18.5 bits (36), Expect = 957<br>Id = 5/5 (100%), Positives = 5/5 (100%),<br>Gaps = 0/5 (0%)<br>Query 1<br>GDPNS 5<br>GDPNS<br>Sbjct 216<br>GDPNS 220 |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | 43<br>Id = 91/91 (100%)<br>Gaps = 0/91 (0%)<br>Strand = Plus/Minus | | | protein phosphatase 2C, magnesium-dependent, catalytic subunit, isoform<br>gi\|119588281\|gb\|EAW67875.1 protein tyrosine phosphatase, receptor type, J, isoform CRA_c<br>gi\|113420339\|ref\|XP_944412.2\|PREDICTED: similar to growth inhibition and differentiation related protein 86 | |
| 3 | 10_C3 | gi\|19807899\|gb\|AC11076 9.2\|Homo sapiens BAC clone RPII-141B14 from 2, complete sequence<br>Length = 135317<br>Score = 599 bits (302)<br>Expect = 2e-168<br>Id = 312/317 (98%)<br>Gaps = 0/317 (0%)<br>Strand = Plus/Plus | EMKRHIST LRWKTCLN ANMKELLE IKVTGKIRY NQGL | 37 | gi\|585487\|sp\|Q07325\|SCYB9_HUMAN Small inducible cytokine B9 precursor (CXCL9) Gamma interferon induced monokine (MIG) (27.8)<br>gi\|62898822\|dbj\|BAD97265.1 Serologically defined colon cancer antigen 33 variant Antigen NY-CO-33 (26.1)<br>gi\|31077164\|sp\|O95757/HS74L_HUMAN Heat shock 70 kDa protein 4L<br>gi\|21315086\|gb\|AAH30792.1\| Cyclin-dependent kinase 5, regulatory subunit 1<br>Transient receptor potential cation channel subfamily V member 3 Vanilloid receptor-like 3 (VRL-3)<br>Dehydrodolichyl diphosphatc synthase<br>Tyrosyl-tRNA synthetase<br>Putative mitochondrial outer membrane protein import receptor | Score = 27.8 bits (58), Expect = 5.1<br>Id = 14/28 (50%), Pos = 17/28 (60%), Gaps = 11/28 (39%)<br>Query 12 ISTLRWK----TCLN---ANMKELLEIK 32<br>I+TL K    TCLN   A++ KEL IK<br>Sbjct 64 IATL--KNGVQTCLNPDSADVKEL--IK 87<br>Score = 26.1 bits (54), Expect = 9.0<br>Id = 9/13 (69%), Pos = 12/13 (92%), Gaps = 1/13 (7%)<br>Query 19 MKELLEIKVTGKI 31<br>M+EL+E KVTGK+<br>Sbjct 270 MEELVE-KVTGKV 281<br>Score = 24.0 bits (49), Expect = 39<br>Id = 6/6 (100%), Pos = 6/6 (100%), Gaps = 0/6 (0%)<br>Query 8 TLRWKT 13<br>TLRWKT<br>Sbjct 403 TLRWKT 408 |
| 5 | 10_G8 | gi\|21686938\|gb\|AC11605 0.3\|Homo sapiens BAC clone RP11-427F2 from 2, complete sequence<br>Length = 165225 | CINMDSPPK QC | 11 | gi\|57208724\|emb\|CA142568.1 GNAS complex locus (OTTHUMP00000031737) Guanine nucleotide binding protein, alpha stimulating activity polypeptide 1 | Score = 24.8 bits (51), Expect = 338<br>Id = 6/7 (85%), Pos = 7/7 (100%), Gaps = 0/7 (0%)<br>Query 2 INMDSPP 8<br>+NMDSPP<br>Sbjct 195 VNMDSPP 201<br>Score = 22.3 bits (45), Expect = 131<br>Id = 7/9 (77%), Pos = 7/9 (77%), |

TABLE 6b-continued

| Rank | Clone | Description of the genes that are in Mimotope clones | Peptide sequences of Mimotopes, in-frame with T7 10 B gene | Size of peptide | Description of the sequences that Mimotopes mimic | Region of similarity of peptide |
|---|---|---|---|---|---|---|
| | | Score = 343 bits (173) Expect = 3e-92 Id = 179/182 (98%) Gaps = 0/182 (0%) Strand = Plus/Plus | | | gi|68565390|sp| Q14676|MDC1_HUMAN Mediator of DNA damage checkpoint protein 1 (Nuclear factor with BRCT domains 1) gi|50400452|sp| Q7Z569/BRAP _HUMANBRCA1-associ- ated protein (Impedes mitogenic signal propagation) (IMP) gi|739072|prf|| 2002263A E1A-assoc protein gp130 Retinoblastoma-like protein 2 gi|55957867|emb| CA113220.1 E74-like factor 1 (ets domain trans- cription factor) RUN and SH3 domain containing protein 2 Ezrin-radixin- moesin binding phosphoprotein 50 Impedes mitogenic signal propagation (IMP) Membrane-associated nucleic acid bind- ing protein E1A-associated protein gp130 | Gaps = 2/9 (22%) Query 4 MDSPP--KQ 10 MDSPP  KQ Sbjct 1818 MDSPPHQKQ 1826 Score 22.3 bits (45), Expect = 131 Id = 8/12 (66%), Pos = 8/12 (66%), Gaps = 2/12 (16%) Query 1 CINM--DSPPKQ 10 CIN   DSP KQ Sbjct 110 CINAAPDSPSKQ 121 |
| 13 | 6_C8 | gi|21263318| gb|AC10444 1.2|*Homo sapiens* chromosome 3 clone RP11- 901H12, complete se- quence Length = 2177320 Score = 262 bits (132) Expect = 4e-67 Id = 160/171 (93%) Gaps = 1/171 (0%) Strand = Plus/Minus | GAGWEWV | 7 | gi|18089035|gb| AAH20586.1| SERS14 protein gi|49256613|gb| AAH73912.1| ACCN4 protein Regenerating islet derived protein 3 alpha precursor Pancreatitis associated protein 1 (PAP) (21.8) ELAM-1 ligand fucosyltransferase Mitochondrial ri- bosomal protein bMRP64 | Score = 23.1 bits (47), Expect = 38 Id = 5/5 (100%), Pos = 5/5 (100%), Gaps = 0/5 (0%) Query 3 GWEWV 7 GWENV Sbjct 946 GWEWV 950 Score = 22.7 bits (46), Expect = 50 Id = 5/5 (100%), Positives = 5/5 (100%), Gaps = 0/5 (0%) Query 2 AGWEW 6 AGWEW Sbjct 255 AGWEW 259 |
| 14 | 6_D4 | gi|15004913| gb|AC00947 5.5|*Homo sapiens* BAC clone RP11- 285F23 from 2, complete sequence Score = 835 bits(421) | PLCLASLLS FIVCLFHFR YLPTILLPP I LKHKCNDR MHLTCFGS AKALMYSL SNNRC | 57 | gi|57209194|emb| CAI41407.1 Dedicator of cytokinesis 11 DOCK11 protein Cdc42-associated guanine nucleotide exchange factor ACG|DOCK11 gi|13634012|sp| | Score = 32.9 bits (70), Expect = 0.19 Id = 8/9 (88%), Positives = 9/9 (100%), Gaps = 0/9 (0%) Query 12 VCLFHFRYL 20 VCLFHFRY+ Sbjct 1319 VCLFHFRYM 1327 Score = 30.3 bits (64), Expect = 1.7 Id = 14/44 (31%), Pos = 20/44 (45%), |

TABLE 6b-continued

| Rank | Clone | Description of the genes that are in Mimotope clones | Peptide sequences of Mimo-topes, in-frame with T7 10 B gene | Size of pep-tide | Description of the sequences that Mimotopes mimic | Region of similarity of peptide |
|---|---|---|---|---|---|---|
| | | Expect = 0.0<br>Id = 424/425 (99%)<br>Gaps = 0/425 (0%)<br>Strand = Plus/Minus | | | Q15884\|C161_HUMAN Protein C9orf61 (Protein X123) Probable G-protein coupled receptor 113 precursor (G-protein coupled receptor PGR23) Wingless-type MMTV integration site family | Gaps = 21/44 (47%)<br>6<br>SPLCLA-------SLLSFIVCLFHFR-------------YLPT 28<br>S+ C+A        S+LSF+VC F +R           +LPT 37<br>SRMCMAISICQMLSMLSFVVCAFRYRHMFKRGWPMGTCCLFLPT 80 |
| 20 | 10_B 11 | gi\|21747795\| gb\|AC12486 4.3\|Homo sapiens BAC clone RPd11-570J4 from 4, complete sequence Length = 166797 Score = 224 bits (113) Expect = 4e-56 Id = 113/113 (100%) Gaps = 0/113 (0%) Strand = Plus/Plus | NSFHN | 5 | gi\|119626686\|gb\| EAX06281.1\| hCG21296, isoform CRA_c gi\|119615394\|gb\| EAW94988.1 ubiqititin specific peptidase 48, isoform CRA_b gi\|119584494\|gb\| EAW64090.1 solute carrier family 6 (neurotransmitter transporter, GABA), member 1, isoform CRA_a | Score = 20.2 bits (40), Expect = 295<br>Id = 5/5 (100%), Positives = 5/5 (100%),<br>Gaps = 0/5 (0%)<br>Query 1<br>NSFHN 5<br>NSFHN<br>Sbjct 310<br>NSFHN 314 |
| 25 | 9_C4 | gi\|22657585\| gb\|AC09156 4.12\|Homo sapiens chromosome 11, clone RP11-732A19, complete sequence Length = 211735 Score = 317 bits (160) Expect = 4e-84 Id = 193/204 (94%) Gaps = 3/204 (1%) Strand = Plus/Plus | GITGSRPA WPTW | 12 | gi\|119623989\|gb\| EAX03584.1\| cAMP responsive element binding protein-like 1 gi\|14250004\|gb\| AAH08394.1\| CREBL1 protein gi\|119625915\|gb\| EAX05510.1\| homeodomain-only protein gi\|24286115\|gb\| AAN46678.1\| hyypothetical protein HGRHSVI | Score 29.9 bits (63), Expect = 0.68<br>Id = 7/7 (100%), Positives = 7/7 (100%),<br>Gaps = 0/7 (0%)<br>Query 6<br>RPAWPTW 12<br>RPAWPTW<br>Sbjct 312<br>RPAWPTW 318<br><br>RPAWPTW |

REFERENCES

1. Alizadeh A A, et al. Distinct types of diffuse large B-cell lymphoma identified by gene expression profiling. Nature 403:503-511, (2000).
2. An, A, et al. A learning system for more accurate classifications. Lecture Notes in Artificial Intelligence, Vancouver. 1418:426-441, (1998).
3. Aunoble B, et al. Major oncogenes and tumor suppressor genes involved in epithelial ovarian cancer. Int J Oncol 16:567-76, (2000).
4. Baron A T, et al. Serum sErbB1 and Epidermal Growth Factor Levels As Tumor Biomarkers in Women with Stage III or IV Epithelial Ovarian Cancer Epidemiology. Biomarkers & Prevention 8:129-137, 1999.
5. Bauer R, et al. Cloning and characterization of the Drosophila homologue of the AP-2 transcription factor. Oncogene 17:1911-1922 (1998).
6. Bast R C, et al. Reactivity of a monoclonal antibody with human ovarian carcinoma. J. Clin Invest 68:1331-1337 (1981).

7. Bast R C et al. A radioimmunoassay using a monoclonal antibody to monitor the course of epithelial ovarian cancer. N Engl J Med 309: 883-887 (1983).
8. Berek, J S et al. Serum interleukins-6 levels correlate with disease status in patients with epithelial ovarian cancer. Am J Obstet Gynecol 164: 1038-1043 (1991).
9. Bittner, M et al. Molecular Classification of Cutaneous Malignant Melanoma by Gene Expression Profiling. Nature 406:536-540 (2000).
10. Blake C, et al. UCI respitory of machine learning databases (1998).
11. Boyd J, et al. Molecular genetic and clinical implications [Review]. Gynecol Oncol 64:196-206 (1997).
12. Breiman L, et al. Classification and regression trees, Wadsworth and Brooks (1984).
13. Buettner R, et al. An alternatively spliced form of AP-2 encodes a negative regulator of transcriptional activation by AP-2. Mol. Cell. Biol 13:4174-4185 (1993).
14. Chiao P J, et al. Elevated expression of the human ribosomal S2 gene in human tumors. Molecular Carcinogenesis 5:219-231 (1992).
15. Clark P, et al. The CN2 induction algorithm. Machine Learning 3:261-283 (1989).
16. Coleman M P, et al. Trends in cancer incidence and mortality. Lyon, France: IARC Scientific Publications 121:477-498 (1993).
17. Deyo J, et al. A novel protein expressed at high cell density but not during growth arrest. DNA and Cell Biol 17:437-447 (1998).
18. Draghici S. The Constraint Based Decomposition, accepted for publication in Neural Networks, to appear (2001).
19. Einhorn, N. et al. Prospective evaluation of serum CA 125 levels for early detection of ovarian cancer. Obstet Gynecol 80:14-18 (1992).
20. Golub T R, et al. Molecular classification of cancer: class discovery and class prediction by gene expression monitoring. Science 286:531-537 (1999).
21. Gotlieb W H, et al. Presence of interleukins in the ascites of patients with ovarian and other intrabdominal cancers. Cytokine 4:385-390 (1992).
22. Greenlee R T, et al. Cancer Statistics. CA Cancer J Clin 50:7-33 (2000).
23. Heath, S. et al. Induction of oblique decision tree. In IJCAI-93. Washington, D.C. (1993).
24. Hogdall E V, et al. Predictive values of serum tumour markers tetranectin, OVX1, CASA and CA125 in patients with a pelvic mass. Int J serum tumour markers tectranectin, OVX1, CASA and CA125 in patients with a pelvic mass. Int J Cancer 89:519-523 (2000).
25. Holschneider C H, et al. Ovarian cancer: epidemiology, biology, and prognostic factors. Semin Surg Oncol 1:3-10 (2000).
26. Houts T M: Improved 2-Color Normalization For Microarray Analyses Employing Cyanine Dyes, CAMDA (2000). Critical Assessment of Techniques for Microarray Data Mining. Duke University Medical Center, Dec. 18-19 (2000).
27. Jacobs I J, et al. Potential screening tests for ovarian cancer, in Sharp F, Mason W P, Leake R E (eds). Ovarian Cancer. London, Chapman and Hall Medical, 197-205 (1997).
28. Jacobs, I. Et al. Multimodal approach to screening for ovarian cancer. Lancet 1268-271 (1988).
29. Jacobs I, et al. The CA 125 tumor-associated antigen: a review of the literature. Hum Reprod 4:1-12 (1989).
30. Kacinski B M et al. Macrophage colony-stimulating factor is produced by human ovarian and endometrial adenocarcinoma-derived cell lines and is present at abnormally high levels in the plasma of ovarian carcinoma patients with active disease. Cancer Cells 7:333-337 (1989).
31. Kerr, Martin, Churchill. Analysis of variance for gene expression microarray data. Journal of Computational Biology (2000).
32. Kim, S Y et al. Coordinate Control of Growth and Cytokeratin 13 Expression by Retinoic Acid. Molecular Carcinogenesis 16:6-11 (1996).
33. Kohonen T. Learning vector quantization. Neural Networks, 1 (suppl. 1):303 (1988).
34. Kohonen T. Learning vector quantization. In the handbook of brain theory and neural networks pp. 537-540. Cambridge Mass.: MIT press (1995).
35. MacBeath G. et al. Printing proteins as microarrays for high-throughput function determination. Science 289: 1760-3 (2000).
36. Murthy K. On growing better decision trees from data. Unpublished doctoral dissertation. John Hopkins University (1995).
37. Musavi M. et al. On the training of radial basis functions classifiers. Neural Networks 5:595-603 (1992).
38. Patsner B. et al. Comparison of serum CA 125 and lipid associated sialic acid (LASA-P) in monitoring patients with invasive ovarian adenocarcinoma. Gynecol Oncol 30(1): 98-103 (1988).
39. Peng Y S, et al. ARHI is the center of allelic deletion on chromosome lp31 in ovarian and breast cancers. Int J Cancer 86:690-4 (2000).
40. Precup D, et al. Classification using $/Phi$-machines and constructive function approximation. In Proc. 15th International Conf. On Machine Learning, pages 439-444. Morgan Kaufmann, San Francisco, Calif. (1998).
41. Poggio T, et al. Networks for approximation and learning. Proceedings of IEEE 78(9):1481-149 (1990).
42. Quinlan J R: C4.5: Programs for machine learning, Morgan-Kaufmann (1993).
43. Rumelhart, D E, et al. Learning internal representations by error backpropagation. Parallel Distributed Processing: Explorations in the Microstructures of Cognition, MIT Press/Bradford Books (1986).
44. Schwartz P E, et al. Circulating tumor markers in the monitoring of gynecologic malignancies. Cancer 60:353-361 (1987).
45. Schmittgen T D et al. Quantitative reverse transcription-polymerase chain reaction to study mRNA decay: comparison of endpoint and real-time methods. Anal Biochem, 285:194-204 (2000).
46. Sonoda K, Nakashima M, Kaku T, Kamura T, Nakano H, Watanabe T. A novel tumor-associated antigen expressed in human uterine and ovarian carcinomas. Cancer 1996 77:1501-9,
47. Nakashima M, Sonoda K, Watanabe T. Inhibition of cell growth and induction of apoptotic cell death by the human tumor-associated antigen RCAS1. Nat. Med. 1999 5:938-42.
48. Lindstrom M S, Klangby U, Wiman K G. p14ARF homozygous deletion or MDM2 overexpression in Burkitt lymphoma lines carrying wild type p53. Oncogene. 20(17):2171-7, 2001.

What is claimed is:

1. A diagnostic device for use in detecting the presence of head and neck squamous cell carcinoma (HNSCC) in a patient comprising an immunoassay incorporating at least one polypeptide marker antigen for HNSCC, for detecting a presence of at least one antibody in a patient's serum indicative of HNSCC and reactive with at least one of the following polypeptide marker antigens for HNSCC, each of said polypeptide marker antigens comprising a SEQ ID NO. selected from SEQ ID NO:3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35, SEQ ID NO: 45, SEQ ID NO: 59, SEQ ID NO: 69, SEQ ID NO: 79, SEQ ID NO: 98, SEQ ID NO: 102, SEQ ID NO: 112, SEQ ID NO: 122, SEQ ID NO: 136, SEQ ID NO: 146, SEQ ID NO: 156, SEQ ID NO: 164, SEQ ID NO: 168, SEQ ID NO: 178, SEQ ID NO: 188, SEQ ID NO: 198, SEQ ID NO: 208, SEQ ID NO: 218, SEQ ID NO: 228, SEQ ID NO: 235, SEQ ID NO: 245, SEQ ID NO: 255, SEQ ID NO: 265, SEQ ID NO: 275, SEQ ID NO: 292, SEQ ID NO: 305, SEQ ID NO: 327, SEQ ID NO: 337, SEQ ID NO: 347, SEQ ID NO: 351, SEQ ID NO: 361, SEQ ID NO: 375, SEQ ID NO: 385, SEQ ID NO: 389, SEQ ID NO: 399, SEQ ID NO: 422, SEQ ID NO: 432, SEQ ID NO: 442, SEQ ID NO: 452, SEQ ID NO: 456, SEQ ID NO: 460, SEQ ID NO: 473, SEQ ID NO: 483, SEQ ID NO: 490, SEQ ID NO: 497, SEQ ID NO: 507, SEQ ID NO: 517, SEQ ID NO: 527, SEQ ID NO: 537, SEQ ID NO: 547, SEQ ID NO: 554, SEQ ID NO: 564, SEQ ID NO: 574, SEQ ID NO: 578, SEQ ID NO: 600, SEQ ID NO: 607, SEQ ID NO: 614, SEQ ID NO: 625, SEQ ID NO: 632, SEQ ID NO: 642, SEQ ID NO: 646, SEQ ID NO: 653, SEQ ID NO: 663, SEQ ID NO: 670, SEQ ID NO: 683, SEQ ID NO: 687, SEQ ID NO: 698, SEQ ID NO: 705, SEQ ID NO: 712, SEQ ID NO: 719, SEQ ID NO: 743, SEQ ID NO: 753, SEQ ID NO: 763, SEQ ID NO: 770, SEQ ID NO: 781, SEQ ID NO: 785, SEQ ID NO: 795, SEQ ID NO: 802, SEQ ID NO: 812, SEQ ID NO: 822, SEQ ID NO: 843, SEQ ID NO: 852, SEQ ID NO: 859, SEQ ID NO: 869, SEQ ID NO: 882, SEQ ID NO: 892, SEQ ID NO: 896, SEQ ID NO: 909, SEQ ID NO: 919, SEQ ID NO: 938, SEQ ID NO: 948, SEQ ID NO: 966, SEQ ID NO: 976, SEQ ID NO: 986, SEQ ID NO: 996, SEQ ID NO: 1016, SEQ ID NO: 1029, SEQ ID NO: 1039, SEQ ID NO: 1072, SEQ ID NO: 1080, SEQ ID NO: 1093, SEQ ID NO: 1103, or SEQ ID NO: 1119, or consisting of a SEQ ID NO. selected from SEQ ID NO: 55, SEQ ID NO: 371, SEQ ID NO: 621, SEQ ID NO: 694, SEQ ID NO: 962, SEQ ID NO: 777, SEQ ID NO: 1129, or SEQ ID NO: 1076; each of said polypeptides being expressed as an insert in frame with the T7 10B phage capsid gene product as a fusion polypeptide.

2. The diagnostic device of claim 1, wherein said immunoassay is selected from the group consisting of a microarray immunoassay, a macroarray immunoassay, a bead array immunoassay, an ELISA, a slide immunoassay, and a filter immunoassay.

3. A diagnostic device for use in staging head and neck squamous cell carcinoma (HNSCC) in a patient comprising an immunoassay incorporating at least one polypeptide marker antigen for HNSCC, for detecting a presence of at least one antibody in a patient's serum indicative of HNSCC and reactive with at least one of the following peptide markers for HNSCC, each of said polypeptide marker antigens comprising a SEQ ID NO. selected from SEQ ID NO:3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35, SEQ ID NO: 45, SEQ ID NO: 59, SEQ ID NO: 69, SEQ ID NO: 79, SEQ ID NO: 98, SEQ ID NO: 102, SEQ ID NO: 112, SEQ ID NO: 122, SEQ ID NO: 136, SEQ ID NO: 146, SEQ ID NO: 156, SEQ ID NO: 164, SEQ ID NO: 168, SEQ ID NO: 178, SEQ ID NO: 188, SEQ ID NO: 198, SEQ ID NO: 208, SEQ ID NO: 218, SEQ ID NO: 228, SEQ ID NO: 235, SEQ ID NO: 245, SEQ ID NO: 255, SEQ ID NO: 265, SEQ ID NO: 275, SEQ ID NO: 292, SEQ ID NO: 305, SEQ ID NO: 327, SEQ ID NO: 337, SEQ ID NO: 347, SEQ ID NO: 351, SEQ ID NO: 361, SEQ ID NO: 375, SEQ ID NO: 385, SEQ ID NO: 389, SEQ ID NO: 399, SEQ ID NO: 422, SEQ ID NO: 432, SEQ ID NO: 442, SEQ ID NO: 452, SEQ ID NO: 456, SEQ ID NO: 460, SEQ ID NO: 473, SEQ ID NO: 483, SEQ ID NO: 490, SEQ ID NO: 497, SEQ ID NO: 507, SEQ ID NO: 517, SEQ ID NO: 527, SEQ ID NO: 537, SEQ ID NO: 547, SEQ ID NO: 554, SEQ ID NO: 564, SEQ ID NO: 574, SEQ ID NO: 578, SEQ ID NO: 600, SEQ ID NO: 607, SEQ ID NO: 614, SEQ ID NO: 625, SEQ ID NO: 632, SEQ ID NO: 642, SEQ ID NO: 646, SEQ ID NO: 653, SEQ ID NO: 663, SEQ ID NO: 670, SEQ ID NO: 683, SEQ ID NO: 687, SEQ ID NO: 698, SEQ ID NO: 705, SEQ ID NO: 712, SEQ ID NO: 719, SEQ ID NO: 743, SEQ ID NO: 753, SEQ ID NO: 763, SEQ ID NO: 770, SEQ ID NO: 781, SEQ ID NO: 785, SEQ ID NO: 795, SEQ ID NO: 802, SEQ ID NO: 812, SEQ ID NO: 822, SEQ ID NO: 843, SEQ ID NO: 852, SEQ ID NO: 859, SEQ ID NO: 869, SEQ ID NO: 882, SEQ ID NO: 892, SEQ ID NO: 896, SEQ ID NO: 909, SEQ ID NO: 919, SEQ ID NO: 938, SEQ ID NO: 948, SEQ ID NO: 966, SEQ ID NO: 976, SEQ ID NO: 986, SEQ ID NO: 996, SEQ ID NO: 1016, SEQ ID NO: 1029, SEQ ID NO: 1039, SEQ ID NO: 1072, SEQ ID NO: 1080, SEQ ID NO: 1093, SEQ ID NO: 1103, or SEQ ID NO: 1119, or consisting of a SEQ ID NO. selected from SEQ ID NO: 55, SEQ ID NO: 371, SEQ ID NO: 621, SEQ ID NO: 694, SEQ ID NO: 962, SEQ ID NO: 777, SEQ ID NO: 1129, or SEQ ID NO: 1076; each of said polypeptides being expressed as an insert in frame with the T7 10B phage capsid gene product as a fusion polypeptide.

4. The diagnostic device of claim 3, wherein said immunoassay is selected from the group consisting of a microarray immunoassay, a macroarray immunoassay, a bead array immunoassay, an ELISA, a slide immunoassay, and a filter immunoassay.

5. Isolated polypeptide marker antigens for head and neck squamous cell carcinoma, each of said polypeptide marker antigens comprising a SEQ ID NO. selected from SEQ ID NO:3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35, SEQ ID NO: 45, SEQ ID NO: 59, SEQ ID NO: 69, SEQ ID NO: 79, SEQ ID NO: 98, SEQ ID NO: 102, SEQ ID NO: 112, SEQ ID NO: 122, SEQ ID NO: 136, SEQ ID NO: 146, SEQ ID NO: 156, SEQ ID NO: 164, SEQ ID NO: 168, SEQ ID NO: 178, SEQ ID NO: 188, SEQ ID NO: 198, SEQ ID NO: 208, SEQ ID NO: 218, SEQ ID NO: 228, SEQ ID NO: 235, SEQ ID NO: 245, SEQ ID NO: 255, SEQ ID NO: 265, SEQ ID NO: 275, SEQ ID NO: 292, SEQ ID NO: 305, SEQ ID NO: 327, SEQ ID NO: 337, SEQ ID NO: 347, SEQ ID NO: 351, SEQ ID NO: 361, SEQ ID NO: 375, SEQ ID NO: 385, SEQ ID NO: 389, SEQ ID NO: 399, SEQ ID NO: 422, SEQ ID NO: 432, SEQ ID NO: 442, SEQ ID NO: 452, SEQ ID NO: 456, SEQ ID NO: 460, SEQ ID NO: 473, SEQ ID NO: 483, SEQ ID NO: 490, SEQ ID NO: 497, SEQ ID NO: 507, SEQ ID NO: 517, SEQ ID NO: 527, SEQ ID NO: 537, SEQ ID NO: 547, SEQ ID NO: 554, SEQ ID NO: 564, SEQ ID NO: 574, SEQ ID NO: 578, SEQ ID NO: 600, SEQ ID NO: 607, SEQ ID NO: 614, SEQ ID NO: 625, SEQ ID NO: 632, SEQ ID NO: 642, SEQ ID NO: 646, SEQ ID NO: 653, SEQ ID NO: 663, SEQ ID NO: 670, SEQ ID NO: 683, SEQ ID NO: 687, SEQ ID NO: 698, SEQ ID NO: 705, SEQ ID NO: 712, SEQ ID NO: 719, SEQ ID NO: 743, SEQ ID NO: 753, SEQ ID NO: 763, SEQ ID NO: 770, SEQ ID NO: 781, SEQ ID NO: 785, SEQ ID NO: 795, SEQ ID NO: 802, SEQ ID NO: 812, SEQ ID NO: 822, SEQ ID NO: 843, SEQ ID NO: 852, SEQ ID NO: 859, SEQ ID NO: 869, SEQ ID NO: 882, SEQ ID NO: 892, SEQ ID NO: 896, SEQ ID NO: 909, SEQ ID NO: 919, SEQ ID NO: 938, SEQ ID NO: 948, SEQ ID NO: 966, SEQ ID NO: 976, SEQ ID NO: 986, SEQ ID NO: 996, SEQ ID NO: 1016, SEQ ID NO: 1029, SEQ ID NO: 1039, SEQ ID NO: 1072, SEQ ID NO: 1080, SEQ ID NO: 1093, SEQ ID NO: 1103, or SEQ ID NO: 1119, or consisting of a SEQ ID NO. selected from SEQ ID NO: 55, SEQ ID NO: 371, SEQ ID NO: 621, SEQ ID NO: 694, SEQ ID NO: 962, SEQ ID NO: 777, SEQ ID NO: 1129, or SEQ ID NO: 1076; each of said polypeptides being expressed as an insert in frame with the T7 10B phage capsid gene product as a fusion polypeptide.

6. A method of diagnosing head and neck squamous cell carcinoma (HNSCC), including the steps of:
   detecting an antibody reactive with a polypeptide marker antigen of claim 1 in the serum of a patient indicative of the presence of HNSCC with the diagnostic device of claim 1; and
   diagnosing the patient with HNSCC.

7. The method of claim 6, wherein said polypeptide marker antigens are chosen from the group consisting of SEQ ID NOs: 3, 7, 11, 15, 19, 23, 27 and 31, wherein each of said polypeptides are expressed as an insert in frame with the T7 10B phage capsid gene product as a fusion polypeptide.

8. A method of staging head and neck squamous cell carcinoma (HNSCC), including the steps of:
   detecting an antibody reactive with a polypeptide marker antigen of claim 3 in the serum of a patient indicative of a stage of HNSCC with the diagnostic device of claim 3; and
   determining the stage of HNSCC.

9. The method of claim 8, wherein said polypeptide marker antigens are chosen from the group consisting of SEQ ID NOs: 3, 7, 11, 15, 19, 23, 27 and 31, wherein each of said polypeptides are expressed as an insert in frame with the T7 10B phage capsid gene product as a fusion polypeptide.

* * * * *